(12) United States Patent
Barawkar et al.

(10) Patent No.: US 10,745,397 B2
(45) Date of Patent: Aug. 18, 2020

(54) 1-SUBSTITUTED 1,2,3,4-TETRAHYDRO-1,7-NAPHTHYRIDIN-8-AMINE DERIVATIVES AND THEIR USE AS EP4 RECEPTOR ANTAGONISTS

(71) Applicant: TAKEDA PHARMACEUTICAL COMPANY LIMITED, Osaka-shi, Osaka (JP)

(72) Inventors: Dinesh Barawkar, Maharashtra (IN);
Anil M Deshpande, Maharashtra (IN);
Santosh Patil, Maharashtra (IN);
Yogesh Waman, Maharashtra (IN);
Anil Panmand, Maharashtra (IN); Dilip Jadhav, Maharashtra (IN);
Bheemashankar Kulkarni, Karnataka (IN)

(73) Assignee: TAKEDA PHARMACEUTICAL COMPANY LIMITED, Osaka-shi, Osaka (JP)

( * ) Notice: Subject to any disclaimer, the term of this patent is extended or adjusted under 35 U.S.C. 154(b) by 0 days.

(21) Appl. No.: 15/746,828

(22) PCT Filed: Jul. 26, 2016

(86) PCT No.: PCT/JP2016/072244
§ 371 (c)(1),
(2) Date: Jan. 23, 2018

(87) PCT Pub. No.: WO2017/014323
PCT Pub. Date: Jan. 26, 2017

(65) Prior Publication Data
US 2018/0215754 A1    Aug. 2, 2018

(30) Foreign Application Priority Data
Jul. 23, 2015 (IN) .......................... 2244/DEL/2015

(51) Int. Cl.
*C07D 498/04* (2006.01)
*C07D 471/04* (2006.01)
*C07D 513/04* (2006.01)
*A61P 19/02* (2006.01)

(52) U.S. Cl.
CPC ............ *C07D 471/04* (2013.01); *A61P 19/02* (2018.01); *C07D 498/04* (2013.01); *C07D 513/04* (2013.01)

(58) Field of Classification Search
CPC .................................................... C07D 498/04
USPC ...................................... 544/105; 514/230.5
See application file for complete search history.

(56) References Cited

FOREIGN PATENT DOCUMENTS

| EP | 0752421 A1 | 1/1997 |
|---|---|---|
| EP | 2172447 A1 | 4/2010 |
| EP | 2277858 A1 | 1/2011 |
| WO | 9744038 A1 | 11/1997 |
| WO | 0132632 A2 | 5/2001 |
| WO | 2006011670 A1 | 2/2006 |
| WO | 2006065703 A1 | 6/2006 |
| WO | 2010019796 A1 | 2/2010 |
| WO | 2010080864 A1 | 7/2010 |
| WO | 2012039972 A1 | 3/2012 |
| WO | 2016021742 A1 | 2/2016 |
| WO | 2016088903 A1 | 6/2016 |

OTHER PUBLICATIONS

International search report dated Oct. 20, 2016 for corresponding international application PCT/JP2016/072244.
Woodward, D.F., et al.; "International Union of Basic and Clinical Pharmacology. LXXXIII: Classification of Prostanoid Receptors, Updating 15 Years of Progress"; Pharmacological Reviews 2011 vol. 63 No. 3; pp. 471-539.
Aoki, Tomohiro, et al.; "Prostaglandins and chronic inflammation"; Trends in Pharmacological Sciences Jun. 2012 vol. 33 No. 6; pp. 304-311.
Konya, Viktoria, et al.; "Endothelial E-type prostanoid 4 receptors promote barrier function and inhibit neutrophil trafficking"; J Allergy Clin Immunol Feb. 2013 vol. 131 No. 2; pp. 532-540.
Ahern, Philip, et al.; "Interleukin-23 Drives Intestinal Inflammation through Direct Activity on T Cells"; Immunity 33 Aug. 27, 2010; pp. 279-288.
Huber, Samuel, et al.; "Checks and Balances: IL-23 in the Intestine"; Immunity 33 Aug. 27, 2010; pp. 150-152.

(Continued)

*Primary Examiner* — Patricia L Morris
(74) *Attorney, Agent, or Firm* — Nath, Goldberg & Meyer; Joshua B. Goldberg; Scott H. Blackman

(57) ABSTRACT

The present invention provides a compound represented by the formula (I):

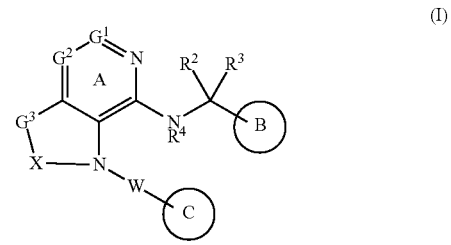

(I)

wherein each symbol is as defined in the specification, or a salt thereof has an EP4 receptor antagonistic action, and is useful as an agent for the prophylaxis or treatment of EP4 receptor associated diseases (e.g., rheumatoid arthritis, aortic aneurysm (e.g. abdominal aortic aneurysm, thoracic aortic aneurysm, thoracoabdominal aortic aneurysm etc.), endometriosis, ankylosing spondylitis, inflammatory breast cancer etc.) and the like.

5 Claims, 2 Drawing Sheets

(56) References Cited

OTHER PUBLICATIONS

Zimecki, Michal; "Potential therapeutic interventions via EP2/EP4 prostaglandin receptors"; Postepy Hig Med Dosw 66, 2012; pp. 287-294.
Chen, Q, et al.; "A novel antagonist of the prostaglandin E2 EP4 receptor inhibits Th1 differentiation and Th17 expansion and is orally active in arthritis models"; British Journal of Pharmacology 160, 2010; pp. 292-310.
Prentice, Andrew; "Endometriosis"; BMJ vol. 323, Jul. 14, 2001; pp. 93-95.
Harirforoosh, Sam, et al.; "Adverse Effects of Nonsteroidal Antiinflammatory Drugs: An Update of Gastrointestinal, Cardiovascular and Renal Complications"; J. Pharm. Pharm. Sci. vol. 16 No. 5, Dec. 31, 2013; pp. 821-847.
Olive, David L.; "Gonadotropin-Releasing Hormone Agonists for Endometriosis"; The New England Journal of Medicine vol. 359 No. 11, 2008; pp. 1136-1142.
Banu, Sakhila K., et al.; "Selective Inhibition of Prostaglandin E2 Receptors EP2 and EP4 Induces Apoptosis of Human Endometriotic Cells through Suppression of ERK1/2, AKT, NFkB, and B-Catenin Pathways and Activation of Intrinsic Apoptotic Mechanisms"; Mol Endocrinol vol. 23 No. 8, Aug. 2009; pp. 1291-1305.
Lee, JeHoon, et al.; "Selective blockade of prostaglandin E2 receptors EP2 and EP4 signaling inhibits proliferation of human endometriotic epithelial cells and stromal cells through distinct cell cycle arrest"; Fertil Steril vol. 93 No. 8, May 15, 2010; pp. 2498-2506.
Lee, JeHoon, et al.; "Selective inhibition of prostaglandin E2 receptors EP2 and EP4 inhibits invasion of human immortalized endometriotic epithelial and stromal cells through suppression of metalloproteinases"; Molecular and Cellular Endocrinology vol. 332, 2011; pp. 306-313.
Lee, JeHoon, et al.; "Selective Inhibition of Prostaglandin E2 Receptors EP2 and EP4 Inhibits Adhesion of Human Endometriotic Epithelial and Stromal Cells Through Suppression of Integrin-Mediated Mechanisms"; Biology of Reproduction vol. 88 No. 3, 2013; Article 77; pp. 1-11.
Alcorn, Hope G., et al.; "Risk Factors for Abdominal Aortic Aneurysms in Older Adults Enrolled in the Cardiovascular Health Study"; Arteriosclerosis, Thrombosis, and Vascular Biology vol. 16 No. 8 Aug. 1996; pp. 963-970.
Ernst, Calvin B.; "Abdominal Aortic Aneurysm"; The New England Journal of Medicine vol. 328 No. 16, Apr. 22, 1993; pp. 1167-1172.
Curci, John A., et al.; "Expression and Localization of Macrophage Elastase (Matrix Metalloproteinase-12) in Abdominal Aortic Aneurysms"; The Journal of Clinical Investigation vol. 102 No. 11, Dec. 1998; pp. 1900-1910.
Longo, G. Matthew, et al.; "Matrix metalloproteinases 2 and 9 work in concert to produce aortic aneurysms"; The Journal of Clinical Investigation vol. 110 No. 5, Sep. 2002; pp. 625-632.
Xiong, Wanfen, et al.; "Key Roles of CD4 T Cells and IFN-y in the Development of Abdominal Aortic Aneurysms in a Murine Model"; The Journal of Immunology vol. 172 No. 4 2004; pp. 2607-2612.
Annambhotla, Suman, et al.; "Recent Advances in Molecular Mechanisms of Abdominal Aortic Aneurysm Formation"; World Journal of Surgery vol. 32 No. 6 2008; pp. 976-986.
Walton, Lesley J., et al.; "Inhibition of Prostaglandin E2 Synthesis in Abdominal Aortic Aneurysms Implications for Smooth Muscle Cell Viability, Inflammatory Processes, and the Expansion of Abdominal Aortic Aneurysms"; Circulation vol. 100, 1999; pp. 48-54.
Yokoyama, Utako, et al.; "Inhibition of EP4 Attenuates Aortic Aneurysm Formation"; PLoS One vol. 7 No. 5, 2012; pp. e36724.
Bayston, T., et al.; "Prostaglandin E2 receptors in abdominal aortic aneurysm and human aortic smooth muscle cells"; Journal of Vascular Surgery vol. 38 No. 2, Aug. 2003; pp. 354-359.
Cao, Richard Y., et al.; "Prostagladin Receptor EP4 in Abdominal Aortic Aneurysms"; American Journal of Pathology vol. 181, Jul. 2012; pp. 313-321.
Pederson, OB, et al.; "Ankylosing Spondylitis in Danish and Norwegian twins: occurrence and the relative importance of genetic vs. environmental effectors in disease causation"; Scandinavian Journal of Rheumatology vol. 37, 2008; pp. 120-126.
Brown, Matthew A., et al.; "Susceptibility to Ankylosing Spondylitis in Twins"; Arthritis and Rheumatism vol. 40, 1997; pp. 1823-1828.
Brown, M A, et al.; "Recurrence risk modelling of the genetic susceptibility to ankylosing spondylitis"; Ann Rheum Dis vol. 59, 2000; pp. 883-886.
Evans, David M, et al.; "Interaction between ERAP1 and HLA-B27 in ankylosing spondylitis implicates peptide handling in the mechanism for HLA-B27 in disease susceptibility"; Nature Genetics vol. 43 No. 8, Aug. 2011; pp. 761-767.
Murase, Akio, et al.; "Effect of prostanoid EP4 receptor antagonist, CJ-042,794, in rat models of pain and inflammation"; European Journal of Pharmacology vol. 580, 2008; pp. 116-121.
Colucci, John, et al.; "Discovery of 4-{1-[({1-[4-(trifluoromethyl)benzyl]-1H-indol-7-yl}carbonyl)amino]cyclopropyl}benzoic acid (MF-766), a highly potent and selective EP4 antagonist for treating inflammatory pain"; Bioorganic & Medicinal Chemistry Letters vol. 20, 2010; pp. 3760-3763.

1-SUBSTITUTED 1,2,3,4-TETRAHYDRO-1,7-NAPHTHYRIDIN-8-AMINE DERIVATIVES AND THEIR USE AS EP4 RECEPTOR ANTAGONISTS

This is a National Phase Application filed under 35 U.S.C. 371 as a national stage of PCT/JP2016/072244, filed Jul. 22, 2016, an application claiming the benefit of Indian Application No. 2244/DEL/2015, filed Jul. 23, 2015, the content of each of which is hereby incorporated by reference in its entirety.

TECHNICAL FIELD

The present invention relates to a novel heterocyclic compound having an EP4 receptor antagonistic action, and may be useful an agent for the prophylaxis or treatment of EP4 receptor associated diseases (e.g., rheumatoid arthritis, aortic aneurysm (e.g. abdominal aortic aneurysm, thoracic aortic aneurysm, thoracoabdominal aortic aneurysm etc.), endometriosis, ankylosing spondylitis, inflammatory breast cancer etc.) and the like.

BACKGROUND OF THE INVENTION

Prostaglandin E2 (PGE2) is one of the most broadly distributed prostanoids throughout animal species and widely produced within the body by the actions of cyclooxygenases (COX) on arachidonic acid. PGE2 is involved in a number of physiological and pathophysiological responses such as fever, pain, inflammation (non-patent document 1) and elicits its biological functions through four receptor subtypes EP1-4, all G-protein-coupled receptor.

Emerging biology has revealed important roles of EP4 receptors in immune system (non-patent documents 2 and 3). For example, EP4 receptor activation stimulates dendritic cells and promotes IL-23 production synergistically with CD40 and Toll-like receptor signaling. PGE2 then enhances the expansion of Th17 cells with IL-23. EP4 receptor activation promotes the differentiation of Th1 from naive T cells synergistically with IL-12. PGE2 synergistically induces IL-6 and IL-13 expression with LPS via EP4 receptors in macrophages. Th1, Th17 and macrophage cells play key roles in the development of autoimmune/inflammatory diseases. Thus, a selective EP4 receptor antagonist is expected to inhibit IL-23 & IL-6 production and suppression of Th1 & Th17 function (non-patent documents 4 and 5), reduce inflammatory pain and offers an attractive therapeutic approach for rheumatoid arthritis (RA), inflammatory bowel diseases and other autoimmune/inflammatory diseases.

Non-steroidal anti-inflammatory drugs (NSAIDs) and COX-2 inhibitors are clinically proven to relieve inflammation and pain by inhibiting the synthesis of arachidonic acid pathway metabolites including PGE2. However, their use is associated with adverse effects due to pleiotropic function of arachidonic acid pathway metabolites and imbalance in their levels. An imbalance between TXA2 and PGI2, for example, has been implicated in the vasospasm, hyperaggregability and thromboembolism that are associated with many cardiovascular diseases (non-patent document 6). As EP4 selective antagonists specifically block PGE2 function through only EP4 receptor, leaving functions through other receptors intact, it is expected that they will not exhibit the adverse effects similar to that of NSAIDs and COX-2 inhibitors (non-patent document 7). Further, compared to other targeted therapies (e.g. JAK, TNFα, IL-6) for RA, EP4 antagonist has been shown to improve both joint damage and inflammatory pain in animal models. Thus, this mechanism has potential to "complete symptom management" for RA in clinic (non-patent document 8).

In addition to autoimmune diseases, endometriosis, aortic aneurysm (e.g. abdominal aortic aneurysm, thoracic aortic aneurysm, thoracoabdominal aortic aneurysm etc.) and ankylosing spondylitis are other indications for EP4 antagonist. Endometriosis (EM) is a chronic, estrogen-dependent inflammatory disease and defined as the presence of functional endometrial tissue at ectopic sites. It is a common disease that 10-20% of women of reproductive age are affected. The most common symptom is a dysmenorrhea. Chronic pelvic pain, dyspareunia, dyschezia (pain on defecation), loin pain, lower abdominal pain or back pain, pain on micturition, pain on exercise are also part of the symptoms of EM (non-patent document 9). Current treatments include surgical intervention, pharmacotherapies using NSAIDs, COX-2 inhibitors and hormonal therapies, or a combination of both. NSAIDs or COX-2 inhibitors are effective in relieving pelvic pain, but can cause severe side effects including gastrointestinal injury, nephropathy, and increase cardiovascular risk (non-patent document 10). Hormonal therapy controls disease conditions, but has side effect such as pseudomenopause and decreased bone density due to suppression of estrogen production (non-patent document 11). Development of a safer, but equally efficacious treatment is highly demanded. EP4 receptor proteins were abundantly expressed in human endometriosis tissues (ectopic and eutopic endometrium) during the proliferative phase of the menstrual cycle (non-patent document 12). In human immortalized endometriotic epithelial and stromal cells selective inhibition of EP4 induced apoptosis (non-patent document 12), inhibited proliferation (non-patent document 13), inhibited migration and invasion (non-patent document 14) and inhibited adhesion (non-patent document 15). These studies suggest that inhibition of EP4 signaling is a potential therapeutic option for women with EM (non-patent document 15).

Abdominal aortic aneurysm (AAA) is a common, progressive, and life-threatening degenerative vascular disease (non-patent documents 16 and 17). It is an inflammatory disorder characterized by localized connective tissue degeneration and smooth muscle cell apoptosis, leading to aortic dilatation and rupture (non-patent documents 18-20). After rupture occurs, the probability of mortality is greater than 60% (non-patent document 21). No pharmacotherapy has been found to be effective at decreasing the growth rate or rupture rate of AAAs except. In aneurysm walls, COX-2 is widely expressed in macrophages and smooth muscle cells, along with locally synthesized PGE2 (non-patent document 22). EP4 expression is increased in the aneurysm areas of human AAA tissues, both in human aortic aneurysm smooth muscle cell as well as in macrophages in the lesion (non-patent documents 23 and 24). EP4 receptor antagonist or global gene deletion of the EP4 receptor significantly decreased MMP-2 activation and IL-6 production in human AAA tissues and the rate of AAA formation in preclinical mouse models (non-patent document 23 and 25).

Ankylosing spondylitis is the prototypic spondyloarthropathy, one of a group of conditions which also includes psoriatic arthritis, reactive arthritis and arthritis complicating inflammatory bowel disease. Ankylosing spondylitis is highly heritable (non-patent documents 26 and 27) and familial (non-patent document 28). Men are affected 2-3 times more frequently than women. The disease is known to be strongly associated with HLA-B27. Since association between EP4 receptor gene (PTGER4) and ankylosing spondylitis has been also demonstrated (non-patent document 29), EP4 receptor is likely to be involved in disease pathogenesis. There is no cure for ankylosing spondylitis as yet, but the patient's back pain and stiffness usually show good symptomatic response to NSAIDs. Since EP4 antagonists are known to possess analgesic activity at least in animal models (non-patent documents 30 and 31), a safe and chronically-treatable EP4 antagonist may be an alternative symptom-relieving pharmacotherapy for ankylosing spondylitis.

Examples of the compound having a structure similar to the compound described in the present specification include the following compounds.

(1) Patent document 1 describes a compound represented by the formula:

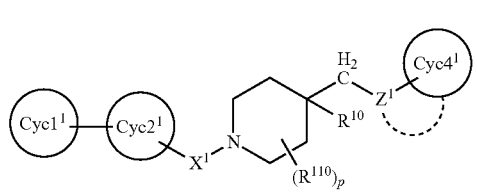

(I-1)

wherein each symbol is as defined in the specification, which is useful as an agent for the prophylaxis or treatment of metabolic disease, cerebrovascular disease and the like.

(2) Patent document 2 describes a compound represented by the formula:

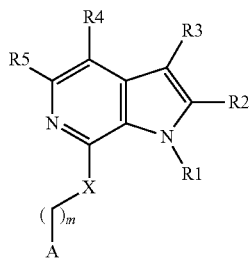

wherein each symbol is as defined in the specification, as a proton pump inhibitor (PPI), which is useful as an agent for the prophylaxis or treatment of peptic ulcer and the like.

(3) Patent document 3 describes a compound represented by the formula:

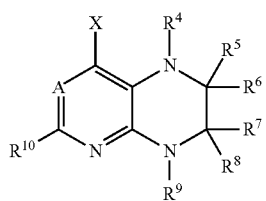

(I)

wherein each symbol is as defined in the specification, as a corticotropin releasing factor (CRF), which is useful as an agent for the prophylaxis or treatment of anxiety, depression, other psychiatric and neurological disorders, and the like.

(4) Patent document 4 describes a compound represented by the formula:

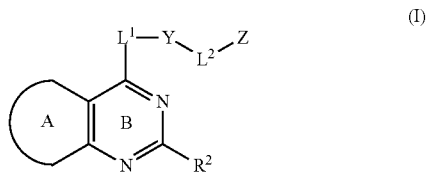

(I)

wherein each symbol is as defined in the specification, as a RAF kinase inhibitor, which is useful as an agent for the prophylaxis or treatment of cancer.

(5) Patent document 5 describes a compound represented by the formula:

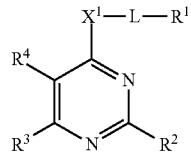

wherein each symbol is as defined in the specification, as a mGluR1 antagonist, which is useful an agent for the prophylaxis or treatment of pain.

DOCUMENT LIST

Patent Document

[Patent Document 1] WO 2010/080864 A1
[Patent Document 2] WO 2006/011670 A1
[Patent Document 3] WO 97/44038 A1
[Patent Document 4] WO 2006/065703 A1
[Patent Document 5] WO 2001/032632 A2

Non-Patent Document

[Non-Patent Document 1] Pharmacol. Rev., 2011. 63(3): p. 471-538
[Non-Patent Document 2] Trends Pharmacol. Sci., 2012. 33(6): p. 304-11
[Non-Patent Document 3] J. Allergy Clin. Immunol., 2013. 131(2): p. 532-40 e1-2
[Non-Patent Document 4] Immunity, 2010. 33(2): p. 279-88
[Non-Patent Document 5] Immunity, 2010. 33(2): p. 150-2
[Non-Patent Document 6] Thromb. Res., 2013. 132(1): p. 56-62
[Non-Patent Document 7] Postepy Hig. Med. Dosw., (Online), 2012. 66: p. 287-94
[Non-Patent Document 8] Br. J. Pharmacol., 2010. 160(2): p. 292-310
[Non-Patent Document 9] BMJ, 2001. 323(7304): p. 93-5
[Non-Patent Document 10] J. Pharm. Pharm. Sci., 2013. 16(5): p. 821-47
[Non-Patent Document 11] N. Engl. J. Med., 2008. 359(11): p. 1136-42
[Non-Patent Document 12] Mol. Endocrinol., 2009. 23(8): p. 1291-305
[Non-Patent Document 13] Fertil Steril, 2010. 93(8): p. 2498-506
[Non-Patent Document 14] Mol. Cell Endocrinol., 2011. 332(1-2): p. 306-13

[Non-Patent Document 15] Biol. Reprod, 2013. 88(3): p. 77

[Non-Patent Document 16] Arterioscler. Thromb. Vasc. Biol., 1996. 16(8): p. 963-70

[Non-Patent Document 17] N. Engl. J. Med., 1993. 328(16): p. 1167-72

[Non-Patent Document 18] J. Clin. Invest., 1998. 102(11): p. 1900-10

[Non-Patent Document 19] J. Clin. Invest., 2002. 110(5): p. 625-32

[Non-Patent Document 20] J. Immunol., 2004. 172(4): p. 2607-12

[Non-Patent Document 21] World J. Surg., 2008. 32(6): p. 976-86

[Non-Patent Document 22] Circulation, 1999. 100(1): p. 48-54

[Non-Patent Document 23] PLoS One, 2012. 7(5): p. e36724

[Non-Patent Document 24] J. Vasc. Surg., 2003. 38(2): p. 354-9

[Non-Patent Document 25] Am. J. Pathol., 2012. 181(1): p. 313-21

[Non-Patent Document 26] Scand. J. Rheumatol., 2008. 37: p. 120-126

[Non-Patent Document 27] Arthritis Rheum., 1997. 40: p. 1823-1828

[Non-Patent Document 28] Ann. Rheum. Dis., 2000. 59: p. 883-886

[Non-Patent Document 29] Nature Genetics, 2011. 43: p. 761-767

[Non-Patent Document 30] Eur J Pharmacol., 2008, 580: p. 116-121

[Non-Patent Document 31] Bioorg Med Chem Lett., 2010. 15: p. 3760-3

SUMMARY OF THE INVENTION

Problems to be Solved by the Invention

The present invention aims to provide a novel heterocyclic compound having an EP4 receptor antagonistic action, and useful as an agent for the prophylaxis or treatment of EP4 receptor associated diseases (e.g., rheumatoid arthritis, aortic aneurysm (e.g. abdominal aortic aneurysm, thoracic aortic aneurysm, thoracoabdominal aortic aneurysm etc.), endometriosis, ankylosing spondylitis, inflammatory breast cancer etc.) and the like.

Means of Solving the Problems

The present inventors have conducted intensive studies, and have found that a compound represented by the below-mentioned formula (I) unexpectedly has an EP4 receptor antagonistic action, and therefore, may be useful as an agent for the prophylaxis or treatment of EP4 receptor associated diseases (e.g., rheumatoid arthritis, aortic aneurysm (e.g. abdominal aortic aneurysm, thoracic aortic aneurysm, thoracoabdominal aortic aneurysm etc.), endometriosis, ankylosing spondylitis, inflammatory breast cancer etc.) and the like, and completed the present invention based on these findings.

Accordingly, the present invention provides the following.

[1] A compound represented by the formula (I):

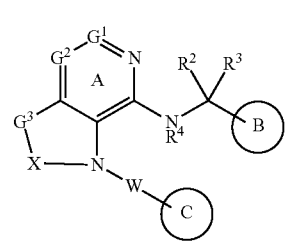

wherein
$G^1$ is a carbon atom or a nitrogen atom,
$G^2$ is a carbon atom or a nitrogen atom,
Ring A is an optionally further substituted 6-membered nitrogen-containing heterocycle,
$G^3$ is an oxygen atom, an optionally substituted methylene, $NR^1$, a sulfur atom, $S(O)$ or $S(O)_2$,
$R^1$ is a hydrogen atom or a substituent,
X is an optionally substituted ethylene,
$R^2$ and $R^3$ are each independently a hydrogen atom or an optionally substituted $C_{1-6}$ alkyl group, or $R^2$ and $R^3$ are joined together to form a cycloalkane or a heterocycle, each of which is optionally substituted,
$R^4$ is a hydrogen atom or a substituent,
Ring B is an optionally further substituted ring,
Ring C is an optionally further substituted ring, and
W is a bond, or a spacer in which the number of atoms in the main chain is 1 to 4,
or a salt thereof (hereinafter to be referred to as compound (I).

[2] The compound or salt of the above-mentioned [1], wherein
$G^1$ is a carbon atom,
$G^2$ is a carbon atom or a nitrogen atom,
Ring A is pyridine or pyrimidine, each of which is optionally further substituted by 1 to 2 substituents selected from the group consisting of
(a) a halogen atom,
(b) a $C_{1-6}$ alkyl group, and
(c) a $C_{3-10}$ cycloalkyl group,
$G^3$ is an oxygen atom, $NR^1$ wherein $R^1$ is a $C_{1-6}$ alkyl group, methylene or a sulfur atom,
X is ethylene optionally substituted by an oxo group,
$R^2$ and $R^3$ are each a hydrogen atom or a $C_{1-6}$ alkyl group, or $R^2$ and $R^3$ are joined together to form a $C_{3-10}$ cycloalkane,
$R^4$ is a hydrogen atom,
Ring B is
(1) a $C_{6-14}$ aromatic hydrocarbon ring optionally further substituted by 1 to 3 substituents selected from the group consisting of
(a) a carboxy group,
(b) a $C_{1-6}$ alkoxy-carbonyl group,
(c) a cyano group,
(d) a carbamoyl group,
(e) a mono- or di-$C_{1-6}$ alkyl-carbamoyl group,
(f) a mono- or di-$C_{1-6}$ alkoxy-carbamoyl group,
(g) a mono- or di-$C_{7-16}$ aralkyloxy-carbamoyl group,
(h) 5-tetrazolyl, and
(i) a $C_{1-6}$ alkoxy group,
(2) a $C_{3-10}$ cycloalkane, or
(3) a 5- to 10-membered aromatic heterocycle optionally further substituted by 1 to 3 $C_{1-6}$ alkyl groups, Ring C is a $C_{6-14}$ aromatic hydrocarbon ring, a $C_{3-10}$ cycloalkane or a 5- to 14-membered aromatic heterocycle, each of which is optionally further substituted by 1 to 3 substituents selected from the group consisting of
  (1) a halogen atom,
  (2) an optionally halogenated $C_{1-6}$ alkyl group,
  (3) a $C_{1-6}$ alkoxy group, and
  (4) a $C_{6-14}$ aryl group, and
W is
(1) a $C_{1-4}$ alkylene group optionally substituted by an oxo group, or
(2) —$(CH_2)_{m1}$—O— wherein m1 is an integer of 0 to 3.

[3] 4-[(1S)-1-[[4-[(3-Chlorophenyl)methyl]-2,3-dihydropyrido[4,3-b][1,4]oxazin-5-yl]amino]ethyl]benzoic acid or a salt thereof.

[4] 4-[1-[[4-[(3,4-Difluorophenyl)methyl]-2,3-dihydropyrido[4,3-b][1,4]oxazin-5-yl]amino]cyclopropyl]benzoic acid or a salt thereof.

[5] 4-[(1S)-1-[[4-[(4-Methoxyphenyl)methyl]-2,3-dihydropyrido[4,3-b][1,4]oxazin-5-yl]amino]ethyl]benzoic acid or a salt thereof.

[6] A medicament comprising the compound or salt of the above-mentioned [1].

[7] The medicament according to the above-mentioned [6], which is an EP4 receptor antagonist.

[8] The medicament according to the above-mentioned [6], which is an agent for the prophylaxis or treatment of EP4 receptor associated diseases.

[9] The medicament according to the above-mentioned [8], wherein the EP4 receptor associated diseases are selected from rheumatoid arthritis, aortic aneurysm, endometriosis, ankylosing spondylitis and inflammatory breast cancer.

[10] The compound or salt of the above-mentioned [1] for use in the prophylaxis or treatment of EP4 receptor associated diseases.

[11] The compound or salt of the above-mentioned [10], wherein the EP4 receptor associated diseases are selected from rheumatoid arthritis, aortic aneurysm, endometriosis, ankylosing spondylitis and inflammatory breast cancer.

[12] A method of inhibiting EP4 receptor in a mammal, which comprises administering an effective amount of the compound or salt of the above-mentioned [1] to the mammal.

[13] A method for the prophylaxis or treatment of EP4 receptor associated diseases in a mammal, which comprises administering an effective amount of the compound or salt of the above-mentioned [1] to the mammal.

[14] The method of the above-mentioned [13], wherein the EP4 receptor associated diseases are selected from rheumatoid arthritis, aortic aneurysm, endometriosis, ankylosing spondylitis and inflammatory breast cancer.

[15] Use of the compound or salt of the above-mentioned [1] for the production of an agent for the prophylaxis or treatment of EP4 receptor associated diseases.

[16] Use of the above-mentioned [15], wherein the EP4 receptor associated diseases are selected from rheumatoid arthritis, aortic aneurysm, endometriosis, ankylosing spondylitis and inflammatory breast cancer.

EFFECT OF THE INVENTION

Figure 1:
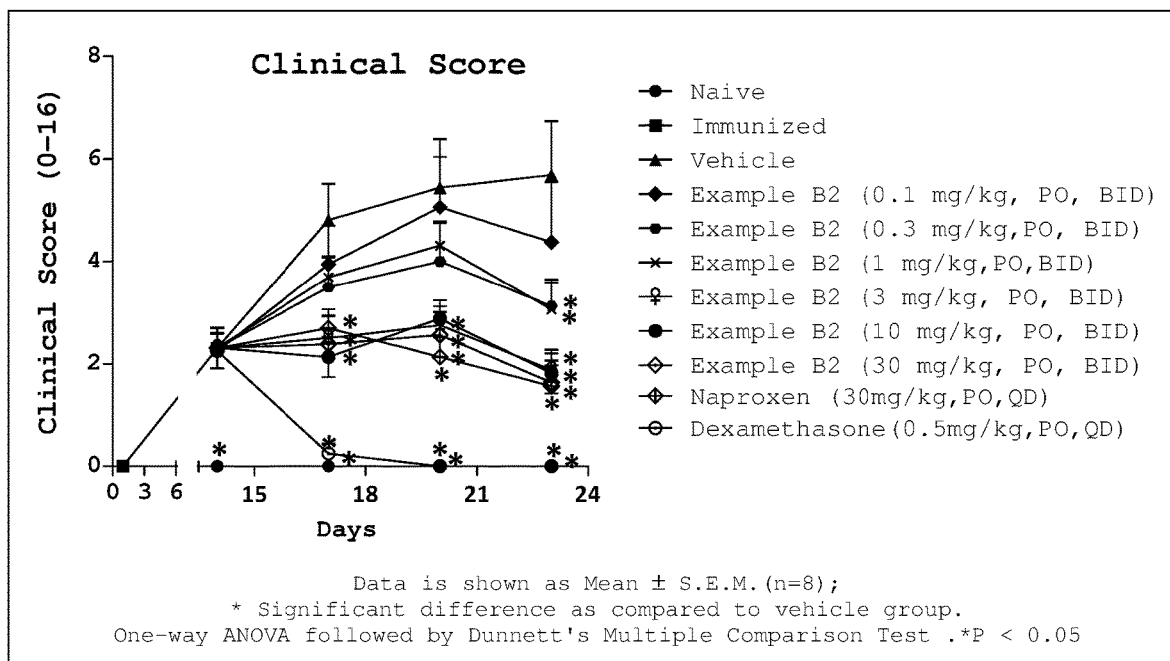
FIG. 1 shows suppression of arthritis development in adjuvant induced arthritis model when treated with the compound of Example B2.

Compound (I) has a superior EP4 receptor antagonistic action, which may be useful as an agent for the prophylaxis or treatment of EP4 receptor associated diseases (e.g., rheumatoid arthritis, aortic aneurysm (e.g. abdominal aortic aneurysm, thoracic aortic aneurysm, thoracoabdominal aortic aneurysm etc.), endometriosis, ankylosing spondylitis, inflammatory breast cancer etc.) and the like.

DETAILED DESCRIPTION OF THE INVENTION

The definition of each substituent used in the present specification is described in detail in the following. Unless otherwise specified, each substituent has the following definition.

In the present specification, examples of the "halogen atom" include fluorine, chlorine, bromine and iodine.

In the present specification, examples of the "$C_{1-6}$ alkyl group" include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl and 2-ethylbutyl.

In the present specification, examples of the "optionally halogenated $C_{1-6}$ alkyl group" include a $C_{1-6}$ alkyl group optionally having 1 to 7, preferably 1 to 5, halogen atoms. Specific examples thereof include methyl, chloromethyl, difluoromethyl, trichloromethyl, trifluoromethyl, ethyl, 2-bromoethyl, 2,2,2-trifluoroethyl, tetrafluoroethyl, pentafluoroethyl, propyl, 2,2-difluoropropyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl and 6,6,6-trifluorohexyl.

In the present specification, examples of the "$C_{2-6}$ alkenyl group" include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl and 5-hexenyl.

In the present specification, examples of the "$C_{2-6}$ alkynyl group" include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and 4-methyl-2-pentynyl.

In the present specification, examples of the "$C_{3-10}$ cycloalkyl group" include cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl and adamantyl.

In the present specification, examples of the "optionally halogenated $C_{3-10}$ cycloalkyl group" include a $C_{3-10}$ cycloalkyl group optionally having 1 to 7, preferably 1 to 5, halogen atoms. Specific examples thereof include cyclopropyl, 2,2-difluorocyclopropyl, 2,3-difluorocyclopropyl, cyclobutyl, difluorocyclobutyl, cyclopentyl, cyclohexyl, cycloheptyl and cyclooctyl.

In the present specification, examples of the "$C_{3-10}$ cycloalkenyl group" include cyclopropenyl, cyclobutenyl, cyclopentenyl, cyclohexenyl, cycloheptenyl and cyclooctenyl.

In the present specification, examples of the "$C_{6-14}$ aryl group" include phenyl, 1-naphthyl, 2-naphthyl, 1-anthryl, 2-anthryl and 9-anthryl.

In the present specification, examples of the "C$_{7-16}$ aralkyl group" include benzyl, phenethyl, naphthylmethyl and phenylpropyl.

In the present specification, examples of the "C$_{1-6}$ alkoxy group" include methoxy, ethoxy, propoxy, isopropoxy, butoxy, isobutoxy, sec-butoxy, tert-butoxy, pentyloxy and hexyloxy.

In the present specification, examples of the "optionally halogenated C$_{1-6}$ alkoxy group" include a C$_{1-6}$ alkoxy group optionally having 1 to 7, preferably 1 to 5, halogen atoms. Specific examples thereof include methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy and hexyloxy.

In the present specification, examples of the "C$_{3-10}$ cycloalkyloxy group" include cyclopropyloxy, cyclobutyloxy, cyclopentyloxy, cyclohexyloxy, cycloheptyloxy and cyclooctyloxy.

In the present specification, examples of the "C$_{1-6}$ alkylthio group" include methylthio, ethylthio, propylthio, isopropylthio, butylthio, sec-butylthio, tert-butylthio, pentylthio and hexylthio.

In the present specification, examples of the "optionally halogenated C$_{1-6}$ alkylthio group" include a C$_{1-6}$ alkylthio group optionally having 1 to 7, preferably 1 to 5, halogen atoms. Specific examples thereof include methylthio, difluoromethylthio, trifluoromethylthio, ethylthio, propylthio, isopropylthio, butylthio, 4,4,4-trifluorobutylthio, pentylthio and hexylthio.

In the present specification, examples of the "C$_{1-6}$ alkyl-carbonyl group" include acetyl, propanoyl, butanoyl, 2-methylpropanoyl, pentanoyl, 3-methylbutanoyl, 2-methylbutanoyl, 2,2-dimethylpropanoyl, hexanoyl and heptanoyl.

In the present specification, examples of the "optionally halogenated C$_{1-6}$ alkyl-carbonyl group" include a C$_{1-6}$ alkyl-carbonyl group optionally having 1 to 7, preferably 1 to 5, halogen atoms. Specific examples thereof include acetyl, chloroacetyl, trifluoroacetyl, trichloroacetyl, propanoyl, butanoyl, pentanoyl and hexanoyl.

In the present specification, examples of the "C$_{1-6}$ alkoxy-carbonyl group" include methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl and hexyloxycarbonyl.

In the present specification, examples of the "C$_{6-14}$ aryl-carbonyl group" include benzoyl, 1-naphthoyl and 2-naphthoyl.

In the present specification, examples of the "C$_{7-16}$ aralkyl-carbonyl group" include phenylacetyl and phenylpropionyl.

In the present specification, examples of the "5- to 14-membered aromatic heterocyclylcarbonyl group" include nicotinoyl, isonicotinoyl, thenoyl and furoyl.

In the present specification, examples of the "3- to 14-membered non-aromatic heterocyclylcarbonyl group" include morpholinylcarbonyl, piperidinylcarbonyl and pyrrolidinylcarbonyl.

In the present specification, examples of the "mono- or di-C$_{1-6}$ alkyl-carbamoyl group" include methylcarbamoyl, ethylcarbamoyl, dimethylcarbamoyl, diethylcarbamoyl and N-ethyl-N-methylcarbamoyl.

In the present specification, examples of the "mono- or di-C$_{7-16}$ aralkyl-carbamoyl group" include benzylcarbamoyl and phenethylcarbamoyl.

In the present specification, examples of the "C$_{1-6}$ alkylsulfonyl group" include methylsulfonyl, ethylsulfonyl, propylsulfonyl, isopropylsulfonyl, butylsulfonyl, sec-butylsulfonyl and tert-butylsulfonyl.

In the present specification, examples of the "optionally halogenated C$_{1-6}$ alkylsulfonyl group" include a C$_{1-6}$ alkylsulfonyl group optionally having 1 to 7, preferably 1 to 5, halogen atoms. Specific examples thereof include methylsulfonyl, difluoromethylsulfonyl, trifluoromethylsulfonyl, ethylsulfonyl, propylsulfonyl, isopropylsulfonyl, butylsulfonyl, 4,4,4-trifluorobutylsulfonyl, pentylsulfonyl and hexylsulfonyl.

In the present specification, examples of the "C$_{6-14}$ arylsulfonyl group" include phenylsulfonyl, 1-naphthylsulfonyl and 2-naphthylsulfonyl.

In the present specification, examples of the "substituent" include a halogen atom, a cyano group, a nitro group, an optionally substituted hydrocarbon group, an optionally substituted heterocyclic group, an acyl group, an optionally substituted amino group, an optionally substituted carbamoyl group, an optionally substituted thiocarbamoyl group, an optionally substituted sulfamoyl group, an optionally substituted hydroxy group, an optionally substituted sulfanyl (SH) group and an optionally substituted silyl group.

In the present specification, examples of the "hydrocarbon group" (including "hydrocarbon group" of "optionally substituted hydrocarbon group") include a C$_{1-6}$ alkyl group, a C$_{2-6}$ alkenyl group, a C$_{2-6}$ alkynyl group, a C$_{3-10}$ cycloalkyl group, a C$_{3-10}$ cycloalkenyl group, a C$_{6-14}$ aryl group and a C$_{7-16}$ aralkyl group.

In the present specification, examples of the "optionally substituted hydrocarbon group" include a hydrocarbon group optionally having substituent(s) selected from the following substituent group A.

[Substituent Group A]
(1) a halogen atom,
(2) a nitro group,
(3) a cyano group,
(4) an oxo group,
(5) a hydroxy group,
(6) an optionally halogenated C$_{1-6}$ alkoxy group,
(7) a C$_{6-14}$ aryloxy group (e.g., phenoxy, naphthoxy),
(8) a C$_{7-16}$ aralkyloxy group (e.g., benzyloxy),
(9) a 5- to 14-membered aromatic heterocyclyloxy group (e.g., pyridyloxy),
(10) a 3- to 14-membered non-aromatic heterocyclyloxy group (e.g., morpholinyloxy, piperidinyloxy),
(11) a C$_{1-6}$ alkyl-carbonyloxy group (e.g., acetoxy, propanoyloxy),
(12) a C$_{6-14}$ aryl-carbonyloxy group (e.g., benzoyloxy, 1-naphthoyloxy, 2-naphthoyloxy),
(13) a C$_{1-6}$ alkoxy-carbonyloxy group (e.g., methoxycarbonyloxy, ethoxycarbonyloxy, propoxycarbonyloxy, butoxycarbonyloxy),
(14) a mono- or di-C$_{1-6}$ alkyl-carbamoyloxy group (e.g., methylcarbamoyloxy, ethylcarbamoyloxy, dimethylcarbamoyloxy, diethylcarbamoyloxy),
(15) a C$_{6-14}$ aryl-carbamoyloxy group (e.g., phenylcarbamoyloxy, naphthylcarbamoyloxy),
(16) a 5- to 14-membered aromatic heterocyclylcarbonyloxy group (e.g., nicotinoyloxy),
(17) a 3- to 14-membered non-aromatic heterocyclylcarbonyloxy group (e.g., morpholinylcarbonyloxy, piperidinylcarbonyloxy),
(18) an optionally halogenated C$_{1-6}$ alkylsulfonyloxy group (e.g., methylsulfonyloxy, trifluoromethylsulfonyloxy),

(19) a $C_{6-14}$ arylsulfonyloxy group optionally substituted by a $C_{1-6}$ alkyl group (e.g., phenylsulfonyloxy, toluenesulfonyloxy),
(20) an optionally halogenated $C_{1-6}$ alkylthio group,
(21) a 5- to 14-membered aromatic heterocyclic group,
(22) a 3- to 14-membered non-aromatic heterocyclic group,
(23) a formyl group,
(24) a carboxy group,
(25) an optionally halogenated $C_{1-6}$ alkyl-carbonyl group,
(26) a $C_{6-14}$ aryl-carbonyl group,
(27) a 5- to 14-membered aromatic heterocyclylcarbonyl group,
(28) a 3- to 14-membered non-aromatic heterocyclylcarbonyl group,
(29) a $C_{1-6}$ alkoxy-carbonyl group,
(30) a $C_{6-14}$ aryloxy-carbonyl group (e.g., phenyloxycarbonyl, 1-naphthyloxycarbonyl, 2-naphthyloxycarbonyl),
(31) a $C_{7-16}$ aralkyloxy-carbonyl group (e.g., benzyloxycarbonyl, phenethyloxycarbonyl),
(32) a carbamoyl group,
(33) a thiocarbamoyl group,
(34) a mono- or di-$C_{1-6}$ alkyl-carbamoyl group,
(35) a $C_{6-14}$ aryl-carbamoyl group (e.g., phenylcarbamoyl),
(36) a 5- to 14-membered aromatic heterocyclylcarbamoyl group (e.g., pyridylcarbamoyl, thienylcarbamoyl),
(37) a 3- to 14-membered non-aromatic heterocyclylcarbamoyl group (e.g., morpholinylcarbamoyl, piperidinylcarbamoyl),
(38) an optionally halogenated $C_{1-6}$ alkylsulfonyl group,
(39) a $C_{6-14}$ arylsulfonyl group,
(40) a 5- to 14-membered aromatic heterocyclylsulfonyl group (e.g., pyridylsulfonyl, thienylsulfonyl),
(41) an optionally halogenated $C_{1-6}$ alkylsulfinyl group,
(42) a $C_{6-14}$ arylsulfinyl group (e.g., phenylsulfinyl, 1-naphthylsulfinyl, 2-naphthylsulfinyl),
(43) a 5- to 14-membered aromatic heterocyclylsulfinyl group (e.g., pyridylsulfinyl, thienylsulfinyl),
(44) an amino group,
(45) a mono- or di-$C_{1-6}$ alkylamino group (e.g., methylamino, ethylamino, propylamino, isopropylamino, butylamino, dimethylamino, diethylamino, dipropylamino, dibutylamino, N-ethyl-N-methylamino),
(46) a mono- or di-$C_{6-14}$ arylamino group (e.g., phenylamino),
(47) a 5- to 14-membered aromatic heterocyclylamino group (e.g., pyridylamino),
(48) a $C_{7-16}$ aralkylamino group (e.g., benzylamino),
(49) a formylamino group,
(50) a $C_{1-6}$ alkyl-carbonylamino group (e.g., acetylamino, propanoylamino, butanoylamino),
(51) a ($C_{1-6}$ alkyl) ($C_{1-6}$ alkyl-carbonyl)amino group (e.g., N-acetyl-N-methylamino),
(52) a $C_{6-14}$ aryl-carbonylamino group (e.g., phenylcarbonylamino, naphthylcarbonylamino),
(53) a $C_{1-6}$ alkoxy-carbonylamino group (e.g., methoxycarbonylamino, ethoxycarbonylamino, propoxycarbonylamino, butoxycarbonylamino, tert-butoxycarbonylamino),
(54) a $C_{7-16}$ aralkyloxy-carbonylamino group (e.g., benzyloxycarbonylamino),
(55) a $C_{1-6}$ alkylsulfonylamino group (e.g., methylsulfonylamino, ethylsulfonylamino),
(56) a $C_{6-14}$ arylsulfonylamino group optionally substituted by a $C_{1-6}$ alkyl group (e.g., phenylsulfonylamino, toluenesulfonylamino),
(57) an optionally halogenated $C_{1-6}$ alkyl group,
(58) a $C_{2-6}$ alkenyl group,
(59) a $C_{2-6}$ alkynyl group,
(60) a $C_{3-10}$ cycloalkyl group,
(61) a $C_{3-10}$ cycloalkenyl group and
(62) a $C_{6-14}$ aryl group.

The number of the above-mentioned substituents in the "optionally substituted hydrocarbon group" is, for example, 1 to 5, preferably 1 to 3. When the number of the substituents is two or more, the respective substituents may be the same or different.

In the present specification, examples of the "heterocyclic group" (including "heterocyclic group" of "optionally substituted heterocyclic group") include (i) an aromatic heterocyclic group, (ii) a non-aromatic heterocyclic group and (iii) a 7- to 10-membered bridged heterocyclic group, each containing, as a ring-constituting atom besides carbon atom, 1 to 4 hetero atoms selected from a nitrogen atom, a sulfur atom and an oxygen atom.

In the present specification, examples of the "aromatic heterocyclic group" (including "5- to 14-membered aromatic heterocyclic group") include a 5- to 14-membered (preferably 5- to 10-membered) aromatic heterocyclic group containing, as a ring-constituting atom besides carbon atom, 1 to 4 hetero atoms selected from a nitrogen atom, a sulfur atom and an oxygen atom.

Preferable examples of the "aromatic heterocyclic group" include 5- or 6-membered monocyclic aromatic heterocyclic groups such as thienyl, furyl, pyrrolyl, imidazolyl, pyrazolyl, thiazolyl, isothiazolyl, oxazolyl, isoxazolyl, pyridyl, pyrazinyl, pyrimidinyl, pyridazinyl, 1,2,4-oxadiazolyl, 1,3,4-oxadiazolyl, 1,2,4-thiadiazolyl, 1,3,4-thiadiazolyl, triazolyl, tetrazolyl, triazinyl and the like; and 8- to 14-membered fused polycyclic (preferably bi or tricyclic) aromatic heterocyclic groups such as benzothiophenyl, benzofuranyl, benzimidazolyl, benzoxazolyl, benzisoxazolyl, benzothiazolyl, benzisothiazolyl, benzotriazolyl, imidazopyridinyl, thienopyridinyl, furopyridinyl, pyrrolopyridinyl, pyrazolopyridinyl, oxazolopyridinyl, thiazolopyridinyl, imidazopyrazinyl, imidazopyrimidinyl, thienopyrimidinyl, furopyrimidinyl, pyrrolopyrimidinyl, pyrazolopyrimidinyl, oxazolopyrimidinyl, thiazolopyrimidinyl, pyrazolotriazinyl, naphtho[2,3-b]thienyl, phenoxathiinyl, indolyl, isoindolyl, 1H-indazolyl, purinyl, isoquinolyl, quinolyl, phthalazinyl, naphthyridinyl, quinoxalinyl, quinazolinyl, cinnolinyl, carbazolyl, 3-carbolinyl, phenanthridinyl, acridinyl, phenazinyl, phenothiazinyl, phenoxazinyl and the like.

In the present specification, examples of the "non-aromatic heterocyclic group" (including "3- to 14-membered non-aromatic heterocyclic group") include a 3- to 14-membered (preferably 4- to 10-membered) non-aromatic heterocyclic group containing, as a ring-constituting atom besides carbon atom, 1 to 4 hetero atoms selected from a nitrogen atom, a sulfur atom and an oxygen atom.

Preferable examples of the "non-aromatic heterocyclic group" include 3- to 8-membered monocyclic non-aromatic heterocyclic groups such as aziridinyl, oxiranyl, thiiranyl, azetidinyl, oxetanyl, thietanyl, tetrahydrothienyl, tetrahydrofuranyl, pyrrolinyl, pyrrolidinyl, imidazolinyl, imidazolidinyl, oxazolinyl, oxazolidinyl, pyrazolinyl, pyrazolidinyl, thiazolinyl, thiazolidinyl, tetrahydroisothiazolyl, tetrahydrooxazolyl, tetrahydroisooxazolyl, piperidinyl, piperazinyl, tetrahydropyridinyl, dihydropyridinyl, dihydrothiopyranyl, tetrahydropyrimidinyl, tetrahydropyridazinyl, dihydropyranyl, tetrahydropyranyl, tetrahydrothiopyranyl, morpholinyl, thiomorpholinyl, azepanyl, diazepanyl, azepinyl, oxepanyl, azocanyl, diazocanyl and the like; and 9- to 14-membered fused polycyclic (preferably bi or tricyclic) non-aromatic heterocyclic groups such as dihydrobenzofuranyl, dihydrobenzimidazolyl, dihydrobenzoxazolyl, dihydrobenzothiazolyl, dihydrobenzisothiazolyl, dihydronaphtho[2,3-b]thienyl, tetrahydroisoquinolyl, tetrahydroquinolyl, 4H-quinolizinyl, indolinyl, isoindolinyl, tetrahydrothieno[2,3-c]pyridinyl, tetrahydrobenzazepinyl, tetrahydroquinoxalinyl, tetrahydrophenanthridinyl, hexahydrophenothiazinyl, hexahydrophenoxazinyl, tetrahydrophthalazinyl, tetrahydronaphthyridinyl, tetrahydroquinazolinyl, tetrahydrocinnolinyl, tetrahydrocarbazolyl, tetrahydro-3-carbolinyl, tetrahydroacrydinyl, tetrahydrophenazinyl, tetrahydrothioxanthenyl, octahydroisoquinolyl and the like.

In the present specification, preferable examples of the "7- to 10-membered bridged heterocyclic group" include quinuclidinyl and 7-azabicyclo[2.2.1]heptanyl.

In the present specification, examples of the "nitrogen-containing heterocyclic group" include a "heterocyclic group" containing at least one nitrogen atom as a ring-constituting atom.

In the present specification, examples of the "optionally substituted heterocyclic group" include a heterocyclic group optionally having substituent(s) selected from the aforementioned substituent group A.

The number of the substituents in the "optionally substituted heterocyclic group" is, for example, 1 to 3. When the number of the substituents is two or more, the respective substituents may be the same or different.

In the present specification, examples of the "acyl group" include a formyl group, a carboxy group, a carbamoyl group, a thiocarbamoyl group, a sulfino group, a sulfo group, a sulfamoyl group and a phosphono group, each optionally having "1 or 2 substituents selected from a $C_{1-6}$ alkyl group, a $C_{2-6}$ alkenyl group, a $C_{3-10}$ cycloalkyl group, a $C_{3-10}$ cycloalkenyl group, a $C_{6-14}$ aryl group, a $C_{7-16}$ aralkyl group, a 5- to 14-membered aromatic heterocyclic group and a 3- to 14-membered non-aromatic heterocyclic group, each of which optionally has 1 to 3 substituents selected from a halogen atom, an optionally halogenated $C_{1-6}$ alkoxy group, a hydroxy group, a nitro group, a cyano group, an amino group and a carbamoyl group".

Examples of the "acyl group" also include a hydrocarbon-sulfonyl group, a heterocyclylsulfonyl group, a hydrocarbon-sulfinyl group and a heterocyclylsulfinyl group.

Here, the hydrocarbon-sulfonyl group means a hydrocarbon group-bonded sulfonyl group, the heterocyclylsulfonyl group means a heterocyclic group-bonded sulfonyl group, the hydrocarbon-sulfinyl group means a hydrocarbon group-bonded sulfinyl group and the heterocyclylsulfinyl group means a heterocyclic group-bonded sulfinyl group.

Preferable examples of the "acyl group" include a formyl group, a carboxy group, a $C_{1-6}$ alkyl-carbonyl group, a $C_{2-6}$ alkenyl-carbonyl group (e.g., crotonoyl), a $C_{3-10}$ cycloalkyl-carbonyl group (e.g., cyclobutanecarbonyl, cyclopentanecarbonyl, cyclohexanecarbonyl, cycloheptanecarbonyl), a $C_{3-10}$ cycloalkenyl-carbonyl group (e.g., 2-cyclohexenecarbonyl), a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a $C_{6-14}$ aryloxy-carbonyl group (e.g., phenyloxycarbonyl, naphthyloxycarbonyl), a $C_{7-16}$ aralkyloxy-carbonyl group (e.g., benzyloxycarbonyl, phenethyloxycarbonyl), a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl), a mono- or di-$C_{6-14}$ aryl-carbamoyl group (e.g., phenylcarbamoyl), a mono- or di-$C_{7-16}$ aralkyl-carbamoyl group, a 5- to 14-membered aromatic heterocyclylcarbamoyl group (e.g., pyridylcarbamoyl), a thiocarbamoyl group, a mono- or di-$C_{1-6}$ alkyl-thiocarbamoyl group (e.g., methylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a 5- to 14-membered aromatic heterocyclylthiocarbamoyl group (e.g., pyridylthiocarbamoyl), a sulfino group, a $C_{1-6}$ alkylsulfinyl group (e.g., methylsulfinyl, ethylsulfinyl), a sulfo group, a $C_{1-6}$ alkylsulfonyl group, a $C_{6-14}$ arylsulfonyl group, a phosphono group and a mono- or di-$C_{1-6}$ alkyl-phosphono group (e.g., dimethylphosphono, diethylphosphono, diisopropylphosphono, dibutylphosphono).

In the present specification, examples of the "optionally substituted amino group" include an amino group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from substituent group A".

Preferable examples of the optionally substituted amino group include an amino group, a mono- or di-(optionally halogenated $C_{1-6}$ alkyl)amino group (e.g., methylamino, trifluoromethylamino, dimethylamino, ethylamino, diethylamino, propylamino, dibutylamino), a mono- or di-$C_{2-6}$ alkenylamino group (e.g., diallylamino), a mono- or di-$C_{3-10}$ cycloalkylamino group (e.g., cyclopropylamino, cyclohexylamino), a mono- or di-$C_{6-14}$ arylamino group (e.g., phenylamino), a mono- or di-$C_{7-16}$ aralkylamino group (e.g., benzylamino, dibenzylamino), a mono- or di-(optionally halogenated $C_{1-6}$ alkyl)-carbonylamino group (e.g., acetylamino, propionylamino), a mono- or di-$C_{6-14}$ aryl-carbonylamino group (e.g., benzoylamino), a mono- or di-$C_{7-16}$ aralkyl-carbonylamino group (e.g., benzylcarbonylamino), a mono- or di-5- to 14-membered aromatic heterocyclylcarbonylamino group (e.g., nicotinoylamino, isonicotinoylamino), a mono- or di-3- to 14-membered non-aromatic heterocyclylcarbonylamino group (e.g., piperidinylcarbonylamino), a mono- or di-$C_{1-6}$ alkoxy-carbonylamino group (e.g., tert-butoxycarbonylamino), a 5- to 14-membered aromatic heterocyclylamino group (e.g., pyridylamino), a carbamoylamino group, a (mono- or di-$C_{1-6}$ alkyl-carbamoyl) amino group (e.g., methylcarbamoylamino), a (mono- or di-$C_{7-16}$ aralkyl-carbamoyl)amino group (e.g., benzylcarbamoylamino), a $C_{1-6}$ alkylsulfonylamino group (e.g., methylsulfonylamino, ethylsulfonylamino), a $C_{6-14}$ arylsulfonylamino group (e.g., phenylsulfonylamino), a ($C_{1-6}$ alkyl) ($C_{1-6}$ alkyl-carbonyl)amino group (e.g., N-acetyl-N-methylamino) and a ($C_{1-6}$ alkyl) ($C_{6-14}$ aryl-carbonyl)amino group (e.g., N-benzoyl-N-methylamino).

In the present specification, examples of the "optionally substituted carbamoyl group" include a carbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from substituent group A".

Preferable examples of the optionally substituted carbamoyl group include a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl, cyclohexylcarbamoyl), a mono- or di-$C_{6-14}$ aryl-carbamoyl group (e.g., phenylcarbamoyl), a mono- or di-$C_{7-16}$ aralkyl-carbamoyl group, a mono- or di-$C_{1-6}$ alkyl-carbonyl-carbamoyl group (e.g., acetylcarbamoyl, propionylcarbamoyl), a mono- or di-$C_{6-14}$ aryl-carbonyl-carbamoyl group (e.g., benzoylcarbamoyl) and a 5- to 14-membered aromatic heterocyclylcarbamoyl group (e.g., pyridylcarbamoyl).

In the present specification, examples of the "optionally substituted thiocarbamoyl group" include a thiocarbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from substituent group A".

Preferable examples of the optionally substituted thiocarbamoyl group include a thiocarbamoyl group, a mono- or di-$C_{1-6}$ alkyl-thiocarbamoyl group (e.g., methylthiocarbamoyl, ethylthiocarbamoyl, dimethylthiocarbamoyl, diethylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a mono- or di-$C_{1-6}$ alkyl-carbonyl-thiocarbamoyl group (e.g., acetylthiocarbamoyl, propionylthiocarbamoyl), a mono- or di-$C_{6-14}$ aryl-carbonyl-thiocarbamoyl group (e.g., benzoylthiocarbamoyl) and a 5- to 14-membered aromatic heterocyclylthiocarbamoyl group (e.g., pyridylthiocarbamoyl).

In the present specification, examples of the "optionally substituted sulfamoyl group" include a sulfamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from substituent group A".

Preferable examples of the optionally substituted sulfamoyl group include a sulfamoyl group, a mono- or di-$C_{1-6}$ alkyl-sulfamoyl group (e.g., methylsulfamoyl, ethylsulfamoyl, dimethylsulfamoyl, diethylsulfamoyl, N-ethyl-N-methylsulfamoyl), a mono- or di-$C_{2-6}$ alkenyl-sulfamoyl group (e.g., diallylsulfamoyl), a mono- or di-$C_{3-10}$ cycloalkyl-sulfamoyl group (e.g., cyclopropylsulfamoyl, cyclohexylsulfamoyl), a mono- or di-$C_{6-14}$ aryl-sulfamoyl group (e.g., phenylsulfamoyl), a mono- or di-$C_{7-16}$ aralkyl-sulfamoyl group (e.g., benzylsulfamoyl, phenethylsulfamoyl), a mono- or di-$C_{1-6}$ alkyl-carbonyl-sulfamoyl group (e.g., acetylsulfamoyl, propionylsulfamoyl), a mono- or di-$C_{6-14}$ aryl-carbonyl-sulfamoyl group (e.g., benzoylsulfamoyl) and a 5- to 14-membered aromatic heterocyclylsulfamoyl group (e.g., pyridylsulfamoyl).

In the present specification, examples of the "optionally substituted hydroxy group" include a hydroxyl group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from substituent group A".

Preferable examples of the optionally substituted hydroxy group include a hydroxy group, a $C_{1-6}$ alkoxy group, a $C_{2-6}$ alkenyloxy group (e.g., allyloxy, 2-butenyloxy, 2-pentenyloxy, 3-hexenyloxy), a $C_{3-10}$ cycloalkyloxy group (e.g., cyclohexyloxy), a $C_{6-14}$ aryloxy group (e.g., phenoxy, naphthyloxy), a $C_{7-16}$ aralkyloxy group (e.g., benzyloxy, phenethyloxy), a $C_{1-6}$ alkyl-carbonyloxy group (e.g., acetyloxy, propionyloxy, butyryloxy, isobutyryloxy, pivaloyloxy), a $C_{6-14}$ aryl-carbonyloxy group (e.g., benzoyloxy), a $C_{7-16}$ aralkyl-carbonyloxy group (e.g., benzylcarbonyloxy), a 5- to 14-membered aromatic heterocyclylcarbonyloxy group (e.g., nicotinoyloxy), a 3- to 14-membered non-aromatic heterocyclylcarbonyloxy group (e.g., piperidinylcarbonyloxy), a $C_{1-6}$ alkoxy-carbonyloxy group (e.g., tert-butoxycarbonyloxy), a 5- to 14-membered aromatic heterocyclyloxy group (e.g., pyridyloxy), a carbamoyloxy group, a $C_{1-6}$ alkyl-carbamoyloxy group (e.g., methylcarbamoyloxy), a $C_{7-16}$ aralkyl-carbamoyloxy group (e.g., benzylcarbamoyloxy), a $C_{1-6}$ alkylsulfonyloxy group (e.g., methylsulfonyloxy, ethylsulfonyloxy) and a $C_{6-14}$ arylsulfonyloxy group (e.g., phenylsulfonyloxy).

In the present specification, examples of the "optionally substituted sulfanyl group" include a sulfanyl group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group and a 5- to 14-membered aromatic heterocyclic group, each of which optionally has 1 to 3 substituents selected from substituent group A" and a halogenated sulfanyl group.

Preferable examples of the optionally substituted sulfanyl group include a sulfanyl (—SH) group, a $C_{1-6}$ alkylthio group, a $C_{2-6}$ alkenylthio group (e.g., allylthio, 2-butenylthio, 2-pentenylthio, 3-hexenylthio), a $C_{3-10}$ cycloalkylthio group (e.g., cyclohexylthio), a $C_{6-14}$ arylthio group (e.g., phenylthio, naphthylthio), a $C_{7-16}$ aralkylthio group (e.g., benzylthio, phenethylthio), a $C_{1-6}$ alkyl-carbonylthio group (e.g., acetylthio, propionylthio, butyrylthio, isobutyrylthio, pivaloylthio), a $C_{6-14}$ aryl-carbonylthio group (e.g., benzoylthio), a 5- to 14-membered aromatic heterocyclylthio group (e.g., pyridylthio) and a halogenated thio group (e.g., pentafluorothio).

In the present specification, examples of the "optionally substituted silyl group" include a silyl group optionally having "1 to 3 substituents selected from a $C_{1-6}$ alkyl group, a $C_{2-6}$ alkenyl group, a $C_{3-10}$ cycloalkyl group, a $C_{6-14}$ aryl group and a $C_{7-16}$ aralkyl group, each of which optionally has 1 to 3 substituents selected from substituent group A".

Preferable examples of the optionally substituted silyl group include a tri-$C_{1-6}$ alkylsilyl group (e.g., trimethylsilyl, tert-butyl(dimethyl)silyl).

In the present specification, examples of the "hydrocarbon ring" include a $C_{6-14}$ aromatic hydrocarbon ring, $C_{3-10}$ cycloalkane and $C_{3-10}$ cycloalkene.

In the present specification, examples of the "$C_{6-14}$ aromatic hydrocarbon ring" include benzene and naphthalene.

In the present specification, examples of the "$C_{3-10}$ cycloalkane" include cyclopropane, cyclobutane, cyclopentane, cyclohexane, cycloheptane and cyclooctane.

In the present specification, examples of the "$C_{3-10}$ cycloalkene" include cyclopropene, cyclobutene, cyclopentene, cyclohexene, cycloheptene and cyclooctene.

In the present specification, examples of the "heterocycle" include an aromatic heterocycle and a non-aromatic heterocycle, each containing, as a ring-constituting atom besides carbon atom, 1 to 4 hetero atoms selected from a nitrogen atom, a sulfur atom and an oxygen atom.

In the present specification, examples of the "aromatic heterocycle" include a 5- to 14-membered (preferably 5- to 10-membered) aromatic heterocycle containing, as a ring-constituting atom besides carbon atom, 1 to 4 hetero atoms selected from a nitrogen atom, a sulfur atom and an oxygen atom. Preferable examples of the "aromatic heterocycle" include 5- or 6-membered monocyclic aromatic heterocycles such as thiophene, furan, pyrrole, imidazole, pyrazole, thiazole, isothiazole, oxazole, isoxazole, pyridine, pyrazine, pyrimidine, pyridazine, 1,2,4-oxadiazole, 1,3,4-oxadiazole, 1,2,4-thiadiazole, 1,3,4-thiadiazole, triazole, tetrazole, triazine and the like; and 8- to 14-membered fused polycyclic (preferably bi or tricyclic) aromatic heterocycles such as benzothiophene, benzofuran, benzimidazole, benzoxazole, benzisoxazole, benzothiazole, benzisothiazole, benzotriazole, imidazopyridine, thienopyridine, furopyridine, pyrrolopyridine, pyrazolopyridine, oxazolopyridine, thiazolopyridine, imidazopyrazine, imidazopyrimidine, thienopyrimidine, furopyrimidine, pyrrolopyrimidine, pyrazolopyrimidine, oxazolopyrimidine, thiazolopyrimidine, pyrazolopyrimidine, pyrazolotriazine, naphtho[2,3-b]thiophene, phenoxathiin, indole, isoindole, 1H-indazole, purine, isoquinoline, quinoline, phthalazine, naphthyridine, quinoxaline, quinazoline, cinnoline, carbazole, β-carboline, phenanthridine, acridine, phenazine, phenothiazine, phenoxazine and the like.

In the present specification, examples of the "non-aromatic heterocycle" include a 3- to 14-membered (preferably 4- to 10-membered) non-aromatic heterocycle containing, as a ring-constituting atom besides carbon atom, 1 to 4 hetero atoms selected from a nitrogen atom, a sulfur atom and an oxygen atom. Preferable examples of the "non-aromatic heterocycle" include 3- to 8-membered monocyclic non-aromatic heterocycles such as aziridine, oxirane, thiirane, azetidine, oxetane, thietane, tetrahydrothiophene, tetrahydrofuran, pyrroline, pyrrolidine, imidazoline, imidazolidine, oxazoline, oxazolidine, pyrazoline, pyrazolidine, thiazoline, thiazolidine, tetrahydroisothiazole, tetrahydrooxazole, tetrahydroisoxazole, piperidine, piperazine, tetrahydropyridine, dihydropyridine, dihydrothiopyran, tetrahydropyrimidine, tetrahydropyridazine, dihydropyran, tetrahydropyran, tetrahydrothiopyran, morpholine, thiomorpholine, azepanine, diazepane, azepine, azocane, diazocane, oxepane and the like; and 9- to 14-membered fused polycyclic (preferably bi or tricyclic) non-aromatic heterocycles such as dihydrobenzofuran, dihydrobenzimidazole, dihydrobenzoxazole, dihydrobenzothiazole, dihydrobenzisothiazole, dihydronaphtho[2,3-b]thiophene, tetrahydroisoquinoline, tetrahydroquinoline, 4H-quinolizine, indoline, isoindoline, tetrahydrothieno[2,3-c]pyridine, tetrahydrobenzazepine, tetrahydroquinoxaline, tetrahydrophenanthridine, hexahydrophenothiazine, hexahydrophenoxazine, tetrahydrophthalazine, tetrahydronaphthyridine, tetrahydroquinazoline, tetrahydrocinnoline, tetrahydrocarbazole, tetrahydro-3-carboline, tetrahydroacridine, tetrahydrophenazine, tetrahydrothioxanthene, octahydroisoquinoline and the like.

In the present specification, examples of the "nitrogen-containing heterocycle" include a "heterocycle" containing at least one nitrogen atom as a ring-constituting atom.

The definition of each symbol in the formula (I) is explained in detail in the following.

$G^1$ is a carbon atom or a nitrogen atom.

$G^1$ is preferably a carbon atom.

$G^2$ is a carbon atom or a nitrogen atom.

$G^2$ is preferably a carbon atom.

Ring A is an optionally further substituted 6-membered nitrogen-containing heterocycle.

Examples of the "6-membered nitrogen-containing heterocycle" of the "optionally further substituted 6-membered nitrogen-containing heterocycle" for Ring A include 6-membered heterocycles containing at least one nitrogen atom, from among of the above-mentioned heterocycle, specifically, pyridine, pyrimidine, pyridazine.

The "6-membered nitrogen-containing heterocycle" of the "optionally further substituted 6-membered nitrogen-containing heterocycle" for Ring A is preferably pyridine or pyrimidine, more preferably pyridine.

The "6-membered nitrogen-containing heterocycle" of the "optionally further substituted 6-membered nitrogen-containing heterocycle" for Ring A optionally has 1 or 2 substituents at substitutable position(s), in addition to —N($R^4$)—C($R^1$)($R^2$)—Ring B. Examples of the substituent include substituents selected from the aforementioned substituent group A. When the number of the substituents is plural, the respective substituents may be the same or different.

Ring A is preferably an optionally further substituted pyridine.

Ring A is more preferably pyridine optionally further substituted by 1 to 3 halogen atoms (e.g., a chlorine atom).

In another embodiment, Ring A is preferably an optionally further substituted pyridine or an optionally further substituted pyrimidine.

In this embodiment, Ring A is more preferably pyridine or pyrimidine, each of which is optionally further substituted by 1 to 2 substituents selected from the group consisting of
(a) a halogen atom (e.g., a chlorine atom),
(b) a $C_{1-6}$ alkyl group (e.g., methyl), and
(c) a $C_{3-10}$ cycloalkyl group (e.g., cyclopropyl)

In this embodiment, Ring A is still more preferably (1) pyridine optionally further substituted by 1 to 2 substituents selected from the group consisting of
(a) a halogen atom (e.g., a chlorine atom),
(b) a $C_{1-6}$ alkyl group (e.g., methyl), and
(c) a $C_{3-10}$ cycloalkyl group (e.g., cyclopropyl), or (2) pyrimidine.

In this embodiment, Ring A is particularly preferably pyridine.

$G^3$ is an oxygen atom, an optionally substituted methylene, NR, a sulfur atom, S(O) or S(O)$_2$.

$R^1$ is a hydrogen atom or a substituent.

The "methylene" of the "optionally substituted methylene" for $G^3$ optionally has 1 or 2 substituents at substitutable position(s). Examples of the substituent include substituents selected from the aforementioned substituent group A. When the number of the substituents is plural, the respective substituents may be the same or different.

$G^3$ is preferably an oxygen atom or $NR^1$ wherein $R^1$ is as defined above.

$G^3$ is more preferably an oxygen atom or $NR^1$ wherein $R^1$ is a $C_{1-6}$ alkyl group (e.g., methyl).

In another embodiment, $G^3$ is preferably an oxygen atom, an optionally substituted methylene, $NR^1$ wherein $R^1$ is as defined above, or a sulfur atom.

In this embodiment, $G^3$ is more preferably an oxygen atom, $NR^1$ wherein $R^1$ is a $C_{1-6}$ alkyl group (e.g., methyl), methylene or a sulfur atom.

In this embodiment, $G^3$ is particularly an oxygen atom.

X is an optionally substituted ethylene.

The "ethylene" of the "optionally substituted ethylene" for X optionally has 1 to 4 substituents at substitutable position(s). Examples of the substituent include substituents selected from the aforementioned substituent group A. When the number of the substituents is plural, the respective substituents may be the same or different.

X is preferably ethylene.

In another embodiment, X is preferably ethylene optionally substituted by an oxo group.

In this embodiment, X is particularly preferably ethylene.

$R^2$ and $R^3$ are each independently a hydrogen atom or an optionally substituted $C_{1-6}$ alkyl group, or $R^2$ and $R^3$ are joined together to form a cycloalkane or a heterocycle, each of which is optionally substituted.

The "$C_{1-6}$ alkyl group" of the "optionally substituted $C_{1-6}$ alkyl group" optionally has 1 to 5 substituents (preferably 1 to 3) at substitutable position(s). Examples of the substituent include substituents selected from the aforementioned substituent group A. When the number of the substituents is plural, the respective substituents may be the same or different.

Examples of the "cycloalkane" of the "cycloalkane or heterocycle, each of which is optionally substituted" formed by $R^1$ and $R^2$ include a $C_{3-10}$ cycloalkane (preferably a $C_{3-6}$ cycloalkane).

The "cycloalkane or heterocycle" of the "cycloalkane or heterocycle, each of which is optionally substituted" formed by $R^2$ and $R^3$ has 1 to 5 substituents (preferably 1 to 3) at substitutable position(s). Examples of the substituent include substituents selected from the aforementioned substituent group A. When the number of the substituents is plural, the respective substituents may be the same or different.

Preferably, $R^2$ and $R^3$ are each a hydrogen atom or an optionally substituted $C_{1-6}$ alkyl group (e.g., methyl), or $R^2$ and $R^3$ are joined together to form an optionally substituted cycloalkane (preferably a $C_{3-10}$ cycloalkane, more preferably a $C_{3-6}$ cycloalkane (e.g., cyclopropane)).

More preferably, $R^2$ and $R^3$ are each a hydrogen atom or a $C_{1-6}$ alkyl group (e.g., methyl), or $R^2$ and $R^3$ are joined together to form a $C_{3-10}$ cycloalkane (preferably a $C_{3-6}$ cycloalkane (e.g., cyclopropane)).

Still more preferably, $R^2$ is a $C_{1-6}$ alkyl group (e.g., methyl), and $R^3$ is a hydrogen atom, or $R^2$ and $R^3$ are joined together to form a $C_{3-10}$ cycloalkane (preferably a $C_{3-6}$ cycloalkane (e.g., cyclopropane)).

In another embodiment, still more preferably, $R^2$ is a hydrogen atom or a $C_{1-6}$ alkyl group (e.g., methyl), and $R^3$ is a hydrogen atom, or $R^2$ and $R^3$ are joined together to form a $C_{3-10}$ cycloalkane (preferably a $C_{3-6}$ cycloalkane (e.g., cyclopropane)).

In this embodiment, particularly preferably, $R^2$ is a $C_{1-6}$ alkyl group (e.g., methyl), and $R^3$ is a hydrogen atom, or $R^2$ and $R^3$ are joined together to form a $C_{3-6}$ cycloalkane (e.g., cyclopropane).

$R^4$ is a hydrogen atom or a substituent.

$R^4$ is preferably a hydrogen atom.

Ring B is an optionally further substituted ring.

Examples of the "ring" of the "optionally further substituted ring" for Ring B include a hydrocarbon ring and a heterocycle (preferably a $C_{6-14}$ aromatic hydrocarbon ring (preferably a $C_{6-10}$ aromatic hydrocarbon ring, more preferably benzene), a $C_{3-10}$ cycloalkane (preferably a $C_{3-6}$ cycloalkane, more preferably cyclohexane) or a 5- to 14-membered (preferably 5- to 10-membered) aromatic heterocycle (preferably a 5- or 6-membered monocyclic aromatic heterocycle, more preferably pyridine), more preferably a $C_{6-10}$ aromatic hydrocarbon ring (preferably benzene), a $C_{3-6}$ cycloalkane (preferably cyclohexane) or a 5- or 6-membered monocyclic aromatic heterocycle (preferably pyridine), particularly preferably benzene).

The "ring" of the "optionally further substituted ring" for Ring B optionally has 1 to 5 (preferably 1 to 3) substituents at substitutable position(s), in addition to —C($R^1$)($R^2$)—N($R^4$)—Ring A. Examples of the substituent include an optionally further substituted pyridine substituents selected from the aforementioned substituent group A. When the number of the substituents is plural, the respective substituents may be the same or different.

Ring B is preferably an optionally further substituted $C_{6-14}$ aromatic hydrocarbon ring (preferably benzene).

Ring B is more preferably a $C_{6-14}$ aromatic hydrocarbon ring (preferably benzene) optionally further substituted by 1 to 3 (preferably one) substituents selected from the group consisting of
  (a) a carboxy group,
  (b) a $C_{1-6}$ alkoxy-carbonyl group (e.g., methoxycarbonyl),
  (c) a cyano group,
  (d) a carbamoyl group,
  (e) a mono- or di-$C_{1-6}$ alkyl-carbamoyl group (e.g., methylcarbamoyl),
  (f) a mono- or di-$C_{1-6}$ alkoxy-carbamoyl group (e.g., methoxycarbamoyl, ethoxycarbamoyl),
  (g) a mono- or di-$C_{7-16}$ aralkyloxy-carbamoyl group (e.g., benzyloxycarbamoyl), and
  (h) 5-tetrazolyl,
[preferably optionally further substituted by 1 to 3 (preferably one) carboxy groups].

Ring B is still more preferably benzene optionally further substituted by 1 to 3 (preferably one) substituents selected from the group consisting of
  (a) a carboxy group,
  (b) a $C_{1-6}$ alkoxy-carbonyl group (e.g., methoxycarbonyl),
  (c) a cyano group,
  (d) a carbamoyl group,
  (e) a mono- or di-$C_{1-6}$ alkyl-carbamoyl group (e.g., methylcarbamoyl),
  (f) a mono- or di-$C_{1-6}$ alkoxy-carbamoyl group (e.g., methoxycarbamoyl, ethoxycarbamoyl),
  (g) a mono- or di-$C_{7-16}$ aralkyloxy-carbamoyl group (e.g., benzyloxycarbamoyl), and
  (h) 5-tetrazolyl,
[preferably optionally further substituted by 1 to 3 (preferably one) carboxy groups].

In another embodiment, Ring B is preferably an optionally further substituted $C_{6-14}$ aromatic hydrocarbon ring (preferably a $C_{6-10}$ aromatic hydrocarbon ring, more preferably benzene), an optionally further substituted $C_{3-10}$ cycloalkane (preferably a $C_{3-6}$ cycloalkane, more preferably cyclohexane) or an optionally further substituted 5- to 10-membered aromatic heterocycle (preferably a 5- or 6-membered monocyclic aromatic heterocycle, more preferably pyridine).

In this embodiment, Ring B is more preferably
(1) a $C_{6-14}$ aromatic hydrocarbon ring (preferably a $C_{6-10}$ aromatic hydrocarbon ring, more preferably benzene) optionally further substituted by 1 to 3 (preferably one) substituents selected from the group consisting of
  (a) a carboxy group,
  (b) a $C_{1-6}$ alkoxy-carbonyl group (e.g., methoxycarbonyl),
  (c) a cyano group,
  (d) a carbamoyl group,
  (e) a mono- or di-$C_{1-6}$ alkyl-carbamoyl group (e.g., methylcarbamoyl),
  (f) a mono- or di-$C_{1-6}$ alkoxy-carbamoyl group (e.g., methoxycarbamoyl, ethoxycarbamoyl),
  (g) a mono- or di-$C_{7-16}$ aralkyloxy-carbamoyl group (e.g., benzyloxycarbamoyl),
  (h) 5-tetrazolyl, and
  (i) a $C_{1-6}$ alkoxy group (e.g., methoxy)
[preferably optionally further substituted by 1 to 3 (preferably one) carboxy groups],
(2) a $C_{3-10}$ cycloalkane (preferably a $C_{3-6}$ cycloalkane, more preferably cyclohexane), or
(3) a 5- to 10-membered aromatic heterocycle (preferably a 5- or 6-membered monocyclic aromatic heterocycle, more preferably pyridine) optionally further substituted by 1 to 3 (preferably one) $C_{1-6}$ alkyl groups (e.g., methyl).

In this embodiment, Ring B is still more preferably
(1) a $C_{6-10}$ aromatic hydrocarbon ring (preferably benzene) optionally further substituted by 1 to 3 (preferably one) substituents selected from the group consisting of
  (a) a carboxy group,
  (b) a $C_{1-6}$ alkoxy-carbonyl group (e.g., methoxycarbonyl),
  (c) a cyano group,
  (d) a carbamoyl group,
  (e) a mono- or di-$C_{1-6}$ alkyl-carbamoyl group (e.g., methylcarbamoyl),
  (f) a mono- or di-$C_{1-6}$ alkoxy-carbamoyl group (e.g., methoxycarbamoyl, ethoxycarbamoyl),
  (g) a mono- or di-$C_{7-16}$ aralkyloxy-carbamoyl group (e.g., benzyloxycarbamoyl),
  (h) 5-tetrazolyl, and
  (i) a $C_{1-6}$ alkoxy group (e.g., methoxy)
[preferably optionally further substituted by 1 to 3 (preferably one) carboxy groups],
(2) a $C_{3-6}$ cycloalkane (preferably cyclohexane), or
(3) a 5- or 6-membered monocyclic aromatic heterocycle (preferably pyridine) optionally further substituted by 1 to 3 (preferably one) $C_{1-6}$ alkyl groups (e.g., methyl).

In this embodiment, Ring B is particularly preferably benzene further substituted by one carboxy group.

Ring C is an optionally further substituted ring.

Examples of the "ring" of the "optionally further substituted ring" for Ring C include a hydrocarbon ring and a heterocycle (preferably a $C_{6-14}$ aromatic hydrocarbon ring (preferably a $C_{6-10}$ aromatic hydrocarbon ring, more preferably benzene, naphthalene), a $C_{3-10}$ cycloalkane (preferably a $C_{3-6}$ cycloalkane, more preferably cyclohexane) or a 5- to 14-membered (preferably 5- to 10-membered) aromatic heterocycle (preferably a 5- or 6-membered monocyclic aromatic heterocycle, more preferably pyridine, furan, isoxazole), more preferably a $C_{6-10}$ aromatic hydrocarbon ring (preferably benzene, naphthalene), a $C_{3-6}$ cycloalkane (preferably cyclohexane) or a 5- or 6-membered monocyclic aromatic heterocycle (preferably pyridine, furan, isoxazole)).

The "ring" of the "optionally further substituted ring" for Ring C optionally has 1 to 5 (preferably 1 to 3) substituents at substitutable position(s), in addition to —W—. Examples of the substituent include substituents selected from the aforementioned substituent group A. When the number of the substituents is plural, the respective substituents may be the same or different.

Ring C is preferably a $C_{6-14}$ aromatic hydrocarbon ring (preferably benzene, naphthalene) or a 5- to 14-membered (preferably 5- to 10-membered) aromatic heterocycle (preferably pyridine, furan) (preferably a $C_{6-14}$ aromatic hydrocarbon ring (preferably benzene, naphthalene) or a 5- or 6-membered monocyclic aromatic heterocycle (preferably pyridine, furan)), each of which is optionally further substituted.

Ring C is more preferably a $C_{6-14}$ aromatic hydrocarbon ring (preferably benzene, naphthalene) or a 5- to 14-membered (preferably 5- to 10-membered) aromatic heterocycle (preferably pyridine, furan) (preferably a $C_{6-14}$ aromatic hydrocarbon ring (preferably benzene, naphthalene) or a 5- or 6-membered monocyclic aromatic heterocycle (preferably pyridine, furan)), each of which is optionally further substituted by 1 to 3 (preferably 1 or 2) substituents selected from the group consisting of
  (1) a halogen atom (e.g., a fluorine atom, a chlorine atom),
  (2) an optionally halogenated $C_{1-6}$ alkyl group (e.g., methyl, trifluoromethyl),
  (3) a $C_{1-6}$ alkoxy group (e.g., methoxy), and
  (4) a $C_{6-14}$ aryl group (e.g., phenyl).

Ring C is still more preferably benzene, naphthalene, pyridine or furan, each of which is optionally further substituted by 1 to 3 (preferably 1 or 2) substituents selected from the group consisting of
  (1) a halogen atom (e.g., a fluorine atom, a chlorine atom),
  (2) an optionally halogenated $C_{1-6}$ alkyl group (e.g., methyl, trifluoromethyl),
  (3) a $C_{1-6}$ alkoxy group (e.g., methoxy), and
  (4) a $C_{6-14}$ aryl group (e.g., phenyl).

In another embodiment, Ring C is preferably a $C_{6-14}$ aromatic hydrocarbon ring (preferably a $C_{6-10}$ aromatic hydrocarbon ring, more preferably benzene, naphthalene), a $C_{3-10}$ cycloalkane (preferably a $C_{3-6}$ cycloalkane, more preferably cyclohexane) or a 5- to 14-membered (preferably 5- to 10-membered) aromatic heterocycle (preferably a 5- or 6-membered monocyclic aromatic heterocycle, more preferably pyridine, furan, isoxazole) (preferably a $C_{6-10}$ aromatic hydrocarbon ring (preferably benzene, naphthalene), a $C_{3-6}$ cycloalkane (preferably cyclohexane) or a 5- or 6-membered monocyclic aromatic heterocycle (preferably pyridine, furan, isoxazole)), each of which is optionally further substituted.

In this embodiment, Ring C is more preferably a $C_{6-14}$ aromatic hydrocarbon ring (preferably a $C_{6-10}$ aromatic hydrocarbon ring, more preferably benzene, naphthalene), a $C_{3-10}$ cycloalkane (preferably a $C_{3-6}$ cycloalkane, more preferably cyclohexane) or a 5- to 14-membered (preferably 5- to 10-membered) aromatic heterocycle (preferably a 5- or 6-membered monocyclic aromatic heterocycle, more preferably pyridine, furan, isoxazole) (preferably a $C_{6-10}$ aromatic hydrocarbon ring (preferably benzene, naphthalene), a $C_{3-6}$ cycloalkane (preferably cyclohexane) or a 5- or 6-membered monocyclic aromatic heterocycle (preferably pyridine, furan, isoxazole)), each of which is optionally further substituted by 1 to 3 (preferably 1 or 2) substituents selected from the group consisting of
  (1) a halogen atom (e.g., a fluorine atom, a chlorine atom),
  (2) an optionally halogenated $C_{1-6}$ alkyl group (e.g., methyl, trifluoromethyl),
  (3) a $C_{1-6}$ alkoxy group (e.g., methoxy), and
  (4) a $C_{6-14}$ aryl group (e.g., phenyl).

In this embodiment, Ring C is further more preferably benzene, naphthalene, cyclohexane, pyridine, furan or isoxazole, each of which is optionally further substituted by 1 to 3 (preferably 1 or 2) substituents selected from the group consisting of
  (1) a halogen atom (e.g., a fluorine atom, a chlorine atom),
  (2) an optionally halogenated $C_{1-6}$ alkyl group (e.g., methyl, trifluoromethyl),
  (3) a $C_{1-6}$ alkoxy group (e.g., methoxy), and
  (4) a $C_{6-14}$ aryl group (e.g., phenyl).

In this embodiment, Ring C is still more preferably benzene further substituted by 1 or 2 substituents selected from the group consisting of
  (1) a halogen atom (e.g., a fluorine atom, a chlorine atom), and
  (2) a $C_{1-6}$ alkoxy group (e.g., methoxy).

In this embodiment, Ring C is particularly preferably benzene further substituted by 1 or 2 halogen atoms (e.g., a fluorine atom, a chlorine atom).

W is a bond, or a spacer in which the number of atoms in the main chain is 1 to 4.

Examples of the "spacer in which the number of atoms in the main chain is 1 to 4" for W include spacers wherein the main chain consists of 1 to 4 atoms selected from a carbon atom, a nitrogen atom, a sulfur atom (optionally oxidized) and an oxygen atom, each of which optionally has substituent(s) selected from the aforementioned substituent group A at substitutable position(s).

Specific examples of the "spacer in which the number of atoms in the main chain is 1 to 4" for W include
(1) a bond;
(2) a $C_{1-4}$ alkylene group (e.g., —$CH_2$—, —$(CH_2)_2$—, —$CH_2$—$CH(CH_3)$—, —$CH(CH_3)$—$CH_2$—, —$(CH_2)_3$—, —$(CH_2)_4$— etc.) optionally substituted by the aforementioned substituent group A (preferably a halogen atom (e.g., a fluorine atom, a chlorine atom), an oxo group and a hydroxy group);
(3) a $C_{2-4}$ alkenylene group (e.g., —CH=CH—, —CH=CH—$CH_2$—, —$CH_2$—CH=CH— etc.) optionally substituted by the aforementioned substituent group A;
(4) —Z— wherein Z is O, $NR^6$ ($R^6$ is a hydrogen atom or a substituent), S, S(O), or $S(O)_2$;
(5) —$(CH_2)_{m1}$—Z—$(CH_2)_{m2}$— wherein Z is as defined above, m1 and m2 are each independently an integer of 0 to 3, and m1+m2 is an integer of 1 to 3;
(6) —$Z$—$(CH_2)_m$—$Z^2$— wherein $Z^1$ and $Z^2$ are each independently O, C(O), $NR^6$ ($R^6$ is a hydrogen atom or a substituent), S, S(O) or $S(O)_2$, and m is an integer of 1 to 2;
(7) —CO—$NR^6$— or —$NR^6$—CO— wherein $R^6$ is as defined above;
(8) —$S(O)_2$—$NR^6$— or —$NR^6$—$S(O)_2$— wherein $R^6$ is as defined above;
(9) a $C_{3-6}$ cycloalkylene (e.g., cyclopropylene, cyclobutylene, cyclopentylene, cyclohexylene etc.);
(10) a divalent non-aromatic heterocyclic group (e.g., 1,2-aziridinediyl, 1,3-azetidinediyl, 1,3-pyrrolidinediyl, 1,3-piperidinediyl, 1,4-piperidinediyl, 1,4-morpholinediyl etc.);
(11) —$Z^1$—Y—$Z^2$— wherein $Z^1$ and $Z^2$ are as defined above, and Y is a divalent non-aromatic heterocyclic group (e.g., 1,2-aziridinediyl, 1,3-azetidinediyl, 1,3-pyrrolidinediyl, 1,3-piperidinediyl etc.);
and the like.

W is preferably a spacer in which the number of atoms in the main chain is 1 to 4.

W is more preferably
(1) a $C_{1-4}$ alkylene group (e.g., —$CH_2$—), or
(2) —$(CH_2)_{m1}$—O— wherein m1 is an integer of 0 to 3 (e.g., —$CH_2CH_2O$—).

W is still more preferably —$CH_2$— or —$CH_2CH_2O$— (wherein the left bond is bonded to the nitrogen atom, and the right bond is bonded to Ring C).

In another embodiment, W is more preferably
(1) a $C_{1-4}$ alkylene group (e.g., —$CH_2$—, —$(CH_2)_2$—) optionally substituted by an oxo group, or
(2) —$(CH_2)_{m1}$—O— wherein m1 is an integer of 0 to 3 (e.g., —$CH_2CH_2O$—).

In this embodiment, W is still more preferably —$CH_2$—, —$(CH_2)_2$—, —$CH_2CH_2O$— (wherein the left bond is bonded to the nitrogen atom, and the right bond is bonded to Ring C) or —C(=O)—.

In this embodiment, W is particularly preferably —$CH_2$—.

Preferable examples of compound (I) include the following compounds.

[Compound A-1]
  Compound (I) wherein
  $G^1$ is a carbon atom or a nitrogen atom,
  $G^2$ is a carbon atom or a nitrogen atom,
  Ring A is an optionally further substituted pyridine,
  $G^3$ is an oxygen atom or $NR^1$ wherein $R^1$ is as defined above,
  X is an optionally substituted ethylene,
  $R^2$ and $R^3$ are each a hydrogen atom or an optionally substituted $C_{1-6}$ alkyl group (e.g., methyl), or $R^2$ and $R^3$ are joined together to form an optionally substituted cycloalkane (preferably a $C_{3-10}$ cycloalkane, more preferably a $C_{3-6}$ cycloalkane (e.g., cyclopropane)),
  $R^4$ is a hydrogen atom,
  Ring B is an optionally further $C_{6-14}$ aromatic hydrocarbon ring (preferably benzene),
  Ring C is a $C_{6-14}$ aromatic hydrocarbon ring (preferably benzene, naphthalene) or a 5- to 14-membered (preferably 5- to 10-membered) aromatic heterocycle (preferably pyridine, furan) (preferably a $C_{6-14}$ aromatic hydrocarbon ring (preferably benzene, naphthalene) or a 5- or 6-membered monocyclic aromatic heterocycle (preferably pyridine, furan)), each of which is optionally further substituted, and
  W is a spacer in which the number of atoms in the main chain is 1 to 4.

[Compound B-1]
  Compound (I) wherein
  $G^1$ is a carbon atom,
  $G^2$ is a carbon atom,
  Ring A is pyridine optionally further substituted by 1 to 2 halogen atoms (e.g., a chlorine atom),
  $G^3$ is an oxygen atom or $NR^1$ wherein $R^1$ is a $C_{1-6}$ alkyl group (e.g., methyl),
  X is ethylene, $R^2$ and $R^3$ are each a hydrogen atom or a $C_{1-6}$ alkyl group (e.g., methyl), or $R^2$ and $R^3$ are joined together to form a $C_{3-10}$ cycloalkane (preferably a $C_{3-6}$ cycloalkane (e.g., cyclopropane)), $R^4$ is a hydrogen atom, Ring B is a $C_{6-14}$ aromatic hydrocarbon ring (preferably benzene) optionally further substituted by 1 to 3 (preferably one) substituents selected from the group consisting of
  (a) a carboxy group,
  (b) a $C_{1-6}$ alkoxy-carbonyl group (e.g., methoxycarbonyl),
  (c) a cyano group,
  (d) a carbamoyl group,
  (e) a mono- or di-$C_{1-6}$ alkyl-carbamoyl group (e.g., methylcarbamoyl),
  (f) a mono- or di-$C_{1-6}$ alkoxy-carbamoyl group (e.g., methoxycarbamoyl, ethoxycarbamoyl),
  (g) a mono- or di-$C_{7-16}$ aralkyloxy-carbamoyl group (e.g., benzyloxycarbamoyl), and
  (h) 5-tetrazolyl,
[preferably optionally further substituted by 1 to 3 (preferably one) carboxy groups], Ring C is a $C_{6-14}$ aromatic hydrocarbon ring (preferably benzene, naphthalene) or a 5- to 14-membered (preferably 5- to 10-membered) aromatic heterocycle (preferably pyridine, furan) (preferably a $C_{6-14}$ aromatic hydrocarbon ring (preferably benzene, naphthalene) or a 5- or 6-membered monocyclic aromatic heterocycle (preferably pyridine, furan)), each of which is optionally further substituted by 1 to 3 (preferably 1 or 2) substituents selected from the group consisting of
  (1) a halogen atom (e.g., a fluorine atom, a chlorine atom),
  (2) an optionally halogenated $C_{1-6}$ alkyl group (e.g., methyl, trifluoromethyl),
  (3) a $C_{1-6}$ alkoxy group (e.g., methoxy),
  (4) a $C_{6-14}$ aryl group (e.g., phenyl), and W is
(1) a $C_{1-4}$ alkylene group (e.g., —$CH_2$—), or
(2) —$(CH_2)_{m1}$—O— wherein m1 is an integer of 0 to 3 (e.g., —$CH_2CH_2O$—)

[Compound C-1]
Compound (I) wherein
  $G^1$ is a carbon atom,
  $G^2$ is a carbon atom,
  Ring A is pyridine optionally further substituted by 1 to 2 halogen atoms (e.g., a chlorine atom),
  $G^3$ is an oxygen atom or $NR^1$ wherein $R^1$ is a $C_{1-6}$ alkyl group (e.g., methyl),
  X is ethylene,
  $R^2$ is a $C_{1-6}$ alkyl group (e.g., methyl), and $R^3$ is a hydrogen atom, or $R^2$ and $R^3$ are joined together to form a $C_{3-10}$ cycloalkane (preferably a $C_{3-6}$ cycloalkane (e.g., cyclopropane)),
  $R^4$ is a hydrogen atom,
  Ring B is benzene optionally further substituted by 1 to 3 (preferably one) substituents selected from the group consisting of
    (a) a carboxy group,
    (b) a $C_{1-6}$ alkoxy-carbonyl group (e.g., methoxycarbonyl),
    (c) a cyano group,
    (d) a carbamoyl group,
    (e) a mono- or di-$C_{1-6}$ alkyl-carbamoyl group (e.g., methylcarbamoyl),
    (f) a mono- or di-$C_{1-6}$ alkoxy-carbamoyl group (e.g., methoxycarbamoyl, ethoxycarbamoyl),
    (g) a mono- or di-$C_{7-16}$ aralkyloxy-carbamoyl group (e.g., benzyloxycarbamoyl), and
    (h) 5-tetrazolyl,
  [preferably optionally further substituted by 1 to 3 (preferably one) carboxy groups], Ring C is benzene, naphthalene, pyridine or furan, each of which is optionally further substituted by 1 to 3 (preferably 1 or 2) substituents selected from the group consisting of
    (1) a halogen atom (e.g., a fluorine atom, a chlorine atom),
    (2) an optionally halogenated $C_{1-6}$ alkyl group (e.g., methyl, trifluoromethyl),
    (3) a $C_{1-6}$ alkoxy group (e.g., methoxy),
    (4) a $C_{6-14}$ aryl group (e.g., phenyl), and
  W is —$CH_2$— or —$CH_2CH_2O$— (wherein the left bond is bonded to the nitrogen atom, and the right bond is bonded to Ring C).

[Compound A-2]
Compound (I) wherein
  $G^1$ is a carbon atom or a nitrogen atom,
  $G^2$ is a carbon atom or a nitrogen atom,
  Ring A is an optionally further substituted pyridine or an optionally further substituted pyrimidine,
  $G^3$ is an oxygen atom, an optionally substituted methylene, $NR^1$ wherein $R^1$ is as defined above, or a sulfur atom,
  X is an optionally substituted ethylene,
  $R^2$ and $R^3$ are each a hydrogen atom or an optionally substituted $C_{1-6}$ alkyl group (e.g., methyl), or $R^2$ and $R^3$ are joined together to form an optionally substituted cycloalkane (preferably a $C_{3-10}$ cycloalkane, more preferably a $C_{3-6}$ cycloalkane (e.g., cyclopropane)),
  $R^4$ is a hydrogen atom,
  Ring B is an optionally further substituted $C_{6-14}$ aromatic hydrocarbon ring (preferably a $C_{6-10}$ aromatic hydrocarbon ring, more preferably benzene), an optionally further substituted $C_{3-10}$ cycloalkane (preferably a $C_{3-6}$ cycloalkane, more preferably cyclohexane) or an optionally further substituted 5- to 10-membered aromatic heterocycle (preferably a 5- or 6-membered monocyclic aromatic heterocycle, more preferably pyridine),
  Ring C is a $C_{6-14}$ aromatic hydrocarbon ring (preferably a $C_{6-10}$ aromatic hydrocarbon ring, more preferably benzene, naphthalene), a $C_{3-10}$ cycloalkane (preferably a $C_{3-6}$ cycloalkane, more preferably cyclohexane) or a 5- to 14-membered (preferably 5- to 10-membered) aromatic heterocycle (preferably a 5- or 6-membered monocyclic aromatic heterocycle, more preferably pyridine, furan, isoxazole) (preferably a $C_{6-10}$ aromatic hydrocarbon ring (preferably benzene, naphthalene), a $C_{3-6}$ cycloalkane (preferably cyclohexane) or a 5- or 6-membered monocyclic aromatic heterocycle (preferably pyridine, furan, isoxazole)), each of which is optionally further substituted, and
  W is a spacer in which the number of atoms in the main chain is 1 to 4.

[Compound B-2]
Compound (I) wherein
  $G^1$ is a carbon atom,
  $G^2$ is a carbon atom or a nitrogen atom,
  Ring A is pyridine or pyrimidine, each of which is optionally further substituted by 1 to 2 substituents selected from the group consisting of
    (a) a halogen atom (e.g., a chlorine atom),
    (b) a $C_{1-6}$ alkyl group (e.g., methyl), and
    (c) a $C_{3-10}$ cycloalkyl group (e.g., cyclopropyl),
  $G^3$ is an oxygen atom, $NR^1$ wherein $R^1$ is a $C_{1-6}$ alkyl group (e.g., methyl), methylene or a sulfur atom, X is ethylene optionally substituted by an oxo group,
$R^2$ and $R^3$ are each a hydrogen atom or a $C_{1-6}$ alkyl group (e.g., methyl), or $R^2$ and $R^3$ are joined together to form a $C_{3-10}$ cycloalkane (preferably a $C_{3-6}$ cycloalkane (e.g., cyclopropane)),
$R^4$ is a hydrogen atom,
Ring B is
(1) a $C_{6-14}$ aromatic hydrocarbon ring (preferably a $C_{6-10}$ aromatic hydrocarbon ring, more preferably benzene) optionally further substituted by 1 to 3 (preferably one) substituents selected from the group consisting of
  (a) a carboxy group,
  (b) a $C_{1-6}$ alkoxy-carbonyl group (e.g., methoxycarbonyl),
  (c) a cyano group,
  (d) a carbamoyl group,
  (e) a mono- or di-$C_{1-6}$ alkyl-carbamoyl group (e.g., methylcarbamoyl),
  (f) a mono- or di-$C_{1-6}$ alkoxy-carbamoyl group (e.g., methoxycarbamoyl, ethoxycarbamoyl),
  (g) a mono- or di-$C_{7-16}$ aralkyloxy-carbamoyl group (e.g., benzyloxycarbamoyl),
  (h) 5-tetrazolyl, and
  (i) a $C_{1-6}$ alkoxy group (e.g., methoxy)
[preferably optionally further substituted by 1 to 3 (preferably one) carboxy groups],
(2) a $C_{3-10}$ cycloalkane (preferably a $C_{3-6}$ cycloalkane, more preferably cyclohexane), or
(3) a 5- to 10-membered aromatic heterocycle (preferably a 5- or 6-membered monocyclic aromatic heterocycle, more preferably pyridine) optionally further substituted by 1 to 3 (preferably one) $C_{1-6}$ alkyl groups (e.g., methyl),
Ring C is a $C_{6-14}$ aromatic hydrocarbon ring (preferably a $C_{6-10}$ aromatic hydrocarbon ring, more preferably benzene, naphthalene), a $C_{3-10}$ cycloalkane (preferably a $C_{3-6}$ cycloalkane, more preferably cyclohexane) or a 5- to 14-membered (preferably 5- to 10-membered) aromatic heterocycle (preferably a 5- or 6-membered monocyclic aromatic heterocycle, more preferably pyridine, furan, isoxazole) (preferably a $C_{6-10}$ aromatic hydrocarbon ring (preferably benzene, naphthalene), a $C_{3-6}$ cycloalkane (preferably cyclohexane) or a 5- or 6-membered monocyclic aromatic heterocycle (preferably pyridine, furan, isoxazole)), each of which is optionally further substituted by 1 to 3 (preferably 1 or 2) substituents selected from the group consisting of
  (1) a halogen atom (e.g., a fluorine atom, a chlorine atom),
  (2) an optionally halogenated $C_{1-6}$ alkyl group (e.g., methyl, trifluoromethyl),
  (3) a $C_{1-6}$ alkoxy group (e.g., methoxy), and
  (4) a $C_{6-14}$ aryl group (e.g., phenyl), and
W is
(1) a $C_{1-4}$ alkylene group (e.g., —$CH_2$—, —$(CH_2)_2$—) optionally substituted by an oxo group, or
(2) —$(CH_2)_{m1}$—O— wherein m1 is an integer of 0 to 3 (e.g., —$CH_2CH_2O$—)

[Compound C-2]
Compound (I) wherein
$G^1$ is a carbon atom,
$G^2$ is a carbon atom or a nitrogen atom,
Ring A is
(1) pyridine optionally further substituted by 1 to 2 substituents selected from the group consisting of
  (a) a halogen atom (e.g., a chlorine atom),
  (b) a $C_{1-6}$ alkyl group (e.g., methyl), and
  (c) a $C_{3-10}$ cycloalkyl group (e.g., cyclopropyl), or
(2) pyrimidine,
$G^3$ is an oxygen atom, $NR^1$ wherein $R^1$ is a $C_{1-6}$ alkyl group (e.g., methyl), methylene or a sulfur atom, X is ethylene optionally substituted by an oxo group,
$R^2$ and $R^3$ are each a hydrogen atom or a $C_{1-6}$ alkyl group (e.g., methyl), or $R^2$ and $R^3$ are joined together to form a $C_{3-10}$ cycloalkane (preferably a $C_{3-6}$ cycloalkane (e.g., cyclopropane)),
$R^4$ is a hydrogen atom,
Ring B is
(1) a $C_{6-14}$ aromatic hydrocarbon ring (preferably a $C_{6-10}$ aromatic hydrocarbon ring, more preferably benzene) optionally further substituted by 1 to 3 (preferably one) substituents selected from the group consisting of
  (a) a carboxy group,
  (b) a $C_{1-6}$ alkoxy-carbonyl group (e.g., methoxycarbonyl),
  (c) a cyano group,
  (d) a carbamoyl group,
  (e) a mono- or di-$C_{1-6}$ alkyl-carbamoyl group (e.g., methylcarbamoyl),
  (f) a mono- or di-$C_{1-6}$ alkoxy-carbamoyl group (e.g., methoxycarbamoyl, ethoxycarbamoyl),
  (g) a mono- or di-$C_{7-16}$ aralkyloxy-carbamoyl group (e.g., benzyloxycarbamoyl),
  (h) 5-tetrazolyl, and
  (i) a $C_{1-6}$ alkoxy group (e.g., methoxy)
[preferably optionally further substituted by 1 to 3 (preferably one) carboxy groups],
(2) a $C_{3-10}$ cycloalkane (preferably a $C_{3-6}$ cycloalkane, more preferably cyclohexane), or
(3) a 5- to 10-membered aromatic heterocycle (preferably a 5- or 6-membered monocyclic aromatic heterocycle, more preferably pyridine) optionally further substituted by 1 to 3 (preferably one) $C_{1-6}$ alkyl groups (e.g., methyl),
Ring C is a $C_{6-14}$ aromatic hydrocarbon ring (preferably a $C_{6-10}$ aromatic hydrocarbon ring, more preferably benzene, naphthalene), a $C_{3-10}$ cycloalkane (preferably a $C_{3-6}$ cycloalkane, more preferably cyclohexane) or a 5- to 14-membered (preferably 5- to 10-membered) aromatic heterocycle (preferably a 5- or 6-membered monocyclic aromatic heterocycle, more preferably pyridine, furan, isoxazole) (preferably a $C_{6-10}$ aromatic hydrocarbon ring (preferably benzene, naphthalene), a $C_{3-6}$ cycloalkane (preferably cyclohexane) or a 5- or 6-membered monocyclic aromatic heterocycle (preferably pyridine, furan, isoxazole)), each of which is optionally further substituted by 1 to 3 (preferably 1 or 2) substituents selected from the group consisting of
  (1) a halogen atom (e.g., a fluorine atom, a chlorine atom),
  (2) an optionally halogenated $C_{1-6}$ alkyl group (e.g., methyl, trifluoromethyl),
  (3) a $C_{1-6}$ alkoxy group (e.g., methoxy), and
  (4) a $C_{6-14}$ aryl group (e.g., phenyl), and W is
(1) a $C_{1-4}$ alkylene group (e.g., —$CH_2$—, —$(CH_2)_2$—) optionally substituted by an oxo group, or
(2) —$(CH_2)_{m1}$—O— wherein m1 is an integer of 0 to 3 (e.g., —$CH_2CH_2O$—)

[Compound D-2]
Compound (I) wherein
$G^1$ is a carbon atom,
$G^2$ is a carbon atom or a nitrogen atom,
Ring A is
(1) pyridine optionally further substituted by 1 to 2 substituents selected from the group consisting of
  (a) a halogen atom (e.g., a chlorine atom),
  (b) a $C_{1-6}$ alkyl group (e.g., methyl), and
  (c) a $C_{3-10}$ cycloalkyl group (e.g., cyclopropyl), or
(2) pyrimidine,
$G^3$ is an oxygen atom, $NR^1$ wherein $R^1$ is a $C_{1-6}$ alkyl group (e.g., methyl), methylene or a sulfur atom, X is ethylene optionally substituted by an oxo group,
R² is a hydrogen atom or a $C_{1-6}$ alkyl group (e.g., methyl), and R³ is a hydrogen atom, or R² and R³ are joined together to form a $C_{3-10}$ cycloalkane (preferably a $C_{3-6}$ cycloalkane (e.g., cyclopropane)),
R⁴ is a hydrogen atom,
Ring B is
(1) a $C_{6-10}$ aromatic hydrocarbon ring (preferably benzene) optionally further substituted by 1 to 3 (preferably one) substituents selected from the group consisting of
  (a) a carboxy group,
  (b) a $C_{1-6}$ alkoxy-carbonyl group (e.g., methoxycarbonyl),
  (c) a cyano group,
  (d) a carbamoyl group,
  (e) a mono- or di-$C_{1-6}$ alkyl-carbamoyl group (e.g., methylcarbamoyl),
  (f) a mono- or di-$C_{1-6}$ alkoxy-carbamoyl group (e.g., methoxycarbamoyl, ethoxycarbamoyl),
  (g) a mono- or di-$C_{7-16}$ aralkyloxy-carbamoyl group (e.g., benzyloxycarbamoyl),
  (h) 5-tetrazolyl, and
  (i) a $C_{1-6}$ alkoxy group (e.g., methoxy)
[preferably optionally further substituted by 1 to 3 (preferably one) carboxy groups],
(2) a $C_{3-6}$ cycloalkane (preferably cyclohexane), or
(3) a 5- or 6-membered monocyclic aromatic heterocycle (preferably pyridine) optionally further substituted by 1 to 3 (preferably one) $C_{1-6}$ alkyl groups (e.g., methyl),
  Ring C is benzene, naphthalene, cyclohexane, pyridine, furan or isoxazole, each of which is optionally further substituted by 1 to 3 (preferably 1 or 2) substituents selected from the group consisting of
  (1) a halogen atom (e.g., a fluorine atom, a chlorine atom),
  (2) an optionally halogenated $C_{1-6}$ alkyl group (e.g., methyl, trifluoromethyl),
  (3) a $C_{1-6}$ alkoxy group (e.g., methoxy), and
  (4) a $C_{6-14}$ aryl group (e.g., phenyl), and
W is —$CH_2$—, —$(CH_2)_2$—, —$CH_2CH_2O$— (wherein the left bond is bonded to the nitrogen atom, and the right bond is bonded to Ring C) or —C(=O)—.
[Compound E-2]
  Compound (I) wherein
  G¹ is a carbon atom,
  G² is a carbon atom,
  Ring A is pyridine,
  G³ is an oxygen atom,
  X is ethylene,
  R² is a $C_{1-6}$ alkyl group (e.g., methyl), and R³ is a hydrogen atom, or R² and R³ are joined together to form a $C_{3-6}$ cycloalkane (e.g., cyclopropane),
  R⁴ is a hydrogen atom,
  Ring B is benzene further substituted by one carboxy group,
  Ring C is benzene further substituted by 1 or 2 substituents selected from the group consisting of
  (1) a halogen atom (e.g., a fluorine atom, a chlorine atom), and
  (2) a $C_{1-6}$ alkoxy group (e.g., methoxy), and
  W is —$CH_2$—.
[Compound F-2]
  Compound (I) wherein
  G¹ is a carbon atom,
  G² is a carbon atom,
  Ring A is pyridine,
  G³ is an oxygen atom,
  X is ethylene,
  R² is a $C_{>6}$ alkyl group (e.g., methyl), and R³ is a hydrogen atom, or R² and R³ are joined together to form a $C_{3-6}$ cycloalkane (e.g., cyclopropane),
  R⁴ is a hydrogen atom,
  Ring B is benzene further substituted by one carboxy group,
  Ring C is benzene further substituted by 1 to 2 halogen atoms (e.g., a fluorine atom, a chlorine atom), and
  W is —$CH_2$—.

When compound (I) is in a form of a salt, examples thereof include metal salts, an ammonium salt, salts with organic base, salts with inorganic acid, salts with organic acid, salts with basic or acidic amino acid, and the like. Preferable examples of the metal salt include alkali metal salts such as sodium salt, potassium salt and the like; alkaline earth metal salts such as calcium salt, magnesium salt, barium salt and the like; an aluminum salt, and the like. Preferable examples of the salt with organic base include salts with trimethylamine, triethylamine, pyridine, picoline, 2,6-lutidine, ethanolamine, diethanolamine, triethanolamine, cyclohexylamine, dicyclohexylamine, N,N'-dibenzylethylenediamine and the like. Preferable examples of the salt with inorganic acid include salts with hydrochloric acid, hydrobromic acid, nitric acid, sulfuric acid, phosphoric acid and the like. Preferable examples of the salt with organic acid include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like. Preferable examples of the salt with basic amino acid include salts with arginine, lysine, ornithine and the like. Preferable examples of the salt with acidic amino acid include salts with aspartic acid, glutamic acid and the like.

Among them, a pharmaceutically acceptable salt is preferable. For example, when a compound has an acidic functional group, examples thereof include inorganic salts such as alkali metal salts (e.g., sodium salt, potassium salt etc.), alkaline earth metal salts (e.g., calcium salt, magnesium salt etc.) and the like, ammonium salt etc., and when a compound has a basic functional group, examples thereof include salts with inorganic acid such as hydrochloric acid, hydrobromic acid, nitric acid, sulfuric acid, phosphoric acid and the like, and salts with organic acid such as acetic acid, phthalic acid, fumaric acid, oxalic acid, tartaric acid, maleic acid, citric acid, succinic acid, methanesulfonic acid, benzenesulfonic acid, p-toluenesulfonic acid and the like.

Compound (I) may be prepared by any process known to be applicable to the preparation of chemically-related compounds. Such processes are provided as one embodiment of the invention, and are illustrated by the following representative process. Necessary starting materials may be obtained by standard procedure of organic chemistry. The preparation of such starting materials is described in conjunction with the following representative process and within the following examples. Alternatively, necessary starting materials are obtained by a method known per se or a method analogous thereto.

The starting material and/or the production intermediate for the compound (I) may form a salt. While the salt is not particularly limited as long as the reaction can be performed, examples thereof include those similar to the salts of compound (I) and the like.

When the starting material has an amino group, a carboxyl group, a hydroxy group or a heterocyclic group, these groups may be protected by a protecting group generally used in peptide chemistry and the like. By removing the protecting group as necessary after the reaction, the objective compound can be obtained. The protection and deprotection can be performed according to a method known per se, for example, the method described in "Protective Groups in Organic Synthesis, 3rd Ed", John Wiley and Sons, Inc. (1999) (Theodora W. Greene, Peter G. M. Wuts). Preferable examples of the protecting group include a tert-butylcarbamate group, a benzylcarbamate group, a benzyl group, a methyl group, an ethyl group, a tert-butyl and the like.

The compound obtained in each step can be used directly as the reaction mixture or as a crude product for the next reaction. It can also be isolated from a reaction mixture by a conventional method, and can be easily purified by a separation means such as recrystallization, distillation, chromatography and the like. When the compound in the formula is commercially available, a commercially available product can also be used directly.

Unless otherwise specified, each symbol in the general formulas in the schemes is as defined above.

Compound (I) is prepared as outlined in Schemes below:

Scheme 1: Synthesis of Compound (I)

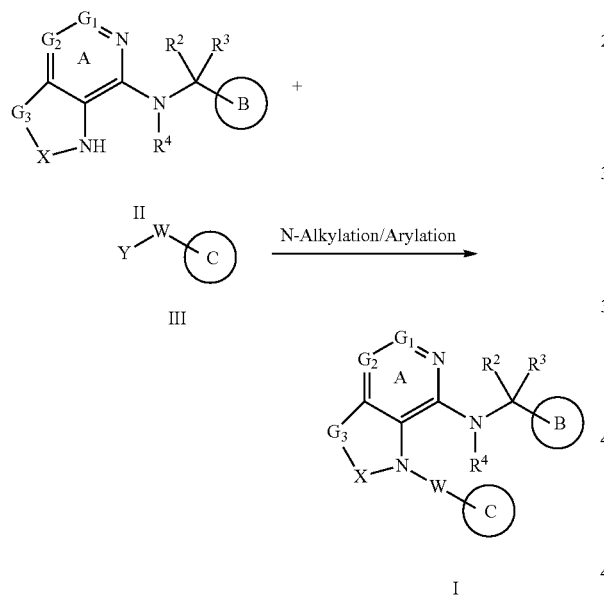

As shown in Scheme 1, compound (I) may be prepared by reacting compound (II) with compound (III) wherein W is as defined above, and Y is a leaving group such as a halogen atom, a $C_{1-6}$ alkylsulfonyl group or a $C_{6-14}$ arylsulfonyl group, or Y/WY may be a formyl group (reductive alkylation/amination), or Y may be a hydroxy group (cross coupling reaction), or WY may be a halogen atom or a triflate (Ullman or Buchwald coupling) or a boronic acid or a boronate ester (Chan-Evans-Lam coupling). The functional group in compound (II) or (III) may be protected if necessary, and after the N-alkylation reaction or N-arylation reaction, it can be removed by a conventional means. Compound (I) having an ester moiety may be further hydrolyzed to obtain the corresponding carboxylic acid or its salt, which may be further derivatized. Compound (I) may be further derivatized by introducing substituent(s) according known methods reported in literature. Compound (III) may be a commercially available product, or can also be prepared according to a method known per se or a method analogous thereto.

Scheme 2: Synthesis of compound (I) wherein W is C(O) or $S(O)_2$

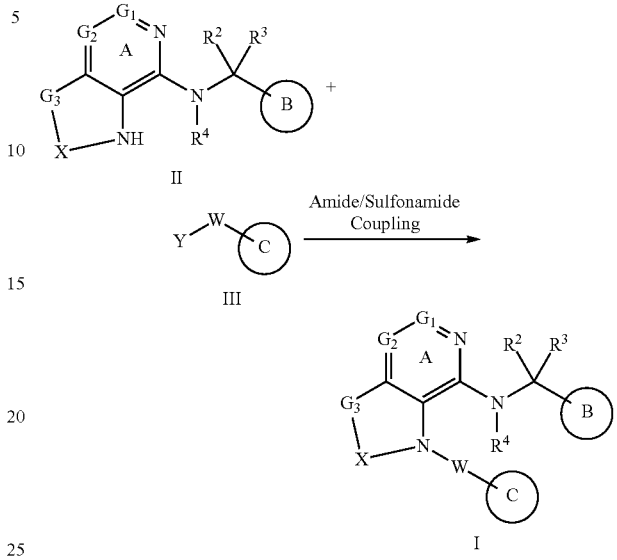

As shown in Scheme 2, compound (I) may be prepared by coupling compound (II) with compound (III) wherein WY is —C(O)OH or —S(O)₂OH, or a reactive derivative thereof such as an acid halide (e.g., an acid chloride, an acid bromide, sulfonyl chloride) or a mixed anhydride (e.g., a mixed anhydride with a chloroformate). The functional group in compound (II) or (III) may be protected if necessary, and after the amide/sulfonamide coupling reaction, it can be removed by a conventional means. Compound (I) having an ester moiety may be further hydrolyzed to obtain the corresponding carboxylic acid or its salt, which may be further derivatized.

Scheme 3: Synthesis of compound (I) wherein W is C(O)NH

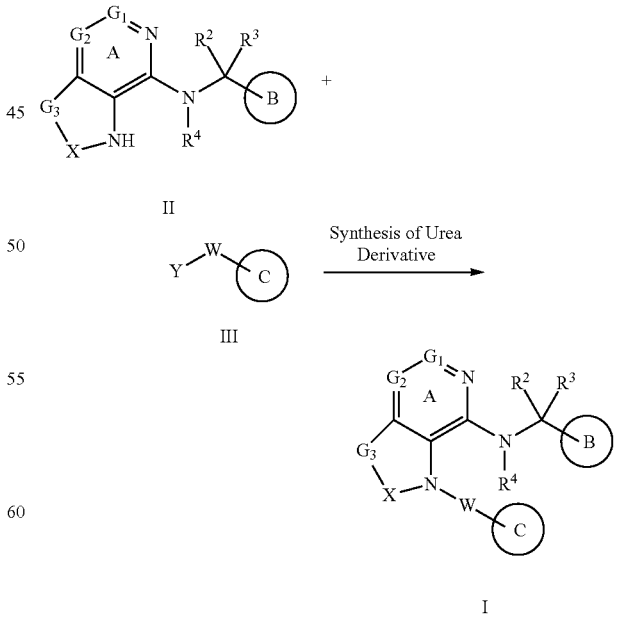

As shown in Scheme 3, compound (I) may be prepared by coupling compound (II) with compound (III) wherein WY is —NC(O), or with compound (III) wherein WY is NH$_2$ and reagents such as carbonylimidazolide (CDI), or with compound (III) wherein WY is a C$_{1-6}$ alkoxy-carbonylamino group. The functional group in compound (II) or (III) may be protected if necessary, and after the synthesis of urea derivative, it can be removed by a conventional means. Compound (I) having an ester moiety may be further hydrolyzed to obtain the corresponding carboxylic acid or its salt, which may be further derivatized.

Scheme 4: Synthesis of compound (I)

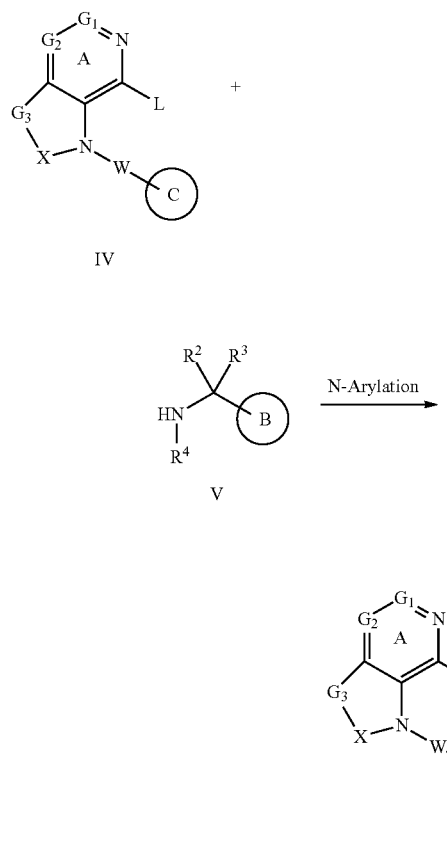

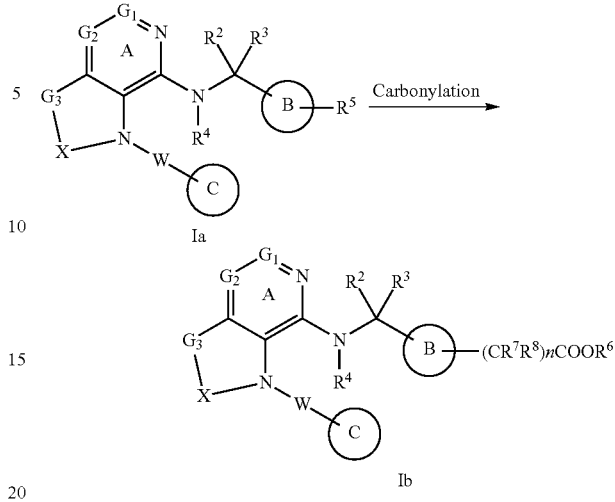

As shown in Scheme 5, compound (Ib) may be prepared by carbonylation of compound (Ia) wherein R$^5$ is a halogen atom, preferably a bromine atom. The functional group in compound (Ia) may be protected if necessary, and after the carbonylation, it can be removed by a conventional means. Compound (Ia) may be prepared according to the method Schemes 1 to 4 wherein ring B is substituted by R$^5$. Alternatively, compound (Ib) may also be prepared according to the method Schemes 1 to 4 wherein ring B is substituted by a group of the formula: —(CR$^7$R$^8$)$_n$C(O)OR$^6$.

Scheme 6: Synthesis of compound (Ic), which is compound (I) wherein Ring B is further substituted by a group of the formula: —(CR$^7$R$^8$)$_n$(CO)OH wherein R$^7$, R$^8$ and n are as defined above

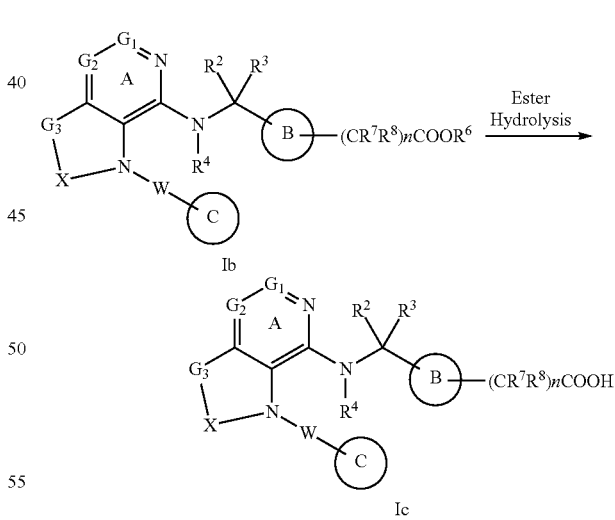

As shown in Scheme 4, compound (I) may be prepared by reacting compound (IV) wherein L is a leaving group such as a halogen atom, a C$_{1-6}$ alkoxy group, a C$_{6-14}$ aryloxy group, a sulfanyl group, a C$_{1-6}$ alkylthio group, a C$_{6-14}$ arylthio group, a C$_{1-6}$ alkylsulfinyl group, a C$_{6-14}$ arylsulfinyl group, a C$_{1-6}$ alkylsulfonyl group, a C$_{6-14}$ arylsulfonyl group and a boronic acid group, with compound (V) (N-arylation reaction). Functional groups in compound (IV) or (V) may be protected if necessary, and after the N-arylation reaction, it can be removed by conventional means. Compound (I) having an ester moiety may be further hydrolyzed to obtain the corresponding carboxylic acid, which may be further derivatized.

Scheme 5: Synthesis of compound (Ib), which is compound (I) wherein Ring B is further substituted by a group of the formula: —(CR$^7$R$^8$)$_n$C(O)OR$^6$ wherein R$^7$ and R$^8$ are each independently a hydrogen atom or a C$_{1-6}$ alkyl group, or R$^7$ and R$^8$ are joined together to form a C$_{3-6}$ cycloalkane, R$^6$ is a C$_{1-6}$ alkyl group, and n is 0-1

As shown in Scheme 6, compound (Ic) may be prepared by ester hydrolysis of compound (Ib) by a conventional means.

Scheme 7: Synthesis of compound (Id), which is compound (I) wherein Ring B is further substituted by a group of the formula: —(CR$^7$R$^8$)$_n$(CO)NHR$^9$ wherein R$^7$, R$^8$ and n are as defined above, and R$^9$ is a hydrogen atom, a C$_{1-6}$ alkyl group, a C$_{3-10}$ cycloalkyl group, a C$_{6-14}$ aryl group, a heteroaryl group, a C$_{1-6}$ alkoxy group, a C$_{3-10}$ cycloalkoxy group, a $C_{1-6}$ alkylsulfonyl group, a $C_{3-10}$ cycloalkylsulfonyl group, a $C_{6-14}$ arylsulfonyl group or a heteroarylsulfonyl group

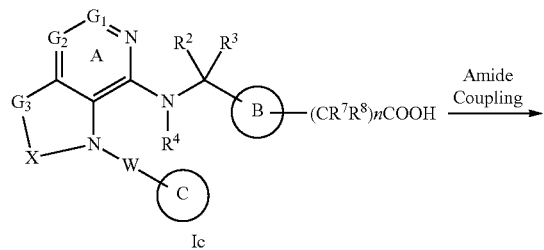

Ic

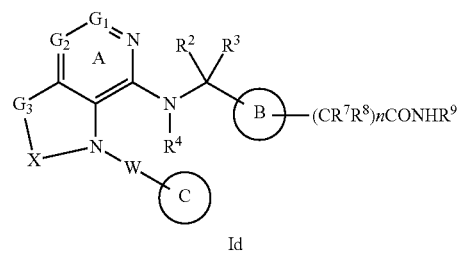

Id

As shown in Scheme 7, compound (Id) may be prepared by amide coupling of compound (Ic) with the corresponding amine or amine derivative.

Scheme 8: Synthesis of compound (Ie), which is compound (I) wherein Ring B is further substituted by a 5-tetrazolyl group

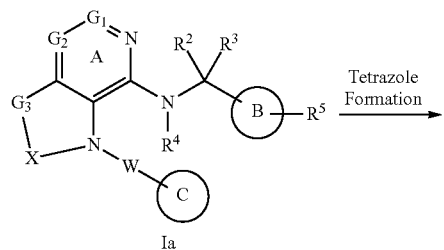

Ia

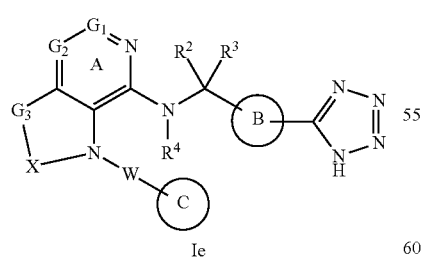

Ie

As shown in Scheme 8, compound (Ie) may be prepared from compound (Ia) wherein Ring B is further substituted by a cyano group, by conversion of the cyano group to a 5-tetrazolyl group by a conventional means (Tetrazole formation).

Scheme 9: Synthesis of compound (II) wherein $G_3$ is an oxygen atom, a sulfur atom and $NR^1$ wherein $R^1$ is as defined above

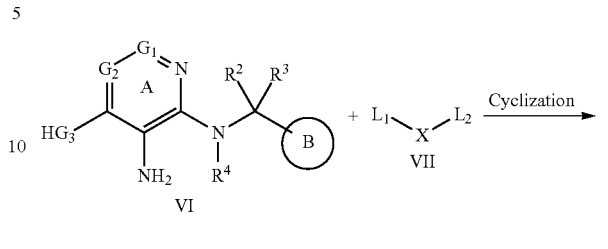

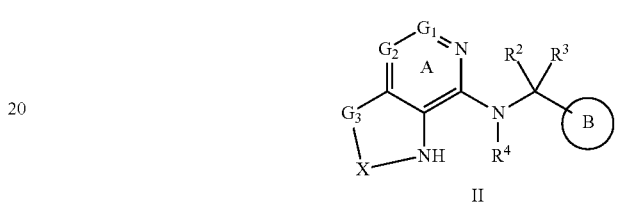

II

As shown in Scheme 9, compound (II) may be prepared by reacting compound (VI) with compound (VII), wherein $L_1$ and $L_2$ are each independently a leaving group, preferably a bromine atom. The functional group in compound (VI) may be protected if necessary, and after the cyclization it can be removed by a conventional means.

Scheme 10: Synthesis of compound (VI) wherein $G_3$ is an oxygen atom, a sulfur atom and $NR^1$ wherein $R^1$ is as defined above

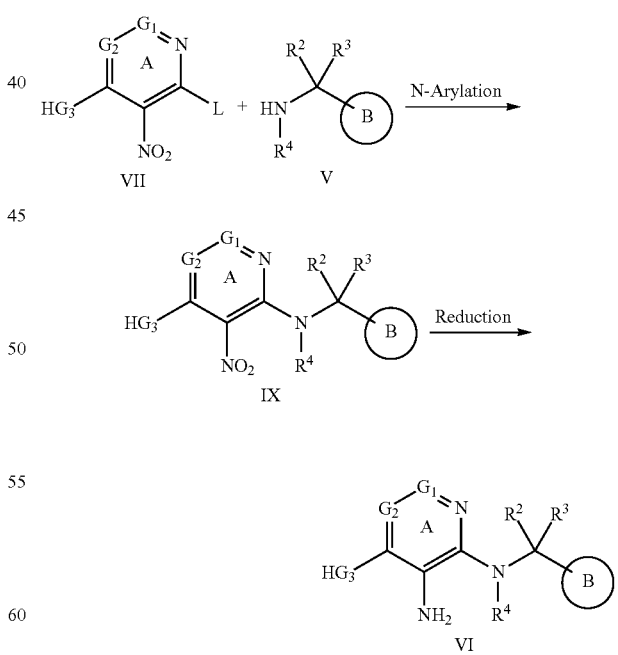

As shown in Scheme 10, compound (VI) may be prepared by reacting compound (VIII) wherein L is as defined above, with compound (V) (N-arylation reaction), and subjecting the resulting compound (IX) to reduction.

Scheme 11: Synthesis of compound (II) wherein $G_3$ is methylene, and X is ethylene

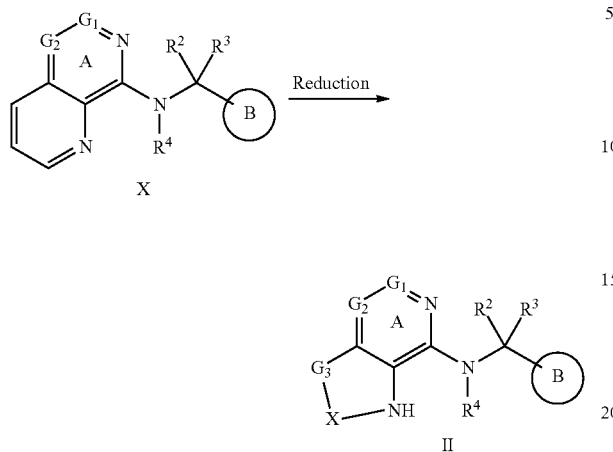

As shown in Scheme 11, compound (II) may be prepared by reduction of compound (X). The functional group in compound (X) may be protected if necessary, and after the reduction it can be removed by a conventional means.

Scheme 12: Synthesis of Compound (IV)

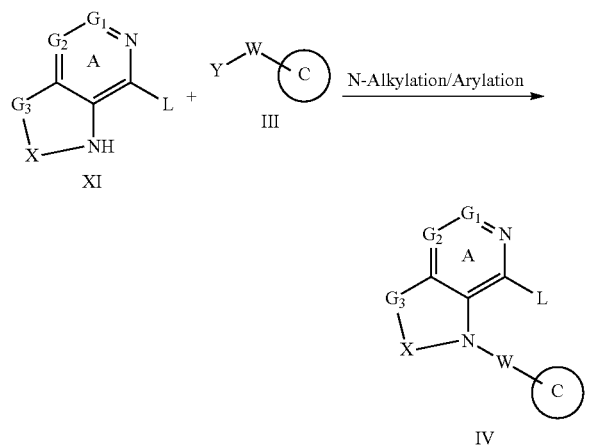

As shown in Scheme 12, compound (IV) may be prepared by reacting compound (XI) with compound (III) wherein W is as defined above, and Y is a leaving group such as a halogen atom, a $C_{1-6}$ alkylsulfonyl group or a $C_{6-14}$ arylsulfonyl group, or Y/WY may be a formyl group (reductive alkylation/amination), or Y may be a hydroxy group (cross coupling reaction), or WY may be a halogen atom or a triflate (Ullman or Buchwald coupling) or a boronic acid or a boronate ester (Chan-Evans-Lam coupling), or WY is —C(O)OH or —S(O)$_2$OH, or a reactive derivative thereof such as an acid halide (e.g., an acid chloride, an acid bromide, and sulfonyl chloride) or a mixed anhydride (e.g., a mixed anhydride with a chloroformate), or WY is —NC(O), NH$_2$ or a $C_{1-6}$ alkoxy-carbonylamino group. The functional group in compound (XI) or (III) may be protected if necessary, and after the synthesis of compound (IV), it can be removed by a conventional means.

Scheme 13: Synthesis of compound (XI) wherein L is a leaving group and $G_3$ is oxygen, Sulfur and NR$^1$

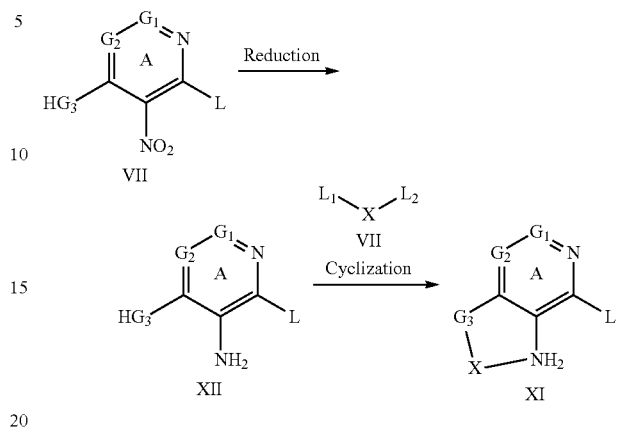

As shown in scheme 13, compound (XI) may be prepared by reduction of compound (VIII) wherein L is as defined above to obtain compound (XII), and subjecting the resulting compound (XII) to cyclization with compound (VII).

N-Alkylation:

Alkyl compounds having a suitable leaving group such as a halogen atom, a $C_{1-6}$ alkylsulfonyl group and a $C_{6-14}$ arylsulfonyl group may be reacted with an amine. The reaction may be carried out in the absence or presence of a base, in an appropriate solvent or without solvent.

Preferred base is selected from organic non-nucleophilic bases such as triethylamine, diisopropylethylamine (Hünig's base), pyridine, 2,6-lutidine, collidine, 4-dimethylaminopyrimidine, N-methylpyrrolidine and diazabicyclo[5.4.0]undec-7ene (DBU); alkali or alkaline earth metal carbonates such as sodium carbonate and potassium carbonate; alkali metal hydrides such as sodium hydride; and phosphazene bases such as 2-tert-butylimino-2-diethylamino-1,3-dimethylperhydro-1,3,2-diazaphosphorine (BEMP). Preferred examples of the solvent inert to the reaction include polar solvents such as acetonitrile, alcohols (e.g., methanol, ethanol, propanol, n-butanol etc.), chlorinated solvents (e.g., chloroform, dichloromethane, 1,2-dichloroethane etc.), ethers (e.g., tetrahydrofuran (THF), 1,4-dioxane, dimethoxyethane (DME) etc.) and amides (e.g., N,N-dimethylformamide (DMF), N,N-dimethylacetamide (DMA), N-methylpyrrolidine (NMP) etc.), and non-polar solvents (e.g., toluene etc.), along with a phase transfer catalyst. Additionally, the N-alkylation may be carried out in presence of an ionic liquid such as 1-butyl-3-methylimidazolium tetrafluorophosphate [Bmim(PF4)], 1-butyl-3-methylimidazolium hexafluorophosphate [Bmim(PF6)] and tetrabutylammonium chloride [TBAC]. The ionic liquid may be used as a reaction solvent, or it may be used as an additive when the N-alkylation is carried out in the above-mentioned solvent. In addition, microwave irradiation may be employed to enhance the rate of the N-alkylation.

Alternatively, N-alkylation may be carried out by cross coupling of an appropriate amine and alcohol under Mitsunobu reaction condition using a phosphine (e.g., triarylphosphine, tricycloalkylphosphine etc.) and a dialkyl azodicarboxylate (e.g., diethyl azodicarboxylate (DEAD), diisopropyl azodicarboxylate (DIAD) etc.). The cross coupling is carried out in an appropriate solvent such as THF and dioxane at 0 to 40° C. to reflux temperature.

Alternatively, N-alkylation may be carried out by using reductive amination (reductive alkylation) using an appropriate amine, aldehyde and reducing agent (e.g., sodium borohydride, sodium cyanoborohydride (NaBH$_3$CN), sodium triacetoxyborohydride (NaBH(OCOCH$_3$)$_3$) etc.). The preferred solvents for this reaction are toluene, 1,4-dioxane, chlorinated solvents such as dichloromethane, 1,2-dichloroethane etc.

N-Arylation:

Aromatic compounds having a suitable leaving group such as a halogen atom, a C$_{1-6}$ alkoxy group, a C$_{6-14}$ aryloxy group, a sulfanyl group, a C$_{1-6}$ alkylthio group, a C$_{6-14}$ arylthio group, a C$_{1-6}$ alkylsulfinyl group, a C$_{6-14}$ arylsulfinyl group, a C$_{1-6}$ alkylsulfonyl group, a C$_{6-14}$ arylsulfonyl group and a boronic acid group, may be reacted with a primary or secondary amine. The reaction may be carried in presence of a metal catalyst such as copper, palladium, iron and rhodium, and a ligand such as diamines, amino acids, xanthphos. The reaction may be carried out in the absence or presence of a base, in an appropriate solvent or without solvent.

Preferred base is selected from organic non-nucleophilic bases such as triethylamine, diisopropylethylamine (Hünig's base), pyridine, 2,6-lutidine, collidine, 4-dimethylaminopyrimidine, N-methylpyrrolidine and diazabicyclo[5.4.0]undec-7ene (DBU); alkali or alkaline earth metal carbonates such as sodium carbonate and potassium carbonate; alkali metal hydrides such as sodium hydride; and phosphazene bases such as 2-tert-butylimino-2-diethylamino-1,3-dimethylperhydro-1,3,2-diazaphosphorine (BEMP). Preferred polar solvent inert to the reaction includes alcohols (e.g., methanol, ethanol, propanol, n-butanol etc.), ethers (e.g., tetrahydrofuran (THF), 1,4-dioxane, dimethoxyethane (DME) etc.), and amides (e.g., N,N-dimethylformamide (DMF), N,N-dimethylacetamide (DMA), N-methylpyrrolidine (NMP) etc.). Alternatively, the reaction may be carried out in a melt without addition of a solvent. The reaction is carried out at elevated temperatures, preferably from approximately 60° C. to reflux temperature. When WY or L is a boronic acid group, the reaction may be carried out in the presence of a suitable catalyst.

Amide Coupling:

Condition-I:

Amide coupling may be carried out using any suitable amide coupling reagents such as oxalyl chloride, thionyl chloride, BOP—Cl, DCC, HOBt, HOAt, HATU, EDCI, propylphosphonic anhydride (T3P), alkyl chloroformate and the like. Preferred base is selected from organic non-nucleophillic bases such as triethylamine, diisopropylethyl amine, pyridine, N-methylpyrrolidine, N,N-dimethylaminopyridine, DBU, other hindered amines and pyridines. The amide coupling may be carried out in the presence of a solvent such as dichloromethane, dichloroethane, DMF, N,N-dimethylacetamide, THF, acetonitrile and mixtures thereof. The reaction may be carried out at a temperature ranging from −20° C. to 150° C., preferably from about 0° C. to 100° C. The reaction may be carried out optionally in presence of a catalytic amount of DMF.

Condition-II:

When R$^6$ is not H, amide coupling may be carried out by heating ester and amine either in the absence of a solvent or in presence of a high boiling solvent such as toluene, xylene and DMSO. The amide coupling may be carried out in presence of a trialkyl aluminium (Chem. Commun., 2008, 1100-1102).

Sulfonamide Coupling:

Sulfonamide may be prepared by reacting an appropriate amine with an appropriate sulfonyl halide in the presence of a base such as organic non-nucleophillic bases (e.g., triethylamine, diisopropylethylamine, N-methylpyrrolidine, N,N-dimethylaminopyridine, DBU etc.), other hindered amines and pyridines. The sulfonamide coupling may be carried out in the presence of a solvent such as dichloromethane, dichloroethane, THF, 1,4-dioxane, acetonitrile, N,N-dimethylformamide (DMF) and mixtures thereof.

Synthesis of Urea Derivatives:

Urea derivatives (unsymmetrical) may be prepared by reacting amine with an appropriate coupling regent such as alkyl chloroformate, CDI, triphosgene, S,S-dimethyl dithiocarbonate (DMDTC), carbonylimidazolide, phenyl 4,5-dichloro-6-oxopyridazine-1(6H)-carboxylate etc. Then the intermediate may be coupled with different amine (e.g., substituted aniline, substituted alkylamine, substituted cycloalkylamine etc.).

Alternatively, urea formation may be carried out using any suitable coupling regent (e.g., substituted alkoxycarbonylamino group, substituted isocyanate etc.). The reaction may be carried out in the absence or presence of a base. Preferred base is selected from organic non-nucleophillic bases (e.g., triethylamine, diisopropylethylamine, pyridine, N-methylpyrrolidine, N,N-dimethylaminopyridine, DBU etc.). The urea formation may be carried out in the presence of a solvent such as chlorobenzene, dichloromethane, dichloroethane, DMF, N,N-dimethylacetamide, THF, acetonitrile, water and mixtures thereof. The urea formation may be carried out at a temperature ranging from −20° C. to 150° C., preferably from about 0° C. to 100° C. The urea formation may be carried out optionally in presence of a catalytic amount of N,N-dimethylformamide (DMF).

Carbonylation Reaction:

Carbonylation reaction may be carried out by reacting an aryl halide with carbon monoxide in presence of a catalyst and/or a base in an inert solvent. Examples of the suitable catalyst include palladium reagents such as palladium acetate and palladium dibenzylacetone; and nickel catalysts. Preferred base is selected from N,N-diisopropylethylamine, N-methylmorpholine, triethylamine etc. If required, this reaction may be carried out in the presence or absence of an additive such as 1,1'-bis(diphenylphosphino)ferrocene, triphenylphosphine and 1,3-bis-(diphenylphosphine)propane. The reaction may be carried out in a suitable solvent such as acetone, nitromethane, DMF, DMSO, NMP, acetonitrile, DCM, EDC, THF, methanol, ethanol and 1,4-dioxane. While the reaction temperature varies depending on the kind of the solvent and reagent used for the reaction, it is generally −20° C. to 150° C., preferably 50° C. to 80° C.

Ester Hydrolysis:

Ester hydrolysis may be carried out under general saponification conditions employing an inorganic base such as alkali and alkaline earth metal hydroxides, carbonates and bicarbonates (e.g., lithium hydroxide, sodium hydroxide, potassium hydroxide, sodium hydride, sodium carbonate, potassium carbonate, cesium carbonate etc.) in the presence of a solvent such as water, methanol, ethanol, diethyl ether, THF, DME, DMF, DMSO and mixtures thereof. These reactions may be carried out at 0° C. to refluxing temperature.

Alternatively, ester hydrolysis may be carried out under acidic condition, for example, in presence of a hydrogen halide (e.g., hydrochloric acid, hydrobromic acid etc.), a sulfonic acid (e.g., sulfuric acid, p-toluenesulfonic acid, benzenesulfonic acid, pyridium p-toluenesulfonate etc.) or a carboxylic acid (e.g., acetic acid, trifluoroacetic acid etc.) The suitable solvent includes alcohols (e.g., methanol, ethanol, propanol, butanol, 2-methoxyethanol, ethylene glycol etc.); ethers (e.g., diethyl ether, THF, 1,4-dioxane, DME etc.); halogenated solvents (e.g., DCM, EDC, chloroform etc.); hexamethylphosphoramide and DMSO. The reaction may be carried out at temperature in the range from −20° C. to 100° C., preferably from 20° C. to 35° C.

Tetrazole Formation:

Aryl tetrazole (5H-substituted tetrazole) may be prepared by converting a cyano group into a tetrazole group in absence or presence of an inert solvent such as acetone, DMF, DMSO, NMP and water. Suitable tetrazole forming reagent includes sodium azide, lithium azide, trialkyltin azide and trimethylsilylazide. This reaction may be carried out in presence or absence of a catalyst such as dialkyltin oxide (alkyl is methyl or butyl), alkylamino hydrochloride or hydrobromide, lithium chloride and copper sulphate. The reaction may be carried out in the presence or absence of an acid or a base. Examples of the suitable base include trimethylamine, triethylamine and N,N-diisopropylethylamine, and examples of the suitable acid include ammonium chloride, hydrogen chloride, aluminium chloride and zinc bromide. The reaction may be carried out at temperature 50° C. to 200° C.

Cyclization for Formation of a Fused Ring Containing Ring A:

Cyclization reaction is used for formation of a fused ring containing Ring A. The fused ring may be prepared by reacting appropriately substituted pyridine ring with 1,2-dibromoethane, 1-bromo-2-chloroethane, 2-chloroacetyl chloride, sulfonium (2-bromoethyl)diphenyl salt with trifluoromethanesulfonic acid, 2-bromoacetyl chloride, 2-bromoacetyl bromide and 1-bromo-2,2-diethoxyethane, 2-bromoethanol, 2-bromoethyl methanesulfonate and 2-bromoethyl 4-methylbenzenesulfonate.

Alternatively, the fused ring may be prepared by reacting appropriately substituted pyridine ring with ethyl bromoacetate, followed by ester hydrolysis and cyclization. If required, the product obtained after cyclization may be further subjected to a reaction such as reduction with preferred reducing agent such as lithium aluminium hydride, borane and THF. The cyclization reaction may be carried out in the absence or presence of a base and in an appropriate solvent.

A preferred base is selected from organic non-nucleophilic bases such as triethylamine, N,N-diisopropylethylamine (Hünig's base), pyridine, 2,6-lutidine, collidine, 4-dimethylaminopyrimidine, N-methylpyrrolidine and diazabicyclo[5.4.0]undec-7ene (DBU); alkali or alkaline earth metal carbonates such as sodium carbonate, potassium carbonate, sodium bicarbonate, cesium carbonate, potassium acetate and potassium fluoride; alkali metal hydrides such as sodium hydride, and phosphazene bases such as 2-tert-butylimino-2-diethylamino-1,3-dimethylperhydro-1,3,2-diazaphosphorine (BEMP). The preferred polar solvent inert to the reaction includes alcohols (e.g., methanol, ethanol, propanol, tert-butanol and n-butanol) or ethers (e.g., tetrahydrofuran (THF), 1,4-dioxane, dimethoxyethane (DME)), dimethylformamide (DMF), dimethylacetamide (DMA), N-methylpyrrolidine (NMP), dimethyl sulfoxide (DMSO), water, acetonitrile, acetone and 1,2-dichloroethane. The reaction may be carried out at elevated temperatures, preferably from approximately 30° C. to 150° C. or at reflux temperature of solvent.

Reduction:

Reduction may be carried out using any suitable catalyst such as Pd/C, Pd(OH)$_2$, platinum(IV) oxide(PtO$_2$), Raney nickel in presence of hydrogen atmosphere. Alternatively, reduction may be carried out using any suitable reducing reagent such as lithium aluminium hydride, sodium dithionite, iron in acetic acid, stannous chloride, samarium dichloride, tin(II) chloride, titanium (III) chloride, zinc/acetic acid etc. The reaction may be carried out in the presence of a solvent such as methanol, ethanol, ethyl acetate, acetic acid, HCl, THF, acetone, dichloromethane, dichloroethane, acetonitrile and mixtures thereof. The reaction may be carried out at a temperature ranging from −20° C. to 150° C., preferably from about 0° C. to 100° C. The Reduction may be carried out optionally in presence of a catalytic amount of acid and/or base.

Compound (I) contains a stereoisomer depending to the kind of a substituent, and each stereoisomer and a mixture thereof are encompassed in the present invention.

Compound (I) may be a hydrate or a non-hydrate.

When desired, compound (I) can be synthesized by performing deprotection reaction, acylation reaction, alkylation reaction, hydrogenation reaction, oxidation reaction, reduction reaction, reaction of carbon chain extension, substituent exchange reaction singly or two or more thereof in combination.

When the objective product is obtained as a free form by the above-mentioned reaction, it can be converted to a salt according to a conventional method, or when the objective product is obtained as a salt, it can be converted to a free form or other salt according to a conventional method. The thus-obtained compound (I) can also be isolated and purified from a reaction mixture according to a known method such as phase transfer, concentration, solvent extraction, distillation, crystallization, recrystallization, chromatography and the like.

When compound (I) contains a configurational isomer, a diastereomer, a conformer and the like, each can be isolated according to the above-mentioned separation and purification methods, if desired. In addition, when compound (I) is racemic, d-form and l-form can be isolated according to a conventional optical resolution.

In each of the above-mentioned reactions, when the compound has a functional group such as an amino group, a hydroxy group or a carboxyl group, the reaction can be carried out after a protecting group generally used in peptide chemistry and the like is introduced into these groups. By removing the protecting group as necessary after the reaction, the objective compound can be obtained.

Examples of the protecting group include formyl, $C_{1-6}$ alkyl-carbonyl (e.g., acetyl, propionyl etc.), phenylcarbonyl, $C_{1-6}$ alkoxy-carbonyl (e.g., methoxycarbonyl, ethoxycarbonyl etc.), phenyloxycarbonyl, $C_{7-10}$ aralkyloxy-carbonyl (e.g., benzyloxycarbonyl etc.), trityl, phthaloyl and the like, each of which is optionally substituted. Examples of the substituent include a halogen atom (e.g., fluorine, chlorine, bromine, iodine etc.), $C_{1-6}$ alkyl-carbonyl (e.g., acetyl, propionyl, valeryl etc.), nitro and the like. The number of substituents is, for example, 1 to 3.

The removal method of the protecting group can be carried out according to a method known per se, and for example, a method using acid, base, ultraviolet rays, hydrazine, phenylhydrazine, sodium N-methyldithiocarbamate, tetrabutylammonium fluoride, palladium acetate and the like, a reduction method, and the like can be employed.

The thus-obtained compound (I), other reaction intermediate therefor and starting materials thereof can be isolated and purified from a reaction mixture according to a method known per se, for example, extraction, concentration, neutralization, filtration, distillation, recrystallization, column chromatography, thin layer chromatography, preparative high performance liquid chromatography (preparative HPLC), moderate-pressure preparative liquid chromatography (moderate-pressure preparative LC) and the like.

A salt of compound (I) can be produced according to a method known per se. For example, when compound (I) is a basic compound, it can be produced by adding an inorganic acid or organic acid, or when compound (I) is an acidic compound, by adding an organic base or inorganic base.

When compound (I) contains an optical isomer, each optical isomer and a mixture thereof are encompassed in the scope of the present invention, and these isomers can be subjected to optical resolution or can be produced respectively, according to a method known per se, if desired.

When compound (I) contains a configurational isomer, a diastereomer, a conformer and the like, each can be isolated according to the above-mentioned separation and purification methods, if desired. In addition, when compound (I) is racemic, S-form and R-form can be isolated according to a conventional optical resolution.

When compound (I) contains a stereoisomer, each isomer and a mixture thereof are encompassed in the present invention.

Compound (I) may be a prodrug, and the prodrug of compound (I) refers to a compound which is converted to compound (I) as a result of a reaction with an enzyme, gastric acid, etc. under physiological conditions in vivo, thus a compound that undergoes enzymatic oxidation, reduction, hydrolysis etc. to convert to compound (I) and a compound that undergoes hydrolysis and the like by gastric acid, etc. to convert to compound (I).

Examples of the prodrug for compound (I) include
(1) a compound obtained by subjecting an amino group in compound (I) to acylation, alkylation or phosphorylation (e.g., a compound obtained by subjecting an amino group in compound (I) to eicosanoylation, alanylation, pentylaminocarbonylation, (5-methyl-2-oxo-1,3-dioxolen-4-yl)methoxycarbonylation, tetrahydrofurylation, pyrrolidylmethylation, pivaloyloxymethylation, tert-butylation, ethoxycarbonylation, tert-butoxycarbonylation, acetylation, cyclopropylcarbonylation and the like);
(2) a compound obtained by subjecting a hydroxy group in compound (I) to acylation, alkylation, phosphorylation or boration (e.g., a compound obtained by subjecting a hydroxy group in compound (I) to acetylation, palmitoylation, propanoylation, pivaloylation, succinylation, fumarylation, alanylation or dimethylaminomethylcarbonylation and the like);
(3) a compound obtained by subjecting a carboxyl group in compound (I) to esterification or amidation (e.g., a compound obtained by subjecting a carboxyl group in compound (I) to ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification or methylamidation and the like) and the like. Any of these compounds can be produced from compound (I) according to a method known per se.

A prodrug of compound (I) may also be one which is converted to compound (I) under physiological conditions as described in "IYAKUHIN no KAIHATSU (Development of Pharmaceuticals)", Vol. 7, Design of Molecules, p. 163-198, Published by HIROKAWA SHOTEN (1990).

In the present specification, compound (I) and a prodrug thereof are sometimes collectively abbreviated as "the compound of the present invention".

When compound (I) has isomers such as optical isomer, stereoisomer, positional isomer, rotamer and the like, such isomers and a mixture thereof are also encompassed in compound (I). For example, when compound (I) has optical isomers, an optical isomer resolved from this compound is also encompassed in compound (I). These isomers can be obtained as a single product according to synthesis methods or separation methods known per se (e.g., concentration, solvent extraction, column chromatography, recrystallization, etc.).

Compound (I) may be a crystal, and a single crystal form and a mixture of crystal forms are both encompassed in compound (I). The crystal can be produced by crystallizing according to a crystallization method known per se.

Compound (I) may be a hydrate, a non-hydrate, a solvate or a non-solvate.

Compound (I) may be labeled with an isotope (e.g., $^3$H, $^{11}$C, $^{14}$C, $^{18}$F, $^{35}$S, $^{125}$I etc.) and the like.

Compound (I) also encompasses a deuterium conversion form wherein $^1$H is converted to $^2$H(D).

Compound (I) may be a pharmaceutically acceptable cocrystal or a salt thereof. The cocrystal or a salt thereof means a crystalline substance constituted with two or more special solids at room temperature, each having different physical properties (e.g., structure, melting point, melting heat, hygroscopicity, solubility and stability etc.). The cocrystal or a salt thereof can be produced according to a cocrystallization a method known per se.

Compound (I) may also be used as a PET tracer.

The compound of the present invention has low toxicity, and may be used as it is or in the form of a pharmaceutical composition by mixing with a pharmacologically acceptable carrier etc. to mammals (e.g., human, mouse, rat, rabbit, dog, cat, bovine, horse, swine, monkey) as an agent for the prophylaxis or treatment of various diseases mentioned below.

As pharmacologically acceptable carriers, various organic or inorganic carrier substances conventionally used as preparation materials can be used. These are incorporated as excipient, lubricant, binder and disintegrant for solid preparations, or solvent, solubilizing agent, suspending agent, isotonicity agent, buffer and soothing agent for liquid preparations, and the like, and preparation additives such as preservative, antioxidant, colorant, sweetening agent and the like can be added as necessary.

Preferable examples of the excipient include lactose, sucrose, D-mannitol, D-sorbitol, starch, gelatinated starch, dextrin, crystalline cellulose, low-substituted hydroxypropylcellulose, sodium carboxymethylcellulose, gum arabic, pullulan, light anhydrous silicic acid, synthesis aluminum silicate and magnesium alumino metasilicate.

Preferable examples of the lubricant include magnesium stearate, calcium stearate, talc and colloidal silica.

Preferable examples of the binder include gelatinated starch, sucrose, gelatin, gum arabic, methylcellulose, carboxymethylcellulose, sodium carboxymethylcellulose, crystalline cellulose, sucrose, D-mannitol, trehalose, dextrin, pullulan, hydroxypropylcellulose, hydroxypropylmethylcellulose and polyvinylpyrrolidone.

Preferable examples of the disintegrant include lactose, sucrose, starch, carboxymethylcellulose, calcium carboxymethylcellulose, croscarmellose sodium, sodium carboxymethyl starch, light anhydrous silicic acid and low-substituted hydroxypropylcellulose.

Preferable examples of the solvent include water for injection, physiological brine, Ringer's solution, alcohol, propylene glycol, polyethylene glycol, sesame oil, corn oil, olive oil and cottonseed oil.

Preferable examples of the solubilizing agents include polyethylene glycol, propylene glycol, D-mannitol, trehalose, benzyl benzoate, ethanol, trisaminomethane, cholesterol, triethanolamine, sodium carbonate, sodium citrate, sodium salicylate and sodium acetate.

Preferable examples of the suspending agent include surfactants such as stearyltriethanolamine, sodium lauryl sulfate, lauryl aminopropionate, lecithin, benzalkonium chloride, benzethonium chloride, glycerol monostearate and the like; hydrophilic polymers such as polyvinyl alcohol, polyvinylpyrrolidone, sodium carboxymethylcellulose, methylcellulose, hydroxymethylcellulose, hydroxyethylcellulose, hydroxypropylcellulose and the like; polysorbates, and polyoxyethylene hydrogenated castor oil.

Preferable examples of the isotonicity agent include sodium chloride, glycerol, D-mannitol, D-sorbitol and glucose.

Preferable examples of the buffer include buffers such as phosphate, acetate, carbonate, citrate and the like.

Preferable examples of the soothing agent include benzyl alcohol.

Preferable examples of the preservative include p-oxybenzoates, chlorobutanol, benzyl alcohol, phenethyl alcohol, dehydroacetic acid and sorbic acid.

Preferable examples of the antioxidant include sulfite and ascorbate.

Preferable examples of the colorant include aqueous water-soluble food tar colors (e.g., food colors such as Food Color Red Nos. 2 and 3, Food Color Yellow Nos. 4 and 5, Food Color Blue Nos. 1 and 2 and the like), water insoluble lake dyes (e.g., aluminum salt of the above-mentioned water-soluble food tar color) and natural dyes (e.g., β-carotene, chlorophyll, ferric oxide red).

Preferable examples of the sweetening agent include saccharin sodium, dipotassium glycyrrhizinate, aspartame and stevia.

Examples of the dosage form of the pharmaceutical composition include oral preparations such as tablet (including sugar-coated tablet, film-coated tablet, sublingual tablet, orally disintegrating tablet), capsules (including soft capsule, microcapsule), granule, powder, troche, syrup, emulsion, suspension, films (e.g., orally disintegrable films) and the like; and parenteral agents such as injection (e.g., subcutaneous injection, intravenous injection, intramuscular injection, intraperitoneal injection, drip infusion), external preparations (e.g., dermal preparation, ointment), suppository (e.g., rectal suppository, vaginal suppository), pellet, nasal preparation, pulmonary preparation (inhalant), eye drop and the like.

These may be respectively safely administered orally or parenterally (e.g., topically, rectally, intravenously administered).

These preparations may be a release control preparation (e.g., sustained-release microcapsule) such as an immediate-release preparation, a sustained-release preparation and the like.

The pharmaceutical composition can be produced according to a method conventionally used in the field of pharmaceutical formulation, for example, the method described in the Japanese Pharmacopoeia, and the like.

While the content of the compound of the present invention in the pharmaceutical composition may vary depending on the dosage form, dose of the compound of the present invention and the like, it is for example, about 0.1 to 100 wt %.

During production of an oral preparation, coating may be applied as necessary for the purpose of masking of taste, enteric property or durability.

Examples of the coating base to be used for coating include sugar coating base, water-soluble film coating base, enteric film coating base and sustained-release film coating base.

As the sugar coating base, sucrose is used. Moreover, one or more kinds selected from talc, precipitated calcium carbonate, gelatin, gum arabic, pullulan, carnauba wax and the like may be used in combination.

Examples of the water-soluble film coating base include cellulose polymers such as hydroxypropyl cellulose, hydroxypropylmethyl cellulose, hydroxyethyl cellulose, methylhydroxyethyl cellulose etc.; synthetic polymers such as polyvinylacetal diethylaminoacetate, aminoalkyl methacrylate copolymer E [Eudragit E (trade name)], polyvinylpyrrolidone etc.; and polysaccharides such as pullulan etc.

Examples of the enteric film coating base include cellulose polymers such as hydroxypropylmethyl cellulose phthalate, hydroxypropylmethyl cellulose acetate succinate, carboxymethylethyl cellulose, cellulose acetate phthalate etc.; acrylic polymers such as methacrylic acid copolymer L [Eudragit L (trade name)], methacrylic acid copolymer LD [Eudragit L-30D55 (trade name)], methacrylic acid copolymer S [Eudragit S (trade name)] etc.; and naturally occurring substances such as shellac etc.

Examples of the sustained-release film coating base include cellulose polymers such as ethyl cellulose etc.; and acrylic polymers such as aminoalkyl methacrylate copolymer RS [Eudragit RS (trade name)], ethyl acrylate-methyl methacrylate copolymer suspension [Eudragit NE (trade name)] etc.

The above-mentioned coating bases may be used after mixing with two or more kinds thereof at appropriate ratios. For coating, for example, a light shielding agent such as titanium oxide, red ferric oxide and the like can be used.

The compound of the present invention may show low toxicity (e.g., acute toxicity, chronic toxicity, genetic toxicity, reproductive toxicity, cardiotoxicity, carcinogenicity) and a few side effects. Therefore, it may be used as an agent for the prophylaxis or treatment or a diagnostic of various diseases in a mammal (e.g., human, bovine, horse, dog, cat, monkey, mouse, rat).

Since the compound of the present invention have superior EP4 receptor antagonistic action, they may be also useful as safe medicaments based on such action.

For example, the medicament of the present invention containing the compound of the present invention may be used for a mammal (e.g., mouse, rat, hamster, rabbit, cat, dog, bovine, sheep, monkey, human etc.) as an agent for the prophylaxis or treatment of EP4 receptor associated diseases, specifically, the diseases described in (1)-(7) below.

(1) inflammatory diseases (e.g., acute pancreatitis, chronic pancreatitis, asthma, adult respiratory distress syndrome, chronic obstructive pulmonary disease (COPD), inflammatory bone disease, inflammatory pulmonary disease, inflammatory bowel disease, celiac disease, hepatitis, systemic inflammatory response syndrome (SIRS), postoperative or posttraumatic inflammation, pneumonia, nephritis, meningitis, cystitis, pharyngolaryngitis, gastric mucosal injury, meningitis, spondylitis, arthritis, dermatitis, chronic pneumonia, bronchitis, pulmonary infarction, silicosis, pulmonary sarcoidosis etc.), (2) autoimmune diseases (e.g., psoriasis, rheumatoid arthritis, inflammatory bowel disease (e.g., Crohn's disease, ulcerative colitis etc.), Sjogren's syndrome, Behcet's disease, multiple sclerosis, systemic lupus erythematosus, ankylopoietic spondylarthritis, polymyositis, dermatomyositis (DM), polyarteritis nodosa (PN), mixed connective tissue disease (MCTD), scleroderma, profundus lupus erythematosus, chronic thyroiditis, Graves' disease, autoimmune gastritis, type I and type II diabetes, autoimmune hemolytic anemia, autoimmune neutropenia, thrombocytopenia, atopic dermatitis, chronic active hepatitis, myasthenia gravis, graft versus host disease, Addison's disease, abnormal immunoresponse, arthritis, dermatitis, radiodermatitis etc.)(especially, psoriasis, rheumatoid arthritis, inflammatory bowel disease, Sjogren's syndrome, Behcet's disease, multiple sclerosis and systemic lupus erythematosus), (3) osteoarticular degenerative disease (e.g., rheumatoid arthritis, osteoporosis, osteoarthritis etc.), (4) neoplastic diseases [e.g., malignant tumor, angiogenesis glaucoma, infantile hemangioma, multiple myeloma, acute myeloblastic leukemia, chronic sarcoma, multiple myeloma, chronic myelogenous leukemia, metastasis melanoma, Kaposi's sacroma, vascular proliferation, cachexia, metastasis of the breast cancer, cancer (e.g., colorectal cancer (e.g., familial colorectal cancer, hereditary nonpolyposis colorectal cancer, gastrointestinal stromal tumor etc.), lung cancer (e.g., non-small cell lung cancer, small cell lung cancer, malignant mesothelioma etc.), mesothelioma, pancreatic cancer (e.g., pancreatic duct cancer etc.), gastric cancer (e.g., mucinous adenocarcinoma, adenosquamous carcinoma etc.), papillary adenocarcinoma, breast cancer (e.g., invasive ductal carcinoma, ductal carcinoma in situ, inflammatory breast cancer etc.), ovarian cancer (e.g., ovarian epithelial carcinoma, extragonadal germ cell tumor, ovarian germ cell tumor, ovarian low malignant potential tumor etc.), prostate cancer (e.g., hormone-dependent prostate cancer, non-hormone dependent prostate cancer etc.), liver cancer (e.g., primary liver cancer, extrahepatic bile duct cancer etc.), thyroid cancer (e.g., medullary thyroid carcinoma etc.), kidney cancer (e.g., renal cell carcinoma, transitional cell carcinoma in kidney and urinary duct etc.), uterine cancer, brain tumor (e.g., pineal astrocytoma, pilocytic astrocytoma, diffuse astrocytoma, anaplastic astrocytoma etc.), melanoma, sarcoma, urinary bladder cancer, hematologic cancer and the like including multiple myeloma, hypophyseal adenoma, glioma, acoustic neurinoma, retinoblastoma, pharyngeal cancer, laryngeal cancer, cancer of the tongue, thymoma, esophagus cancer, duodenal cancer, colorectal cancer, rectal cancer, hepatoma, pancreatic endocrine tumor, bile duct cancer, gallbladder cancer, penile cancer, urinary duct cancer, testis tumor, vulvar cancer, cervix cancer, endometrial cancer, uterus sarcoma, cholionic disease, vaginal cancer, skin cancer, fungoid mycosis, basal cell tumor, soft tissue sarcoma, malignant lymphoma, Hodgkin's disease, myelodysplastic syndrome, acute lymphocytic leukemia, chronic lymphocytic leukemia, adult T cell leukemia, chronic bone marrow proliferative disease, pancreatic endocrine tumor, fibrous histiocytoma, leiomyosarcoma, rhabdomyosarcoma, cancer of unknown primary), (5) cardiovascular disease (e.g., heart disease (e.g., cardiac hypertrophy, acute heart failure and chronic heart failure including congestive, cardiomyopathy, angina pectoris, myocarditis, arrhythmia, tachycardia, myocardial infarction), myocardial ischemia, venous insufficiency, heart failure after myocardial infarction, hypertension, cor pulmonale, arteriosclerosis including atherosclerosis (e.g., aortic aneurysm (e.g., abdominal aortic aneurysm, thoracic aortic aneurysm, thoracoabdominal aortic aneurysm), coronary atherosclerosis, cerebral atherosclerosis, peripheral arterial disease, arteriosclerosis obliterans, chronic arterial occlusion), intervention (e.g., percutaneous transluminal coronary angioplasty, stent placement, coronary angioscopy, intravascular ultrasound, thrombolysis therapy), vascular hypertrophy or vascular occlusion and organ dysfunction after heart transplant, vascular reocclusion and restenosis after bypass surgery), (6) hormone-dependent diseases (sex hormone-dependent cancers (e.g., prostate cancer, uterine cancer, breast cancer, pituitary tumor), prostatic hyperplasia, endometriosis, uterine fibroid, precocious puberty, dysmenorrhea, amenorrhea, premenstrual syndrome, polycystic ovary syndrome), (7) acute and chronic pain (e.g., neuropathic pain (e.g., peripheral neuropathy, diabetic neuropathy, post herpetic neuralgia, trigeminal neuralgia, back pain, cancer neuropathy, HIV neuropathy, phantom limb pain, carpal tunnel syndrome, central post-stroke pain, and pain associated with chronic alcoholism, hypothyroidism, uremia, multiple sclerosis, spinal cord injury, Parkinson's disease, epilepsy and vitamin deficiency), inflammatory pain (e.g., osteoarthritis, ankylosing spondylitis), visceral pain (e.g., pain associated with gastrointestinal disorders (gastro-esophageal reflux, dyspepsia, irritable bowel syndrome (IBS), functional abdominal pain syndrome (FAPS), inflammatory bowel disease (IBD), Crohn's disease, ileitis, ulcerative colitis)), pain from central nervous system trauma, strains/sprains, burns, myocardial infarction and acute pancreatitis, postoperative pain, renal colic, posttraumatic pain, back pain, cancer pain (e.g., tumor related pain (e.g., bone pain, headache, facial pain or visceral pain), pain associated with cancer therapy (e.g., pain associated with postchemotherapy syndrome, chronic postsurgical pain syndrome, post radiation syndrome), chemotherapy, immunotherapy, hormonal therapy or radiotherapy), pain resulting from musculo-skeletal disorders (e.g., myalgia, fibromyalgia, spondylitis, sero-negative (non-rheumatoid) arthropathies, non-articular rheumatism, dystrophinopathy, glycogenosis, polymyositis and pyomyositis), heart and vascular pain (e.g., pain caused by angina, myocardial infarction, mitral stenosis, pericarditis, Raynaud's phenomenon, scleroderma and skeletal muscle ischemia), head pain (e.g., migraine (including migraine with aura and migraine without aura), cluster headache, tension-type headache, mixed headache and headache associated with vascular disorders), orofacial pain (e.g., dental pain, otic pain, burning mouth syndrome and temporomandibular myofascial pain)).

The medicament of the present invention may be preferably used as an agent for the prophylaxis or treatment of rheumatoid arthritis, aortic aneurysm (e.g. abdominal aortic aneurysm, thoracic aortic aneurysm, thoracoabdominal aortic aneurysm etc.), endometriosis, ankylosing spondylitis, inflammatory breast cancer and the like.

Here, the above-mentioned "prophylaxis" of a disease means, for example, administration of a medicament containing the compound of the present invention to patients who are expected to have a high risk of the onset due to some factor relating to the disease but have not developed the disease or patients who have developed the disease but do not have a subjective symptom, or administration of a medicament containing the compound of the present invention to patients who are feared to show recurrence of the disease after treatment of the disease.

The dose of the compound of the present invention may vary depending on the administration subject, route of administration, target disease, symptoms, etc. For example, when it is administered orally to an adult patient (body weight 60 kg), its dose may be about 0.01 to 100 mg/kg body weight per dose, preferably 0.05 to 30 mg/kg body weight per dose, more preferably 0.1 to 10 mg/kg body weight per dose and this amount is desirably administered in 1 to 3 portions daily.

The compound of the present invention can also be used together with other medicaments.

Hereinafter, a medicament to be used in combination with the compound of the present invention is referred to as "concomitant drug", and a combination of the compound of the present invention and concomitant drug is referred to as "the combination agent of the present invention".

For example, when the compound of the present invention is used as a prophylactic or therapeutic agent for EP4 receptor associated disease, it can be used in combination with the following drugs.

(1) non-steroidal anti-inflammatory drug (NSAIDs)
(i) classical NSAIDs
alcofenac, aceclofenac, sulindac, tolmetin, etodolac, fenoprofen, thiaprofenic acid, meclofenamic acid, meloxicam, tenoxicam, lornoxicam, nabumeton, acetaminophen, phenacetin, ethenzamide, sulpyrine, antipyrine, migrenin, aspirin, mefenamic acid, flufenamic acid, diclofenac sodium, loxoprofen sodium, phenylbutazone, indomethacin, ibuprofen, ketoprofen, naproxen, oxaprozin, flurbiprofen, fenbufen, pranoprofen, floctafenine, piroxicam, epirizole, tiaramide hydrochloride, zaltoprofen, gabexate mesylate, camostat mesylate, ulinastatin, colchicine, probenecid, sulfinpyrazone, benzbromarone, allopurinol, sodium aurothiomalate, hyaluronate sodium, sodium salicylate, morphine hydrochloride, salicylic acid, atropine, scopolamine, morphine, pethidine, levorphanol, oxymorphone or a salt thereof and the like.
(ii) cyclooxygenase inhibitor (COX-1 selective inhibitor, COX-2 selective inhibitor etc.)
salicylic acid derivatives (e.g., celecoxib, aspirin), etoricoxib, valdecoxib, diclofenac, indomethacin, loxoprofen and the like.
(iii) nitric oxide-releasing NSAIDs.
(iv) JAK inhibitor
tofacitinib, ruxolitinib and the like.
(2) disease-modifying anti-rheumatic drugs (DMARDs)
(i) Gold preparation
auranofin and the like.
(ii) penicillamine
D-penicillamine and the like.
(iii) aminosalicylic acid preparation
sulfasalazine, mesalazine, olsalazine, balsalazide and the like.
(iv) antimalarial drug
chloroquine and the like.
(v) pyrimidine synthesis inhibitor
leflunomide and the like.
(vi) prograf
(3) anti-cytokine drug
(I) protein drug
(i) TNF inhibitor
etanercept, infliximab, adalimumab, certolizumab pegol, golimumab, PASSTNF-α, soluble TNF-α receptor, TNF-α binding protein, anti-TNF-α antibody and the like.

(ii) interleukin-1 inhibitor
anakinra (interleukin-1 receptor antagonist), soluble interleukin-1 receptor and the like.
(iii) interleukin-6 inhibitor
tocilizumab (anti-interleukin-6 receptor antibody), anti-interleukin-6 antibody and the like.
(iv) interleukin-10 drug
interleukin-10 and the like.
(i) Interleukin-12/23 inhibitor
ustekinumab, briakinumab (anti-interleukin-12/23 antibody) and the like.
(II) non-protein drug
(i) MAPK inhibitor
BMS-582949 and the like.
(ii) gene modulator
inhibitor of molecule involved in signal transduction, such as NF-κ, NF-κB, IKK-1, IKK-2, AP-1 and the like, and the like.
(iii) cytokine production inhibitor
iguratimod, tetomilast and the like.
(iv) TNF-α converting enzyme inhibitor
(v) interleukin-1β converting enzyme inhibitor
VX-765 and the like.
(vi) interleukin-6 antagonist
HMPL-004 and the like.
(vii) interleukin-8 inhibitor
IL-8 antagonist, CXCR1 & CXCR2 antagonist, reparixin and the like.
(viii) chemokine antagonist
CCR9 antagonist (CCX-282, CCX-025), MCP-1 antagonist and the like.
(ix) interleukin-2 receptor antagonist
denileukin, diftitox and the like.
(x) therapeutic vaccines
TNF-α vaccine and the like.
(xi) gene therapy drug
gene therapy drugs aiming at promoting the expression of gene having an anti-inflammatory action such as interleukin-4, interleukin-10, soluble interleukin-1 receptor, soluble TNF-α receptor and the like.
(xii) antisense compound
ISIS 104838 and the like.
(4) integrin inhibitor
natalizumab, vedolizumab, AJM300, TRK-170, E-6007 and the like.
(5) immunomodulator (immunosuppressant)
methotrexate, cyclophosphamide, MX-68, atiprimod dihydrochloride, BMS-188667, CKD-461, rimexolone, cyclosporine, tacrolimus, gusperimus, azathipurine, anti-lymphocyte serum, freeze-dried sulfonated normal immunoglobulin, erythropoietin, colony stimulating factor, interleukin, interferon and the like.
(6) steroid
dexamethasone, hexestrol, methimazole, betamethasone, triamcinolone, triamcinolone acetonide, fluocinonide, fluocinolone acetonide, predonisolone, methylpredonisolone, cortisone acetate, hydrocortisone, fluorometholone, beclomethasone dipropionate, estriol and the like.
(7) angiotensin converting enzyme inhibitor
enalapril, captopril, ramipril, lisinopril, cilazapril, perindopril and the like.
(8) angiotensin II receptor antagonist
candesartan, candesartan cilexetil, azilsartan, azilsartan medoxomil, valsartan, irbesartan, olmesartan, eprosartan and the like.
(9) diuretic drug
hydrochlorothiazide, spironolactone, furosemide, indapamide, bendrofluazide, cyclopenthiazide and the like.

(10) cardiotonic drug
  digoxin, dobutamine and the like.
(11) β receptor antagonist
  carvedilol, metoprolol, atenolol and the like.
(12) Ca sensitizer
  MCC-135 and the like.
(13) Ca channel antagonist
  nifedipine, diltiazem, verapamil and the like.
(14) anti-platelet drug, anticoagulator
  heparin, aspirin, warfarin and the like.
(15) HMG-CoA reductase inhibitor
  atorvastatin, simvastatin and the like.
(16) Contraceptive
(i) sex hormone or derivatives thereof
  gestagen or a derivative thereof (progesterone, 17α-hydroxy progesterone, medroxyprogesterone, medroxyprogesterone acetate, norethisterone, norethisterone enanthate, norethindrone, norethindrone acetate, norethynodrel, levonorgestrel, norgestrel, ethynodiol diacetate, desogestrel, norgestimate, gestodene, progestin, etonogestrel, drospirenone, dienogest, trimegestone, nestorone, chlormadinone acetate, mifepristone, nomegestrol acetate, Org-30659, TX-525, EMM-310525) or a combination agent of a gestagen or a derivative thereof and an estrogen or a derivative thereof (estradiol, estradiol benzoate, estradiol cypionate, estradiol dipropionate, estradiol enanthate, estradiol hexahydrobenzoate, estradiol phenylpropionate, estradiol undecanoate, estradiol valerate, estrone, ethinylestradiol, mestranol) and the like.
(ii) antiestrogen
  ormeloxifene, mifepristone, Org-33628 and the like.
(iii) spermatocide
  ushercell and the like.
(17) others
(i) T cell inhibitors
(ii) inosine monophosphate dehydrogenase (IMPDH) inhibitor
  mycophenolate mofetil and the like.
(iii) adhesion molecule inhibitor
  ISIS-2302, selectin inhibitor, ELAM-1, VCAM-1, ICAM-1 and the like.
(iv) thalidomide
(v) cathepsin inhibitor
(vi) matrix metalloprotease (MMPs) inhibitor
  V-85546 and the like.
(vii) glucose-6-phosphate dehydrogenase inhibitor
(viii) dihydroorotate dehydrogenase (DHODH) inhibitor
(ix) phosphodiesterase IV(PDE IV) inhibitor
  roflumilast, CG-1088 and the like.
(x) phospholipase $A_2$ inhibitor
(xi) iNOS inhibitor
  VAS-203 and the like.
(xii) microtubule stimulating drug
  paclitaxel and the like.
(xiii) microtubule inhibitor
  reumacon and the like.
(xiv) MHC class II antagonist
(xv) prostacyclin agonist
  iloprost and the like.
(xvi) CD4 antagonist
  zanolimumab and the like.
(xvii) CD23 antagonist
(xviii) LTB4 receptor antagonist
  DW-1305 and the like.
(xix) 5-lipoxygenase inhibitor
  zileuton and the like.
(xx) cholinesterase inhibitor
  galanthamine and the like.
(xxi) tyrosine kinase inhibitor
  Tyk2 inhibitor (the compounds described in WO 2010/142752) and the like.
(xxii) cathepsin B inhibitor
(xxiii) adenosine deaminase inhibitor
  pentostatin and the like.
(xxiv) osteogenesis stimulator
(xxv) dipeptidylpeptidase inhibitor
(xxvi) collagen agonist
(xxvii) capsaicin cream
(xxviii) hyaluronic acid derivative
  synvisc (hylan G-F 20), orthovisc and the like.
(xxix) glucosamine sulfate
(xxx) amiprilose
(xxxi) CD-20 inhibitor rituximab, ibritumomab, tositumomab, ofatumumab and the like.
(xxxii) BAFF inhibitor
  belimumab, tabalumab, atacicept, A-623 and the like.
(xxxiii) CD52 inhibitor
  alemtuzumab and the like.
(xxxiv) IL-17 inhibitor
  secukinumab (AIN-457), LY-2439821, AMG827 and the like Other concomitant drugs besides the above-mentioned include, for example, antibacterial agent, antifungal agent, antiprotozoal agent, antibiotic, antitussive and expectorant drug, sedative, anesthetic, antiulcer drug, antiarrhythmic agent, hypotensive diuretic drug, anticoagulant, tranquilizer, antipsychotic, antitumor drug, hypolipidemic drug, muscle relaxant, antiepileptic drug, antidepressant, antiallergic drug, cardiac stimulants, therapeutic drug for arrhythmia, vasodilator, vasoconstrictor, therapeutic drug for diabetes, antinarcotic, vitamin, vitamin derivative, antiasthmatic, therapeutic agent for pollakisuria/anischuria, antipruritic drug, therapeutic agent for atopic dermatitis, therapeutic agent for allergic rhinitis, hypertensor, endotoxin-antagonist or -antibody, signal transduction inhibitor, inhibitor of inflammatory mediator activity, antibody to inhibit inflammatory mediator activity, inhibitor of anti-inflammatory mediator activity, antibody to inhibit anti-inflammatory mediator activity and the like. Specific examples thereof include the following.
(1) antibacterial agent
(i) sulfa drug
  sulfamethizole, sulfisoxazole, sulfamonomethoxine, sulfamethizole, salazosulfapyridine, silver sulfadiazine and the like.
(ii) quinolone antibacterial agent
  nalidixic acid, pipemidic acid trihydrate, enoxacin, norfloxacin, ofloxacin, tosufloxacin tosylate, ciprofloxacin hydrochloride, lomefloxacin hydrochloride, sparfloxacin, fleroxacin and the like.
(iii) antiphthisic
  isoniazid, ethambutol (ethambutol hydrochloride), p-aminosalicylic acid (calcium p-aminosalicylate), pyrazinamide, ethionamide, protionamide, rifampicin, streptomycin sulfate, kanamycin sulfate, cycloserine and the like.
(iv) antiacidfast bacterium drug
  diaphenylsulfone, rifampicin and the like.
(v) antiviral drug
  idoxuridine, acyclovir, vidarabine, gancyclovir and the like.
(vi) anti-HIV agent
  zidovudine, didanosine, zalcitabine, indinavir sulfate ethanolate, ritonavir and the like.

(vii) antispirochetele
(viii) antibiotic tetracycline hydrochloride, ampicillin, piperacillin, gentamicin, dibekacin, kanendomycin, lividomycin, tobramycin, amikacin, fradiomycin, sisomicin, tetracycline, oxytetracycline, rolitetracycline, doxycycline, ampicillin, piperacillin, ticarcillin, cephalothin, cephapirin, cephaloridine, cefaclor, cephalexin, cefroxadine, cefadroxil, cefamandole, cefotoam, cefuroxime, cefotiam, cefotiam hexetil, cefuroxime axetil, cefdinir, cefditoren pivoxil, ceftazidime, cefpiramide, cefsulodin, cefmenoxime, cefpodoxime proxetil, cefpirome, cefozopran, cefepime, cefsulodin, cefmenoxime, cefmetazole, cefminox, cefoxitin, cefbuperazone, latamoxef, flomoxef, cefazolin, cefotaxime, cefoperazone, ceftizoxime, moxalactam, thienamycin, sulfazecin, aztreonam or a salt a salt thereof, griseofulvin, lankacidin-group [Journal of Antibiotics (J. Antibiotics), 38, 877-885(1985)], azole compound [2-[(1R,2R)-2-(2,4-difluorophenyl)-2-hydroxy-1-methyl-3-(1H-1,2,4-triazol-1-yl)propyl]-4-[4-(2,2,3,3-tetrafluoropropoxy)phenyl]-3(2H, 4H)-1,2,4-triazolone, fluconazole, itraconazole and the like] and the like.

(2) antifungal agent (i) polyethylene antibiotic (e.g., amphotericin B, nystatin, trichomycin)
(ii) griseofulvin, pyrrolnitrin and the like
(iii) cytosine metabolism antagonist (e.g., flucytosine)
(iv) imidazole derivative (e.g., econazole, clotrimazole, miconazole nitrate, bifonazole, croconazole)
(v) triazole derivative (e.g., fluconazole, itraconazole)
(vi) thiocarbamic acid derivative (e.g., trinaphthol) and the like.

(3) antiprotozoal agent metronidazole, tinidazole, diethylcarbamazine citrate, quinine hydrochloride, quinine sulfate and the like.

(4) antitussive and expectorant drug ephedrine hydrochloride, noscapine hydrochloride, codeine phosphate, dihydrocodeine phosphate, isoproterenol hydrochloride, ephedrine hydrochloride, methylephedrine hydrochloride, noscapine hydrochloride, alloclamide, chlophedianol, picoperidamine, cloperastine, protokylol, isoproterenol, salbutamol, terbutaline, oxymetebanol, morphine hydrochloride, dextromethorfan hydrobromide, oxycodone hydrochloride, dimemorphan phosphate, tipepidine hibenzate, pentoxyverine citrate, clofedanol hydrochloride, benzonatate, guaifenesin, bromhexine hydrochloride, ambroxol hydrochloride, acetylcysteine, ethyl cysteine hydrochloride, carbocysteine and the like.

(5) sedative chlorpromazine hydrochloride, atropine sulfate, phenobarbital, barbital, amobarbital, pentobarbital, thiopental sodium, thiamylal sodium, nitrazepam, estazolam, flurazepam, haloxazolam, triazolam, flunitrazepam, bromovalerylurea, chloral hydrate, triclofos sodium and the like.

(6) anesthetic (6-1) local anesthetic cocaine hydrochloride, procaine hydrochloride, lidocaine, dibucaine hydrochloride, tetracaine hydrochloride, mepivacaine hydrochloride, bupivacaine hydrochloride, oxybuprocaine hydrochloride, ethyl aminobenzoate, oxethazaine and the like.

(6-2) general anesthetic (i) inhalation anesthetic (e.g., ether, halothane, nitrous oxide, isoflurane, enflurane),
(ii) intravenous anesthetic (e.g., ketamine hydrochloride, droperidol, thiopental sodium, thiamylal sodium, pentobarbital) and the like.

(7) antiulcer drug histidine hydrochloride, lansoprazole, metoclopramide, pirenzepine, cimetidine, ranitidine, famotidine, urogastrone, oxethazaine, proglumide, omeprazole, sucralfate, sulpiride, cetraxate, gefarnate, aldioxa, teprenone, prostaglandin and the like.

(8) antiarrhythmic agent (i) sodium channel blocker (e.g., quinidine, procainamide, disopyramide, ajmaline, lidocaine, mexiletine, phenytoin),
(ii) β-blocker (e.g., propranolol, alprenolol, bufetolol hydrochloride, oxprenolol, atenolol, acebutolol, metoprolol, bisoprolol, pindolol, carteolol, arotinolol hydrochloride),
(iii) potassium channel blocker (e.g., amiodarone),
(iv) calcium channel blocker (e.g., verapamil, diltiazem) and the like.

(9) hypotensive diuretic drug hexanethonium bromide, clonidine hydrochloride, hydrochlorothiazide, trichlormethiazide, furosemide, ethacrynic acid, bumetanide, mefruside, azosemide, spironolactone, potassium canrenoate, triamterene, amiloride, acetazolamide, D-mannitol, isosorbide, aminophylline and the like.

(10) anticoagulant heparin sodium, sodium citrate, activated protein C, tissue factor pathway inhibitor, antithrombin III, dalteparin sodium, warfarin potassium, argatroban, gabexate, sodium citrate, ozagrel sodium, ethyl icosapentate, beraprost sodium, alprostadil, ticlopidine hydrochloride, pentoxifylline, dipyridamole, tisokinase, urokinase, streptokinase and the like.

(11) tranquilizer diazepam, lorazepam, oxazepam, chlordiazepoxide, medazepam, oxazolam, cloxazolam, clotiazepam, bromazepam, etizolam, fludiazepam, hydroxyzine and the like.

(12) antipsychotic chlorpromazine hydrochloride, prochlorperazine, trifluoperazine, thioridazine hydrochloride, perphenazine maleate, fluphenazine enanthate, prochlorperazine maleate, levomepromazine maleate, promethazine hydrochloride, haloperidol, bromperidol, spiperone, reserpine, clocapramine hydrochloride, sulpiride, zotepine and the like.

(13) antitumor drug

6-O—(N-chloroacetylcarbamoyl)fumagillol, bleomycin, methotrexate, actinomycin D, mitomycin C, daunorubicin, adriamycin, neocarzinostatin, cytosine arabinoside, fluorouracil, tetrahydrofuryl-5-fluorouracil, picibanil, lentinan, levamisole, bestatin, azimexon, glycyrrhizin, doxorubicin hydrochloride, aclarubicin hydrochloride, bleomycin hydrochloride, peplomycin sulfate, vincristine sulfate, vinblastine sulfate, irinotecan hydrochloride, cyclophosphamide, melphalan, busulfan, thiotepa, procarbazine hydrochloride, cisplatin, azathioprine, mercaptopurine, tegafur, carmofur, cytarabine, methyltestosterone, testosterone propionate, testosterone enanthate, mepitiostane, fosfestrol, chlormadinone acetate, leuprorelin acetate, buserelin acetate and the like.

(14) hypolipidemic drug clofibrate, ethyl 2-chloro-3-[4-(2-methyl-2-phenylpropoxy)phenyl]propionate [Chemical and Pharmaceutical Bulletin (Chem. Pharm. Bull), 38, 2792-2796 (1990)], pravastatin, simvastatin, probucol, bezafibrate, clinofibrate, nicomol, cholestyramine, dextran sulfate sodium and the like.

(15) muscle relaxant pridinol, tubocurarine, pancuronium, tolperisone hydrochloride, chlorphenesin carbamate, baclofen, chlormezanone, mephenesin, chlorzoxazone, eperisone, tizanidine and the like.

(16) antiepileptic drug
phenytoin, ethosuximide, acetazolamide, chlordiazepoxide, trimethadione, carbamazepine, phenobarbital, primidone, sulthiame, sodium valproate, clonazepam, diazepam, nitrazepam and the like.
(17) antidepressant
imipramine, clomipramine, noxiptiline, phenelzine, amitriptyline hydrochloride, nortriptyline hydrochloride, amoxapine, mianserin hydrochloride, maprotiline hydrochloride, sulpiride, fluvoxamine maleate, trazodone hydrochloride and the like.
(18) antiallergic drug
diphenhydramine, chlorpheniramine, tripelennamine, metodilamine, clemizole, diphenylpyraline, methoxyphenamine, sodium cromoglicate, tranilast, repirinast, amlexanox, ibudilast, ketotifen, terfenadine, mequitazine, azelastine hydrochloride, epinastine, ozagrel hydrochloride, pranlukast hydrate, seratrodast and the like.
(19) cardiac stimulants
trans-π-oxocamphor, terephyllol, aminophylline, etilefrine, dopamine, dobutamine, denopamine, aminophylline, vesnarinone, amrinone, pimobendan, ubidecarenone, digitoxin, digoxin, methyldigoxin, lanatoside C, G-strophanthin and the like.
(20) vasodilator
oxyfedrine, diltiazem, tolazoline, hexobendine, bamethan, clonidine, methyldopa, guanabenz and the like.
(21) vasoconstrictor
dopamine, dobutamine denopamine and the like.
(22) hypotensive diuretic
hexanethonium bromide, pentolinium, mecamylamine, ecarazine, clonidine, diltiazem, nifedipine and the like.
(23) therapeutic drug for diabetes
tolbutamide, chlorpropamide, acetohexamide, glibenclamide, tolazamide, acarbose, epalrestat, troglitazone, glucagon, glymidine, glipizide, phenformin, buformin, metformin and the like.
(24) antinarcotic
levallorphan, nalorphine, naloxone or a salt thereof and the like.
(25) liposoluble vitamins
(i) vitamin A: vitamin $A_1$, vitamin $A_2$ and retinol palmitate
(ii) vitamin D: vitamin $D_1$, $D_2$, $D_3$, $D_4$ and $D_5$
(iii) vitamin E: α-tocopherol, β-tocopherol, γ-tocopherol, δ-tocopherol, dl-α-tocopherol nicotinate
(iv) vitamin K: vitamin $K_1$, $K_2$, $K_3$ and $K_4$
(v) folic acid (vitamin M) and the like.
(26) vitamin derivative
various derivatives of vitamins, for example, vitamin $D_3$ derivatives such as 5,6-trans-cholecalciferol, 2,5-hydroxycholecalciferol, 1-α-hydroxycholecalciferol and the like, vitamin $D_2$ derivatives such as 5,6-trans-ergocalciferol and the like, and the like.
(27) antiasthmatic
isoprenaline hydrochloride, salbutamol sulfate, procaterol hydrochloride, terbutaline sulfate, trimetoquinol hydrochloride, tulobuterol hydrochloride, orciprenaline sulfate, fenoterol hydrobromide, ephedrine hydrochloride, ipratropium bromide, oxitropium bromide, flutropium bromide, theophylline, aminophylline, sodium cromoglicate, tranilast, repirinast, amlexanox, ibudilast, ketotifen, terfenadine, mequitazine, azelastine, epinastine, ozagrel hydrochloride, pranlkast hydrate, seratrodast, dexamethasone, prednisolone, hydrocortisone, hydrocortisone sodium succinate, beclometasone dipropionate and the like.
(28) therapeutic agent for pollakisuria/anischuria
flavoxate hydrochloride and the like.
(29) therapeutic agent for atopic dermatitis
sodium cromoglicate and the like.
(30) therapeutic agent for allergic rhinitis
sodium cromoglicate, chlorpheniramine maleate, alimemazine tartrate, clemastine fumarate, homochlorcyclizine hydrochloride, fexofenadine, mequitazine and the like.
(31) hypertensor
dopamine, dobutamine, denopamine, digitoxin, digoxin, methyldigoxin, lanatoside C, G-strophanthin and the like.
(32) others
hydroxycam, diacerein, megestrol acetate, nicergoline, prostaglandins and the like.

In another embodiment, when the compound of the present invention is used as an agent for the prophylaxis or treatment of chronic or acute pain, from among EP4 receptor associated disease, it can be used in combination with the following drugs.

(1) opioid analgesic, for example, morphine, heroin, hydromorphone, oxymorphone, levorphanol, levallorphan, methadone, meperidine, fentanyl, cocaine, codeine, dihydrocodeine, oxycodone, hydrocodone, propoxyphene, nalmefene, nalorphine, naloxone, naltrexone, buprenorphine, butorphanol, nalbuphine or pentazocine;
(2) non-steroidal antiinflammatory drug (NSAID), for example, aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, nabumetone, naproxen, oxaprozin, phenylbutazone, piroxicam, sulindac, tolmetin or zomepirac; cyclooxygenase-2 (COX-2) inhibitors, for example, celecoxib, rofecoxib, meloxicam, 4-(4-cyclohexyl-2-methyl-1,3-oxazol-5-yl)-2-fluorobenzenesulfonamide, L-745, L-337, N-[2-(cyclohexyloxy)-4-nitrophenyl]methanesulfonamide, N-(2-cyclohexyloxy-4-nitrophenyl)methanesulfonamide or N-(methylsulfonyl)-2-(cyclohexyloxy)-4-nitroaniline; or a pharmaceutically acceptable salt thereof;
(3) barbiturate sedative, for example, amobarbital, aprobarbital, butabarbital, butabital, mephobarbital, metharbital, methohexital, pentobarbital, phenobartital, secobarbital, talbutal, theamylal or thiopental or a pharmaceutically acceptable salt thereof;
(4) benzodiazepine having a sedative action, for example, chlordiazepoxide, clorazepate, diazepam, flurazepam, lorazepam, oxazepam, temazepam or triazolam or a pharmaceutically acceptable salt thereof;
(5) H1 antagonist having a sedative action, for example, diphenhydramine, pyhlamine, promethazine, chlorpheniramine or chlorcyclizine or a pharmaceutically acceptable salt thereof;
(6) sedative, for example, loxoprofen sodium, acetaminophen, acetylsalicylic acid, glutethimide, meprobamate, methaqualone or dichloralphenazone or a pharmaceutically acceptable salt thereof;
(7) skeletal muscle relaxant, for example, baclofen, cahsoprodol, chlorzoxazone, cyclobenzaphne, methocarbamol or orphrenadine or a pharmaceutically acceptable salt thereof;
(8) NMDA receptor antagonist, for example, dextromethorphan ((+)-3-hydroxy-N-methylmorphinan) or its metabolite dextrorphan ((+)-3-hydroxy-N-methylmorphinan), ketamine, memantine, pyrroloquinoline quinone or cis-4-(phosphonomethyl)-2-piperidinecarboxylic acid or a pharmaceutically acceptable salt thereof;
(9) α-adrenergic, for example, doxazosin, tamsulosin, clonidine or 4-amino-6,7-dimethoxy-2-(5-methanesulfonamido-1,2,3,4-tetrahydroisoquinol-2-yl)-5-(2-pyridyl)quinazoline;

(10) tricyclic antidepressant, for example, desipramine, imipramine, clomipramine, doxepin, amythptiline or nortriptiline;
(11) anticonvulsant, for example, carbamazepine, lamotrigine or valproate;
(12) tachykinin (NK) antagonist (particularly an NK-3, NK-2 or NK-1 antagonist), for example, 5-[[(2R,3S)-2-[(1R)-1-[3,5-bis(trifluoromethyl)phenyl]ethoxy-3-(4-fluorophenyl)-4-morpholinyl]methyl]-1,2-dihydro-3H-1,2,4-triazol-3-one, lanepitant, dapitant or 3-[[2-methoxy-5-(trifluoromethoxy)phenyl]methylamino]-2-phenyl-piperidine (2S,3S);
(13) muscarinic antagonist, for example, oxybutin, tolterodine, propiverine, tropsium chloride or darifenacin;
(14) COX-2 inhibitor, for example, celecoxib, rofecoxib or valdecoxib;
(15) non-selective COX inhibitor (preferably, having a protective effect on the gastrointestinal tract), for example, nitroflurbiprofen;
(16) coal-tar analgesic, particularly paracetamol;
(17) neuroleptic, for example, droperidol;
(18) vanilloid receptor agonist (e.g., resinferatoxin) or antagonist (e.g., capsazepine);
(19) β-adrenergic, for example, propranolol;
(20) local anaesthetic, for example, mexiletine, tocainide or lidocaine;
(21) corticosteriod, for example, dexamethasone or prednisone;
(22) serotonin receptor agonist or antagonist;
(23) cholinergic (nicotinic) analgesic;
(24) tramadol hydrochloride;
(25) PDEV inhibitor, such as sildenafil, vardenafil or taladafil;
(26) α-2-δ ligand, for example, gabapentin or pregabalin;
(27) canabinoid; and
(28) antidepressant (e.g., amitriptyline, trazodone, duloxetine, milnacipran, fluoxetine, paroxetine, sertraline, citalopram and imipramine), anticonvulsant (e.g., phenytoin or carbamazepine), narcotic drug (e.g., methadone, tramadol), Chinese herbal medicine (e.g., gosha-jinki-gan, shakuyaku-kanzoh-toh) and vitamin.

For combined use, the administration time of the compound of the present invention and the concomitant drug is not restricted, and the compound of the present invention or the concomitant drug may be administered to an administration subject simultaneously, or may be administered at different times. The dosage of the concomitant drug may be determined according to the dose clinically used, and can be appropriately selected depending on an administration subject, administration route, disease, combination and the like.

The administration form of the combined use is not particularly limited, and the compound of the present invention and a concomitant drug only need to be combined on administration. Examples of such administration mode include the following:
(1) administration of a single preparation obtained by simultaneously processing the compound of the present invention and the concomitant drug, (2) simultaneous administration of two kinds of preparations of the compound of the present invention and the concomitant drug, which have been separately produced, by the same administration route, (3) administration of two kinds of preparations of the compound of the present invention and the concomitant drug, which have been separately produced, by the same administration route in a staggered manner, (4) simultaneous administration of two kinds of preparations of the compound of the present invention and the concomitant drug, which have been separately produced, by different administration routes, (5) administration of two kinds of preparations of the compound of the present invention and the concomitant drug, which have been separately produced, by different administration routes in a staggered manner (e.g., administration in the order of the compound of the present invention and the concomitant drug, or in the reverse order) and the like.

The mixing ratio of the compound of the present invention and a concomitant drug in the combination agent of the present invention can be appropriately selected based on the subject of administration, administration route, disease and the like.

For example, while the content of the compound of the present invention in the combination agent of the present invention varies depending on the preparation form, it is generally about 0.01-100 wt %, preferably about 0.1-50 wt %, more preferably about 0.5-20 wt %, of the whole preparation.

The content of the concomitant drug in the combination agent of the present invention varies depending on the preparation form, and generally about 0.01 to 100% by weight, preferably about 0.1 to 50% by weight, further preferably about 0.5 to 20% by weight, of the entire preparation.

While the content of the additive such as a carrier and the like in the combination agent of the present invention varies depending on the form of a preparation, it is generally about 1 to 99.99% by weight, preferably about 10 to 90% by weight, based on the preparation.

When the compound of the present invention and the concomitant drug are separately prepared, the same content may be adopted.

The dose of the combination agent varies depending on the kind of the compound of the present invention, administration route, symptom, age of patients and the like. For example, for oral administration to patients (body weight about 60 kg) with inflammatory bowel disease (IBD), about 0.1 mg/kg body weight—about 30 mg/kg body weight, preferably about 1 mg/kg body weight—20 mg/kg body weight, of compound (I) can be administered once to several portions per day.

The dose of the pharmaceutical composition of the present invention as a sustained-release preparation varies depending on the kind and content of compound (I), dosage form, period of sustained drug release, subject animal of administration (e.g., mammals such as mouse, rat, hamster, guinea pig, rabbit, cat, dog, bovine, horse, swine, sheep, monkey, human etc.), and administration object. For example, for application by parenteral administration, about 0.1 to about 100 mg of compound (I) needs to be released from the administered preparation per 1 week.

Any amount of the concomitant drug can be adopted as long as the side effects do not cause a problem. The daily dosage in terms of the concomitant drug varies depending on the severity, age, sex, body weight, sensitivity difference of the subject, administration period, interval, and nature, pharmacology, kind of the pharmaceutical preparation, kind of effective ingredient, and the like, and not particularly restricted, and the amount of a drug is, in the case of oral administration for example, generally about 0.001 to 2000 mg, preferably about 0.01 to 500 mg, further preferably about 0.1 to 100 mg, per 1 kg of a mammal and this is generally administered once to 4-times, divided in a day.

When the combination agent of the present invention is administered, the compound of the present invention and the concomitant drug can be administered simultaneously, or may be administered in a staggered manner. When administered at a time interval, the interval varies depending on the effective ingredient, dosage form and administration method, and, for example, when the concomitant drug is administered first, a method in which the compound of the present invention is administered within time range of from 1 minute to 3 days, preferably from 10 minutes to 1 day, more preferably from 15 minutes to 1 hour, after administration of the concomitant drug is an example. When the compound of the present invention is administered first, a method in which the concomitant drug is administered within time range of from 1 minute to 1 day, preferably from 10 minutes to 6 hours, more preferably from 15 minutes to 1 hour after administration of the compound of the present invention is an example.

EXAMPLES

The present invention is explained in detail in the following by referring to Preparations, Examples, Experimental Examples and Formulation Examples, which are not to be construed as limitative, and the invention may be changed within the scope of the present invention.

In the following Examples, the "room temperature" generally means about 10° C. to about 35° C. The ratios indicated for mixed solvents are volume mixing ratios, unless otherwise specified. % means wt %, unless otherwise specified.

In silica gel column chromatography, basic silica gel means use of aminopropylsilane-bound silica gel. In HPLC (high performance liquid chromatography), C18 means use of octadecyl-bound silica gel. The ratios of elution solvents are volume mixing ratios, unless otherwise specified.

$^1$H NMR (proton nuclear magnetic resonance spectrum) was measured by Fourier-transform type NMR. For the analysis, ACD/SpecManager (trade name) and the like were used. Peaks with very mild protons such as a hydroxy group, an amino group and the like are not described.

MS (mass spectrum) was measured by LC/MS (liquid chromatography mass spectrometer). As ionization method, ESI (Electro Spray Ionization) method or APCI (Atomospheric Pressure Chemical Ionization) method was used. The data indicates those found. Generally, a molecular ion peak is observed. In the case of a salt, a molecular ion peak or fragment ion peak of free form is generally observed.

Preparation 1: 2-Chloro-3-nitropyridin-4-ol

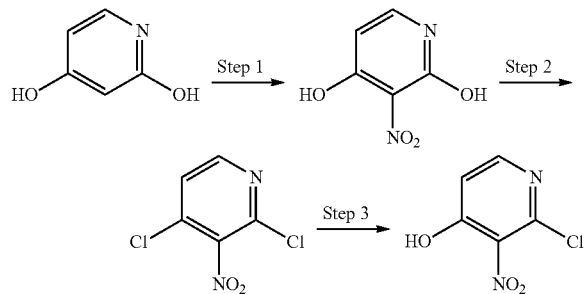

Step 1: 3-Nitropyridine-2,4-diol 2,4-Dihydroxypyridine (100 g, 901 mmol) was added portion wise to cooled (0-10° C.) concentrated sulfuric acid (300 mL) while stirring. The reaction mixture was stirred further for 40 minutes at room temperature. Fuming nitric acid (40 mL) was added slowly thereto over a period of 1 hour, and the reaction temperature was maintained below 5° C. The reaction mixture was poured slowly into cold water (3000 mL) keeping the temperature below 5° C. The resulting suspension was stirred at ambient temperature for 2 hours. The solid was collected by filtration and washed with water (1000 mL). The obtained solid was dried under vacuum to give the title compound (125 g, 88%).

MS (ESI) m/z: 157.1 (M+1). $^1$H NMR (400 MHz, DMSO-d$_6$): δ 6.02 (d, J=7.2 Hz, 1H), 7.44 (d, J=7.2 Hz, 1H), 11.85 (br s, 1H), 12.40 (br s, 1H).

Step 2: 2,4-Dichloro-3-nitropyridine

A mixture of 3-nitropyridine-2,4-diol (100 g, 640 mmol) and phosphorous oxychloride (500 mL) was heated at 120° C. for 18 hours. The reaction completion was confirmed by TLC, then the phosphorous oxychloride was removed under vacuum, and the resulting residue was dissolved in water (1000 mL). The aqueous phase was extracted with ethyl acetate (3×700 mL), and the combined organic layers were washed successively with water (250 mL) and brine (500 mL), dried over sodium sulfate and concentrated under vacuum to give a crude product. The crude product was purified by silica gel (100-200) column chromatography with 5-10% ethyl acetate in hexane as a mobile phase to give the title compound as an off-white solid (100 g, 81%).

MS (ESI) m/z: 192.9 (M+1); $^1$H NMR (400 MHz, CDCl$_3$): δ 7.48 (d, J=5.2 Hz, 1H), 8.45 (d, J=5.2 Hz, 1H).

Step 3: 2-Chloro-3-nitropyridin-4-ol

To a solution of 2,4-dichloro-3-nitropyridine (100 g, 518 mmol) in N,N-dimethylformamide (500 mL) was added sodium acetate (106 g, 1295 mmol) at room temperature. The mixture was stirred at 120° C. for 5 hours. The reaction completion was confirmed by TLC, then the mixture was cooled to room temperature and diluted with water (500 mL) followed by aqueous 2N HCl solution to adjust the pH<4. The aqueous layer was extracted with ethyl acetate (5×750 mL). The combined organic layers were washed with brine, dried over sodium sulfate and under vacuum to give a crude product. The crude product was triturated with water, and the resulting solid was collected by filtration, and dried under vacuum to give the title compound (63 g, 65%).

MS (ESI) m/z: 175.1 (M+1); $^1$H NMR (400 MHz, DMSO-d$_6$): δ 7.10 (d, J=6.0 Hz, 1H), 8.25 (d, J=5.6 Hz, 1H), 13.10 (br s, 1H).

Preparation 2: 2-Chloro-N-methyl-3-nitropyridin-4-amine

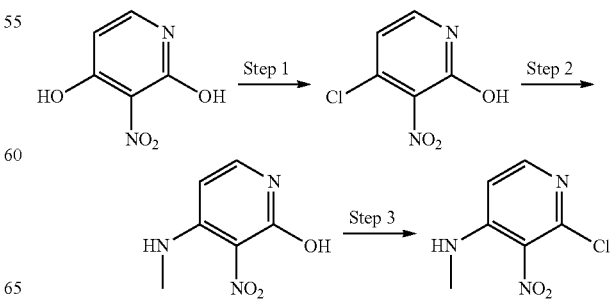

Step 1: 4-Chloro-3-nitropyridin-2-ol

To a mixture of DMF (7 mL) and acetonitrile (75 mL) was added a solution of oxalyl chloride (8.2 mL, 96.15 mmol) in acetonitrile (15 mL) in drop wise manner. After complete addition, the solution was stirred for 10 minute, and 3-nitropyridine-2,4-diol (10 g, 64.10 mmol) was added thereto, and the mixture was continued to stir at room temperature for 30 minutes. The reaction completion was confirmed by TLC, then the acetonitrile was removed under vacuum. The resulting residue was diluted with ice cold water (100 mL), and the precipitated solid was collected by filtration, and washed with cold water (20 mL) followed by n-hexane (20 mL). The obtained solid was dried under vacuum to give the title compound (90 g, 81%).

MS (ESI) m/z: 174.9 (M+1); $^1$H NMR (400 MHz, DMSO-d$_6$): δ 6.59 (d, J=6.8 Hz, 1H), 7.76 (d, J=6.8 Hz, 1H), 13.10 (br s, 1H).

Step 2: 4-(Methylamino)-3-nitropyridin-2-ol

To a solution of 4-chloro-3-nitropyridin-2-ol (4 g, 23 mmol) in acetonitrile (40 mL) were added DIPEA (16.5 mL, 92 mmol) and a solution of methylamine (2 M in THF, 34.5 mL, 69 mmol). The reaction mixture was heated at 100° C. for 2 hours under argon atmosphere. The reaction completion was confirmed by TLC, then the acetonitrile was removed under vacuum. The resulting residue was triturated with diethyl ether (100 mL), and the precipitated solid was collected by filtration, and dried under vacuum to give the title compound (3.7 g, 95%).

MS (ESI) m/z: 169.9 (M+1); $^1$H NMR (400 MHz, DMSO-d$_6$): δ 2.95 (d, J=4.8 Hz, 3H), 5.94 (d, J=7.2 Hz, 1H), 7.39 (d, J=8.0 Hz, 1H), 7.76 (br s, 1H), 8.95 (d, J=3.6 Hz, 1H).

Step 3: 2-Chloro-N-methyl-3-nitropyridin-4-amine

A round bottom flask was charged with 4-(methylamino)-3-nitropyridin-2-ol (3.7 g, 22 mmol) and phosphorous oxychloride (40 mL), and the mixture was heated at 120° C. for 2 hours. The reaction completion was confirmed by TLC, and then the phosphorous oxychloride was removed under vacuum. The resulting residue was diluted with water (100 mL), and the aqueous layer was extracted with ethyl acetate (3×40 mL). The combined organic layers were washed successively with water (50 mL) and brine (40 mL), dried over sodium sulfate and concentrated under vacuum to give the title compound (3.5 g, 85%).

MS (ESI) m/z: 187.9 (M+1); $^1$H NMR (400 MHz, DMSO-d$_6$): δ 2.81 (d, J=4.8 Hz, 3H), 6.87 (d, J=6.4 Hz, 1H), 7.43 (d, J=3.2 Hz, 1H), 8.03 (d, J=6.0 Hz, 1H).

Preparation 3: Methyl 4-[(1S)-1-(3,4-dihydro-2H-pyrido[4,3-b][1,4]oxazin-5-ylamino)ethyl]benzoate

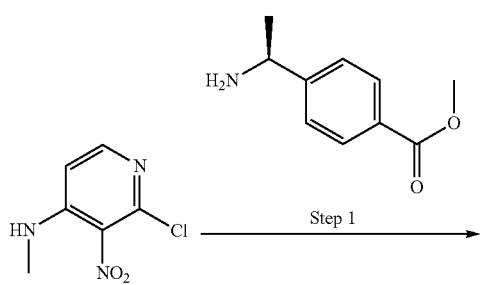

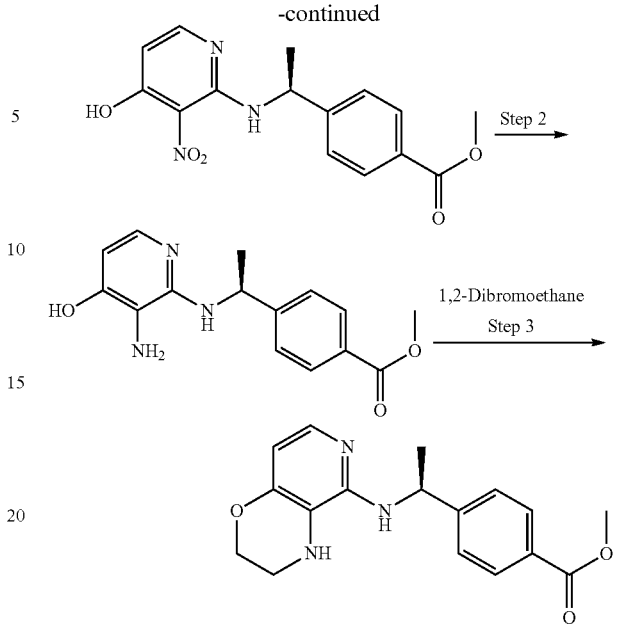

Step 1: Methyl 4-[(1S)-1-[(4-hydroxy-3-nitro-2-pyridyl)amino]ethyl]benzoate

A round bottom flask was charged with a mixture of 2-chloro-3-nitropyridin-4-ol (20 g, 115 mmol) and methyl 4-[(1S)-1-aminoethyl]benzoate (31 g, 173 mmol). The flask was immersed in preheated oil bath at 160° C., and the mixture was stirred for 20-30 mins. The reaction completion was confirmed by TLC, then the mixture was cooled to room temperature, and triturated with ethanol (200 mL). The solid was collected by filtration, washed with cold ethanol (50 mL) and dried under vacuum to give the title compound as a yellow solid (30 g, 83%).

MS (ESI) m/z: 318.1 (M+1); $^1$H NMR (400 MHz, DMSO-d$_6$): δ 1.54 (d, J=6.8 Hz, 3H), 3.83 (s, 3H), 5.25 (br s, 1H), 6.05 (br s, 1H), 7.52 (d, J=8.0 Hz, 2H), 7.93 (d, J=8.4 Hz, 2H), 8.50 (br s, 1H), 11.30 (br s, 1H).

Step 2: Methyl 4-[(1S)-1-[(3-amino-4-hydroxy-2-pyridyl)amino]ethyl]benzoate

A flame dried flask was purged with argon and charged methyl 4-[(1S)-1-[(4-hydroxy-3-nitro-2-pyridyl)amino] ethyl]benzoate (30 g, 95 mmol) and ethyl acetate (600 mL). The flask was degassed for 15 minutes (argon sparge), and Pd/C (6 g, 5.6 mmol, 10% w/w) was added thereto. Hydrogen balloon was placed over it and argon was replaced by hydrogen using vacuum. The reaction mixture was stirred at room temperature for 18 hours under hydrogen atmosphere. After completion of the reaction by TLC, the reaction mixture was passed through celite pad and washed with ethyl acetate (1000 mL). The filtrate and washing were concentrated under vacuum to give the title compound as a light brown solid (25 g, 91%).

MS (ESI) m/z: 288.2 (M+1); $^1$H NMR (400 MHz, DMSO-d$_6$): δ 1.44 (d, J=6.8 Hz, 3H), 3.82 (s, 3H), 5.15-5.30 (m, 1H), 5.76 (d, J=7.2 Hz, 1H), 6.07 (d, J=5.2 Hz, 1H), 7.09 (d, J=5.2 Hz, 1H), 7.48 (d, J=8.4 Hz, 2H), 7.86 (d, J=8.0 Hz, 2H).

Step 3: Methyl 4-[(1S)-1-(3,4-dihydro-2H-pyrido[4,3-b][1,4]oxazin-5-ylamino)ethyl]benzoate To a solution of methyl 4-[(1S)-1-[(3-amino-4-hydroxy-2-pyridyl)amino]ethyl]benzoate (25 g, 87 mmol) in N,N-dimethylformamide (125 mL) were added potassium carbonate (48 g, 348 mmol) and 1,2-dibromoethane (65 g, 348 mmol) at room temperature. The reaction mixture was stirred at 120° C. for 2 hours. The reaction completion was confirmed by TLC, then the mixture was cooled to room temperature. The reaction mixture was diluted with water (500 mL), and the aqueous layer was extracted with ethyl acetate (3×750 mL). The combined organic layers were washed with brine, dried over sodium sulfate and concentrated under vacuum. The obtained residue was dissolved in diethyl ether, and 2M HCl in diethyl ether was added thereto. The resulting solid was collected by filtration and re-dissolved in aqueous bicarbonate solution, and the solution was extracted with ethyl acetate (3×150 mL). The combined organic layers were washed with brine, dried over sodium sulfate and concentrated under vacuum to give the title compound (28 g, 84%).

MS (ESI) m/z: 314.2 (M+1); $^1$H NMR (400 MHz, DMSO-$d_6$): δ 1.56 (d, J=6.8 Hz, 3H), 2.62 (br s, 1H), 3.40 (t, J=3.6 Hz, 2H), 3.89 (s, 3H), 4.16-4.19 (m, 2H), 4.52-4.53 (m, 1H), 5.30-5.31 (m, 1H), 6.21 (d, J=6.0 Hz, 1H), 7.45 (d, J=8.4 Hz, 2H), 7.55 (d, J=5.6 Hz, 1H), 7.97-8.09 (m, 2H).

Preparation 4: Methyl 4-[1-(3,4-dihydro-2H-pyrido[4,3-b][1,4]oxazin-5 ylamino)cyclopropyl]benzoate

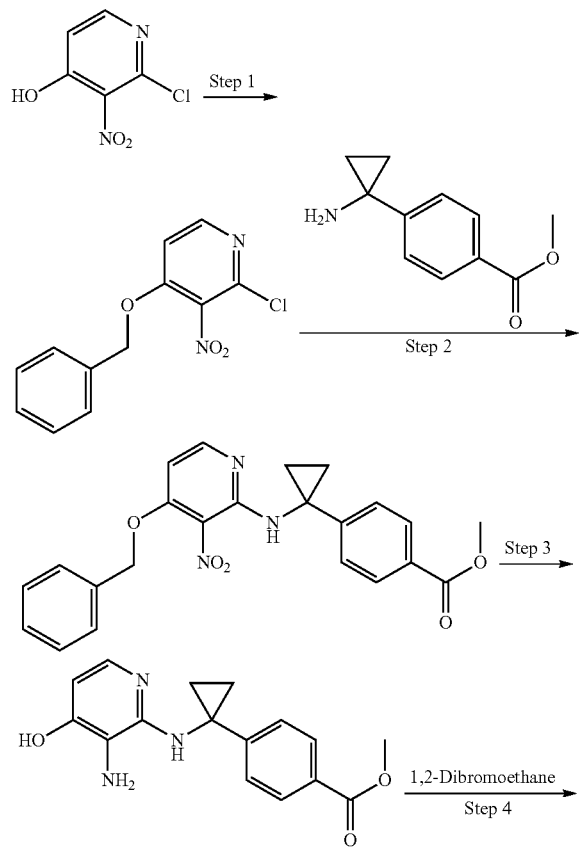

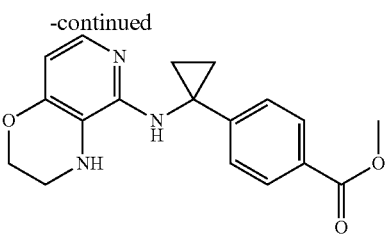

Step 1: 4-Benzyloxy-2-chloro-3-nitropyridine

A round bottom flask was charged with 2-chloro-3-nitropyridin-4-ol (25 g, 144 mmol), benzyl bromide (20.4 mL, 172 mmol), potassium carbonate (39.5 g, 286 mmol) and DMF (125 mL). The reaction mixture was heated at 100° C. for 18 hours, and the reaction completion was confirmed by TLC. The reaction mixture was cooled to room temperature, diluted with water (1.5 L) and extracted with ethyl acetate (3×250 mL). The combined organic layers were washed with brine (500 mL), and dried over sodium sulfate and evaporated under vacuum. The obtained residue was purified by silica gel (100-200) column chromatography with 20-25% ethyl acetate in hexane as a mobile phase to give the title compound as an off-white solid (13 g, 34%).

MS (ESI) m/z: 265.0 (M+1), $^1$H NMR (400 MHz, CDCl$_3$): δ 5.26 (s, 2H), 6.61 (d, J=8.0 Hz, 1H), 7.19-7.21 (m, 2H), 7.42-7.47 (m, 4H).

Step 2: Methyl 4-[1-[(4-benzyloxy-3-nitro-2-pyridyl)amino]cyclopropyl]benzoate A round bottom flask was charged with a mixture of 4-benzyloxy-2-chloro-3-nitropyridine (13.0 g, 49 mmol) and methyl 4-(1-aminocyclopropyl)benzoate (18.8 g, 98 mmol). The flask was immersed in preheated oil bath at 160° C., and the mixture was stirred for 1 hour. The reaction completion was confirmed by TLC, then the mixture was cooled to room temperature, and the residue was triturated with ethanol and filtered to give the title compound as an off-white solid (15 g, 73%).

MS (ESI) m/z: 419.9 (M+1); $^1$H NMR (400 MHz, DMSO-$d_6$); δ 0.64 (dd, J=4.8, 6.8 Hz, 2H), 1.02 (dd, J=6.0, 8.4 Hz, 2H), 3.82 (s, 3H), 5.33 (s, 2H), 6.07 (d, J=7.2 Hz, 1H), 7.04 (d, J=7.6 Hz, 2H), 7.19 (d, J=8.0 Hz, 2H), 7.32-7.36 (m, 1H), 7.42-7.44 (m, 3H), 7.70 (d, J=7.6 Hz, 1H), 7.79 (d, J=8.4 Hz, 2H).

Step 3: Methyl 4-[1-[(3-amino-4-hydroxy-2-pyridyl)amino]cyclopropyl]benzoate A flame dried flask was purged with argon and charged with methyl 4-[1-[(4-benzyloxy-3-nitro-2-pyridyl)amino]cyclopropyl]benzoate (15 g, 35.8 mmol) and methanol:DCM (1:9) (150 mL). The flask was degassed for 15 minutes (argon sparge), and Pd/C (6 g, 5.7 mmol, 10% w/w) was added thereto. Hydrogen balloon was placed over it, and argon was replaced by hydrogen using vacuum. The reaction mixture was stirred at room temperature for 18 hours under hydrogen atmosphere. After completion of the reaction by TLC, the reaction mixture was passed through celite pad and washed with methanol:DCM (1:10) (1500 mL). The filtrate and washing were concentrated under vacuum to give the title compound as a light brown solid (9.3 g, 87%).

MS (ESI) m/z: 300.0 (M+1); $^1$H NMR (400 MHz, DMSO-$d_6$): δ 1.35-1.42 (m, 4H), 3.81 (s, 3H), 6.24 (d, J=6.0 Hz, 1H), 7.11 (d, J=6.4 Hz, 1H), 7.23 (d, J=8.8 Hz, 2H), 7.83 (d, J=8.4 Hz, 2H).

Step 4: Methyl 4-[1-(3,4-dihydro-2H-pyrido[4,3-b][1,4]oxazin-5 ylamino)cyclopropyl]benzoate To a solution of methyl 4-[1-[(3-amino-4-hydroxy-2-pyridyl)amino]cyclopropyl]benzoate (9.3 g, 31 mmol) in N,N-dimethylformamide (90 mL) were added potassium carbonate (17 g, 124 mmol) and 1,2-dibromoethane (23 g, 124 mmol). The reaction mixture was stirred at 120° C. for 2 hours. The reaction completion was confirmed by TLC, then the mixture was cooled to room temperature. The reaction mixture was diluted with water (500 mL), and the aqueous layer was extracted with ethyl acetate (3×350 mL). The combined organic layers were washed with brine, dried over sodium sulfate and concentrated under vacuum. The obtained residue was triturated with diethyl ether, and the solid was collected by filtration and dried under vacuum to give the title compound as an off-white solid (7.44 g, 73%). MS (ESI) m/z: 326.0 (M+1); $^1$H NMR (400 MHz, DMSO-$d_6$): δ 1.26-1.27 (m, 2H), 1.33-1.34 (m, 2H), 3.32-3.33 (m, 2H), 3.81 (s, 3H), 4.12 (t, J=4.0 Hz, 2H), 4.69 (br s, 1H), 6.07 (d, J=6.0 Hz, 1H), 6.40 (br s, 1H), 7.17 (d, J=6.0 Hz, 1H), 7.22 (d, J=8.0 Hz, 2H), 7.80 (d, J=8.4 Hz, 2H).

Preparation 5: Methyl 4-[(1S)-1-[(1-methyl-3,4-dihydro-2H-pyrido[3,4-b]pyrazin-5-yl)amino]ethyl]benzoate

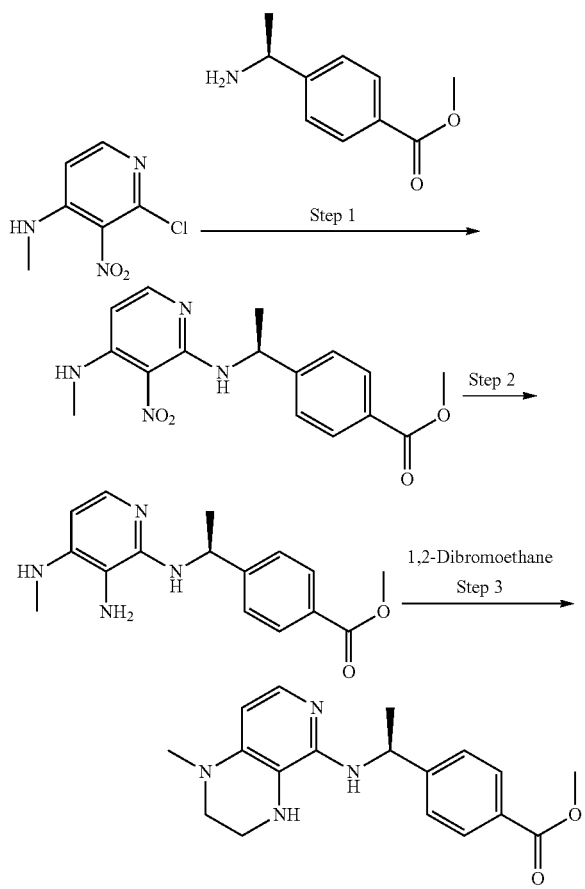

Step 1: Methyl 4-[(1S)-1-[[4-(methylamino)-3-nitro-2-pyridyl]amino]ethyl]benzoate A round bottom flask was charged with a mixture of 2-chloro-N-methyl-3-nitropyridin-4-amine (2.0 g, 16.7 mmol) and methyl 4-[(1S)-1-aminoethyl]benzoate (3.8 g, 21.4 mmol). The flask was immersed in preheated oil bath at 160° C., and the mixture was stirred for 1 hour. The reaction completion was confirmed by TLC, then the mixture was cooled to room temperature, and the residue was diluted with a mixture of methanol and DCM (1:10, 100 mL) to give a crude product. The crude product was purified by silica gel (100-200) column chromatography with 2-5% methanol in DCM as a mobile phase to give the title compound (3.3 g, 94%).

MS (ESI) m/z: 330.9 (M+1); $^1$H NMR (400 MHz, DMSO-$d_6$): δ 1.53 (d, J=6.8 Hz, 3H), 2.91 (d, J=5.2 Hz, 3H), 3.83 (s, 3H), 5.46 (m, J=6.8 Hz, 1H), 6.08 (d, J=6.0 Hz, 1H), 7.50 (d, J=8.0 Hz, 2H), 7.72 (d, J=6.4 Hz, 1H), 7.90 (d, J=8.4 Hz, 2H), 9.11 (d, J=4.8 Hz, 1H), 9.23 (d, J=7.2 Hz, 1H).

Step 2: Methyl 4-[(1S)-1-[[3-amino-4-(methylamino)-2-pyridyl]amino]ethyl]benzoate A flame dried flask was purged with argon and charged with methyl 4-[(1S)-1-[[4-(methylamino)-3-nitro-2-pyridyl]amino]ethyl]benzoate (3.3 g, 10 mmol) and ethyl acetate (65 mL). The flask was degassed for 15 minutes (argon sparge), and Pd/C (0.66 g, 0.63 mmol, 10% w/w) was added thereto. Hydrogen balloon was placed over it, and argon was replaced by hydrogen using vacuum. The reaction mixture was stirred at room temperature for 18 hours under hydrogen atmosphere. After completion of the reaction by TLC, the reaction mixture was passed through celite pad and washed with ethyl acetate (150 mL). The filtrate and washing were concentrated under vacuum to give the title compound as an off-white solid (2.4 g, 80%)

MS (ESI) m/z: 301.0 (M+1); $^1$H NMR (400 MHz, DMSO-$d_6$): δ 1.43 (d, J=7.2 Hz, 3H), 2.69 (d, J=5.2 Hz, 3H), 3.82 (s, 3H), 3.85 (br s, 2H), 5.15 (d, J=4.8 Hz, 1H), 5.23 (m, J=6.8 Hz, 1H); 5.57 (d, J=7.6 Hz, 1H), 5.89 (d, J=5.6 Hz, 1H), 7.21 (d, J=5.6 Hz, 1H), 7.47 (d, J=8.4 Hz, 2H), 7.85 (d, J=8.4 Hz, 2H).

Step 3: Methyl 4-[(1S)-1-[(1-methyl-3,4-dihydro-2H-pyrido[3,4-b]pyrazin-5-yl)amino]ethyl]benzoate To a solution of methyl 4-[(1S)-1-[[3-amino-4-(methylamino)-2-pyridyl]amino]ethyl]benzoate (2.4 g, 8 mmol) in N,N-dimethylformamide (25 mL) were added potassium carbonate (4.4 g, 32 mmol) and 1,2-dibromoethane (2.74 mL, 32 mmol). The reaction mixture was stirred at 120° C. for 2 hours. The reaction completion was confirmed by TLC, then the mixture was cooled to room temperature and diluted with water (200 mL), and the aqueous layer was extracted with ethyl acetate (3×50 mL). The combined organic layers were washed with brine, dried over sodium sulfate and concentrated under vacuum to give the title compound as a solid product (2.1 g, crude), which was used in the next step without further purification.

MS (ESI) m/z: 327.0 (M+1).

The compounds of Preparations 6-8 were synthesized in a similar manner to that of Preparation 3.

TABLE 1

| Pre. No. | Structure | IUPAC Name | MS(ESI)m/z: (M + 1) |
|---|---|---|---|
| 6 | 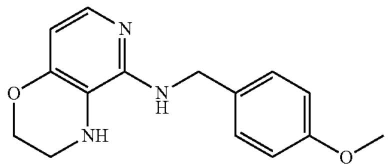 [SMILES: COc1ccc(CNc2nccc3c2NCCO3)cc1] | N-[(4-methoxyphenyl)methyl]-3,4-dihydro-2H-pyrido[4,3-b][1,4]oxazin-5-amine | 271.9 |
| 7 | 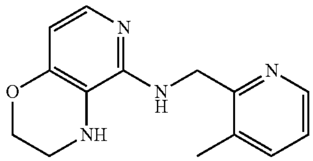 [SMILES: Cc1cccnc1CNc1nccc2c1NCCO2] | N-[(3-methyl-2-pyridyl)methyl]-3,4-dihydro-2H-pyrido[4,3-b][1,4]oxazin-5-amine | 256.8 |
| 8 | 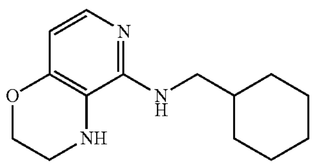 [SMILES: c1cc2c(c(NCC3CCCCC3)n1)NCCO2] | N-(cyclohexylmethyl)-3,4-dihydro-2H-pyrido[4,3-b][1,4]oxazin-5-amine | 247.8 |

Preparation 9: Methyl 4-[(1S)-1-[(3-oxo-4H-pyrido[4,3-b][1,4]thiazin-5-yl)amino]ethyl]benzoate

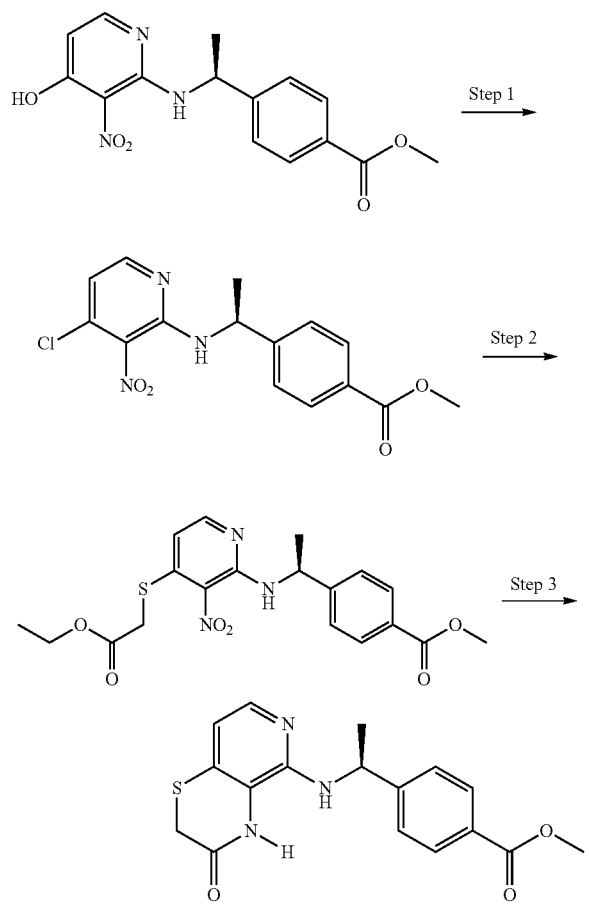

Step 1: Methyl 4-[(1S)-1-[(4-chloro-3-nitro-2-pyridyl)amino]ethyl]benzoate

A mixture of methyl 4-[(1S)-1-[(4-hydroxy-3-nitro-2-pyridyl)amino]ethyl]benzoate (4.5 g, 14.19 mmol) and POCl$_3$ (45 mL) was heated at 110° C. for 1 hour. The product formation was confirmed by TLC. The mixture was evaporated to dryness then quenched by aq. sodium bicarbonate solution, and the obtained solid was collected by thltration, washed with n-hexane and dried to give the title compound (4.0 g, 84%).

MS (EI) m/z: 336.0 (M+1); $^1$H NMR (400 MHz, DMSO-d$_6$): δ 1.48 (d, J=6.8 Hz, 3H), 3.82 (s, 3H), 5.33-5.37 (m, 1H), 6.86 (d, J=5.2 Hz, 1H), 7.50 (d, J=8.4 Hz, 2H), 7.79 (d, J=7.2 Hz, 1H), 7.90 (d, J=8.4 Hz, 2H), 8.08 (d, J=5.2 Hz, 1H).

Step 2: Methyl 4-[(1S)-1-[[4-(2-ethoxy-2-oxoethyl)sulfanyl-3-nitro-2-pyridyl]amino]ethyl]benzoate To a solution of methyl 4-[(1S)-1-[(4-chloro-3-nitro-2-pyridyl)amino]ethyl]benzoate (2.0 g, 5.97 mmol) in acetone (30 mL) were added triethylamine (0.83 mL, 5.97 mmol) and ethyl mercaptoacetate (0.65 mL, 5.97 mmol), and the mixture was heated at 60° C. under nitrogen for 2 hours. The product formation was confirmed by TLC. The reaction mixture was cooled to room temperature, then filtered through celite pad, and washed with acetone, and the filtrate was evaporated under vacuo to give the title compound (2.4 g, 96%).

MS (EI) m/z: 420.2 (M+1); $^1$H NMR (400 MHz, CDCl$_3$): δ 1.24-1.28 (m, 3H), 1.62 (d, J=6.8 Hz, 3H), 3.65 (s, 2H), 3.90 (s, 3H), 4.17-4.24 (m, 2H), 5.49-5.53 (m, 1H), 6.55 (d, J=5.2 Hz, 1H), 7.42 (d, J=8.0 Hz, 2H), 7.97-8.00 (m, 3H), 8.94 (d, J=6.8 Hz, 1H).

Step 3: Methyl 4-[(1S)-1-[(3-oxo-4H-pyrido[4,3-b][1,4]thiazin-5-yl)amino]ethyl]benzoate To a solution of methyl 4-[(1S)-1-[[4-(2-ethoxy-2-oxoethyl)sulfanyl-3-nitro-2-pyridyl]amino]ethyl]benzoate (2.4 g, 5.72 mmol) in acetic acid (30 mL) was added iron powder (5.72 g, 103.10 mmol). The reaction mixture was stirred and heated at 90° C. for 1 hour, and the product formation was confirmed by TLC. The reaction mixture was cooled to room temperature, and evaporated to dryness. Aq. NaHCO$_3$ solution (20 mL) was added thereto, and the mixture was extracted with ethyl acetate (3×25 mL). The combined organic layers were washed with brine (25 mL) and dried over sodium sulfate. The organic layer was evaporated under vacuo to give the title compound (1.85 g, 94%).

MS (EI) m/z: 344.0 (M+1) $^1$H NMR (400 MHz, DMSO-d$_6$): δ 1.47 (d, J=6.8 Hz, 3H), 3.49 (s, 2H), 3.82 (s, 3H), 5.21-5.24 (m, 1H), 5.53 (d, J=4.8 Hz, 1H), 6.68 (d, J=6.8 Hz, 1H), 7.49-7.51 (m, 3H), 7.89 (d, J=8.0 Hz, 2H), 10.06 (br s, 1H).

Preparation 10: Methyl 4-[(1S)-1-(1,2,3,4-tetra-hydro-1,7-naphthyridin-8-ylamino)ethyl]benzoate

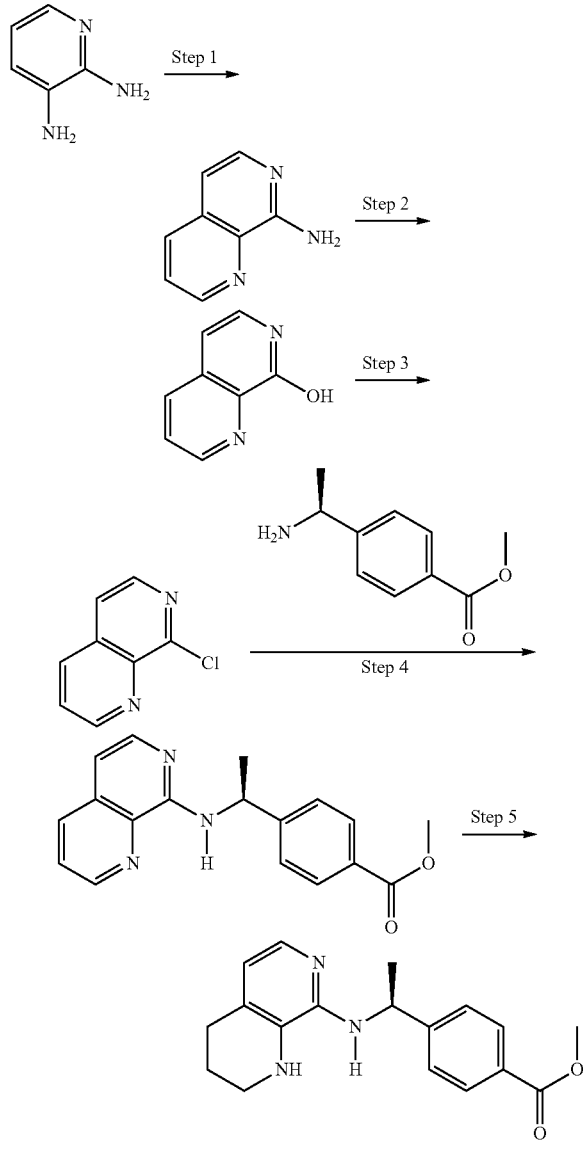

Step 1: 1,7-Naphthyridin-8-amine

To a mixture of pyridine-2,3-diamine (10.0 g, 91.74 mmol), sodium 3-nitrobenzenesulfonate (41.3 g, 183.5 mmol) and glycerol (33.5 mL, 458.7 mmol) were added water (60 mL) and sulfuric acid (40 mL). The reaction mixture was heated at 135° C. for 6 days. The product formation was confirmed by TLC. The mixture was cooled to room temperature, and poured into ice-cold water. The pH of the mixture was adjusted to 8-9 with saturated NaOH solution (aq.). The aqueous layer was extracted with ethyl acetate (3×100 mL). The combined organic layers were washed with brine (100 mL) and dried over sodium sulfate. The organic layer was evaporated under vacuo, then the crude material was purified by column chromatography using 5-10% methanol in DCM as a mobile phase to give the title compound (3.0 g, 22%).

MS (EI) m/z: 145.8 (M+1); $^1$H NMR (400 MHz, DMSO-d$_6$): δ 6.90-6.92 (m, 3H), 7.67 (dd, J=3.6 & 8.0 Hz, 1H), 7.86 (d, J=6.0 Hz, 1H), 8.16 (dd, J=2.0 & 8.4 Hz, 1H), 8.78 (dd, J=1.2, 4.0 Hz, 1H).

Step 2: 1,7-Naphthyridin-8-ol

To a mixture of 1,7-naphthyridin-8-amine (3.0 g, 20.7 mmol) in water (5.6 mL) and sulfuric acid (24 mL, 455.2 mmol) was added sodium nitrite (1.42 g, 20.7 mmol) at 0° C. The reaction mixture was stirred at room temperature for 18 hours. The product formation was confirmed by TLC. To the reaction mixture was added aq. NaHCO$_3$ solution, and the mixture was extracted with chloroform:methanol (9:1) (3×50 mL). The combined organic layers were washed with brine (50 mL) and dried over sodium sulfate. The organic layer was evaporated under vacuo to give the title compound (2.0 g, 67%).

MS (EI) m/z: 147.1 (M+1); $^1$H NMR (400 MHz, DMSO-d$_6$): δ 6.54 (d, J=7.2 Hz, 1H), 7.26 (d, J=6.8 Hz, 1H), 7.67 (dd, J=4.0, 8.0 Hz, 1H), 8.10 (dd, J=2.0, 8.4 Hz, 1H), 8.74-8.75 (m, 1H), 11.55 (br s, 1H).

Step 3: 8-Chloro-1,7-naphthyridine

A solution of 1,7-naphthyridin-8-ol (2.0 g, 13.7 mmol) in POCl$_3$ (20 mL) was heated at 100° C. for 16 hours, and the product formation was confirmed by TLC. The reaction mixture was cooled to room temperature, and evaporated to dryness. Aq. NaHCO$_3$ solution (20 mL) was added thereto, and the mixture was extracted with ethyl acetate (3×25 mL). The combined organic layers were washed with brine (25 mL) and dried over sodium sulfate. The organic layer was evaporated under vacuo, and the residue was purified by column chromatography using 2-5% methanol in DCM as a mobile phase to give the title compound (1.4 g, 62%).

MS (EI) m/z: 165.3 (M+1); $^1$H NMR (400 MHz, DMSO-d$_6$): δ 7.64 (d, J=6.0 Hz, 1H), 7.70 (dd, J=4.0 & 8.4 Hz, 1H), 8.22 (dd, J=1.6 & 8.4 Hz, 1H), 8.40 (d, J=6.0 Hz, 1H), 9.15 (dd, J=1.6 & 4.0 Hz, 1H)

Step 4: Methyl 4-[(1S)-1-(1,7-naphthyridin-8-ylamino)ethyl]benzoate

A mixture of 8-chloro-1,7-naphthyridine (1.4 g, 8.5 mmol) and methyl 4-[(1S)-1-aminoethyl]benzoate (1.52 g, 8.5 mmol) was stirred in preheated oil bath at 150° C. for 6 hours. The product formation was confirmed by TLC. The reaction mixture was cooled to room temperature, diluted with mixture of methanol and DCM (1:10, 20 mL), adsorbed on silica gel, and purified by combiflash column chromatography with 20-25% ethyl acetate in hexane as a mobile phase to give the title compound (1.5 g, 57%).

MS (ESI) m/z: 308.3 (M+1); $^1$H NMR (400 MHz, CDCl$_3$); δ 1.69 (d, J=7.2 Hz, 3H), 3.88 (s, 3H), 4.95-5.15 (m, 1H), 6.79 (d, J=6.0 Hz, 1H), 7.18-7.22 (m, 1H), 7.50-7.54 (m, 3H), 7.92-8.00 (m, 4H), 8.73 (dd, J=2.0 & 4.4 Hz, 1H).

Step 5: Methyl 4-[(1S)-1-(1,2,3,4-tetrahydro-1,7-naphthyridin-8-ylamino)ethyl]benzoate To a suspension of methyl 4-[(1S)-1-(1,7-naphthyridin-8-ylamino)ethyl]benzoate (1.5 g, 4.88 mmol) in methanol (30 mL) was added Pd(OH)$_2$ (0.3 g, 20% w/w) under argon atmosphere. Hydrogen balloon was placed over it and argon was replaced by hydrogen using vacuum. The reaction mixture was stirred at room temperature for 2 days under hydrogen atmosphere, and the product formation was confirmed by TLC. The reaction mixture was filtered through celite pad, washed with methanol:DCM (1:10, 150 mL), and the filtrated was concentrated under vacuum. The residue was purified by combiflash column chromatography using 10-15% ethyl acetate in hexane as mobile phase to give the title compound (1.2 g, 79%).

MS (ESI) m/z: 312.0 (M+1); $^1$H NMR (400 MHz, DMSO-d$_6$): δ 1.44 (d, J=6.8 Hz, 3H), 1.76-1.78 (m, 2H), 2.56 (t, J=6.4 Hz, 2H), 3.26 (t, J=6.0 Hz, 2H), 3.82 (s, 3H), 4.97 (br s, 1H), 5.21-5.24 (m, 1H), 7.78 (d, J=6.8 Hz, 1H), 6.15 (d, J=4.8 Hz, 1H), 7.12 (d, J=4.8 Hz, 1H), 7.48 (d, J=8.4 Hz, 2H), 7.86-7.88 (m, 2H)

Preparation 11: Methyl 4-[(1S)-1-[(6-oxo-5H-pyrimido[4,5-b][1,4]oxazin-4-yl)amino]ethyl]benzoate

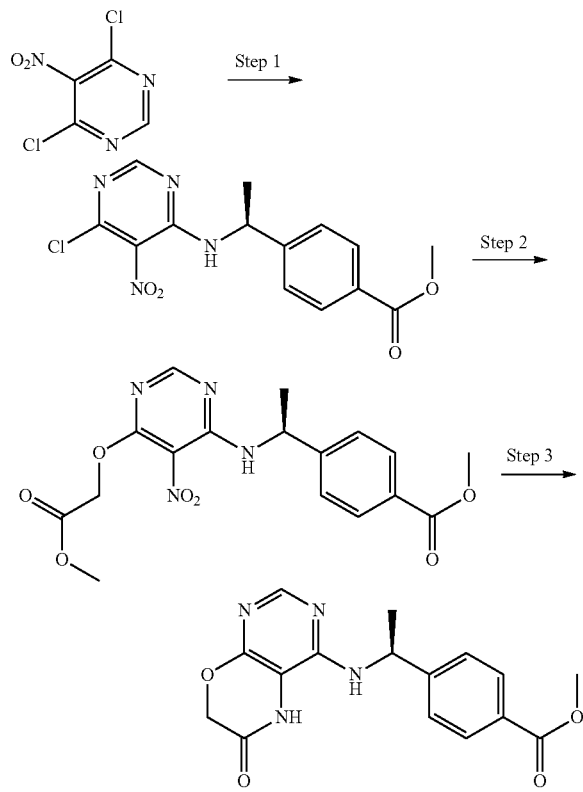

Step 1: Methyl 4-[(1S)-1-[(6-chloro-5-nitropyrimidin-4-yl)amino]ethyl]benzoate A solution of 4,6-dichloro-5-nitropyrimidine (3.0 g, 15.46 mmol) and methyl 4-[(1S)-1-aminoethyl]benzoate (2.77 g, 15.46 mmol) in tetrahydrofuran (60.0 mL) was cooled to 0° C. To the above mixture was added triethylamine (6.5 mL, 46.4 mmol). The reaction mixture was stirred at room temperature for 2.0 hours. Progress of the reaction was monitored by TLC. After completion of the reaction, the reaction mixture was diluted with water (100 mL) and extracted with ethyl acetate (3×100 mL). The combined organic layers were washed with water (100 mL) and brine (100 mL), and dried over sodium sulfate. The organic layer was evaporated under vacuum, and the residue was purified by combiflash with 8-12% ethyl acetate in hexane as a mobile phase to give the title compound as solid (3.5 g, 67%).

MS (ESI) m/z: (M+1) 337.2 [M($^{35}$Cl)+1]; 339.2 [M($^{37}$Cl)+1]; $^1$H NMR CDCl$_3$: δ 1.64 (d, J=6.8 Hz, 3H), 3.91 (s, 3H), 5.48-5.52 (m, 1H), 7.40 (d, J=8.4 Hz, 2H), 7.80 (d, J=7.6 Hz 1H), 8.03 (m, 2H), 8.34 (s, 1H)

Step 2: Methyl 4-[(1S)-1-[[6-(2-methoxy-2-oxoethoxy)-5-nitropyrimidin-4-yl]amino]ethyl]benzoate To a solution of methyl 4-[(1S)-1-[(6-chloro-5-nitropyrimidin-4-yl)amino]ethyl]benzoate (2.9 g, 8.6 mmol) and methyl glycolate (0.8 mL, 10.3 mmol) in tetrahydrofuran (50 mL) was added slowly potassium tert-butoxide (1M in THF) (10.33 mL, 10.33 mmol). The reaction mixture was stirred at room temperature for 3 hours. Progress of the reaction was monitored by TLC. After completion of the reaction, the reaction mixture was diluted with water (25 mL) and extracted with ethyl acetate (3×50 mL). The combined organic layers were washed with water (25 mL) and brine (25 mL), and dried over sodium sulfate. The organic layer was evaporated under vacuum, and the residue was purified by combiflash with 15-20% ethyl acetate in hexane as a mobile phase to give the title compound as solid (2.7 g, 80%).

MS (ESI) m/z: (M+1) 391.2; $^1$H NMR CDCl$_3$: δ 1.63 (d, J=7.6 Hz, 3H), 3.77 (s, 3H), 3.91 (s, 3H), 5.03 (s, 2H), 5.52-5.56 (m, 1H), 7.41 (d, J=8.4 Hz, 2H), 8.02 (m, 2H), 8.14 (s, 1H), 8.71 (d, J=6.8 Hz 1H)

Step 3: Methyl 4-[(1S)-1-[(6-oxo-5H-pyrimido[4,5-b][1,4]oxazin-4-yl)amino]ethyl]benzoate A mixture of methyl 4-[(1S)-1-[[6-(2-methoxy-2-oxoethoxy)-5-nitropyrimidin-4-yl]amino]ethyl]benzoate (2.5 g, 6.4 mmol) and iron powder (1.4 g, 25.6 mmol) in acetic acid (12.5 mL) was heated at 100° C. for 3 hours. Progress of the reaction was monitored by TLC. After completion of the reaction, acetic acid was evaporated, and the residue was dissolved in water, and the solution was basified with saturated sodium bicarbonate solution to pH 9. The aqueous layer was extracted with ethyl acetate (3×50 mL). The combined organic layers were washed with water (25 mL) and brine (25 mL), and dried over sodium sulfate. The organic layer was evaporated under vacuum, and the residue was purified by combiflash with 50% ethyl acetate in hexane as a mobile phase to give the title compound as solid (1.7 g, 74%).

MS (ESI) m/z: (M+1) 329.0;

$^1$H NMR CDCl$_3$: δ 1.59 (d, J=6.8 Hz, 3H), 3.91 (s, 3H), 4.73-4.83 (m, 2H), 5.41-5.45 (m, 1H), 5.95 (d, J=6.8 Hz, 1H), 7.43 (d, J=8.4 Hz, 2H), 7.99 (m, 2H), 8.07 (s, 1H), 10.82 (s, 1H).

Preparation 12: 4-Chloro-5-[(3-chlorophenyl)methyl]-6,7-dihydropyrimido[4,5-b][1,4]oxazine

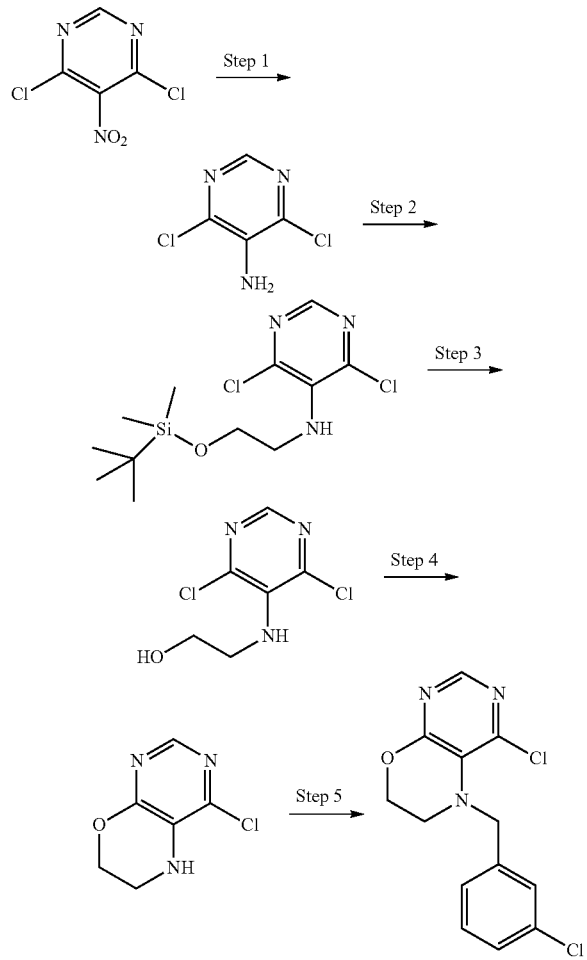

Step 1: 4,6-dichloropyrimidin-5-amine

To a suspension of 4,6-dichloro-5-nitropyrimidine (15 g, 77.3 mmol) in a mixture of ethanol (75 mL) and H$_2$O (4.5 mL) were added iron powder (12.95 g, 231.98 mmol) and CaCl$_2$ (8.58 g, 77.32 mmol). The resulting suspension was stirred at 60° C. for 30 min. Progress of the reaction was monitored by TLC. After completion of the reaction, the reaction mixture was filtered to remove the iron residues, which were washed with ethyl acetate (2×20 mL). The combined organic extracts were washed with H$_2$O (3×10 mL) and brine (2×10 mL), and dried over Na$_2$SO$_4$. The organic layer was evaporated under vacuum, and the residue was directly loaded onto a silica column and eluted using 20% ethyl acetate in hexane to give the title compound (3.6 g, 28%).

MS (ESI) m/z: 164.3 [M($^{35}$Cl)+1], 166.3 [M($^{37}$Cl)+1]; $^1$H NMR CDCl$_3$: δ 4.50 (br s, 2H), 8.21 (s, 1H).

Step 2: N-[2-[tert-butyl(dimethyl)silyl]oxyethyl]-4,6-dichloropyrimidin-5-amine

A solution of 4,6-dichloropyrimidin-5-amine (1.0 g, 6.1 mmol) and 2-bromoethoxy-tert-butyl(dimethyl)silane (1.56 mL, 7.32 mmol) in N,N-dimethylformamide (10.0 mL) was cooled to 0° C. To the above mixture was added sodium hydride (60% on oil) (0.29 g, 7.3 mmol). The reaction mixture was stirred at room temperature for 5 hours. Progress of the reaction was monitored by TLC. After completion of the reaction, the reaction mixture was diluted with water (50 mL). The aqueous layer was extracted with ethyl acetate (3×25 mL). The combined organic layers were washed with water (25 mL) and brine (25 mL), and dried over sodium sulfate. The organic layer was evaporated under vacuum, and the residue was purified by combiflash with 5-10% ethyl acetate in hexane as a mobile phase to give the title compound as oil (0.87 g, 43%).

MS (ESI) m/z: (M+1) 322.0 [M($^{35}$Cl)+1], 323.9 [M($^{37}$Cl)+1]; $^1$H NMR CDCl$_3$: δ 0.07 (s, 6H), 0.90 (s, 9H), 3.57-3.61 (m, 2H), 3.78 (t, J=4.8 Hz, 2H), 4.74 (br s, 1H), 8.24 (s, 1H).

Step 3: 2-[(4,6-dichloropyrimidin-5-yl)amino]ethanol

A solution of N-[2-[tert-butyl(dimethyl)silyl]oxyethyl]-4,6-dichloropyrimidin-5-amine (1.7 g, 5.27 mmol) in tetrahydrofuran (20.0 mL) was cooled to 0° C. To the solution was added slowly tetrabutylammonium fluoride (1M in THF) (5.3 mL, 5.3 mmol). The reaction mixture was stirred at room temperature for 2 hours. Progress of the reaction was monitored by TLC. After completion of the reaction, the reaction mixture was diluted with water (50 mL). The aqueous layer was extracted with ethyl acetate (3×25 mL). The combined organic layers were washed with saturated NaHCO$_3$ (25 mL) and brine (25 mL), and dried over sodium sulfate. The organic layer was evaporated under vacuum, and the residue was purified by combiflash with 20-25% ethyl acetate in hexane as a mobile phase to give the title compound as oil (1.0 g, 91%).

MS (ESI) m/z: 207.5; $^1$H NMR (400 M Hz, CDCl$_3$): δ 1.76 (br s, 1H), 3.62-3.66 (m, 2H), 3.82-3.85 (m, 2H), 4.59 (br s, 1H), 8.28 (s, 1H).

Step 4: 4-Chloro-6,7-dihydro-5H-pyrimido[4,5-b][1,4]oxazine

To a solution of 2-[(4,6-dichloropyrimidin-5-yl)amino]ethanol (1.0 g, 4.80 mmol) in tetrahydrofuran (10.0 mL) was added slowly potassium tert-butoxide (1M in THF) (7.20 mL, 7.20 mmol). The reaction mixture was stirred at room temperature for 4 hours. Progress of the reaction was monitored by TLC. After completion of the reaction, the reaction mixture was diluted with water (25 mL). The aqueous layer was extracted with ethyl acetate (3×25 mL). The combined organic layers were washed with water (25 mL) and brine (25 mL), and dried over sodium sulfate. The organic layer was evaporated under vacuum, and the residue was purified by combiflash with 25-30% ethyl acetate in hexane as a mobile phase to give the title compound as solid (0.4 g, 49%).

MS (ESI) m/z: (M+1) 172.3.0 [M($^{35}$Cl)+1], 174.3 [M($^{37}$Cl)+1]; $^1$H NMR CDCl$_3$: δ 3.53-3.56 (m, 2H), 4.27 (br s, 1H), 4.51 (t, J=4.6 Hz, 2H), 8.06 (s, 1H)

Step 5: 4-Chloro-5-[(3-chlorophenyl)methyl]-6,7-dihydropyrimido[4,5-b][1,4]oxazine A solution of 4-chloro-6,7-dihydro-5H-pyrimido[4,5-b][1,4]oxazine (0.15 g, 0.87 mmol) in N,N-dimethylformamide (5.0 mL) was cooled to 0° C. To the above mixture was added sodium hydride (60% on oil) (0.052 g, 1.31 mmol). 3-Chlorobenzyl bromide (0.16 mL, 1.31 mmol) was added thereto after 15 min. The reaction mixture was stirred at room temperature for 2.0 hours. Progress of the reaction was monitored by TLC. After completion of the reaction, the reaction mixture was diluted with water (50 mL). The aqueous layer was extracted with ethyl acetate (3×25 mL). The combined organic layers were washed with water (25 mL) and brine (25 mL), and dried over sodium sulfate. The organic layer was evaporated under vacuum, and the residue was purified by combiflash with 5-10% ethyl acetate in hexane as a mobile phase to give the title compound as solid (0.2 g, 77%)

MS (ESI) m/z: (M+1) 295.8 [M($^{35}$Cl)+1], 297.8 [M($^{37}$Cl)+1]; $^1$H NMR CDCl$_3$: δ 3.06 (t, J=4.6 Hz, 2H), 4.25 (s, 2H), 4.41 (t, J=4.8 Hz, 2H), 7.26-7.33 (m, 2H), 7.38-7.41 (m, 1H), 7.54 (s. 1H), 8.34 (s, 1H).

Example A1: Methyl 4-[(1S)-1-[(4-benzyl-2,3-dihydropyrido[4,3-b][1,4]oxazin-5-yl)amino]ethyl]benzoate

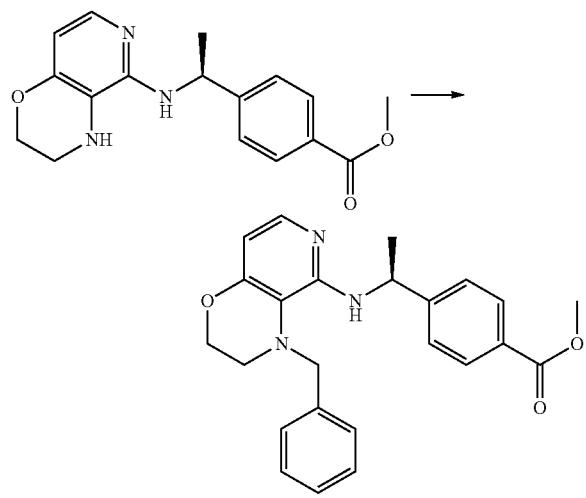

To a solution methyl 4-[(1S)-1-(3,4-dihydro-2H-pyrido[4,3-b][1,4]oxazin-5-ylamino)ethyl]benzoate (Preparation 3, 0.15 g, 0.43 mmol) in N,N-dimethylformamide (10 mL) were added potassium carbonate (0.21 g, 1.50 mmol) and benzyl bromide (0.09 g, 0.52 mmol) at room temperature. The mixture was stirred at 120° C. for 2 hours. The reaction completion was confirmed by TLC, then the mixture was cooled to room temperature, water (20 mL) was added thereto, and the aqueous layer was extracted with ethyl acetate (3×20 mL). The combined organic layers were washed with brine and dried over sodium sulfate. The organic layer was evaporated under vacuum, and the residue was purified by silica gel (100-200) column chromatography with 10-20% ethyl acetate in hexane as a mobile phase to give the title compound as colorless oil (0.115 g, 66%).

MS (ESI) m/z: 404.2 (M+1); $^1$H NMR (400 MHz, CDCl$_3$): δ 1.49 (d, J=6.4 Hz, 3H), 3.04 (t, J=4.0 Hz, 2H), 3.88 (s, 3H), 4.02 (d, J=3.2 Hz, 2H), 4.21 (t, J=4.8 Hz, 2H), 5.11 (d, J=6.4 Hz, 1H), 5.20-5.26 (m, 1H), 6.22 (d, J=6.0 Hz, 1H), 7.36-7.32 (m, 3H), 7.43-7.38 (m, 4H), 7.66 (d, J=5.6 Hz, 1H), 7.92 (d, J=8.0 Hz, 2H).

Example A2: Methyl 4-[(1S)-1-[[4-[(3-chlorophenyl)methyl]-2,3-dihydropyrido[4,3-b][1,4]oxazin-5-yl]amino]ethyl]benzoate

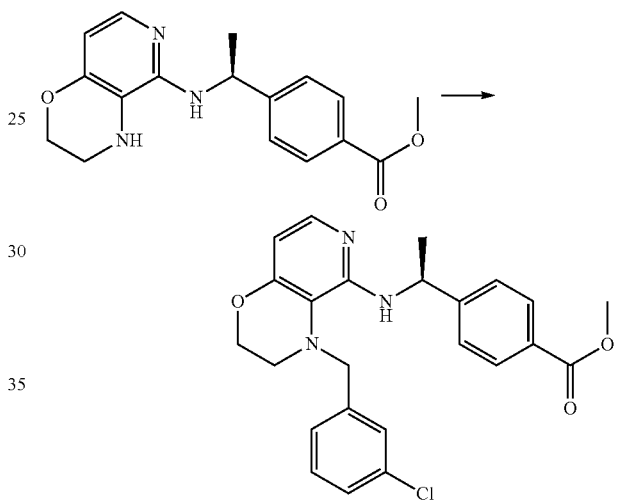

To a solution of methyl 4-[(1S)-1-(3,4-dihydro-2H-pyrido[4,3-b][1,4]oxazin-5-ylamino)ethyl]benzoate (Preparation 3, 20 g, 52 mmol) in N,N-dimethylformamide (200 mL) were added potassium carbonate (60 g, 156 mmol) and 3-chlorobenzyl bromide (12.8 g, 62 mmol) at room temperature. The mixture was stirred at 120° C. for 2 hours. The reaction completion was confirmed by TLC, then the mixture was cooled to room temperature, water (500 mL) was added thereto, and the aqueous layer was extracted with ethyl acetate (3×750 mL). The combined organic layers were washed with brine and dried over sodium sulfate. The organic layer was evaporated under vacuum, and the residue was purified by silica gel (100-200) column chromatography with 10-20% ethyl acetate in hexane as a mobile phase to give the title compound as colorless oil (15 g, 65%).

MS (ESI) m/z: 438.0 (M+1); $^1$H NMR (400 MHz, CDCl$_3$): δ 1.49 (d, J=6.8 Hz, 3H), 3.04 (t, J=4.8 Hz, 2H), 3.89 (s, 3H), 3.98 (s, 2H), 4.21 (m, 2H), 4.98 (d, J=6.8 Hz, 1H), 5.30-5.24 (m, 1H), 6.27 (d, J=5.6 Hz, 1H), 7.35-7.25 (m, 5H), 7.43 (s, 1H), 7.67 (d, J=6.0 Hz, 1H), 7.93 (d, J=8.4 Hz, 2H).

Example A3: Methyl 4-[(1S)-1-[[4-[2-(4-fluorophenoxy)ethyl]-2,3-dihydropyrido[4,3-b][1,4]oxazin-5-yl]amino]ethyl]benzoate Example A4: Methyl 4-[1-[[4-[(3,4-difluorophenyl)methyl]-2,3-dihydropyrido[4,3-b][1,4]oxazin-5-yl]amino]cyclopropyl]benzoate

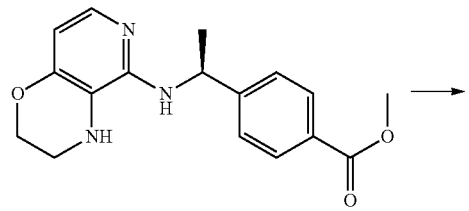

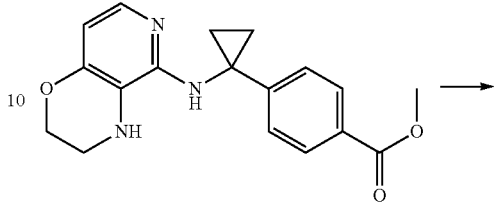

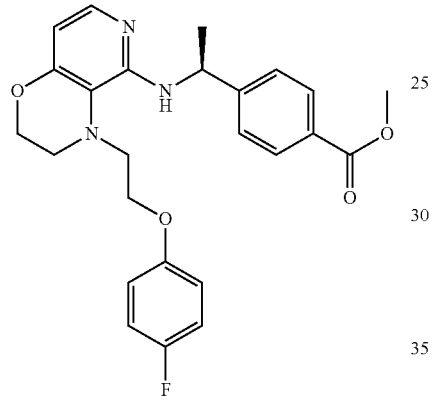

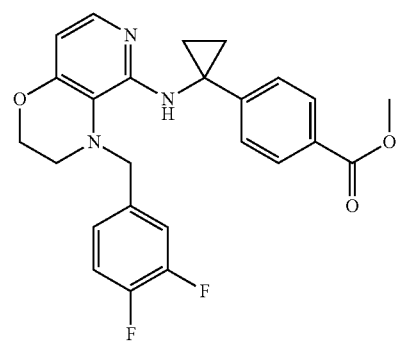

The title compound was obtained as an oil (0.16 g, 62%) in a similar manner to that of Example A2 using the compound obtained in Preparation 3 (0.20 g, 0.57 mmol) and 1-(2-bromoethoxy)-4-fluoro-benzene (0.15 g, 0.68 mmol).

MS (ESI) m/z: 452.3 (M+1).

The title compound was obtained as an off-white solid (6 g, 87%) in a similar manner to that of Example A2 using the compound obtained in Preparation 4 (5.0 g, 15.4 mmol) and 3,4-difluorobenzyl bromide (3.8 g, 18.4 mmol).

MS (ESI) m/z: 451.9 (M+1); $^1$H NMR (400 MHz, CDCl$_3$): δ 1.43-1.46 (m, 2H), 1.31-1.34 (m, 2H), 1.43-1.46 (m, 2H), 3.05 (t, J=4.4 Hz, 2H), 3.87 (s, 3H), 3.96 (s, 2H), 4.22 (t, J=4.4 Hz, 2H), 5.42 (br s, 1H), 6.26 (d, J=6.0 Hz, 1H), 7.15-7.22 (m, 4H), 7.26-7.30 (m, 1H), 7.70 (d, J=6.0 Hz, 1H), 7.89 (d, J=8.4 Hz, 2H).

The compounds of Examples A5-A35 were synthesized in a similar manner to that of Examples A1-A4.

TABLE 2

| Ex. No. | Structure | IUPAC Name | MS(ESI)m/z: (M + 1) |
|---|---|---|---|
| A5 | 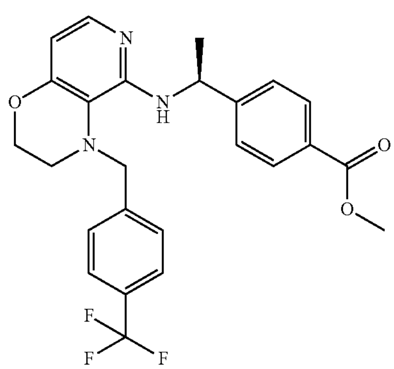 [SMILES: COC(=O)c1ccc([C@H](C)Nc2nccc3c2N(Cc2ccc(C(F)(F)F)cc2)CCO3)cc1] | methyl 4-[(1S)-1-[[4-[[4-(trifluoromethyl)phenyl]methyl]-2,3-dihydropyrido[4,3-b][1,4]oxazin-5-yl]amino]ethyl]benzoate | 472.2 |

TABLE 2-continued

| Ex. No. | Structure | IUPAC Name | MS(ESI)m/z: (M + 1) |
|---|---|---|---|
| A6 | 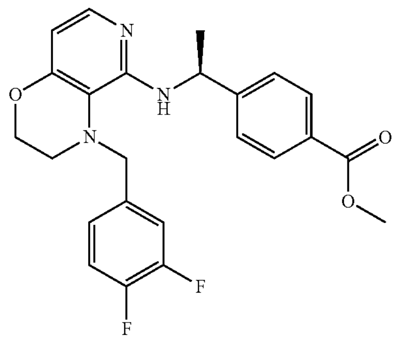 [SMILES: COC(=O)c1ccc([C@H](C)Nc2nccc3c2N(Cc2ccc(F)c(F)c2)CCO3)cc1] | methyl 4-[(1S)-1-[[4-[(3,4-difluorophenyl)methyl]-2,3-dihydropyrido[4,3-b][1,4]oxazin-5-yl]amino]ethyl]benzoate | 440.2 |
| A7 | 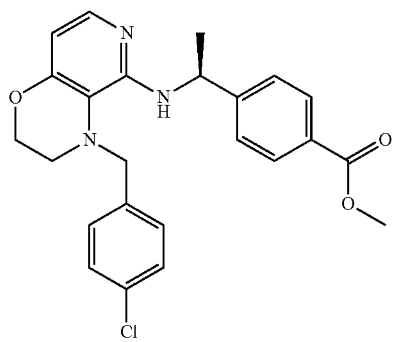 [SMILES: COC(=O)c1ccc([C@H](C)Nc2nccc3c2N(Cc2ccc(Cl)cc2)CCO3)cc1] | methyl 4-[(1S)-1-[[4-[(4-chlorophenyl)methyl]-2,3-dihydropyrido[4,3-b][1,4]oxazin-5-yl]amino]ethyl]benzoate | 438.2 |
| A8 | 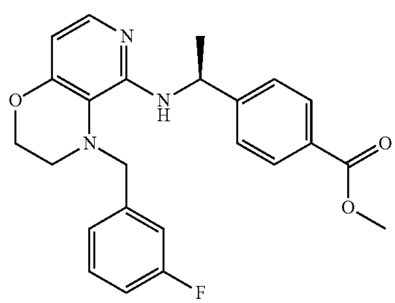 [SMILES: COC(=O)c1ccc([C@H](C)Nc2nccc3c2N(Cc2cccc(F)c2)CCO3)cc1] | methyl 4-[(1S)-1-[[4-[(3-fluorophenyl)methyl]-2,3-dihydropyrido[4,3-b][1,4]oxazin-5-yl]amino]ethyl]benzoate | 422.2 |
| A9 | 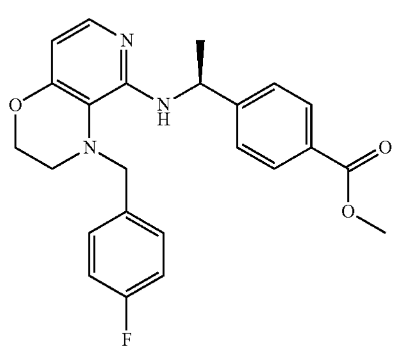 [SMILES: COC(=O)c1ccc([C@H](C)Nc2nccc3c2N(Cc2ccc(F)cc2)CCO3)cc1] | methyl 4-[(1S)-1-[[4-[(4-fluorophenyl)methyl]-2,3-dihydropyrido[4,3-b][1,4]oxazin-5-yl]amino]ethyl]benzoate | 422.2 |

TABLE 2-continued

| Ex. No. | Structure | IUPAC Name | MS(ESI)m/z: (M + 1) |
|---|---|---|---|
| A10 | 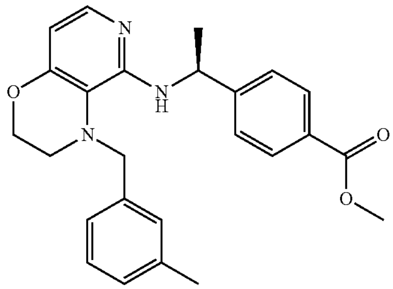 [SMILES: COC(=O)c1ccc([C@H](C)Nc2nccc3c2N(Cc2cccc(C)c2)CCO3)cc1] | methyl 4-[(1S)-1-[[4-(m-tolylmethyl)-2,3-dihydropyrido[4,3-b][1,4]oxazin-5-yl]amino]ethyl]benzoate | 418.3 |
| A11 | 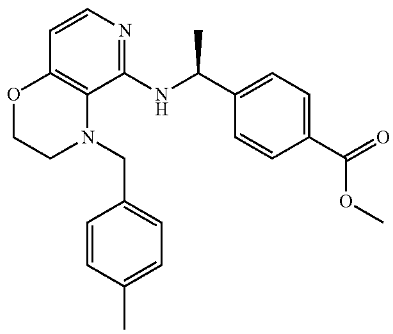 [SMILES: COC(=O)c1ccc([C@H](C)Nc2nccc3c2N(Cc2ccc(C)cc2)CCO3)cc1] | methyl 4-[(1S)-1-[[4-(p-tolylmethyl)-2,3-dihydropyrido[4,3-b][1,4]oxazin-5-yl]amino]ethyl]benzoate | 418.3 |
| A12 | 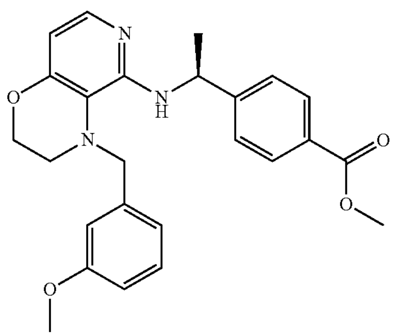 [SMILES: COC(=O)c1ccc([C@H](C)Nc2nccc3c2N(Cc2cccc(OC)c2)CCO3)cc1] | methyl 4-[(1S)-1-[[4-[(3-methoxyphenyl)methyl]-2,3-dihydropyrido[4,3-b][1,4]oxazin-5-yl]amino]ethyl]benzoate | 434.3 |
| A13 | 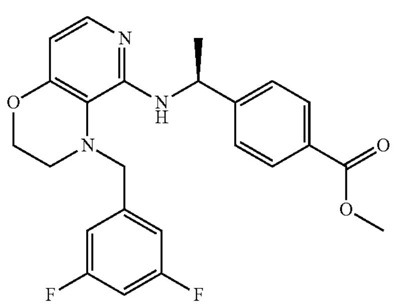 [SMILES: COC(=O)c1ccc([C@H](C)Nc2nccc3c2N(Cc2cc(F)cc(F)c2)CCO3)cc1] | methyl 4-[(1S)-1-[[4-[(3,5-difluorophenyl)methyl]-2,3-dihydropyrido[4,3-b][1,4]oxazin-5-yl]amino]ethyl]benzoate | 440.2 |

TABLE 2-continued

| Ex. No. | Structure | IUPAC Name | MS(ESI)m/z: (M + 1) |
|---|---|---|---|
| A14 | 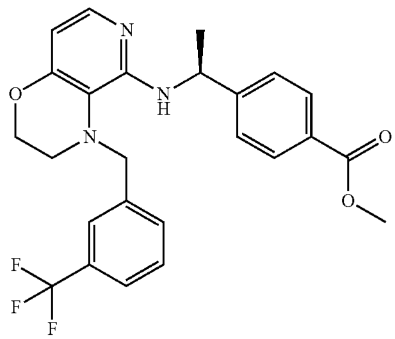 [SMILES: COC(=O)c1ccc([C@H](C)Nc2nccc3c2N(Cc2cccc(C(F)(F)F)c2)CCO3)cc1] | methyl 4-[(1S)-1-[[4-[[3-(trifluoromethyl)phenyl]methyl]-2,3-dihydropyrido[4,3-b][1,4]oxazin-5-yl]amino]ethyl]benzoate | 472.3 |
| A15 | 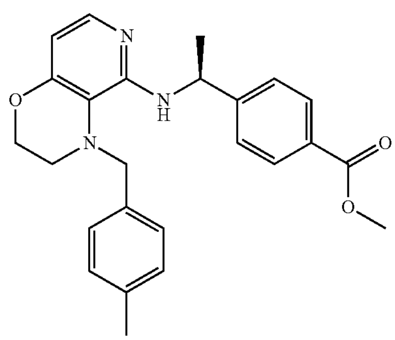 [SMILES: COC(=O)c1ccc([C@H](C)Nc2nccc3c2N(Cc2ccc(C)cc2)CCO3)cc1] | methyl 4-[(1S)-1-[[4-[(4-methoxyphenyl)methyl]-2,3-dihydropyrido[4,3-b][1,4]oxazin-5-yl]amino]ethyl]benzoate | 434.2 |
| A16 | 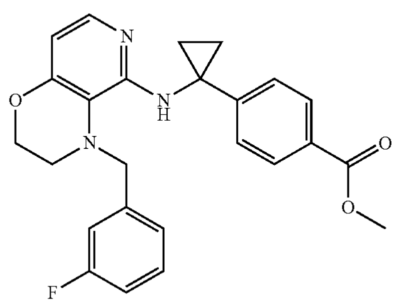 [SMILES: COC(=O)c1ccc(C2(Nc3nccc4c3N(Cc3cccc(F)c3)CCO4)CC2)cc1] | methyl 4-[1-[[4-[(3-fluorophenyl)methyl]-2,3-dihydropyrido[4,3-b][1,4]oxazin-5-yl]amino]cyclopropyl]benzoate | 433.9 |
| A17 | 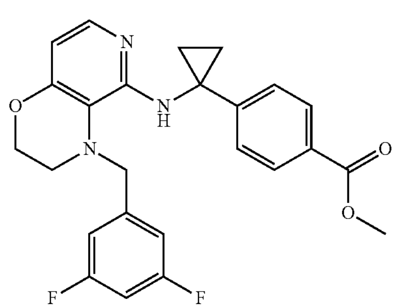 [SMILES: COC(=O)c1ccc(C2(Nc3nccc4c3N(Cc3cc(F)cc(F)c3)CCO4)CC2)cc1] | methyl 4-[1-[[4-[(3,5-difluorophenyl)methyl]-2,3-dihydropyrido[4,3-b][1,4]oxazin-5-yl]amino]cyclopropyl]benzoate | 451.9 |

TABLE 2-continued

| Ex. No. | Structure | IUPAC Name | MS(ESI)m/z: (M + 1) |
|---|---|---|---|
| A18 | 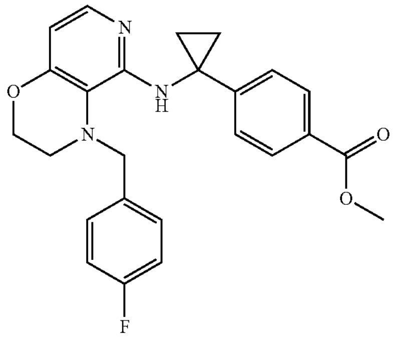 [SMILES: COC(=O)c1ccc(C2(Nc3nccc4c3N(Cc3ccc(F)cc3)CCO4)CC2)cc1] | methyl 4-[1-[[4-[(4-fluorophenyl)methyl]-2,3-dihydropyrido[4,3-b][1,4]oxazin-5-yl]amino]cyclopropyl]benzoate | 433.9 |
| A19 | 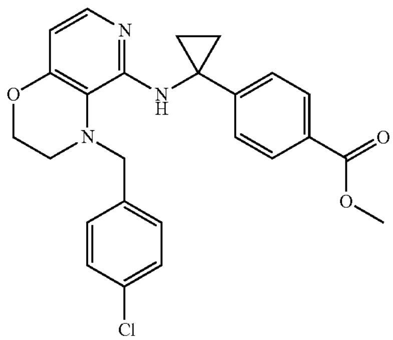 [SMILES: COC(=O)c1ccc(C2(Nc3nccc4c3N(Cc3ccc(Cl)cc3)CCO4)CC2)cc1] | methyl 4-[1-[[4-[(4-chlorophenyl)methyl]-2,3-dihydropyrido[4,3-b][1,4]oxazin-5-yl]amino]cyclopropyl]benzoate | 449.9 |
| A20 | 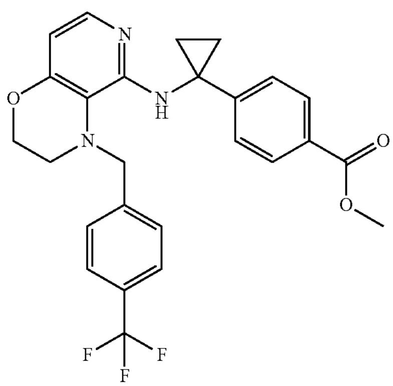 [SMILES: COC(=O)c1ccc(C2(Nc3nccc4c3N(Cc3ccc(C(F)(F)F)cc3)CCO4)CC2)cc1] | methyl 4-[1-[[4-[[4-(trifluoromethyl)phenyl]methyl]-2,3-dihydropyrido[4,3-b][1,4]oxazin-5-yl]amino]cyclopropyl]benzoate | 484.2 |
| A21 | 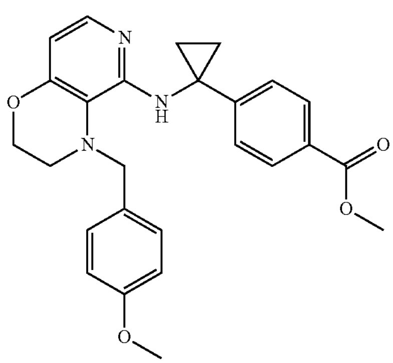 [SMILES: COC(=O)c1ccc(C2(Nc3nccc4c3N(Cc3ccc(OC)cc3)CCO4)CC2)cc1] | methyl 4-[1-[[4-[(4-methoxyphenyl)methyl]-2,3-dihydropyrido[4,3-b][1,4]oxazin-5-yl]amino]cyclopropyl]benzoate | 445.9 |

TABLE 2-continued

| Ex. No. | Structure | IUPAC Name | MS(ESI)m/z: (M + 1) |
| --- | --- | --- | --- |
| A22 | 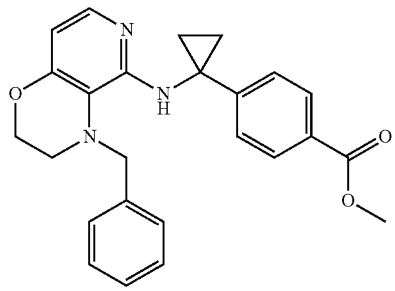 [SMILES: COC(=O)c1ccc(C2(Nc3nccc4c3N(Cc3ccccc3)CCO4)CC2)cc1] | methyl 4-[1-[(4-benzyl-2,3-dihydropyrido[4,3-b][1,4]oxazin-5-yl)amino]cyclopropyl]benzoate | 416.0 |
| A23 | 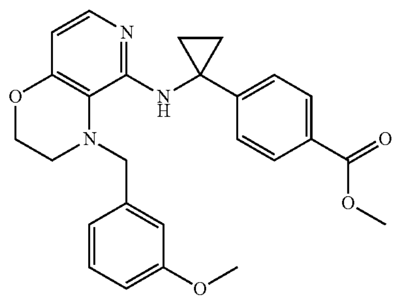 [SMILES: COC(=O)c1ccc(C2(Nc3nccc4c3N(Cc3cccc(OC)c3)CCO4)CC2)cc1] | methyl 4-[1-[[4-[(3-methoxyphenyl)methyl]-2,3-dihydropyrido[4,3-b][1,4]oxazin-5-yl]amino]cyclopropyl]benzoate | 445.9 |
| A24 | 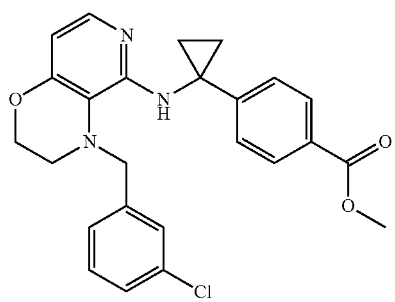 [SMILES: COC(=O)c1ccc(C2(Nc3nccc4c3N(Cc3cccc(Cl)c3)CCO4)CC2)cc1] | methyl 4-[1-[[4-[(3-chlorophenyl)methyl]-2,3-dihydropyrido[4,3-b][1,4]oxazin-5-yl]amino]cyclopropyl]benzoate | 449.9 |
| A25 | 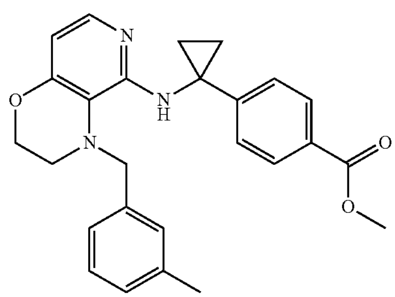 [SMILES: COC(=O)c1ccc(C2(Nc3nccc4c3N(Cc3cccc(C)c3)CCO4)CC2)cc1] | methyl 4-[1-[[4-(m-tolylmethyl)-2,3-dihydropyrido[4,3-b][1,4]oxazin-5-yl]amino]cyclopropyl]benzoate | 430.0 |
| A26 | 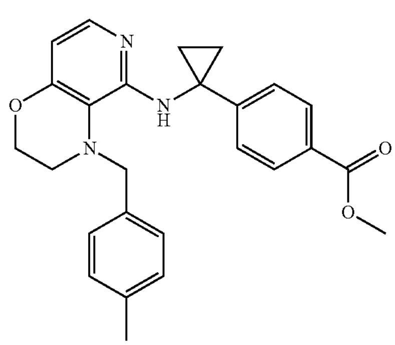 [SMILES: COC(=O)c1ccc(C2(Nc3nccc4c3N(Cc3ccc(C)cc3)CCO4)CC2)cc1] | methyl 4-[1-[[4-(p-tolylmethyl)-2,3-dihydropyrido[4,3-b][1,4]oxazin-5-yl]amino]cyclopropyl]benzoate | 430.0 |

TABLE 2-continued

| Ex. No. | Structure | IUPAC Name | MS(ESI)m/z: (M + 1) |
|---|---|---|---|
| A27 | 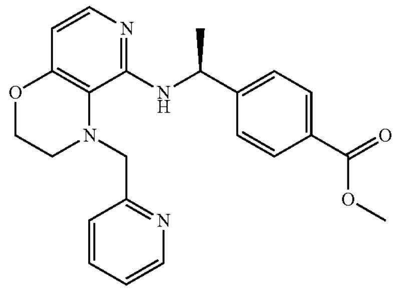 [SMILES: COC(=O)c1ccc([C@H](C)Nc2nccc3c2N(Cc2ccccn2)CCO3)cc1] | methyl 4-[(1S)-1-[[4-(2-pyridylmethyl)-2,3-dihydropyrido[4,3-b][1,4]oxazin-5-yl]amino]ethyl]benzoate | 405.0 |
| A28 | 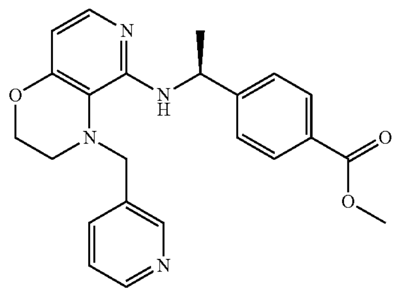 [SMILES: COC(=O)c1ccc([C@H](C)Nc2nccc3c2N(Cc2cccnc2)CCO3)cc1] | methyl 4-[(1S)-1-[[4-(3-pyridylmethyl)-2,3-dihydropyrido[4,3-b][1,4]oxazin-5-yl]amino]ethyl]benzoate | 404.9 |
| A29 | 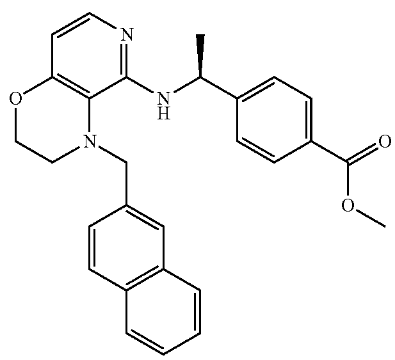 [SMILES: COC(=O)c1ccc([C@H](C)Nc2nccc3c2N(Cc2ccc4ccccc4c2)CCO3)cc1] | methyl 4-[(1S)-1-[[4-(2-naphthylmethyl)-2,3-dihydropyrido[4,3-b][1,4]oxazin-5-yl]amino]ethyl]benzoate | 453.9 |
| A30 | 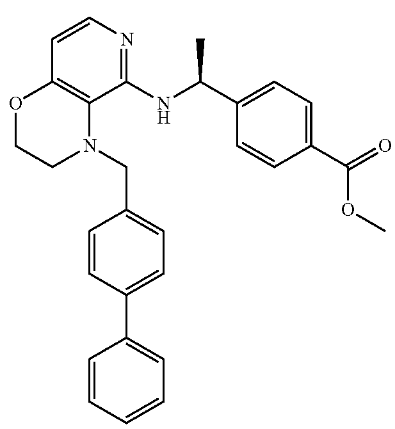 [SMILES: COC(=O)c1ccc([C@H](C)Nc2nccc3c2N(Cc2ccc(-c4ccccc4)cc2)CCO3)cc1] | methyl 4-[(1S)-1-[[4-[(4-phenylphenyl)methyl]-2,3-dihydropyrido[4,3-b][1,4]oxazin-5-yl]amino]ethyl]benzoate | 479.9 |

TABLE 2-continued

| Ex. No. | Structure | IUPAC Name | MS(ESI)m/z: (M + 1) |
|---|---|---|---|
| A31 | 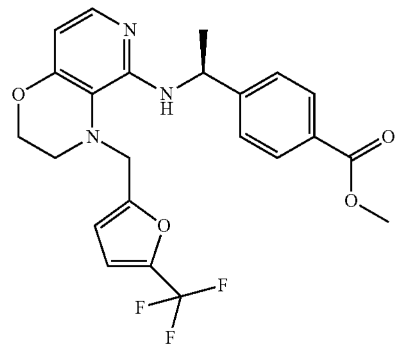 [SMILES: COC(=O)c1ccc([C@H](C)Nc2nccc3c2N(Cc2ccc(C(F)(F)F)o2)CCO3)cc1] | methyl 4-[(1S)-1-[[4-[[5-(trifluoromethyl)-2-furyl]methyl]-2,3-dihydropyrido[4,3-b][1,4]oxazin-5-yl]amino]ethyl]benzoate | 461.9 |
| A32 | 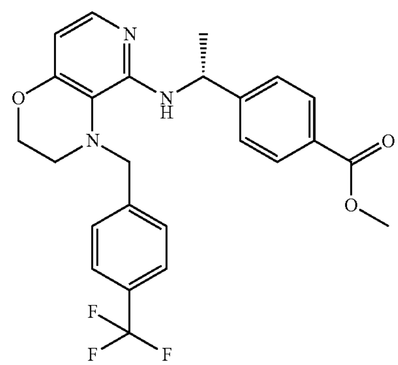 [SMILES: COC(=O)c1ccc([C@@H](C)Nc2nccc3c2N(Cc2ccc(C(F)(F)F)cc2)CCO3)cc1] | methyl 4-[(1R)-1-[[4-[[4-(trifluoromethyl)phenyl]methyl]-2,3-dihydropyrido[4,3-b][1,4]oxazin-5-yl]amino]ethyl]benzoate | 472.0 |
| A33 | 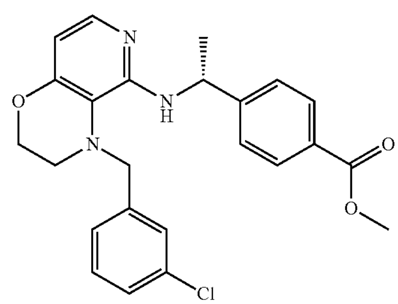 [SMILES: COC(=O)c1ccc([C@@H](C)Nc2nccc3c2N(Cc2cccc(Cl)c2)CCO3)cc1] | methyl 4-[(1R)-1-[[4-[(3-chlorophenyl)methyl]-2,3-dihydropyrido[4,3-b][1,4]oxazin-5-yl]amino]ethyl]benzoate | 438.0 |
| A34 | 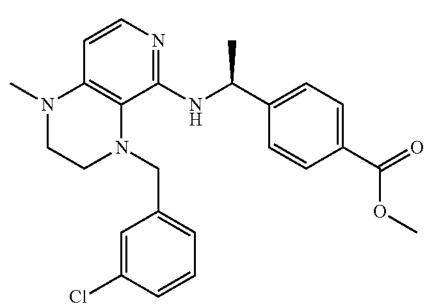 | methyl 4-[(1S)-1-[[4-[(3-chlorophenyl)methyl]-1-methyl-2,3-dihydropyrido[3,4-b]pyrazin-5-yl]amino]ethyl]benzoate | 450.9 |

TABLE 2-continued

| Ex. No. | Structure | IUPAC Name | MS(ESI)m/z: (M + 1) |
|---|---|---|---|
| A35 | 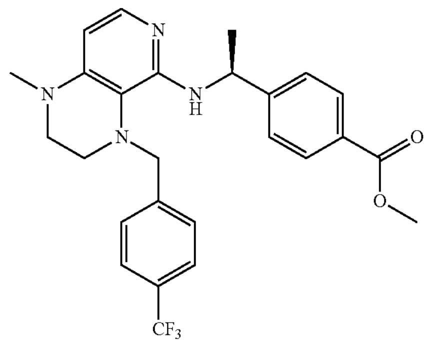 | methyl 4-[(1S)-1-[[1-methyl-4-[[4-(trifluoromethyl)phenyl]methyl]-2,3-dihydropyrido[3,4-b]pyrazin-5-yl]amino]ethyl]benzoate | 485.0 |

Example A36: Methyl 4-[(1S)-1-[[3-oxo-4-[[4-(trifluoromethyl)phenyl]methyl]pyrido[4,3-b][1,4]thiazin-5-yl]amino]ethyl]benzoate]

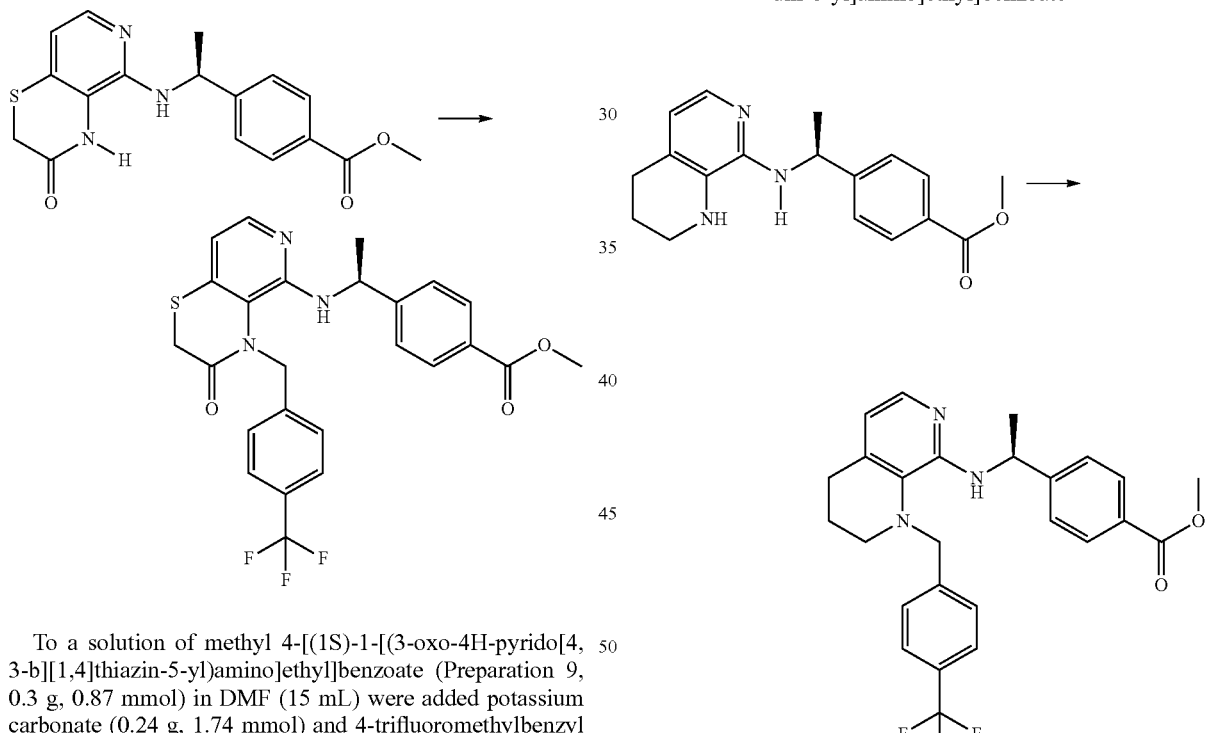

To a solution of methyl 4-[(1S)-1-[(3-oxo-4H-pyrido[4,3-b][1,4]thiazin-5-yl)amino]ethyl]benzoate (Preparation 9, 0.3 g, 0.87 mmol) in DMF (15 mL) were added potassium carbonate (0.24 g, 1.74 mmol) and 4-trifluoromethylbenzyl bromide (0.250 g, 1.05 mmol). The reaction mixture was heated at 120-130° C. under nitrogen atmosphere for 16 hours and the product formation was confirmed by TLC. The reaction mixture was diluted with water (25 mL) and extracted with ethyl acetate (2×15 mL). The combined organic layers were washed with brine and dried over sodium sulfate. The organic layer was evaporated under vacuo, and the obtained crude material was purified by combiflash column chromatography using 10-15% ethyl acetate in hexane as a mobile phase to give the title compound (0.2 g, 46%).

MS (EI) m/z: 502.3 (M+1); $^1$H NMR (400 MHz, CDCl$_3$): δ 1.37 (d, J=6.8 Hz, 3H), 3.32-3.42 (m, 2H), 3.90 (s, 3H), 4.32 (d, J=6.8 Hz, 1H), 5.07-5.09 (m, 2H), 5.19-5.21 (m, 1H), 6.63 (d, J=5.6 Hz, 1H), 7.23-7.27 (m, 3H), 7.46-7.51 (m, 3H), 7.71-7.75 (m, 1H), 7.93-7.95 (m, 2H).

Example A37: Methyl 4-[(1S)-1-[[1-[[4-(trifluoromethyl)phenyl]methyl]-3,4-dihydro-2H-1,7-naphthyridin-8-yl]amino]ethyl]benzoate The title compound was obtained (0.120 g, 40%) in a similar manner to that of Example A36 using the compound obtained in Preparation 10 (0.2 g, 0.64 mmol) and 4-trifluoromethylbenzyl bromide (0.184 g, 0.77 mmol).

MS (ESI) m/z: 470.3 (M+1); $^1$H NMR (400 MHz, DMSO-d$_6$): δ 1.41 (d, J=6.8 Hz, 3H), 1.84-1.86 (m, 2H), 2.71 (t, J=6.0 Hz, 2H), 3.01 (t, J=5.6 Hz, 2H), 3.88 (s, 3H), 4.06 (s, 2H), 5.19-5.23 (m, 1H), 6.34 (d, J=5.2 Hz, 1H), 7.22-7.25 (m, 2H), 7.49 (d, J=8.0 Hz, 1H), 7.54 (d, J=8.0 Hz, 2H), 7.61-7.65 (m, 2H), 7.69 (d, J=5.6 Hz, 1H), 7.86-7.88 (m, 2H)

Example A38: Methyl 4-[(1S)-1-[[5-[(3-chlorophenyl)methyl]-6,7-dihydropyrimido[4,5-b][1,4]oxazin-4-yl]amino]ethyl]benzoate

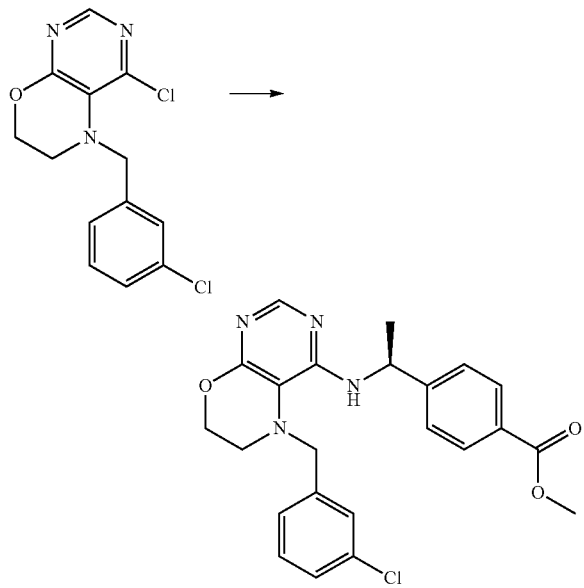

A suspension of 4-chloro-5-[(3-chlorophenyl)methyl]-6,7-dihydropyrimido[4,5-b][1,4]oxazine (Preparation 12, 0.05 g, 0.17 mmol), methyl 4-[(1S)-1-aminoethyl]benzoate (0.045 g, 0.25 mmol) and cesium carbonate (0.08 g, 0.25 mmol) in 1,4-dioxane (2 mL) was degassed with argon for 30 min. To above suspension were added $Pd_2(dba)_3$-$CHCl_3$ (0.008 g, 0.008 mmol) and BINAP (0.016 g, 0.025 mmol). Degassing was continued for another 20 min. The resulting mixture was heated at 100° C. for 18 hours under argon atmosphere. Progress of the reaction was monitored by TLC. After completion of the reaction, the reaction mixture was diluted with water (10 mL). The aqueous layer was extracted with ethyl acetate (3×15 mL). The combined organic layers were washed and brine (15 mL), and dried over sodium sulfate. The organic layer was evaporated under vacuum, and the residue was purified by preparative TLC to give the title compound as solid (0.05 g, 67%).

MS (ESI) m/z: (M+1) 439.3 [M($^{35}$Cl)+1], 441.2 [M($^{37}$Cl)+1]; $^1$H NMR (400 MHz, DMSO-$d_6$): 1.47 (d, J=6.8 Hz, 3H), 3.03-2.99 (t, J=4.0 Hz, 2H), 3.83 (s, 3H), 4.01 (s, 2H), 4.27 (t, J=4.0 Hz, 2H), 5.24-5.28 (m, 1H), 6.09 (d, J=7.2 Hz, 1H), 7.38-7.48 (m. 5H), 7.57 (s, 1H), 7.87-7.89 (m, 3H)

The compounds of Examples A39-A51 were synthesized in a similar manner to that of Examples A1-A4 and A36-A38.

TABLE 3

| Ex. No. | Structure | IUPAC Name | MS(ESI)m/z: (M + 1) |
|---|---|---|---|
| A39 | 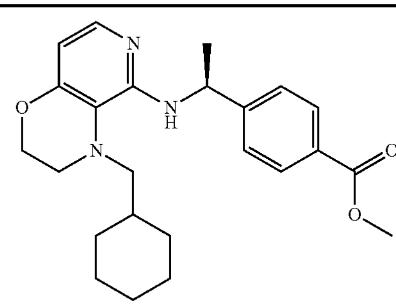 | methyl 4-[(1S)-1-[[4-(cyclohexylmethyl)-2,3-dihydropyrido[4,3-b][1,4]oxazin-5-yl]amino]ethyl]benzoate | 410.3 |
| A40 | 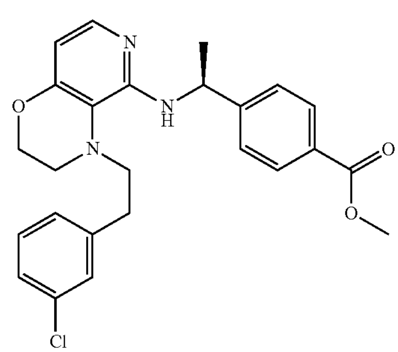 [SMILES: COC(=O)c1ccc([C@H](C)Nc2nccc3c2N(CCc2cccc(Cl)c2)CCO3)cc1] | methyl 4-[(1S)-1-[[4-[2-(3-chlorophenyl)ethyl]-2,3-dihydropyrido[4,3-b][1,4]oxazin-5-yl]amino]ethyl]benzoate | 452.3 |

TABLE 3-continued

| Ex. No. | Structure | IUPAC Name | MS(ESI)m/z: (M + 1) |
|---|---|---|---|
| A41 | 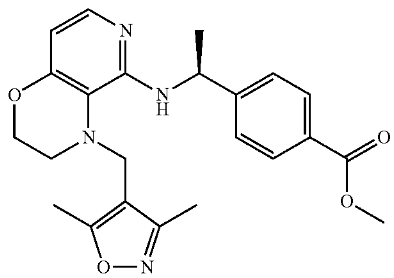 [SMILES: COC(=O)c1ccc([C@H](C)Nc2nccc3c2N(Cc2c(C)noc2C)CCO3)cc1] | methyl 4-[(1S)-1-[[4-[(3,5-dimethylisoxazol-4-yl)methyl]-2,3-dihydropyrido[4,3-b][1,4]oxazin-5-yl]amino]ethyl]benzoate | 423.3 |
| A42 | 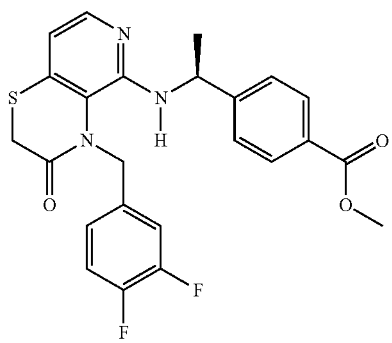 [SMILES: COC(=O)c1ccc([C@H](C)Nc2nccc3c2N(Cc2ccc(F)c(F)c2)C(=O)CS3)cc1] | methyl 4-[(1S)-1-[[4-[(3,4-difluorophenyl)methyl]-3-oxopyrido[4,3-b][1,4]thiazin-5-yl]amino]ethyl]benzoate | 470.2 |
| A43 | 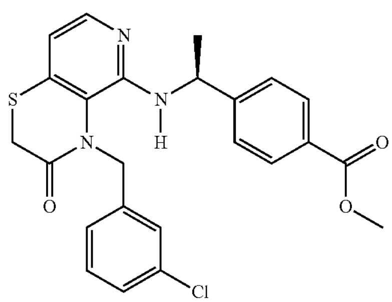 [SMILES: COC(=O)c1ccc([C@H](C)Nc2nccc3c2N(Cc2cccc(Cl)c2)C(=O)CS3)cc1] | methyl 4-[(1S)-1-[[4-[(3-chlorophenyl)methyl]-3-oxopyrido[4,3-b][1,4]thiazin-5-yl]amino]ethyl]benzoate | 468.2 |
| A44 | 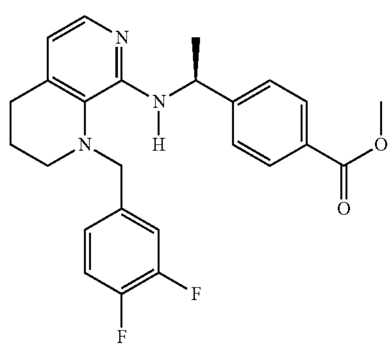 [SMILES: COC(=O)c1ccc([C@H](C)Nc2nccc3c2N(Cc2ccc(F)c(F)c2)CCC3)cc1] | methyl 4-[(1S)-1-[[1-[(3,4-difluorophenyl)methyl]-3,4-dihydro-2H-1,7-naphthyridin-8-yl]amino]ethyl]benzoate | 438.3 |
| A45 | 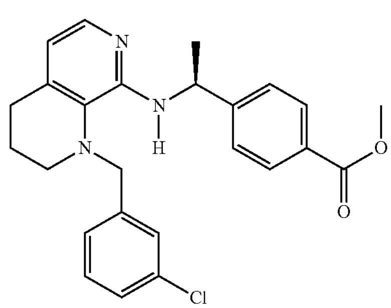 [SMILES: COC(=O)c1ccc([C@H](C)Nc2nccc3c2N(Cc2cccc(Cl)c2)CCC3)cc1] | methyl 4-[(1S)-1-[[1-[(3-chlorophenyl)methyl]-3,4-dihydro-2H-1,7-naphthyridin-8-yl]amino]ethyl]benzoate | 436.3 |

TABLE 3-continued

| Ex. No. | Structure | IUPAC Name | MS(ESI)m/z: (M + 1) |
|---|---|---|---|
| A46 | 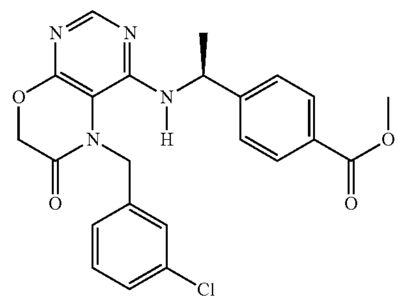 [SMILES: COC(=O)c1ccc([C@H](C)Nc2ncnc3c2N(Cc2cccc(Cl)c2)C(=O)CO3)cc1] | methyl 4-[(1S)-1-[[5-[(3-chlorophenyl)methyl]-6-oxo-pyrimido[4,5-b][1,4]oxazin-4-yl]amino]ethyl]benzoate | 453.2 |
| A47 | 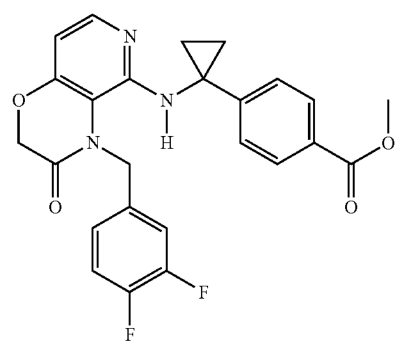 [SMILES: COC(=O)c1ccc(C2(Nc3nccc4c3N(Cc3ccc(F)c(F)c3)C(=O)CO4)CC2)cc1] | methyl 4-[1-[[4-[(3,4-difluorophenyl)methyl]-3-oxopyrido[4,3-b][1,4]oxazin-5-yl]amino]cyclopropyl]benzoate | 466.1 |
| A48 | 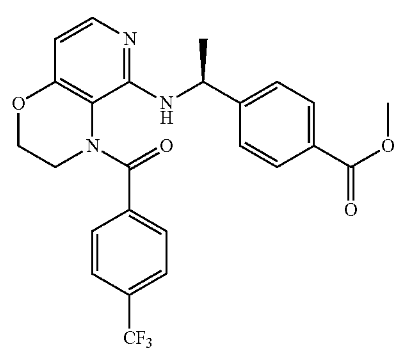 [SMILES: COC(=O)c1ccc([C@H](C)Nc2nccc3c2N(C(=O)c2ccc(C(F)(F)F)cc2)CCO3)cc1] | methyl 4-[(1S)-1-[[4-[4-(trifluoromethyl)benzoyl]-2,3-dihydropyrido[4,3-b][1,4]oxazin-5-yl]amino]ethyl]benzoate | 486.2 |
| A49 | 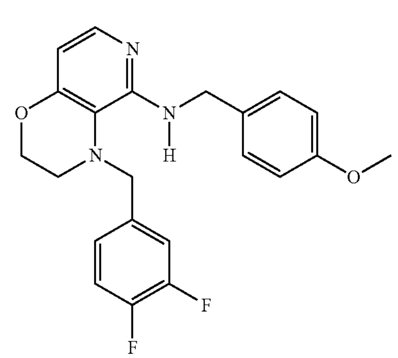 [SMILES: COc1ccc(CNc2nccc3c2N(Cc2ccc(F)c(F)c2)CCO3)cc1] | 4-[(3,4-difluorophenyl)methyl]-N-[(4-methoxyphenyl)methyl]-2,3-dihydropyrido[4,3-b][1,4]oxazin-5-amine | 398.2 |

TABLE 3-continued

| Ex. No. | Structure | IUPAC Name | MS(ESI)m/z: (M + 1) |
|---|---|---|---|
| A50 | 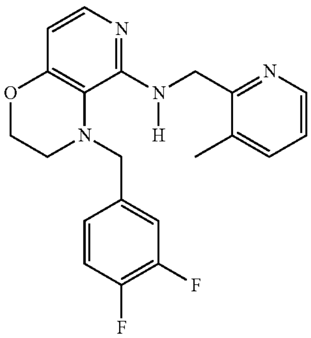 [SMILES: Cc1cccnc1CNc1nccc2c1N(Cc1ccc(F)c(F)c1)CCO2] | 4-[(3,4-difluorophenyl)methyl]-N-[(3-methyl-2-pyridyl)methyl]-2,3-dihydropyrido[4,3-b][1,4]oxazin-5-amine | 383.3 |
| A51 | 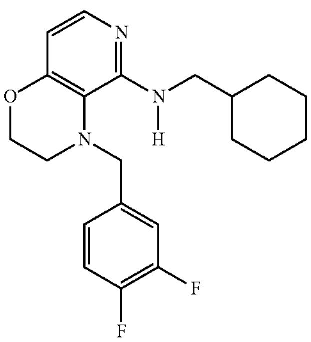 [SMILES: Fc1ccc(CN2CCOc3ccnc(NCC4CCCCC4)c32)cc1F] | N-(cyclohexylmethyl)-4-[(3,4-difluorophenyl)methyl]-2,3-dihydropyrido[4,3-b][1,4]oxazin-5-amine | 374.2 |

Example B1: 4-[(1S)-1-[(4-Benzyl-2,3-dihydropyrido[4,3-b][1,4]oxazin-5-yl)amino]ethyl]benzoic acid

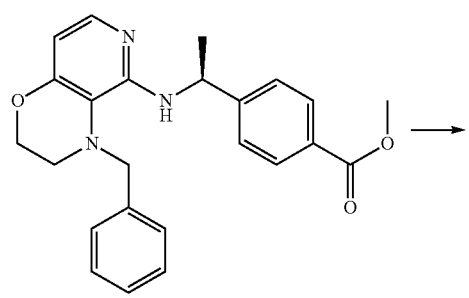

To a solution of methyl 4-[(1S)-1-[(4-benzyl-2,3-dihydropyrido[4,3-b][1,4]oxazin-5-yl)amino]ethyl]benzoate (Example A1, 0.1 g, 0.25 mmol) in ethanol:water (10:1, 6 mL) was added potassium hydroxide (0.042 g, 0.74 mmol). The mixture was stirred at 100° C. for 2 hours. The reaction completion was confirmed by TLC, then the mixture was cooled to room temperature and evaporated to dryness. The residue was dissolved in water (10 mL), and the solution was acidified by 5% aqueous citric acid solution to pH 4-5, and stirred for 30 min. The resulting solid was collected by filtration, washed with water and dried under vacuum to give the title compound as a pale yellow solid (0.023 g, 24%).

MS (ESI) m/z: 390.1 (M+1); $^1$H NMR (400 MHz, DMSO-$d_6$): δ 1.54 (d, J=5.6 Hz, 3H), 3.12 (s, 2H), 4.05 (s, 2H), 4.22 (s, 2H), 5.15-5.25 (m, 1H), 6.57 (s, 1H), 7.34-7.41 (m, 5H), 7.48 (d, J=8.8 Hz, 2H), 7.59 (d, J=6.8 Hz, 1H), 7.89 (d, J=8 Hz, 2H), 13.00 (br s, 1H). [0323]

Example B2: 4-[(1S)-1-[[4-[(3-Chlorophenyl)methyl]-2,3-dihydropyrido[4,3-b][1,4]oxazin-5-yl]amino]ethyl]benzoic acid

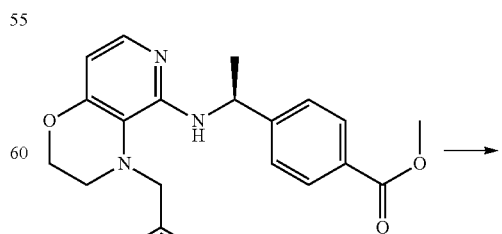

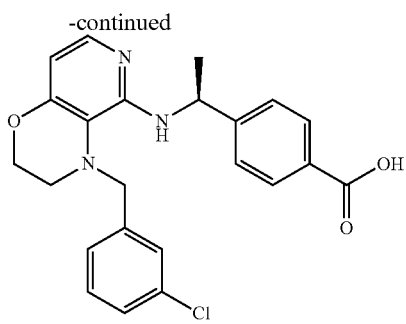

The title compound was obtained as an off-white solid (0.68 g, 88%) in a similar manner to that of Example B1 using the compound obtained in Example A2 (0.8 g, 1.82 mmol) and potassium hydroxide (0.3 g, 5.48 mmol).

MS (ESI) m/z: 423.6 (M+1); $^1$H NMR (400 MHz, DMSO-$d_6$): δ 1.41 (d, to J=6.8 Hz, 3H), 2.98 (d, J=3.2 Hz, 2H), 4.01 (d, J=6.8 Hz, 2H), 4.19 (t, J=4.4 HZ, 2H), 5.12-5.15 (m, 1H), 5.29 (d, J=6.8 Hz, 1H), 6.18 (d, J=5.6 Hz, 1H), 7.39-7.52 (m, 6H), 7.57 (br s, 1H), 7.83 (d, J=8.0 Hz, 2H), 12.75 (br s, 1H).

Example B3: 4-[(1S)-1-[[4-[2-(4-Fluorophenoxy) ethyl]-2,3-dihydropyrido[4,3-b][1,4]oxazin-5-yl] amino]ethyl]benzoic acid The title compound was obtained as brown solid (0.021 g, 14%) in a similar manner to that of Example B1 using the compound obtained in Example A3 (0.15 g, 0.33 mmol) and potassium hydroxide (0.056 g, 0.99 mmol).

MS (ESI) m/z: 438.1 (M+1); $^1$H NMR (400 MHz, DMSO-$d_6$): δ 1.56 (s, 3H), 3.18 (br s, 4H), 4.22 (s, 2H), 4.32 (s, 2H), 5.26 (s, 1H), 6.82-6.96 (m, 2H), 7.10 (t, J=8.8 Hz, 2H), 7.49-7.51 (m, 4H), 7.89 (d, J=8 Hz, 2H), 12.90 (br s, 1H).

Example B4: 4-[1-[[4-[(3,4-Difluorophenyl) methyl]-2,3-dihydropyrido[4,3-b][1,4]oxazin-5-yl] amino]cyclopropyl]benzoic acid

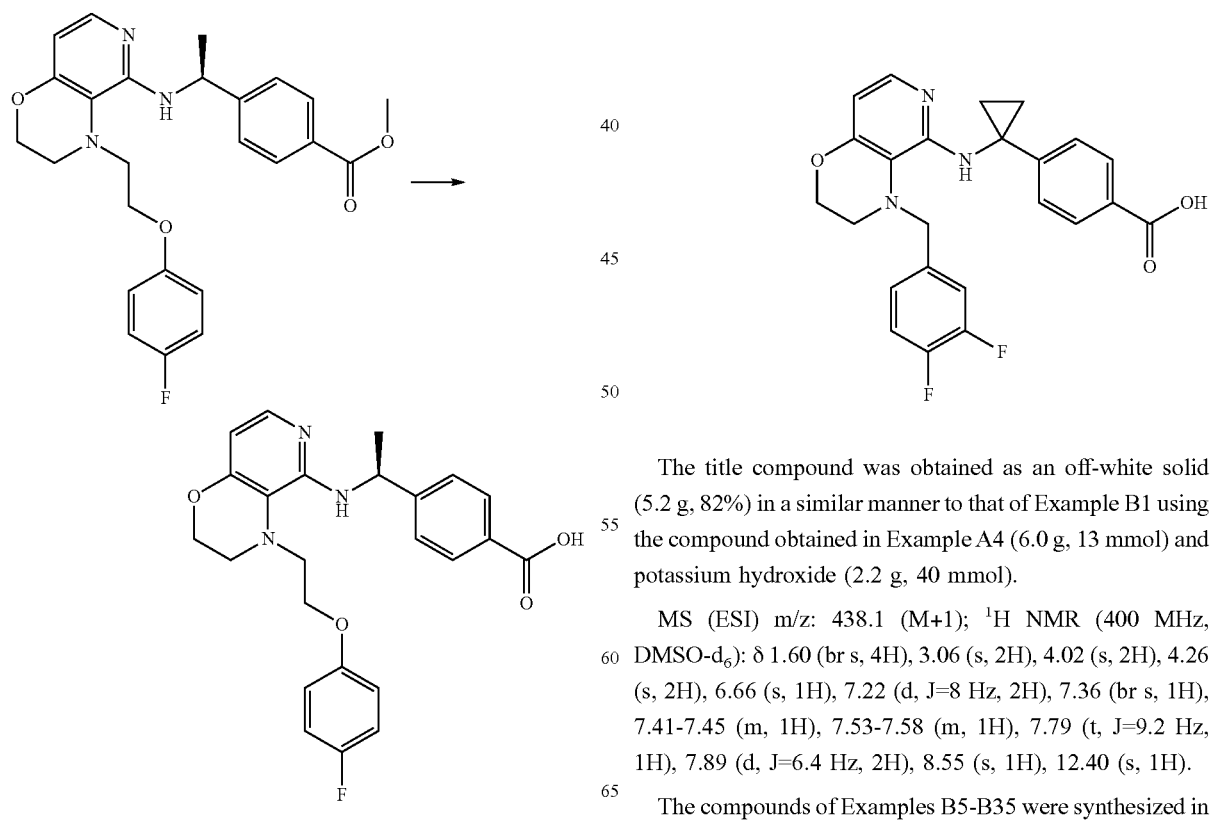

The title compound was obtained as an off-white solid (5.2 g, 82%) in a similar manner to that of Example B1 using the compound obtained in Example A4 (6.0 g, 13 mmol) and potassium hydroxide (2.2 g, 40 mmol).

MS (ESI) m/z: 438.1 (M+1); $^1$H NMR (400 MHz, DMSO-$d_6$): δ 1.60 (br s, 4H), 3.06 (s, 2H), 4.02 (s, 2H), 4.26 (s, 2H), 6.66 (s, 1H), 7.22 (d, J=8 Hz, 2H), 7.36 (br s, 1H), 7.41-7.45 (m, 1H), 7.53-7.58 (m, 1H), 7.79 (t, J=9.2 Hz, 1H), 7.89 (d, J=6.4 Hz, 2H), 8.55 (s, 1H), 12.40 (s, 1H).

The compounds of Examples B5-B35 were synthesized in a similar manner to that of Examples B1-B4.

TABLE 4

| Ex. No. | Structure | IUPAC Name and ¹H NMR data | MS(ESI)m/z: (M + 1) |
|---|---|---|---|
| B5 | 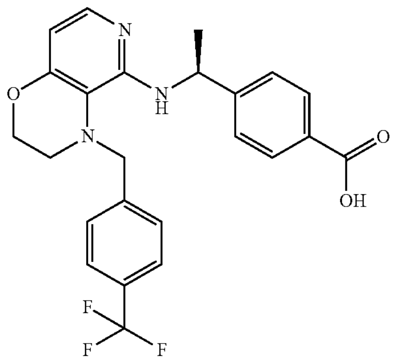 [SMILES: C[C@H](Nc1nccc2c1N(Cc1ccc(C(F)(F)F)cc1)CCO2)c1ccc(C(=O)O)cc1] | 4-[(1S)-1-[[4-[[4-(trifluoromethyl)phenyl]methyl]-2,3-dihydropyrido[4,3-b][1,4]oxazin-5-yl]amino]ethyl]benzoic acid<br>¹H NMR DMSO-$d_6$: δ 1.38 (d, J = 6.8 Hz, 3H), 3.00 (br s, 2H), 4.11 (d, J = 5.2 Hz, 2H), 4.21 (br s, 2H), 5.10-5.20 (br s, 1H), 5.20-5.30 (br s, 1H), 6.19 (d, J = 5.6 Hz, 1H), 7.37 (d, J = 8 Hz, 2H), 7.52 (d, J = 6.0 Hz, 1H), 7.74-7.82 (m, 6H), 12.80 (br s, 1H). | 458.1 |
| B6 | 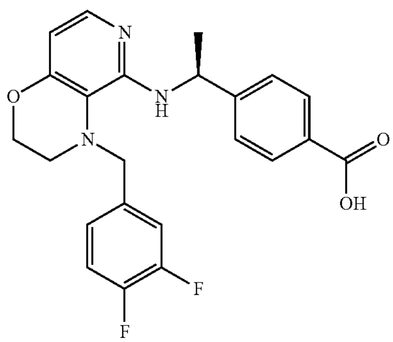 [SMILES: C[C@H](Nc1nccc2c1N(Cc1ccc(F)c(F)c1)CCO2)c1ccc(C(=O)O)cc1] | 4-[(1S)-1-[[4-[(3,4-difluorophenyl)methyl]-2,3-dihydropyrido[4,3-b][1,4]oxazin-5-yl]amino]ethyl]benzoic acid<br>¹H NMR DMSO-$d_6$: δ 1.44 (d, J = 6.8 Hz, 3H); 2.98 (s, 2H); 3.97-4.01 (m, 2H); 4.19 (s, 2H); 5.12-5.60 (m, 1H); 5.40 (br s, 1H); 6.19 (br s, 1H); 7.30-7.64 (m, 7H); 7.83 (d, J = 8 Hz, 1H); 12.80 (br s, 1H). | 426.2 |
| B7 | 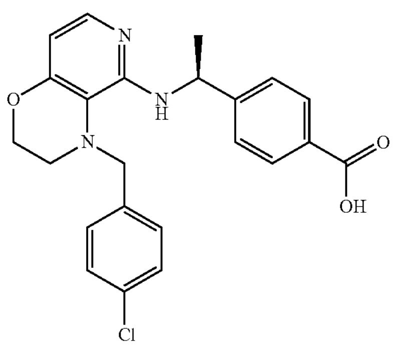 [SMILES: C[C@H](Nc1nccc2c1N(Cc1ccc(Cl)cc1)CCO2)c1ccc(C(=O)O)cc1] | 4-[(1S)-1-[[4-[(4-chlorophenyl)methyl]-2,3-dihydropyrido[4,3-b][1,4]oxazin-5-yl]amino]ethyl]benzoic acid<br>¹H NMR DMSO-$d_6$ (for K-slat): δ 1.40 (d, J = 6.0 Hz, 3H), 2.96 (s, 2H), 3.95 (s, 2H), 4.19 (s, 2H), 5.12-5.14 (m, 2H), 6.16 (d, J = 6.0 Hz, 1H), 7.10 (d, J = 7.2 Hz, 2H), 7.45-7.50 (m, 4H), 7.56 (d, J = 6.0 Hz, 1H), 7.69 (d, J = 8.0 Hz, 2H). | 424.2 |
| B8 | 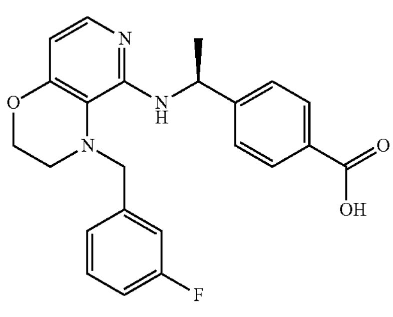 [SMILES: C[C@H](Nc1nccc2c1N(Cc1cccc(F)c1)CCO2)c1ccc(C(=O)O)cc1] | 4-[(1S)-1-[[4-[(3-fluorophenyl)methyl]-2,3-dihydropyrido[4,3-b][1,4]oxazin-5-yl]amino]ethyl]benzoic acid<br>¹H NMR DMSO-$d_6$: δ 1.54 (s, 3H), 3.10 (s, 2H), 4.05 (s, 2H), 4.23 (s, 2H), 5.16-5.19 (m, 1H), 6.50 (br s, 1H), 7.17 (t, J = 6.4 Hz, 1H), 7.28 (d, J = 7.2 Hz, 1H), 7.35 (d, J = 9.6 Hz, 1H), 7.41-7.48 (m, 3H), 7.58 (d, J = 7.2 Hz, 1H), 7.88 (d, J = 8 Hz, 2H), 13.00 (br s, 1H). | 408.1 |

TABLE 4-continued

| Ex. No. | Structure | IUPAC Name and <sup>1</sup>H NMR data | MS(ESI)m/z: (M + 1) |
|---|---|---|---|
| B9 | 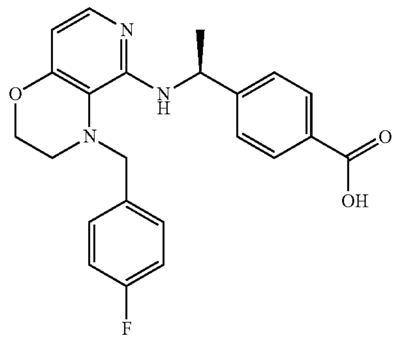 [SMILES: C[C@H](Nc1nccc2c1N(Cc1ccc(F)cc1)CCO2)c1ccc(C(=O)O)cc1] | 4-[(1S)-1-[[4-[(4-fluorophenyl)methyl]-2,3-dihydropyrido[4,3-b][1,4]oxazin-5-yl]amino]ethyl]benzoic acid<br><sup>1</sup>H NMR DMSO-d$_6$: δ 1.57 (d, J = 6 Hz, 3H), 3.10 (br s, 2H), 4.03 (s, 2H), 4.23 (s, 2H), 5.25 (s, 1H), 6.55 (br s, 1H), 7.22 (t, J = 8.4 Hz, 2H), 7.46-7.52 (m, 4H), 7.59 (d, J = 7.2 Hz, 1H), 7.90 (d, J = 8.4 Hz, 2H), 13.20 (br s, 1H). | 408.1 |
| B10 | 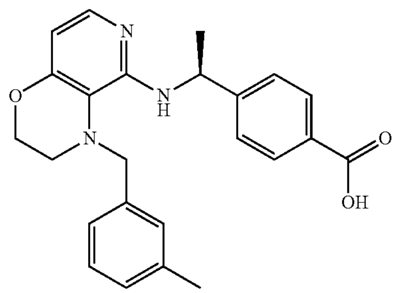 [SMILES: Cc1cccc(CN2CCOc3ccnc(N[C@@H](C)c4ccc(C(=O)O)cc4)c32)c1] | 4-[(1S)-1-[[4-(m-tolylmethyl)-2,3-dihydropyrido[4,3-b][1,4]oxazin-5-yl]amino]ethyl]benzoic acid<br><sup>1</sup>H NMR DMSO-d$_6$: δ 1.55 (d, J = 6.4 Hz, 3H), 2.28 (s, 3H), 3.11 (s, 2H), 4.00 (s, 2H), 4.25 (s, 2H), 5.20-5.30 (m, 1H), 6.55 (br s, 1H), 7.15 (d, J = 7.6 Hz, 2H), 7.19-7.20 (m, 1H), 7.27 (t, J = 7.2 Hz, 1H), 7.49 (d, J = 7.2 Hz, 2H), 7.60 (d, J = 7.2 Hz, 1H), 7.89 (d, J = 8 Hz, 2H), 13.00 (br s, 1H). | 404.1 |
| B11 | 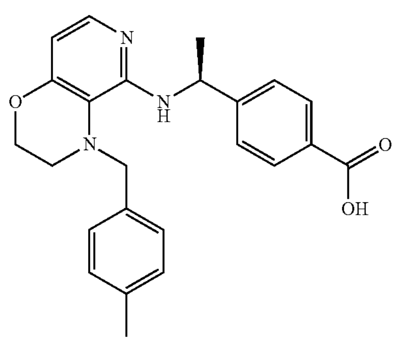 [SMILES: Cc1ccc(CN2CCOc3ccnc(N[C@@H](C)c4ccc(C(=O)O)cc4)c32)cc1] | 4-[(1S)-1-[[4-(p-tolylmethyl)-2,3-dihydropyrido[4,3-b][1,4]oxazin-5-yl]amino]ethyl]benzoic acid<br><sup>1</sup>H NMR DMSO-d$_6$: δ 1.55 (d, J = 7.2 Hz, 3H), 2.30 (s, 3H), 3.11 (br s. 2H), 4.00-4.04 (m, 2H), 4.16-4.22 (m, 2H), 5.30 (br s, 1H), 6.54 (br s, 1H), 7.18 (d, J = 8.0 Hz, 2H), 7.27 (d, J = 8.0 Hz, 2H), 7.50 (d, J = 8.4 Hz, 2H), 7.58 (d, J = 6.8 Hz, 1H), 7.89 (d, J = 8.0 Hz, 2H), 13.40 (br s, 1H). | 404.1 |
| B12 | 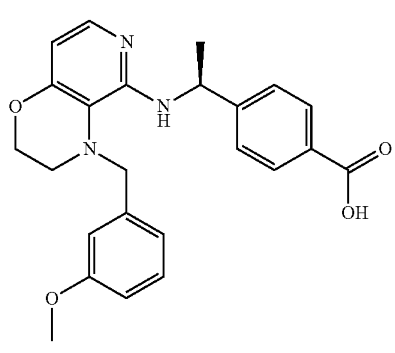 [SMILES: COc1cccc(CN2CCOc3ccnc(N[C@@H](C)c4ccc(C(=O)O)cc4)c32)c1] | 4-[(1S)-1-[[4-[(3-methoxyphenyl)methyl]-2,3-dihydropyrido[4,3-b][1,4]oxazin-5-yl]amino]ethyl]benzoic acid<br><sup>1</sup>H NMR DMSO-d$_6$: δ 1.54 (d, J = 6.4 Hz, 3H), 3.15 (s, 2H), 3.72 (s, 3H), 4.09 (s, 2H), 4.22 (s, 2H), 5.33-5.36 (m, 1H), 6.58 (d, J = 6.4 Hz, 1H), 6.86-6.97 (m, 3H), 7.30 (t, J = 7.6 Hz 1H), 7.50 (d, J = 8.4 Hz, 2H), 7.60 (d, J = 6.4 Hz, 1H), 7.89 (d, J = 8.4 Hz, 2H), 13.40 (br s, 1H). | 420.1 |

TABLE 4-continued

| Ex. No. | Structure | IUPAC Name and ¹H NMR data | MS(ESI)m/z: (M + 1) |
|---|---|---|---|
| B13 | 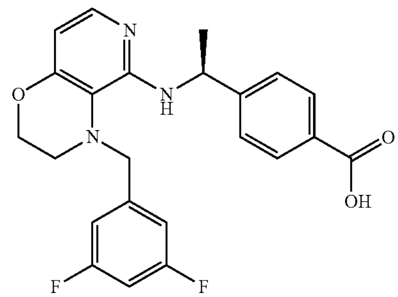 [SMILES: C[C@H](Nc1nccc2c1N(Cc1cc(F)cc(F)c1)CCO2)c1ccc(C(=O)O)cc1] | 4-[(1S)-1-[[4-[(3,5-difluorophenyl)methyl]-2,3-dihydropyrido[4,3-b][1,4]oxazin-5-yl]amino]ethyl]benzoic acid<br>¹H NMR DMSO-d$_6$: δ 1.57 (d, J = 6.8 Hz, 3H), 3.11 (s, 2H), 4.03-4.09 (m, 2H), 4.27-4.28 (m, 2H), 5.24 (br s, 1H), 6.57 (br s, 1H), 7.18-7.27 (m, 3H), 7.50 (d, J = 8 Hz, 2H), 7.61 (d, J = 7.2 Hz, 1H), 7.89 (d, J = 8.0 Hz, 2H), 13.00 (br s, 1H). | 426.1 |
| B14 | 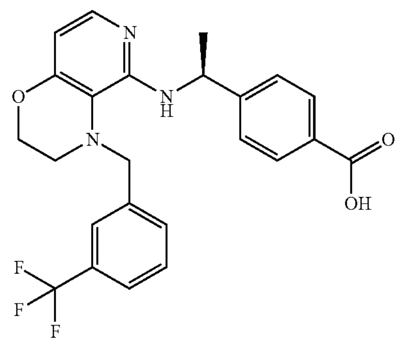 [SMILES: C[C@H](Nc1nccc2c1N(Cc1cccc(C(F)(F)F)c1)CCO2)c1ccc(C(=O)O)cc1] | 4-[(1S)-1-[[4-[[3-(trifluoromethyl)phenyl]methyl]-2,3-dihydropyrido[4,3-b][1,4]oxazin-5-yl]amino]ethyl]benzoic acid<br>¹H NMR DMSO-d$_6$: δ 1.55 (d, J = 6.4 Hz, 3H), 3.13 (s, 2H), 4.14 (dd, J = 19.6, 15.2 Hz, 2H), 4.26 (s, 2H), 5.25 (s, 1H), 6.56 (s, 1H), 7.20 (br s, 1H), 7.50 (d, J = 8 Hz, 2H), 7.61-7.79 (m, 5H), 7.87 (d, J = 8.4 Hz, 2H), 13.20 (br s, 1H). | 458.2 |
| B15 | 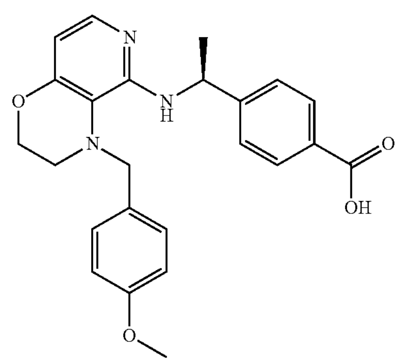 [SMILES: COc1ccc(CN2CCOc3ccnc(N[C@@H](C)c4ccc(C(=O)O)cc4)c32)cc1] | 4-[(1S)-1-[[4-[(4-methoxyphenyl)methyl]-2,3-dihydropyrido[4,3-b][1,4]oxazin-5-yl]amino]ethyl]benzoic acid<br>¹H NMR DMSO-d$_6$: δ 1.45 (d, J = 6.4 Hz, 3H), 2.94-2.95 (m, 2H), 3.76 (s, 3H), 3.92 (q, J = 14.2 Hz, 2H), 4.18 (s, 2H), 5.15-5.18 (m, 1H), 5.37-5.38 (m, 1H), 6.17 (d, J = 5.2 Hz, 1H), 6.96 (d, J = 8.4 Hz, 2H), 7.38-7.44 (m, 4H), 7.50 (d, J = 5.6 Hz, 1H), 7.84 (d, J = 8 Hz, 2H), 12.8 (br s, 1H). | 420.1 |
| B16 | 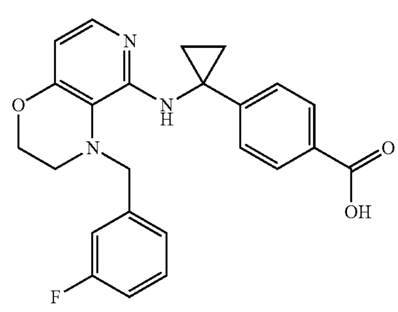 [SMILES: O=C(O)c1ccc(C2(Nc3nccc4c3N(Cc3cccc(F)c3)CCO4)CC2)cc1] | 4-[1-[[4-[(3-fluorophenyl)methyl]-2,3-dihydropyrido[4,3-b][1,4]oxazin-5-yl]amino]cyclopropyl]benzoic acid<br>¹H NMR DMSO-d$_6$: 1.24-1.27 (m, 2H); 1.35 (br s, 2H), 2.98 (br s, 2H), 4.03 (s, 2H), 4.17 (s, 2H), 6.11 (s, 1H), 6.19 (d, J = 5.6 Hz, 1H), 7.13-7.15 (m, 1H), 7.19 (d, J = 8.0 Hz, 2H), 7.36 (d, J = 7.6 Hz, 1H), 7.43-7.50 (m, 3H), 7.77 (d, J = 8.4 Hz, 2H), 12.70 (br s, 1H). | 420.3 |

TABLE 4-continued

| Ex. No. | Structure | IUPAC Name and ¹H NMR data | MS(ESI)m/z: (M + 1) |
|---|---|---|---|
| B17 | 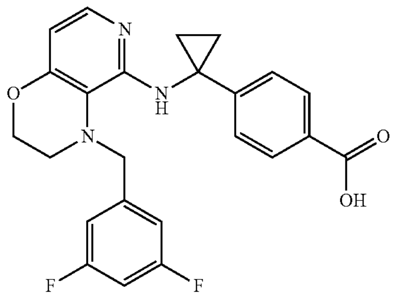 [SMILES: O=C(O)c1ccc(C2(Nc3nccc4c3N(Cc3cc(F)cc(F)c3)CCO4)CC2)cc1] | 4-[1-[[4-[(3,5-difluorophenyl)methyl]-2,3-dihydropyrido[4,3-b][1,4]oxazin-5-yl]amino]cyclopropyl]benzoic acid<br>¹H NMR DMSO-d₆: 1.19-1.24 (m, 2H), 1.36 (br s, 2H), 2.97 (s, 2H), 4.02 (s, 2H), 4.18 (s, 2H), 6.21 (s, 1H), 7.18 (d, J = 8.0 Hz, 2H), 7.36 (d, J = 6.8 Hz, 2H), 7.49 (d, J = 5.2 Hz, 2H), 7.78 (d, J = 7.6 Hz, 2H), 12.60 (br s, 1H). | 438.2 |
| B18 | 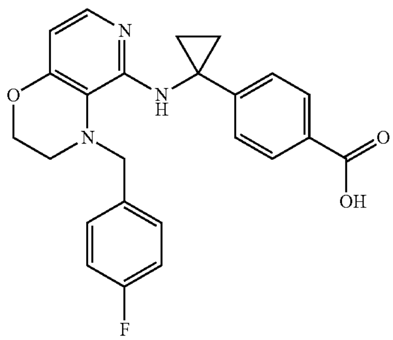 [SMILES: O=C(O)c1ccc(C2(Nc3nccc4c3N(Cc3ccc(F)cc3)CCO4)CC2)cc1] | 4-[1-[[4-[(4-fluorophenyl)methyl]-2,3-dihydropyrido[4,3-b][1,4]oxazin-5-yl]amino]cyclopropyl]benzoic acid<br>¹H NMR DMSO-d₆: δ 1.23-1.38 (m, 4H); 2.95-2.97 (m, 2H), 3.99 (s, 2H), 4.15-4.17 (m, 2H), 6.09 (s, 1H), 6.19 (d, J = 5.2 Hz, 1H), 7.18-7.25 (m, 4H), 7.49 (d, J = 6.0 Hz, 1H), 7.57-7.59 (m, 2H), 7.78 (d, J = 8.4 Hz, 2H), 12.70 (br s, 1H). | 420.3 |
| B19 | 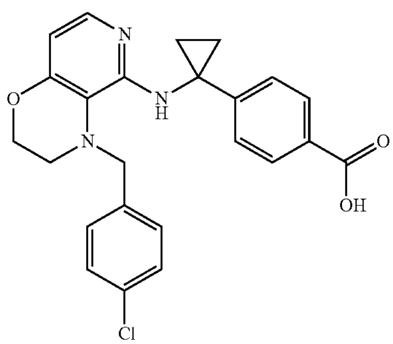 [SMILES: O=C(O)c1ccc(C2(Nc3nccc4c3N(Cc3ccc(Cl)cc3)CCO4)CC2)cc1] | 4-[1-[[4-[(4-chlorophenyl)methyl]-2,3-dihydropyrido[4,3-b][1,4]oxazin-5-yl]amino]cyclopropyl]benzoic acid<br>¹H NMR DMSO-d₆: δ 1.28 (br s, 2H), 1.36 (s, 2H), 2.96 (t, J = 4.4 Hz, 2H), 4.00 (s, 2H), 4.16 (t, J = 4.4 Hz, 2H), 6.06 (s, 1H), 6.19 (d, J = 6 Hz, 1H), 7.19 (d, J = 8.4 Hz, 2H), 7.45-7.50 (m, 3H), 7.56 (d, J = 8.4 Hz, 2H), 7.77 (d, J = 8.0 Hz, 2H), 12.70 (br s, 1H). | 436.2 |
| B20 | 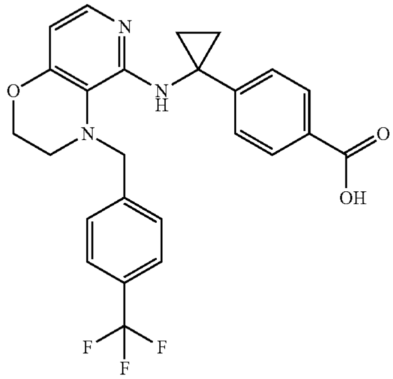 [SMILES: O=C(O)c1ccc(C2(Nc3nccc4c3N(Cc3ccc(C(F)(F)F)cc3)CCO4)CC2)cc1] | 4-[1-[[4-[[4-(trifluoromethyl)phenyl]methyl]-2,3-dihydropyrido[4,3-b][1,4]oxazin-5-yl]amino]cyclopropyl]benzoic acid<br>¹H NMR DMSO-d₆: δ 1.27 (s, 2H), 1.35 (s, 2H), 2.98 (t, J = 4.4 Hz, 2H), 4.11 (s, 2H), 4.18 (t, J = 4.4 Hz, 2H), 6.06 (br s, 1H), 6.21 (d, J = 5.6 Hz, 1H), 7.19 (d, J = 8.4 Hz, 2H), 7.50 (d, J = 6 Hz, 1H), 7.75-7.79 (m, 6H), 12.70 (br s, 1H). | 470.3 |

TABLE 4-continued

| Ex. No. | Structure | IUPAC Name and ¹H NMR data | MS(ESI)m/z: (M + 1) |
|---|---|---|---|
| B21 | 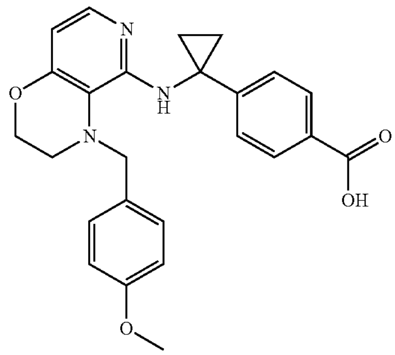 [SMILES: COc1ccc(CN2CCOc3ccnc(NC4(c5ccc(C(=O)O)cc5)CC4)c32)cc1] | 4-[1-[[4-[(4-methoxyphenyl)methyl]-2,3-dihydropyrido[4,3-b][1,4]oxazin-5-yl]amino]cyclopropyl]benzoic acid<br>¹H NMR DMSO-$d_6$: δ 1.30 (s, 2H), 1.37 (s, 2H), 2.96-2.97 (m, 2H); 3.75 (s, 3H), 3.94 (s, 2H), 4.15 (t, J = 4 Hz, 2H), 6.07 (br s, 1H), 6.21 (d, J = 5.2 Hz, 1H), 6.95 (d, J = 8.0 Hz, 2H), 7.20 (d, J = 8.4 Hz, 2H), 7.41 (d, J = 8.0 Hz, 2H), 7.48 (d, J = 6.0 Hz, 1H), 7.78 (d, J = 8.4 Hz, 2H), 12.70 (br s, 1H). | 432.3 |
| B22 | 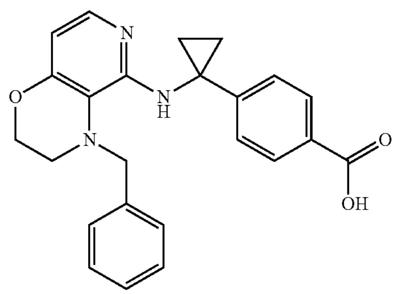 [SMILES: O=C(O)c1ccc(C2(Nc3nccc4c3N(Cc3ccccc3)CCO4)CC2)cc1] | 4-[1-[(4-benzyl-2,3-dihydropyrido[4,3-b][1,4]oxazin-5-yl)amino]cyclopropyl]benzoic acid<br>¹H NMR DMSO-$d_6$: δ 1.29 (s, 2H), 1.37 (s, 2H), 2.99 (s, 2H), 4.02 (s, 2H), 4.16 (t, J = 4.4 Hz, 2H), 6.01 (br s, 1H), 6.22 (s, 1H), 7.19 (d, J = 8 Hz, 2H), 7.32 (t, J = 7.2 Hz, 1H), 7.40 (t, J = 7.6 Hz, 2H), 7.50 (t, J = 7.6 Hz, 3H), 7.78 (d, J = 8.4 Hz, 2H), 12.70 (br s, 1H) | 402.3 |
| B23 | 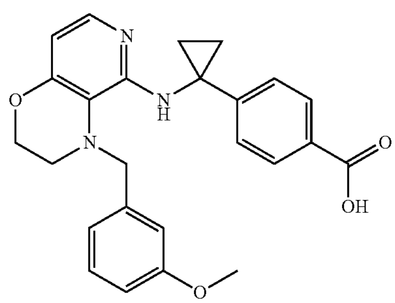 [SMILES: COc1cccc(CN2CCOc3ccnc(NC4(c5ccc(C(=O)O)cc5)CC4)c32)c1] | 4-[1-[[4-[(3-methoxyphenyl)methyl]-2,3-dihydropyrido[4,3-b][1,4]oxazin-5-yl]amino]cyclopropyl]benzoic acid<br>1H NMR DMSO-$d_6$: δ 1.27 (s, 2H), 1.36 (s, 2H), 3.01 (s, 2H), 3.70 (s, 3H), 4.00 (s, 2H), 4.15 (t, J = 4.0 Hz, 2H), 6.01 (br s, 1H), 6.19 (d, J = 5.2 Hz, 1H), 6.88-6.90 (m, 1H), 7.04 (s, 1H), 7.09 (d, J = 7.2 Hz, 1H), 7.19 (d, J = 8.4 Hz, 2H), 7.32 (t, J = 8.0 Hz, 1H), 7.49 (d, J = 5.2 Hz, 1H), 7.78 (d, J = 8.4 Hz, 2H), 12.60 (br s, 1H). | 432.3 |
| B24 | 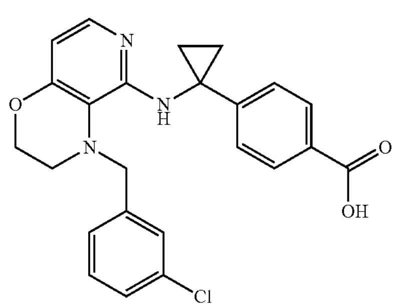 [SMILES: O=C(O)c1ccc(C2(Nc3nccc4c3N(Cc3cccc(Cl)c3)CCO4)CC2)cc1] | 4-[1-[[4-[(3-chlorophenyl)methyl]-2,3-dihydropyrido[4,3-b][1,4]oxazin-5-yl]amino]cyclopropyl]benzoic acid ¹H NMR DMSO-$d_6$: δ 1.27 (s, 2H), 1.36 (s, 2H), 2.98-2.99 (m, 2H), 4.02 (s, 2H), 4.17 (t, J = 4.0 Hz, 2H), 6.13 (br s, 1H), 6.19 (d, J = 5.2 Hz, 1H), 7.19 (d, J = 8.4 Hz, 2H), 7.37-7.52 (m, 4H), 7.65 (s, 1H), 7.78 (d, J = 8.4 Hz, 2H), 12.70 (br s, 1H). | 436.3 |

| Ex. No. | Structure | IUPAC Name and $^1$H NMR data | MS(ESI)m/z: (M + 1) |
|---|---|---|---|
| B25 | 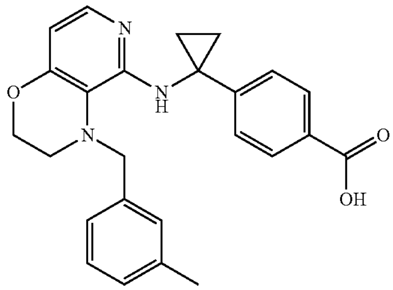 [SMILES: Cc1cccc(CN2CCOc3ccnc(NC4(c5ccc(C(=O)O)cc5)CC4)c32)c1] | 4-[1-[[4-(m-tolylmethyl)-2,3-dihydropyrido[4,3-b][1,4]oxazin-5-yl]amino]cyclopropyl]benzoic acid<br>$^1$H NMR DMSO-d$_6$: δ 1.28-1.29 (m, 2H), 1.35-1.36 (m, 2H), 2.33 (s, 3H), 2.97 (t, J = 3.6 Hz, 2H), 3.97 (s, 2H), 4.17 (t, J = 3.6 Hz, 2H), 5.99 (s, 1H), 6.19 (d, J = 5.2 Hz, 1H), 7.13 (d, J = 7.2 Hz, 1H), 7.19 (d, J = 8.0 Hz, 2H), 7.29-7.32 (m, 3H), 7.49 (d, J = 5.2 Hz, 1H), 7.78 (d, J = 8.0 Hz, 2H), 12.70 (s, 1H). | 416.3 |
| B26 | 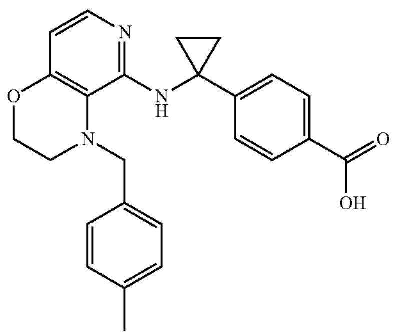 [SMILES: Cc1ccc(CN2CCOc3ccnc(NC4(c5ccc(C(=O)O)cc5)CC4)c32)cc1] | 4-[1-[[4-(p-tolylmethyl)-2,3-dihydropyrido[4,3-b][1,4]oxazin-5-yl]amino]cyclopropyl]benzoic acid<br>$^1$H NMR DMSO-d$_6$: δ 1.28-1.29 (m, 2H), 1.35-1.36 (m, 2H), 2.31 (s, 3H), 2.96 (t, J = 4.0 Hz, 2H), 3.96 (s, 2H), 4.15 (t, J = 4.4 Hz, 2H), 6.01 (s, 1H), 6.19 (d, J = 5.6 Hz, 1H), 7.18-7.21 (m, 4H), 7.38 (d, J = 8.0 Hz, 2H), 7.48 (d, J = 6.0 Hz, 1H), 7.78 (d, J = 8.4 Hz, 2H), 12.70 (br s, 1H). | 416.3 |
| B27 | 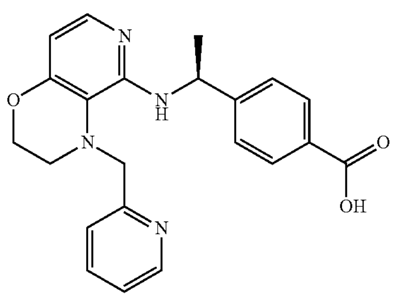 [SMILES: C[C@H](Nc1nccc2c1N(Cc1ccccn1)CCO2)c1ccc(C(=O)O)cc1] | 4-[(1S)-1-[[4-(2-pyridylmethyl)-2,3-dihydropyrido[4,3-b][1,4]oxazin-5-yl]amino]ethyl]benzoic acid<br>$^1$H NMR DMSO-d$_6$: δ 1.58 (d, J = 6.8 Hz, 3H), 2.84-2.88 (m, 2H), 3.91-3.92 (m, 2H), 4.26 (s, 2H), 5.28-5.32 (m, 1H), 6.09 (d, J = 5.2 Hz, 1H), 7.40-7.45 (m, 2H), 7.48-7.52 (m, 3H), 7.84-7.86 (m, 3H), 7.99 (d, J = 6.8 Hz, 1H), 8.65-8.66 (m, 1H), 12.80 (br s, 1H). | 391.3 |
| B28 | 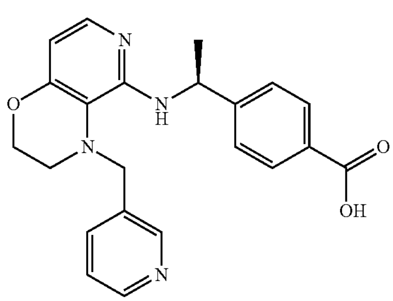 [SMILES: C[C@H](Nc1nccc2c1N(Cc1cccnc1)CCO2)c1ccc(C(=O)O)cc1] | 4-[(1S)-1-[[4-(3-pyridylmethyl)-2,3-dihydropyrido[4,3-b][1,4]oxazin-5-yl]amino]ethyl]benzoic acid<br>$^1$H NMR DMSO-d$_6$: δ 1.44 (d, J = 6.8 Hz, 3H), 2.97-2.98 (m, 2H), 4.03-4.05 (m, 2H), 4.21 (s, 2H), 5.14-5.18 (m, 1H), 5.41 (d, J = 6.4 Hz, 1H), 6.18 (d, J = 5.6 Hz, 1H), 7.43-7.46 (m, 2H), 7.52 (d, J = 5.6 Hz, 1H), 7.83 (d, J = 8 Hz, 2H), 7.94 (d, J = 8 Hz, 1H), 8.40 (s, 1H), 8.55 (d, J = 4.4 Hz, 1H), 8.67 (s, 1H), 12.80 (br s, 1H). | 391.3 |

TABLE 4-continued

| Ex. No. | Structure | IUPAC Name and ¹H NMR data | MS(ESI)m/z: (M + 1) |
|---|---|---|---|
| B29 | 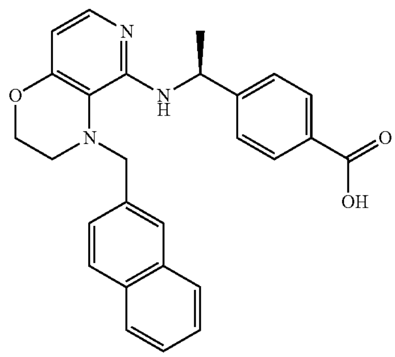 [SMILES: C[C@H](Nc1nccc2c1N(Cc1ccc3ccccc3c1)CCO2)c1ccc(C(=O)O)cc1] | 4-[(1S)-1-[[4-(2-naphthylmethyl)-2,3-dihydropyrido[4,3-b][1,4]oxazin-5-yl]amino]ethyl]benzoic acid<br>¹H NMR DMSO-d$_6$: 1.38 (d, J = 6.4 Hz, 3H), 3.03-3.05 (m. 2H), 4.15-4.18 (m, 2H), 4.23-4.25 (m, 2H), 5.17-5.14 (m, 1H), 5.41 (d, J = 6.4 Hz, 1H), 6.20 (d, J = 6 Hz, 1H), 7.38 (d, J = 8 Hz, 2H), 7.54-7.52 (m, 3H), 7.63 (d, J = 8.4 Hz, 1H), 7.77 (d, J = 7.6 Hz, 2H), 7.98-7.91 (m, 3H), 8.05 (s, 1H), 12.80 (br s, 1H). | 440.4 |
| B30 | 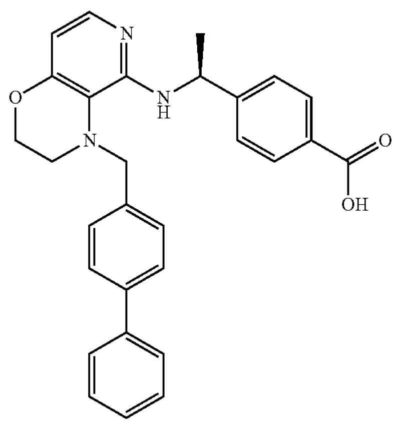 [SMILES: C[C@H](Nc1nccc2c1N(Cc1ccc(-c3ccccc3)cc1)CCO2)c1ccc(C(=O)O)cc1] | 4-[(1S)-1-[[4-[(4-phenylphenyl)methyl]-2,3-dihydropyrido[4,3-b][1,4]oxazin-5-yl]amino]ethyl]benzoic acid<br>¹H NMR DMSO-d$_6$: 1.44 (d, J = 6.8 Hz, 3H), 3.02-3.01 (m. 2H), 4.06-4.04 (m, 2H), 4.23 (s, 2H), 5.40 (br s, 1H), 5.15-5.19 (m, 1H), 6.20 (d, J = 5.2 Hz, 1H), 7.37-7.53 (m, 6H), 7.59 (d, J = 8.4 Hz, 2H), 7.68-7.70 (m, 4H), 7.84 (d, J = 8.4 Hz, 2H), 12.50 (br s, 1H). | 466.3 |
| B31 | 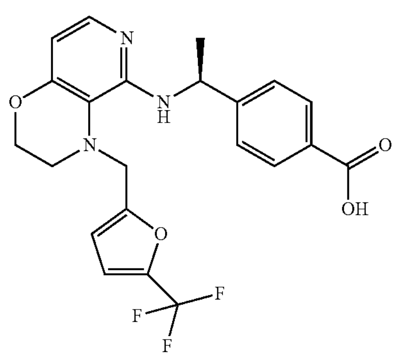 [SMILES: C[C@H](Nc1nccc2c1N(Cc1ccc(C(F)(F)F)o1)CCO2)c1ccc(C(=O)O)cc1] | 4-[(1S)-1-[[4-[[5-(trifluoromethyl)-2-furyl]methyl]-2,3-dihydropyrido[4,3-b][1,4]oxazin-5-yl]amino]ethyl]benzoic acid<br>¹H NMR DMSO-d$_6$: δ 1.51 (d, J = 6.8 Hz, 3H), 2.95-3.05 (m, 2H), 3.99 (s, 2H), 4.22 (s, 2H), 5.22 (m, 1H), 5.59 (d, J = 6.8 Hz, 1H), 6.16 (d, J = 5.2 Hz, 1H), 6.77 (d, J = 3.6 Hz, 1H), 7.25 (d, J = 2.0 Hz, 1H), 7.46 (d, J = 8.4 Hz, 2H), 7.49 (d, J = 6.0 Hz, 1H), 7.85 (d, J = 8.4 Hz, 2H), 12.80 (br s, 1H). | 448.3 |
| B32 | 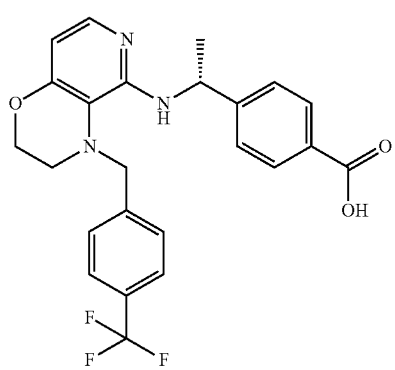 [SMILES: C[C@@H](Nc1nccc2c1N(Cc1ccc(C(F)(F)F)cc1)CCO2)c1ccc(C(=O)O)cc1] | 4-[(1R)-1-[[4-[[4-(trifluoromethyl)phenyl]methyl]-2,3-dihydropyrido[4,3-b][1,4]oxazin-5-yl]amino]ethyl]benzoic acid<br>¹H NMR DMSO-d$_6$: δ 1.38 (d, J = 3.2 Hz, 3H), 2.99 (s, 2H), 4.09-4.15 (m, 2H), 4.19-5.22 (m, 2H), 5.10-5.19 (m, 1H), 5.21 (d, J = 6.8 Hz, 1H), 6.19 (d, J = 5.6 Hz, 1H), 7.32 (d, J = 7.6 Hz, 1H), 7.53 (d, J = 6 Hz, 1H), 7.73-7.80 (m, 6H), 12.90 (br s, 1H). | 458.0 |

TABLE 4-continued

| Ex. No. | Structure | IUPAC Name and ¹H NMR data | MS(ESI)m/z: (M + 1) |
|---|---|---|---|
| B33 | 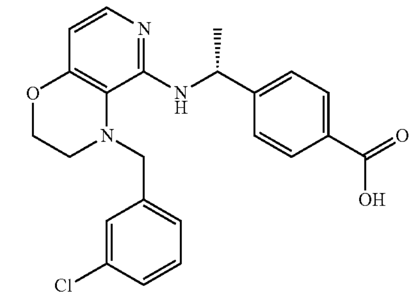 [SMILES: C[C@@H](Nc1nccc2c1N(Cc1cccc(Cl)c1)CCO2)c1ccc(C(=O)O)cc1] | 4-[(1R)-1-[[4-[(3-chlorophenyl)methyl]-2,3-dihydropyrido[4,3-b][1,4]oxazin-5-yl]amino]ethyl]benzoic acid 1H NMR DMSO-d6: δ 1.41 (d, J = 6.8 Hz, 3H), 2.99 (d, J = 3.2 Hz, 2H), 4.00-4.02 (m, 2H), 4.20 (t, J = 4.4 Hz, 2H), 5.12-5.16 (m, 1H), 5.30 (d, J = 6.4 Hz, 1H), 6.18 (d, J = 5.6 Hz, 1H), 7.39-7.52 (m, 6H), 7.58 (s, 1H), 7.83 (d, J = 8.4 Hz, 2H), 12.90 (s, 1H). | 424.3 |
| B34 | 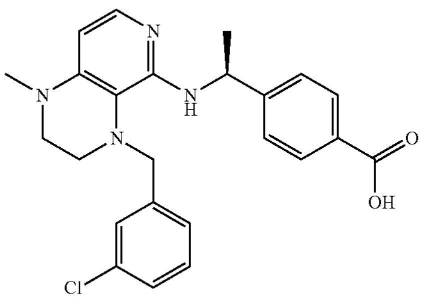 [SMILES: C[C@H](Nc1nccc2c1N(Cc1cccc(Cl)c1)CCN2C)c1ccc(C(=O)O)cc1] | 4-[(1S)-1-[[4-[(3-chlorophenyl)methyl]-1-methyl-2,3-dihydropyrido[3,4-b]pyrazin-5-yl]amino]ethyl]benzoic acid ¹H NMR (400 MHz, DMSO-d₆): δ 1.38 (d, J = 6.8 Hz, 3H), 2.86-2.89 (m, 2H), 2.91 (s, 3H); 3.26 (br s, 2H), 3.82 (br s, 2H), 5.09-5.13 (m, 1H), 5.23 (d, J = 7.6 Hz, 1H), 6.12 (d, J = 6.0 Hz, 1H), 7.35-7.48 (m, 6H), 7.53 (s, 1H), 7.81 (d, J = 8.0 Hz, 2H), 12.76 (br s, 1H). | 437.3 |
| B35 | 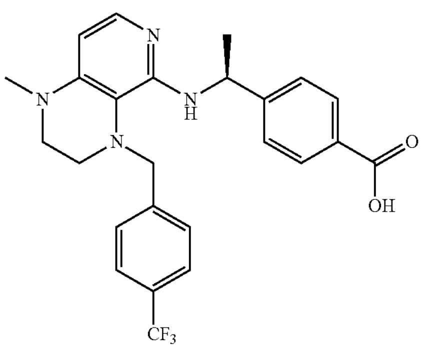 [SMILES: C[C@H](Nc1nccc2c1N(Cc1ccc(C(F)(F)F)cc1)CCN2C)c1ccc(C(=O)O)cc1] | 4-[(1S)-1-[[1-methyl-4-[[4-(trifluoromethyl)phenyl]methyl]-2,3-dihydropyrido[3,4-b]pyrazin-5-yl]amino]ethyl]benzoic acid ¹H NMR (400 MHz, DMSO-d₆): δ 1.36 (d, J = 6.8 Hz, 3H), 2.85-2.88 (m, 2H), 2.92 (s, 3H), 3.27 (br s, 2H), 3.92 (br s, 2H), 5.09-5.21 (m, 2H), 6.14 (d, J = 6.0 Hz, 1H), 7.34 (d, J = 7.6 Hz, 2H), 7.43 (d, J = 5.6 Hz, 1H), 7.68-7.80 (m, 6H), 12.70 (brs, 1H). | 471.3 |

Example B36: 4-[(1S)-1-[[3-oxo-4-[[4-(trifluoromethyl)phenyl]methyl]pyrido[4,3-b][1,4]thiazin-5-yl]amino]ethyl]benzoic acid

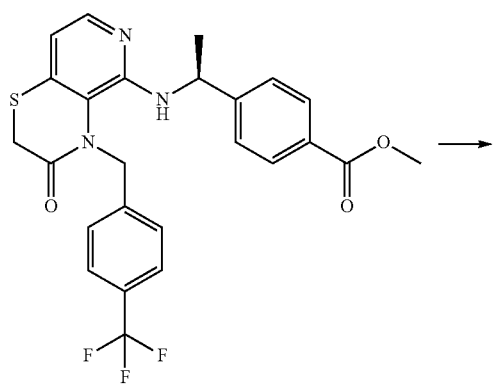

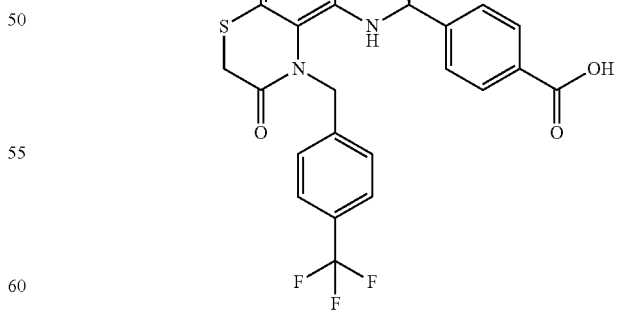

To a solution of methyl 4-[(1S)-1-[[3-oxo-4-[[4-(trifluoromethyl)phenyl]methyl]pyrido[4,3-b][1,4]thiazin-5-yl]amino]ethyl]benzoate (Example A36, 0.2 g, 0.40 mmol) in THF:MeOH:H₂O (3:2:1; 18 mL) was added lithium hydroxide monohydrate (0.049 g, 1.20 mmol), and the mixture was stirred at room temperature for 2 days, and the product formation was confirmed by TLC. The reaction mixture was evaporated under vacuo, diluted with water (5 mL), and then acidified by using 1N HCl to pH 4-5. The obtained solid was collected by filtration, washed with water, n-hexane, dried, and then purified by cobiflash column chromatography using 20-25% ethyl acetate in hexane as a mobile phase to give the title compound (0.11 g, 57%).

MS (EI) m/z: 488.1 (M+1); $^1$H NMR DMSO-$d_6$: δ 1.48 (br s, 3H), 3.50-3.58 (m, 2H), 5.23-5.45 (m, 3H), 6.64 (d, J=5.2 Hz, 1H), 6.72-6.80 (m, 1H), 7.18-7.26 (m, 2H), 7.48-7.52 (m, 2H), 7.55-7.58 (m, 3H), 7.86 (d, J=8.0 Hz, 2H), 12.78 (br s, 1H)

Example B37: 4-[(1S)-1-[[1-[[4-(trifluoromethyl)phenyl]methyl]-3,4-dihydro-2H-1,7-naphthyridin-8-yl]amino]ethyl]benzoic acid

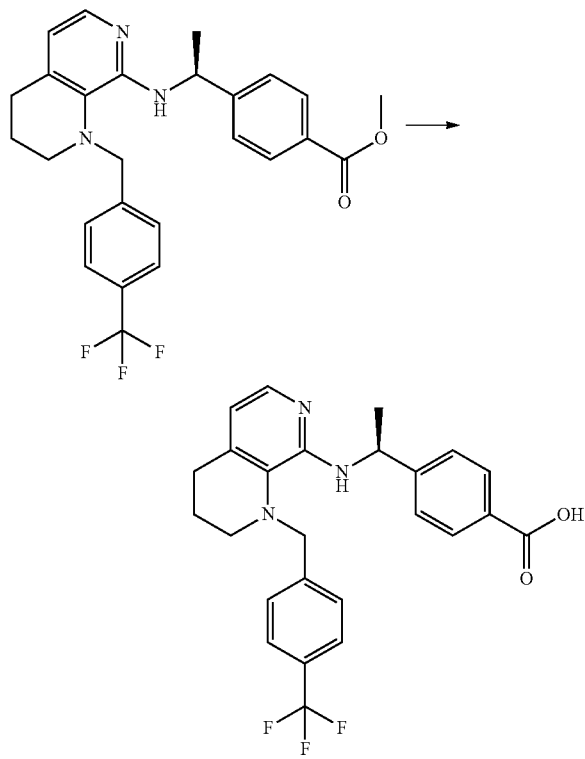

The title compound was obtained as an light brown solid (0.035 g, 30%) in a similar manner to that of Example B36 using the compound obtained in Example A37 (0.12 g, 0.26 mmol) and lithium hydroxide (0.031 g, 0.77 mmol).

MS (EI) m/z: 456.2 (M+1) $^1$H NMR DMSO-$d_6$: δ 1.32 (d, J=6.8 Hz, 3H), 1.77-1.82 (m, 2H), 2.65 (t, J=6.4 Hz, 2H), 2.94 (t, J=4.8 Hz, 2H), 4.07 (s, 2H), 5.08-5.11 (m, 1H), 5.17 (d, J=6.4 Hz, 1H), 6.36 (d, J=4.8 Hz, 1H), 7.30 (d, J=8.4 Hz, 2H), 7.54 (d, J=5.2 Hz, 1H), 7.72-7.79 (m, 6H), 12.78 (br s, 1H).

Example B38: 4-[(1S)-1-[[5-[(3-chlorophenyl)methyl]-6,7-dihydropyrimido[4,5-b][1,4]oxazin-4-yl]amino]ethyl]benzoic acid

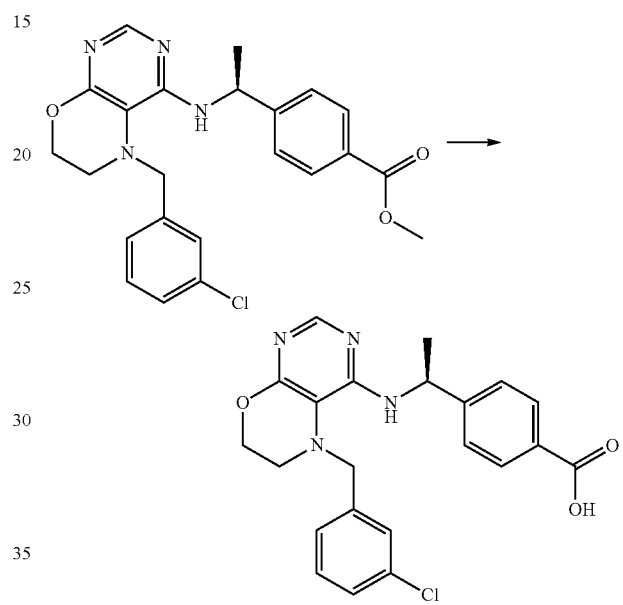

The title compound was obtained as an off-white solid (0.03 g, 62%) in a similar manner to that of Example B1 or B36 using the compound obtained in Example A38 (0.05 g, 0.11 mmol) and lithium hydroxide (0.023 g, 0.56 mmol).

MS (ESI) m/z: 424.8 [M($^{35}$Cl)+1], 426.8 [M($^{37}$Cl)+1]; $^1$H NMR (400 MHz, DMSO-$d_6$): δ 1.46 (d, J=6.8 Hz, 3H), 3.00 (d, J=3.6 Hz, 2H), 4.00 (s, 2H), 4.27 (t, J=4.8 HZ, 2H), 5.20-5.25 (m, 1H), 6.04 (d, J=7.6 Hz, 1H), 7.39-7.45 (m, 5H), 7.57 (s, 1H), 7.85 (d, J=8.4 Hz, 2H), 7.88 (s, 1H), 12.80 (br s, 1H).

The compounds of Examples B39-B45 were synthesized in a similar manner to that of Examples B1-B4 and B36-B38.

TABLE 5

| Ex. No. | Structure | IUPAC Name 1H NMR data | MS (ESI) m/z: (M + 1) |
|---|---|---|---|
| B39 | 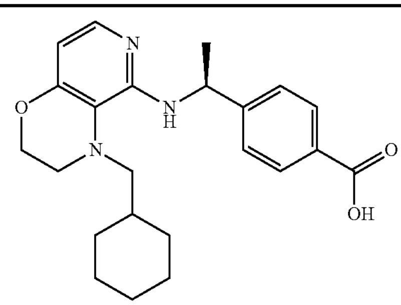 | 4-[(1S)-1-[[4-(cyclohexylmethyl)-2,3-dihydropyrido[4,3-b][1,4]oxazin-5-yl]amino]ethyl]benzoic acid<br>$^1$H NMR (400 MHz, DMSO-$d_6$): δ 0.86-0.94 (m, 2H), 1.10-1.30 (m, 3H), 1.49 (d, J = 6.4 Hz, 3H), 1.60-1.75 (m, 4H), 1.83-1.92 (m, 2H), 2.54 (s, 2H), 2.98-3.09 (m, 2H), 4.15 (t, J = 4.0 Hz, 2H), 5.11-5.15 (m, 2H), 6.11 (d, J = 5.6 Hz, 1H), 7.45 (m, 3H), 7.87 (m, 2H), 12.45 (brs, 1H). | 396.3 |

TABLE 5-continued

| Ex. No. | Structure | IUPAC Name 1H NMR data | MS (ESI) m/z: (M + 1) |
|---|---|---|---|
| B40 | 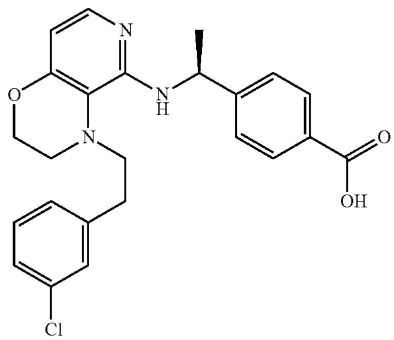 [SMILES: C[C@H](Nc1nccc2c1N(CCc1cccc(Cl)c1)CCO2)c1ccc(C(=O)O)cc1] | 4-[(1S)-1-[[4-[2-(3-chlorophenyl)ethyl]-2,3-dihydropyrido[4,3-b][1,4]oxazin-5-yl]amino]ethyl]benzoic acid<br>$^1$H NMR DMSO-$d_6$: δ 1.18 (d, J = 7.6 Hz, 3H), 2.93-2.95 (m, 4H), 3.15-3.25 (m, 2H), 4.22 (t, J = 4.4 Hz, 2H), 4.74 (d, J = 8.0 Hz, 1H), 5.12-5.16 (m, 1H), 6.10 (d, J = 6.0 Hz, 1H), 7.26-7.32 (m, 5H), 7.41-7.43 (m, 2H), 7.84 (d, J = 8.4 Hz, 2H), 12.70 (s, 1H). | 438.2 |
| B41 | 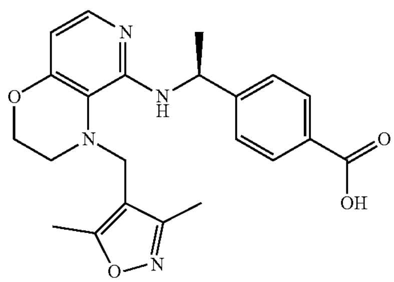 [SMILES: Cc1noc(C)c1CN1CCOc2ccnc(N[C@@H](C)c3ccc(C(=O)O)cc3)c21] | 4-[(1S)-1-[[4-[(3,5-dimethyl-isoxazol-4-yl)methyl]-2,3-dihydro-pyrido[4,3-b][1,4]oxazin-5-yl]amino]ethyl]benzoic acid<br>$^1$H NMR DMSO-$d_6$: δ 1.50 (d, J = 6.8 Hz, 3H), 2.19 (s, 3H), 2.32 (s, 3H), 2.95-2.98 (m, 2H), 3.80-3.95 (m, 2H), 4.17 (t, J = 4.6 Hz, 2H), 5.15-5.18 (m, 1H), 5.42 (d, J = 6.4 Hz, 1H), 6.17 (d, J = 6.0 Hz, 1H), 7.48 (d, J = 8.0 Hz 2H), 7.52 (d, J = 5.6 Hz, 1H), 7.86 (d, J = 8.4 Hz, 2H), 12.80 (s, 1H). | 409.2 |
| B42 | 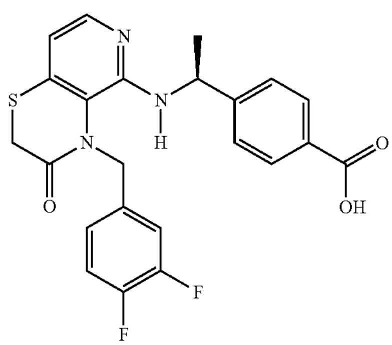 [SMILES: C[C@H](Nc1nccc2c1N(Cc1ccc(F)c(F)c1)C(=O)CS2)c1ccc(C(=O)O)cc1] | 4-[(1S)-1-[[4-[(3,4-difluorophenyl)methyl]-3-oxopyrido[4,3-b][1,4]thiazin-5-yl]amino]ethyl]benzoic acid<br>$^1$H NMR (400 MHz, DMSO-$d_6$): δ 1.50 (br s, 3H), 3.49-3.57 (m, 2H), 4.80-5.27 (m, 3H), 6.40 (br s, 1H), 6.74-7.02 (m, 3H), 7.24-7.26 (m, 1H), 7.46-7.54 (m, 2H), 7.56-7.62 (m, 1H), 7.86 (d, J = 7.6 Hz, 2H), 12.78 (br s, 1H) | 456.2 |
| B43 | 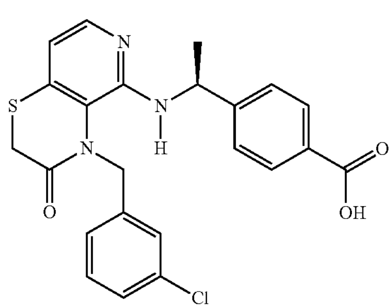 [SMILES: C[C@H](Nc1nccc2c1N(Cc1cccc(Cl)c1)C(=O)CS2)c1ccc(C(=O)O)cc1] | 4-[(1S)-1-[[4-[(3-chlorophenyl)methyl]-3-oxopyrido[4,3-b][1,4]thiazin-5-yl]amino]ethyl]benzoic acid<br>$^1$H NMR (400 MHz, DMSO-$d_6$): δ 1.49 (d, J = 5.2 Hz, 3H), 3.50-3.58 (m, 2H), 4.80-5.27 (m, 3H), 6.63 (d, J = 4.8 Hz, 1H), 6.72-6.78 (m, 1H), 6.90-7.06 (m, 2H), 7.20 (br s, 2H), 7.50 (d, J = 5.6 Hz, 2H), 7.59 (d, J = 4.8 Hz, 1H), 7.86 (d, J = 8.4 Hz, 2H), 12.76 (br s, 1H). | 454.1 |

TABLE 5-continued

| Ex. No. | Structure | IUPAC Name 1H NMR data | MS (ESI) m/z: (M + 1) |
|---|---|---|---|
| B44 | 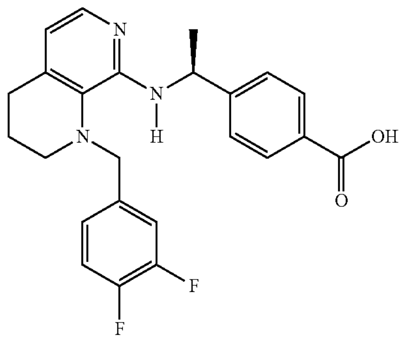 [SMILES: C[C@H](Nc1nccc2c1N(Cc1ccc(F)c(F)c1)CCC2)c1ccc(C(=O)O)cc1] | 4-[(1S)-1-[[1-[(3,4-difluorophenyl)methyl]-3,4-dihydro-2H-1,7-naphthyridin-8-yl]amino]ethyl]benzoic acid<br>$^1$H NMR DMSO-$d_6$: δ 1.37 (d, J = 6.8 Hz, 3H), 1.75-1.79 (m, 2H), 2.64 (t, J = 6.4 Hz, 2H), 2.92 (t, J = 4.4 Hz, 2H), 3.95 (s, 2H), 5.08-5.12 (m, 1H), 5.30-5.40 (m, 1H), 6.35 (d, J = 5.6 Hz, 1H), 7.35-7.37 (m, 3H), 7.42-7.49 (m, 1H), 7.53-7.59 (m, 2H), 7.81 (d, J = 8.4 Hz, 2H), 12.78 (br s, 1H) | 424.3 |
| B45 | 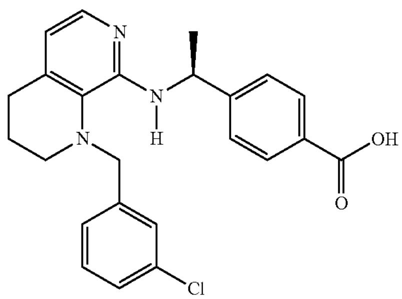 [SMILES: C[C@H](Nc1nccc2c1N(Cc1cccc(Cl)c1)CCC2)c1ccc(C(=O)O)cc1] | 4-[(1S)-1-[[1-[(3-chlorophenyl)methyl]-3,4-dihydro-2H-1,7-naphthyridin-8-yl]amino]ethyl]benzoic acid<br>$^1$H NMR DMSO-$d_6$: δ 1.34 (d, J = 6.8 Hz, 3H), 1.76-1.81 (m, 2H), 2.64 (t, J = 6.4 Hz, 2H), 2.92-2.94 (m, 2H), 3.98 (s, 2H), 5.08-5.12 (m, 1H), 5.24 (d, J = 6.0 Hz, 1H), 6.35 (d, J = 5.6 Hz, 1H), 7.34 (d, J = 8.4 Hz, 2H), 7.37-7.40 (m, 1H), 7.42-7.49 (m, 2H), 7.54 (d, J = 5.2 Hz, 2H), 7.81 (d, J = 8.4 Hz, 2H), 12.78 (br s, 1H) | 422.2 |

Example B46: 4-[(1S)-1-[[8-Methyl-4-[[3-(trifluoromethyl)phenyl]methyl]-2,3-dihydropyrido[4,3-b][1,4]oxazin-5-yl]amino]ethyl]benzoic acid

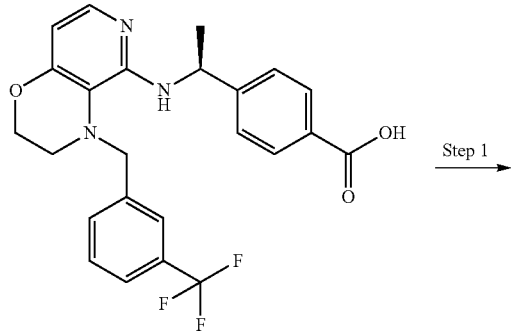

Step 1 →

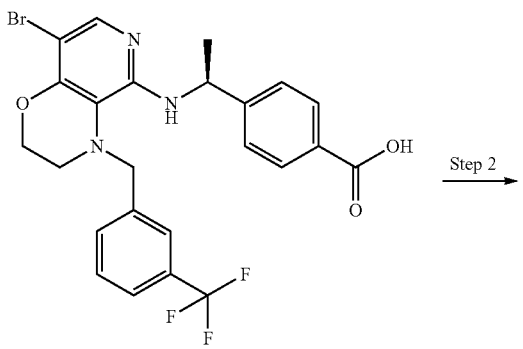

Step 2 →

-continued

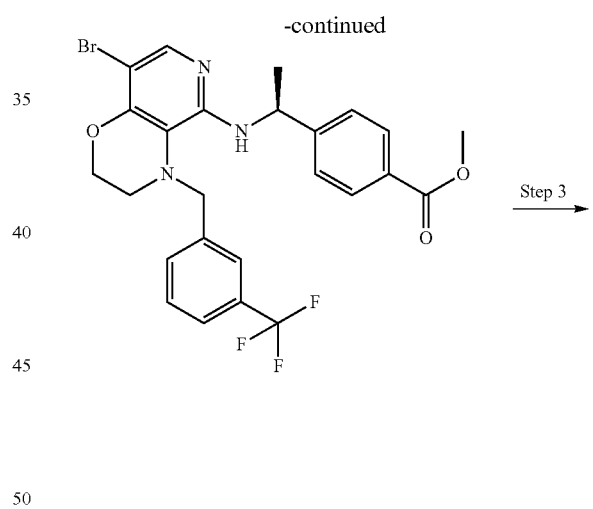

Step 3 →

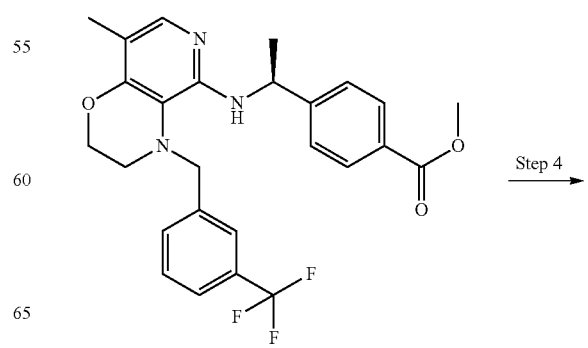

Step 4 →

-continued

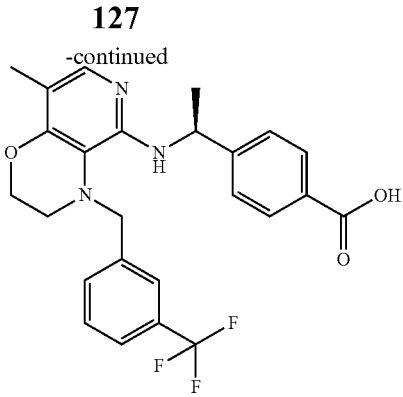

Step 1: 4-[(1S)-1-[[8-Bromo-4-[[3-(trifluoromethyl)phenyl]methyl]-2,3-dihydropyrido[4,3-b][1,4]oxazin-5-yl]amino]ethyl]benzoic acid To a mixture of 4-[(1S)-1-[[4-[[3-(trifluoromethyl)phenyl]methyl]-2,3-dihydropyrido[4,3-b][1,4]oxazin-5-yl]amino]ethyl]benzoic acid (Example B14, 2.0 g, 4.37 mmol) in acetonitrile (50 mL) was added and N-bromosuccinimide (0.93 g, 5.20 mmol) at room temperature, and the mixture was stirred for 2 hours. The reaction completion was confirmed by TLC. To the resulting residue was added water (50 mL), and the mixture was extracted with ethyl acetate (3×50 mL). The combined organic layers were washed with brine (50 mL) and dried over sodium sulfate. The organic layer was evaporated under vacuum, and the residue was purified by combiflash with 50% ethyl acetate in hexane as a mobile phase to give the title compound as solid (1.1 g, 47%).

MS (ESI) m/z: 536.0 [M($^{79}$Br)+1], 538.0 [M($^{81}$Br)+1]; $^1$H NMR (400 MHz, DMSO-d$_6$): δ 1.38 (d, J=6.8 Hz, 3H), 3.05 (s, 2H), 4.13 (s, 2H), 4.31-4.32 (m, 2H), 5.08-5.11 (m, 1H), 5.33 (d, J=6.8 Hz, 1H), 7.35 (d, J=8.4 Hz, 2H), 7.73-7.81 (m, 7H), 12.75 (s, 1H).

Step 2: Methyl 4-[(1S)-1-[[8-bromo-4-[[3-(trifluoromethyl)phenyl]methyl]-2,3-dihydropyrido[4,3-b][1,4]oxazin-5-yl]amino]ethyl]benzoate To a solution of 4-[(1S)-1-[[8-bromo-4-[[3-(trifluoromethyl)phenyl]methyl]-2,3-dihydropyrido[4,3-b][1,4]oxazin-5-yl]amino]ethyl]benzoic acid (1.0 g, 1.86 mmol) in N,N-dimethylformamide (10 mL) was cooled to 0° C., potassium carbonate (0.52 g, 3.72 mmol) and methyl iodide (0.14 mL, 0.22 mmol) were added thereto. The reaction mixture was stirred at room temperature for 2.0 hours. Progress of the reaction was monitored by TLC. After completion of the reaction, water (50 mL) was added thereto. The mixture was extracted with ethyl acetate (3×50 mL). The combined organic layers were washed with water (50 mL) and brine (50 mL), and dried over sodium sulfate. The organic layer was evaporated under vacuum, and the residue was purified by combiflash with 20% ethyl acetate in hexane as a mobile phase to give the title compound as solid (0.78 g, 76%).

MS (ESI) m/z: (M+1) 550.2 [M($^{79}$Br)+1], 552.2 [M($^{81}$Br)+1] $^1$H NMR CDCL$_3$: δ 1.46 (d, J=6.8 Hz, 3H), 3.07 (t, J=4.4 Hz, 2H), 3.89 (s, 3H), 4.07 (s, 2H), 4.33 (m, 2H), 4.90 (d, J=6.4 Hz, 1H), 5.18-5.30 (m, 1H), 7.28 (d, J=8.4 Hz, 2H), 7.54 (d, J=8.4 Hz, 2H), 7.66 (d, J=7.6 Hz, 2H), 7.84 (s. 1H), 7.91 (d, J=8.0 Hz, 2H)

Step 3: Methyl 4-[(1S)-1-[[8-methyl-4-[[3-(trifluoromethyl)phenyl]methyl]-2,3-dihydropyrido[4,3-b][1,4]oxazin-5-yl]amino]ethyl]benzoate A mixture of methyl 4-[(1S)-1-[[8-bromo-4-[[3-(trifluoromethyl)phenyl]methyl]-2,3-dihydropyrido[4,3-b][1,4]oxazin-5-yl]amino]ethyl]benzoate (0.2 g, 0.36 mmol), methyl boronic acid (0.108 g, 1.81 mmol), potassium phosphate (0.269 g, 1.27 mmol), water (0.2 mL) and toluene (4 mL) was degassed with argon for 30 min. To the mixture were added palladium acetate (0.008 g, 0.036 mmol) and tricyclohexylphosphine (0.020 g, 0.073 mmol). Degassing was continued for another 20 min. The resulting mixture was heated at 100° C. for 3 hours under argon atmosphere. The reaction mixture was cooled to room temperature, filtered through celite pad, and washed with ethyl acetate. The filtrate was evaporated under vacuum, and the residue was purified by combiflash with 10-15% ethyl acetate in hexane as a mobile phase to give the title compound (0.09 g. 75,%).

MS (ESI) m/z: 486.3 [M+1]; $^1$H NMR CDCl$_3$: 1.46 (d, J=6.8 Hz, 3H), 2.02 (s, 3H), 3.01-3.03 (m, 2H), 3.88 (s, 3H), 4.07 (m, 2H), 4.24-4.26 (m, 2H), 4.79 (d, J=6.8 Hz, 1H), 5.20-5.24 (m, 1H), 7.30 (d, J=8.0 Hz, 2H), 7.54-7.56 (m, 3H), 7.65 (d, J=8.4 Hz, 2H), 7.90 (d, J=8.4 Hz, 2H).

Step 4: 4-[(1S)-1-[[8-Methyl-4-[[3-(trifluoromethyl)phenyl]methyl]-2,3-dihydropyrido[4,3-b][1,4]oxazin-5-yl]amino]ethyl]benzoic acid To a solution of methyl 4-[(1S)-1-[[8-methyl-4-[[3-(trifluoromethyl)phenyl]methyl]-2,3-dihydropyrido[4,3-b][1,4]oxazin-5-yl]amino]ethyl]benzoate (0.09 g, 0.18 mmol) in THF:water:methanol (3:2:2, 6 mL) was added lithium hydroxide monohydrate (0.039 g, 0.92 mmol). The mixture was stirred at room temperature for 18 hours. The reaction completion was confirmed by TLC, and then the mixture was evaporated to dryness. The residue was dissolved in water (10 mL), and the solution was acidified by 5% aqueous citric acid solution to pH 4-5, and stirred for 30 min. The resulting solid was collected by filtration, washed with water and dried under vacuum to give the title compound as a pale yellow solid (0.065 g, 74%).

MS (ESI) m/z: 472.1 (M+1); $^1$H NMR (400 MHz, DMSO-d$_6$): δ 1.36 (d, J=6.8 Hz, 3H), 1.95 (s, 3H), 2.98 (t, J=3.2 Hz, 2H), 4.09-4.11 (m, 2H), 4.26 (t, J=3.6 Hz, 2H), 5.02-5.15 (m, 2H), 7.34 (d, J=8.0 Hz, 2H), 7.40 (s, 1H), 7.77-7.81 (m, 6H), 12.85 (br S, 1H)

The compounds of Example B47 was synthesized in a similar manner to that of Example B46.

TABLE 6

| Ex. No. | Structure | IUPAC Name / $^1$H NMR data | MS (ESI) m/z: (M + 1) |
|---|---|---|---|
| B47 | 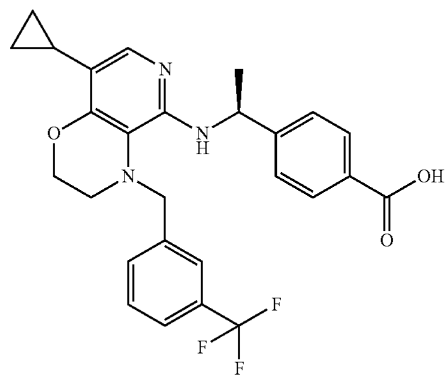 [SMILES: C[C@H](Nc1ncc(C2CC2)c2c1N(Cc1cccc(C(F)(F)F)c1)CCO2)c1ccc(C(=O)O)cc1] | 4-[(1S)-1-[[8-cyclopropyl-4-[[3-(trifluoromethyl)phenyl]methyl]-2,3-dihydropyrido[4,3-b][1,4]oxazin-5-yl]amino]ethyl]benzoic acid<br>$^1$H NMR (400 MHz, DMSO-$d_6$): δ 0.50-0.54 (m, 2H), 0.73-0.75 (m, 2H), 1.35 (d, J = 6.0 Hz, 3H), 1.70-1.74 (m, 1H), 2.99 (s, 2H), 4.05-4.16 (m, 2H), 4.29 (s, 2H), 5.02-5.15 (m, 2H), 7.26 (s, 1H), 7.33 (d, J = 8.0 Hz, 2H), , 7.75-7.80 (m, 6H), 12.85 (br s, 1H). | 498.1 |

Example C1: Potassium salt of 4-[(1S)-1-[[4-[(4-methoxyphenyl)methyl]-2,3-dihydropyrido[4,3-b][1,4]oxazin-5-yl]amino]ethyl]benzoic acid

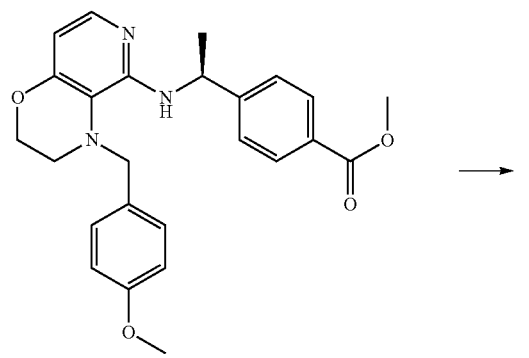

To a solution of methyl 4-[(1S)-1-[[4-[(4-methoxyphenyl)methyl]-2,3-dihydropyrido[4,3-b][1,4]oxazin-5-yl]amino]ethyl]benzoate (Example A15, 0.43 g, 0.99 mmol) in mixture of solvent ethanol:H$_2$O (9:1, 10 mL) was added potassium hydroxide (0.167 g, 2.97 mmol). The mixture was stirred at 100° C. for 2 hours. The reaction completion was confirmed by TLC then, the mixture was cooled to room temperature and evaporated to dryness, and the residue was purified by preparative HPLC using acetonitrile: water to give the title compound as an off-white solid (0.24 g, 53%).

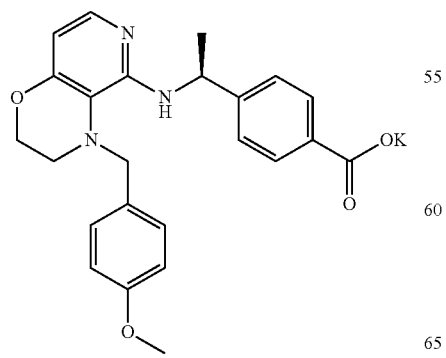

MS (ESI) m/z: 420.1 (M+1); $^1$H NMR DMSO-$d_6$: δ 1.44 (d, J=6.4 Hz, 3H), 2.93-2.94 (m, 2H), 3.76 (s, 3H), 3.88 (s, 2H), 4.18 (s, 2H), 5.13-5.16 (m, 1H), 5.28 (d, J=6.8 Hz, 1H), 6.16 (d, J=5.2 Hz, 1H), 6.95 (d, J=8.0 Hz, 2H), 7.24 (d, J=8.0 Hz, 2H), 7.35 (d, J=8.0 Hz, 2H), 7.54 (d, J=5.6 Hz, 1H), 7.76 (d, J=8.0 Hz, 1H)

The compounds of Examples C2-C7 were synthesized in a similar manner to that of Example C1.

TABLE 7

| Ex. No. | Structure | IUPAC Name / ¹H NMR data | MS(ESI)m/z: (M + 1) |
|---|---|---|---|
| C2 | 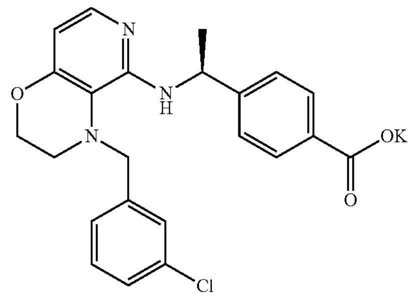 | Potassium salt of 4-[(1S)-1-[[4-[(3-chlorophenyl)methyl]-2,3-dihydropyrido[4,3-b][1,4]oxazin-5-yl]amino]ethyl]benzoic acid<br>¹H NMR (400 MHz, DMSO-$d_6$) δ: 1.35 (d, J = 6.4 Hz, 3H), 2.94 (t, J = 4.0 Hz, 2H), 3.95 (s, 2H), 4.17 (t, J = 4.0 Hz, 2H), 5.05-5.16 (m, 2H), 6.15 (d, J = 6.0 Hz, 1H), 7.10 (d, J = 7.2 Hz, 2H), 7.38-7.42 (m, 3H), 7.53-7.55 (m, 2H), 7.67 (d, J = 8.0 Hz, 2H). | 424.2 |
| C3 | 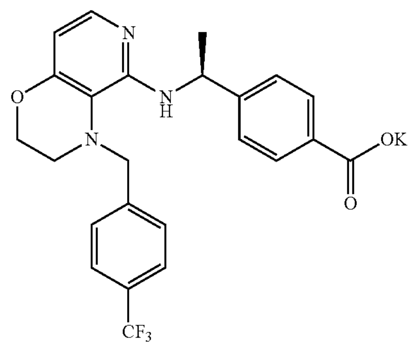 | Potassium salt of 4-[(1S)-1-[[4-[[4-(trifluoromethyl)phenyl]methyl]-2,3-dihydropyrido[4,3-b][1,4]oxazin-5-yl]amino]ethyl]benzoic acid<br>¹H NMR DMSO-$d_6$: δ 1.36 (d, J = 6 Hz, 3H), 2.96-2.98 (m, 2H), 4.06 (s, 2H), 4.19-4.21 (m. 2H), 5.12-5.13 (m, 1H), 6.18 (d, J = 5.6 Hz, 1H), 7.08 (d, J = 8 Hz, 2H), 7.56 (d, J = 6 Hz, 2H), 7.67 (d, J = 8 Hz, 2H), 7.72 (d, J = 8 Hz, 2H), 7.79 (d, J = 8 Hz, 2H). | 458.2 |
| C4 | 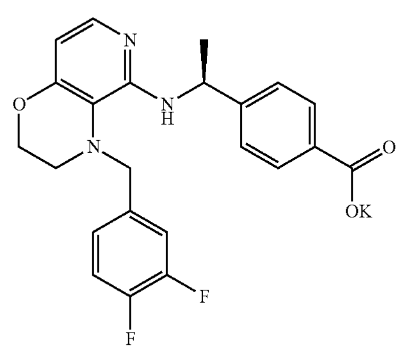 | Potassium salt of 4-[(1S)-1-[[4-[(3,4-difluorophenyl)methyl]-2,3-dihydropyrido[4,3-b][1,4]oxazin-5-yl]amino]ethyl]benzoic acid<br>¹H NMR DMSO-$d_6$: δ 1.40 (d, J = 4.4 Hz, 3H), 2.96 (s, 2H), 3.95 (s, 2H), 4.18 (s, 2H), 5.12 (br s, 1H), 5.21 (br s, 1H), 6.16 (br s, 1H), 7.18 (d, J = 6.4 Hz, 2 H), 7.33 (s, 1H), 7.43-7.62 (br s, 3H), 7.73 (d, J = 6.8 Hz, 2 H). | 426.1 |
| C5 | 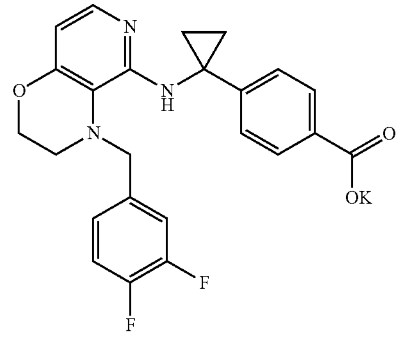 | Potassium salt of 4-[1-[[4-[(3,4-difluorophenyl)methyl]-2,3-dihydropyrido[4,3-b][1,4]oxazin-5-yl]amino]cyclopropyl]benzoic acid<br>¹H NMR DMSO-$d_6$: δ 1.23-1.29 (m, 4H), 2.95 (t, J = 4.0 Hz, 2H), 3.77 (s, 2H), 4.16 (t, J = 4.0 Hz, 1H), 6.12 (s, 1H), 6.17 (d, J = 5.6 Hz, 1H), 7.05 (d, J = 8.0 Hz, 2H), 7.37-7.46 (m, 2H), 7.50 (d, J = 5.6 Hz, 2H), 7.70 (d, J = 8.4 Hz, 3H). | 438.3 |

TABLE 7-continued

| Ex. No. | Structure | IUPAC Name $^1$H NMR data | MS(ESI)m/z: (M + 1) |
|---|---|---|---|
| C6 | 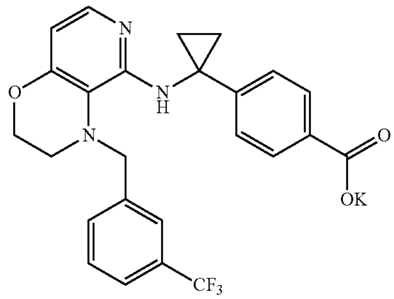 | Potassium salt of 4-[1-[[4-[[3-(trifluoromethyl)phenyl]methyl]-2,3-dihydropyrido[4,3-b][1,4]oxazin-5-yl]amino]cyclopropyl]benzoic acid<br>$^1$H NMR DMSO-d$_6$: δ 1.15-1.65 (m, 2H), 1.21-1.24 (m, 2H), 2.97-2.99 (m, 2H), 4.10 (s, 2H), 4.17 (t, J = 4.4 Hz, 2 H), 5.94 (s, 1H), 6.17 (d, J = 5.2 Hz, 1 H), 6.94 (d, J = 8.8 Hz, 2 H), 7.51 (d, J = 5.2 Hz, 1H), 7.61-7.69 (m, 4H), 7.85-7.88 (m, 2H). | 471.1 |
| C7 | 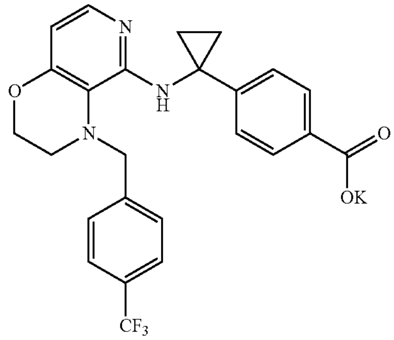 | Potassium salt of 4-[1-[[4-[[4-(trifluoromethyl)phenyl]methyl]-2,3-dihydropyrido[4,3-b][1,4]oxazin-5-yl]amino]cyclopropyl]benzoic acid<br>$^1$H NMR DMSO-d$_6$: δ 1.18 (s, 2H), 1.25 (s, 2H), 2.98 (s, 2H), 4.09 (s, 2H), 4.18 (s, 2H), 5.91 (s, 1H), 6.19 (d, J = 6 Hz, 1H), 6.99 (d, J = 8.4 Hz, 2H), 7.51 (d, J = 6 Hz, 1H), 7.65 (d, J = 8.4 Hz, 2H), 7.7 (s, 4H). | 470.3 |

Example D1: 4-[(1S)-1-[[4-[[4-(Trifluoromethyl)phenyl]methyl]-2,3-dihydropyrido[4,3-b][1,4]oxazin-5-yl]amino]ethyl]benzamide

Example D2: N-Methoxy-4-[(1S)-1-[[4-[[4-(trifluoromethyl)phenyl]methyl]-2,3-dihydropyrido[4,3-b][1,4]oxazin-5-yl]amino]ethyl]benzamide

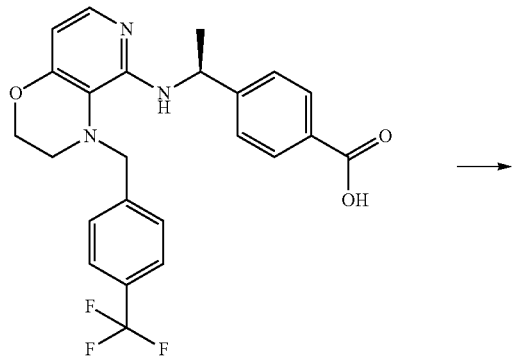

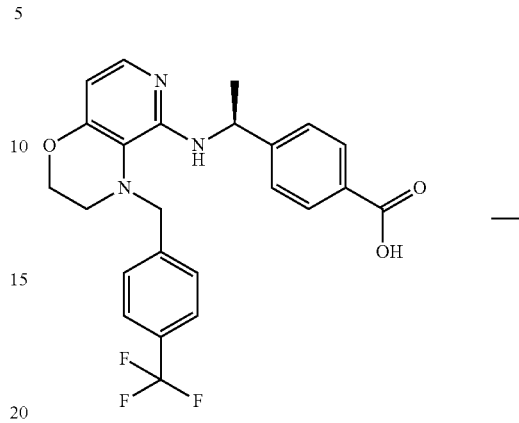

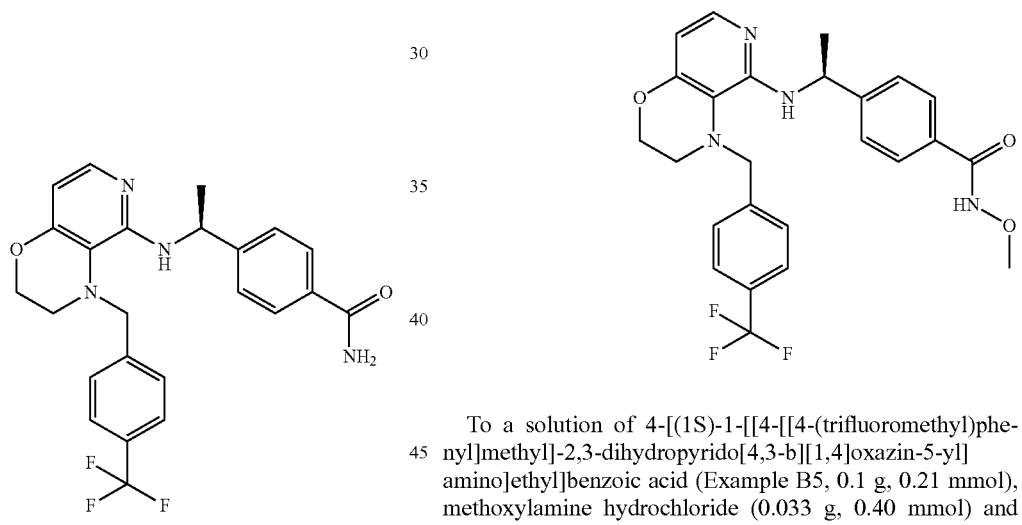

To a solution of 4-[(1S)-1-[[4-[[4-(trifluoromethyl)phenyl]methyl]-2,3-dihydropyrido[4,3-b][1,4]oxazin-5-yl]amino]ethyl]benzoic acid (Example B5, 1.0 g, 2.18 mmol) in THF (10 mL) were added triethylamine (0.61 mL, 4.37 mmol) and ethyl chloroformate (0.31 mL, 3.28 mmol). The reaction mixture was stirred at 0° C. under argon atmosphere. After 15 min stirring at 0° C., 7N ammonia solution in 1.4-dioxane was added thereto, and the mixture was continued to stir for 1 hour. The reaction mixture was concentrated under vacuum, and the residue was obtained was purified by silica gel (100-200) column chromatography with 35% ethyl acetate in hexane to give the title compound as a white solid (0.75 g, 75%).

MS (ESI) m/z: 457.1 (M+1); $^1$H NMR (400 MHz, DMSO-$d_6$): δ 1.38 (d, J=6.4 Hz, 3H), 2.99 (s, 2H), 4.10 (d, J=3.2 Hz, 2H), 4.19-4.21 (m, 2H), 5.12-5.15 (m, 1H), 5.24 (d, J=7.2 Hz, 2H), 6.18 (d, J=5.2 Hz, 1H), 7.33 (d, J=8.4 Hz, 2H), 7.52 (d, J=6.0 Hz, 1H), 7.73-7.78 (m, 6H), 7.79-7.85 (m, 1H).

To a solution of 4-[(1S)-1-[[4-[[4-(trifluoromethyl)phenyl]methyl]-2,3-dihydropyrido[4,3-b][1,4]oxazin-5-yl]amino]ethyl]benzoic acid (Example B5, 0.1 g, 0.21 mmol), methoxylamine hydrochloride (0.033 g, 0.40 mmol) and HATU (0.114 g, 0.30 mmol) in DMF (5 mL) was added DIPEA (0.18 mL, 1.0 mmol). The reaction mixture was stirred at room temperature for 18 hours. The reaction mixture was quenched with water (20 mL), and extracted with ethyl acetate (3×20 mL). The combined organic layers were washed successively with water (20 mL) and brine (20 mL), dried over sodium sulfate and concentrated under vacuum. The crude mixture thus obtained was purified by flash column chromatography using silica gel and 30% ethyl acetate in hexane to give the title compound as an off-white solid (0.08 g, 75%).

MS (ESI) m/z: 487.1 (M+1); $^1$H NMR (400 MHz, DMSO-$d_6$): δ 1.38 (d, J=7.2 Hz, 3H), 2.99 (s, 2H), 3.68 (s, 3H), 4.10 (d, J=4.8 Hz, 2H), 4.20-4.21 (m, 2H), 5.10-5.13 (m, 1H), 5.25 (s, 1H), 6.19 (d, J=5.6 Hz, 1H), 7.35 (d, J=8.0 Hz, 2H), 7.51 (d, J=5.2 Hz, 1H), 7.62 (d, J=8.0 Hz, 2H), 7.74-7.79 (m, 4H), 11.6 (s, 1H).

The compounds of Examples D3-D5 were synthesized in a similar manner to that of Example D2.

TABLE 8

| Ex. No. | Structure | IUPAC Name / ¹H NMR data | MS(ESI)m/z: (M + 1) |
|---|---|---|---|
| D3 | 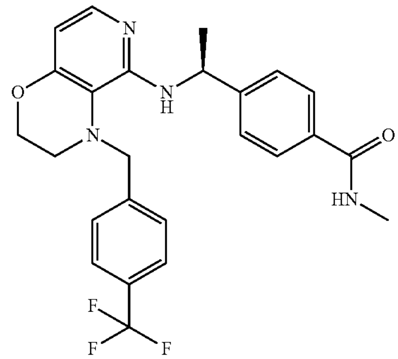 [SMILES: CNC(=O)c1ccc([C@H](C)Nc2nccc3c2N(Cc2ccc(C(F)(F)F)cc2)CCO3)cc1] | N-methyl-4-[(1S)-1-[[4-[[4-(trifluoromethyl)phenyl]methyl]-2,3-dihydropyrido[4,3-b][1,4]oxazin-5-yl]amino]ethyl]benzamide<br>¹H NMR DMSO-$d_6$: δ 1.38 (d, J = 6.3 Hz, 3H), 2.75 (d, J = 4.8 Hz, 3H), 2.99 (s, 2H), 4.10 (d, J = 4.0 Hz, 2H), 4.21 (d, J = 4.0 Hz, 2H), 5.12-5.15 (m, 1H), 5.24 (d, J = 7.2 Hz, 1H), 6.19 (d, J = 8.4 Hz, 1H), 7.33 (d, J = 8.4 Hz, 2H), 7.52 (d, J = 5.6 Hz, 1H), 7.69 (d, J = 8.0 Hz, 2H), 7.74-7.79 (m, 4H), 8.31-8.30 (m, 1H). | 471.1 |
| D4 | 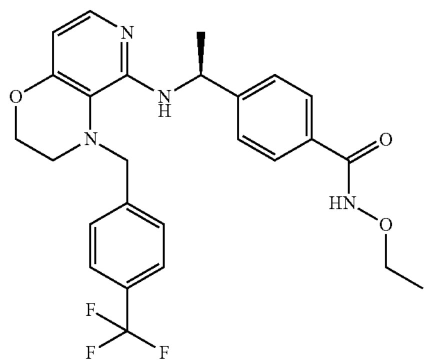 [SMILES: CCONC(=O)c1ccc([C@H](C)Nc2nccc3c2N(Cc2ccc(C(F)(F)F)cc2)CCO3)cc1] | N-ethoxy-4-[(1S)-1-[[4-[[4-(trifluoromethyl)phenyl]methyl]-2,3-dihydropyrido[4,3-b][1,4]oxazin-5-yl]amino]ethyl]benzamide<br>¹H NMR DMSO-$d_6$: δ 1.17-1.29 (m, 3H), 1.38 (d, J = 6.8 Hz, 3H), 2.99 (s, 2H), 3.90 (q, J = 6.8 Hz, 2H), 4.10 (d, J = 3.6 Hz, 2H), 4.20 (s, 2H), 5.09-5.13 (m, 1H), 5.25 (s, 1H), 6.19 (d, J = 5.2 Hz, 1H), 7.35 (d, J = 8.0 Hz, 2H), 7.52 (d, J = 5.2 Hz, 1H), 7.62 (d, J = 8.0 Hz, 2H), 7.73-7.79 (m, 4H). | 501.1 |
| D5 | 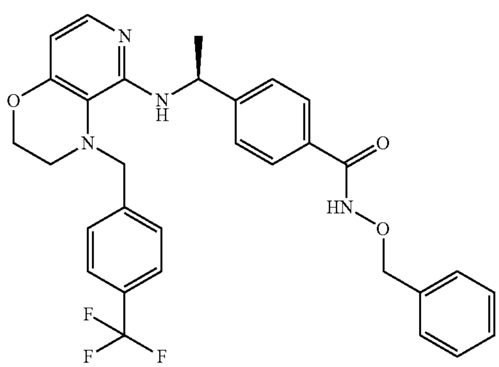 [SMILES: C[C@H](Nc1nccc2c1N(Cc1ccc(C(F)(F)F)cc1)CCO2)c1ccc(C(=O)NOCc2ccccc2)cc1] | N-benzyloxy-4-[(1S)-1-[[4-[[4-(trifluoromethyl)phenyl]methyl]-2,3-dihydropyrido[4,3-b][1,4]oxazin-5-yl]amino]ethyl]benzamide<br>¹H NMR DMSO-$d_6$: δ 1.37 (d, J = 6.4 Hz, 3H); 2.99 (s, 2H), 4.10 (dd, J = 5.6, 15.6 Hz, 2H), 4.20 (s, 2H), 4.89 (s, 2H), 5.10-5.13 (m, 1H), 5.25 (d, J = 6.4 Hz, 1H), 6.19 (d, J = 5.6 Hz, 1H), 7.34-7.45 (m, 7H), 7.51 (d, J = 5.6 Hz, 1H), 7.61 (d, J = 7.6 Hz, 2H), 7.75-7.8 (m, 4H). | 563.2 |

Example E1: 4-[(1S)-1-[[4-[[4-(Trifluoromethyl)phenyl]methyl]-2,3-dihydropyrido[4,3-b][1,4]oxazin-5-yl]amino]ethyl]benzonitrile

Example F1: N-[(1S)-1-[4-(1H-Tetrazol-5-yl)phenyl]ethyl]-4-[[4-(trifluoromethyl)phenyl]methyl]-2,3-dihydropyrido[4,3-b][1,4]oxazin-5-amine

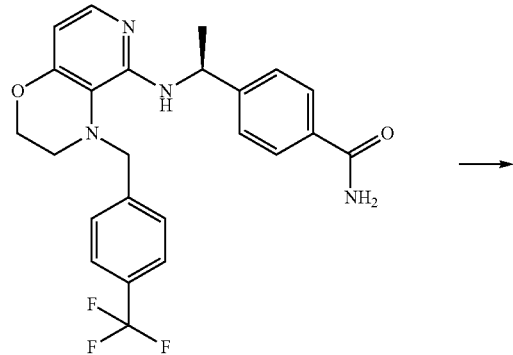

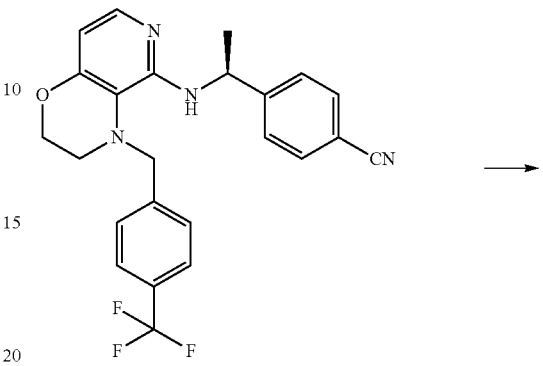

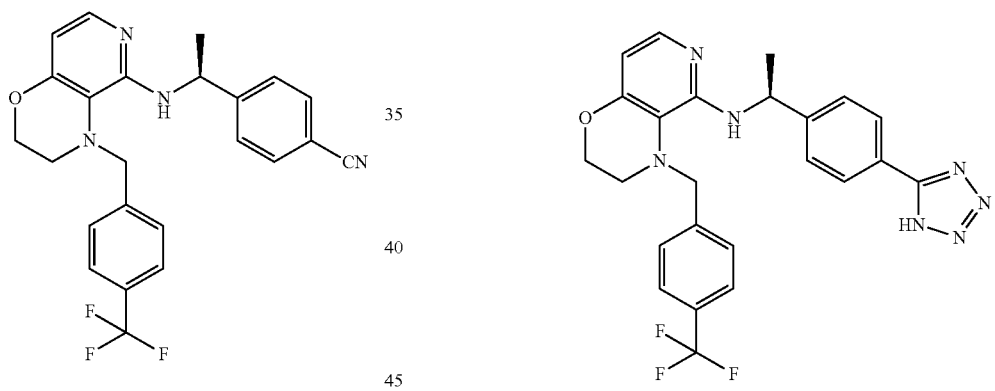

To a solution of 4-[(1S)-1-[[4-[[4-(trifluoromethyl)phenyl]methyl]-2,3-dihydropyrido[4,3-b][1,4]oxazin-5-yl]amino]ethyl]benzamide (Example D1, 0.4 g, 0.87 mmol) in THF (10 mL) were added pyridine (0.18 mL, 2.19 mmol) and trifluoroacetic anhydride (0.3 mL, 2.19 mmol). The reaction mixture was stirred at 0° C. under argon atmosphere for 2 hours. The reaction was quenched with water (20 mL) and extracted with ethyl acetate (3×20 mL). The combined organic layers were washed successively with water (20 mL) and brine (20 mL), dried over sodium sulfate and concentrated under vacuum. The residue was purified by silica gel (100-200) column chromatography with 20-30% ethyl acetate in hexane to give the title compound as an off-white solid (0.335 g, 87%).

MS (ESI) m/z: 439.1 (M+1); $^1$H NMR (400 MHz, DMSO-$d_6$): δ 1.39 (d, J=7.2 Hz, 3H), 2.99 (d, J=3.6 Hz, 2H), 4.12 (dd, J=10.0, 15.6 Hz, 2H), 4.21 (d, J=5.4 Hz, 2H), 5.09-5.12 (m, 1H), 5.32 (d, J=6.4 Hz, 1H), 6.20 (d, J=5.6 Hz, 1H), 7.48-7.50 (m, 3H), 7.70 (d, J=8.4 Hz, 2H), 7.77-7.80 (m, 4H).

A mixture of 4-[(1S)-1-[[4-[[4-(trifluoromethyl)phenyl]methyl]-2,3-dihydropyrido[4,3-b][1,4]oxazin-5-yl]amino]ethyl]benzonitrile (Example E1, 0.1 g, 0.23 mmol) and trimethylsilylazide (0.039 g, 0.34 mmol) was heated at 100° C. under argon atmosphere for 4 hours. After cooling at room temperature, the reaction mixture was diluted with water (10 mL) and extracted with ethyl acetate (3×20 mL). The combined organic layers were washed successively with water (20 mL) and brine (20 mL), dried over sodium sulfate and concentrated under vacuum. The residue was purified by silica gel (100-200) column chromatography with 60-70% ethyl acetate in hexane as a mobile phase to give the title compound as an off-white solid (0.035 g, 32%).

MS (ESI) m/z: 482.1 (M+1

$^1$H NMR (400 MHz, DMSO-$d_6$): δ 1.43 (d, J=6.4 Hz, 3H), 3.00 (s, 2H), 4.13 (dd, J=16.0, 8.2 Hz, 2H), 4.20-4.22 (m, 2H), 5.13-5.17 (m, 1H), 5.34 (s, 1H), 6.21 (d, J=6 Hz, 1H), 7.49-7.54 (m, 3H), 7.75-7.79 (m, 4H), 7.91 (d, J=8.8 Hz, 2H), 16.6 (br s, 1H).

Example G1: 4-[(1S)-1-[[8-Chloro-4-[[4-(trifluoromethyl)phenyl]methyl]-2,3-dihydropyrido[4,3-b][1,4]oxazin-5-yl]amino]ethyl]benzoic acid

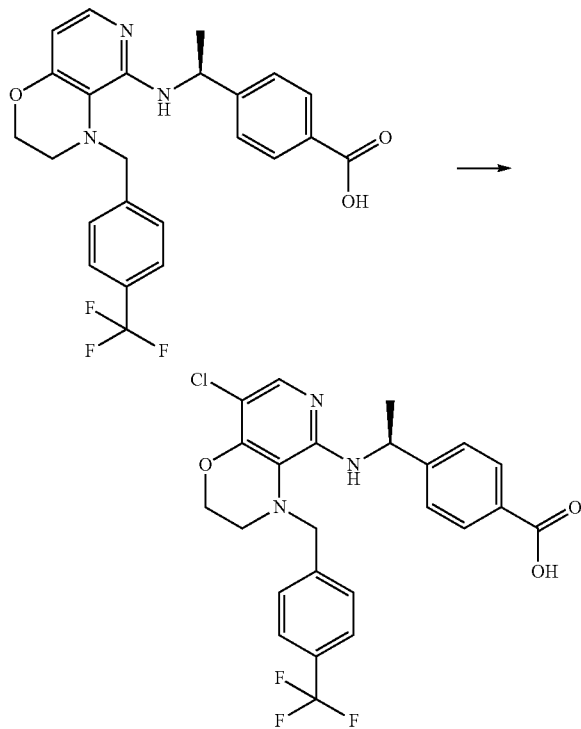

A mixture of 4-[(1S)-1-[[4-[[4-(trifluoromethyl)phenyl]methyl]-2,3-dihydropyrido[4,3-b][1,4]oxazin-5-yl]amino]ethyl]benzoic acid (Example B5, 0.2 g, 0.44 mmol) in acetonitrile (10 mL) and N-chlorosuccinimide (0.058 g, 0.44 mmol) was heated at 70° C. for 2 hours. The reaction completion was confirmed by TLC. To the resulting residue was added water (15 mL), and the mixture was extracted with ethyl acetate (3×15 mL). The combined organic layers were washed with brine (20 mL) and dried over sodium sulfate. The organic layer was evaporated under vacuum, and the residue was purified by LCMS purification technique to give the title compound (0.11 g, 51%).

MS (ESI) m/z: 492.2 (M+1); $^1$H NMR (400 MHz, DMSO-$d_6$): δ 1.38 (d, J=6.8 Hz, 3H), 3.05 (s, 2H), 4.13 (s, 2H), 4.31-4.32 (m, 2H), 5.09-5.12 (m, 1H), 5.32 (d, J=6.8 Hz, 1H), 7.36 (d, J=8.4 Hz, 2H), 7.66 (s, 1H), 7.74-7.82 (m, 6H), 12.75 (s, 1H).

Formulation Example 1 (Production of Capsule)

| 1) compound of Example 1 | 30 mg |
|---|---|
| 2) fine powder cellulose | 10 mg |
| 3) lactose | 19 mg |
| 4) magnesium stearate | 1 mg |
| Total | 60 mg |

1), 2), 3) and 4) are mixed and filled in a gelatin capsule.

Formulation Example 2 (Production of Tablet)

| 1) compound of Example 1 | 30 g |
|---|---|
| 2) lactose | 50 g |
| 3) cornstarch | 15 g |
| 4) calcium carboxymethylcellulose | 44 g |
| 5) magnesium stearate | 1 g |
| 1000 tablets total | 140 g |

The total amount of 1), 2) and 3) and 4) (30 g) is kneaded with water, vacuum dried, and sieved. The sieved powder is mixed with 4) (14 g) and 5) (1 g), and the mixture is punched by a tableting machine, whereby 1000 tablets containing 30 mg of the compound of Example 1 per tablet are obtained.

Experimental Example 1

Membrane Preparation:

The full-length coding sequences for human EP1 (NM_000955), human EP2 (NM_000956), human EP3 (NM_198717) and human EP4 (NM_000958) were cloned into pcDNA3.1(+) vector (Life Technologies, CA, USA). In order to prepare overexpressed EP 1-4 membrane in Freestyle293 cells (Life Technologies, CA, USA), the pcDNA3.1(+) vector encoding a cDNA of the relevant gene was transiently transfected into FreeStyle293 cells using 293Fectin (Life Technologies, CA, USA) according to the manufacturer instruction manual. After 2 days, cultured cells were centrifuged (1,000×g, 10 min, 4° C.) and pellets homogenized by a probe sonicator (Sonics vibracell, Sonics and Materials Inc., USA; 31% Amp, 5 sec pulse, 1min interval, 4 cycles) in ice-cold 50 mM Tris-HCl buffer (pH 7.5 at 25° C.) containing 0.5 mM EDTA, 250 mM Sucrose and 10 mM $MgCl_2$. Cell homogenates were centrifuged (890×g, 10 min, 4° C.), and the supernatant was recovered. Total membrane fractions were isolated by ultracentrifugation (140,000×g, 60 min, 4° C.). Pellets were re-suspended in the same buffer, and stored at −80° C. until use. The protein concentration in homogenate was determined with the BCA Protein Assay Kit (Pierce Biotechnology, Inc., IL, USA) according to the manufacturer protocol.

Primary In Vitro Binding Assay:

The binding affinity of the compounds was evaluated using a competitive radioligand binding assay which measured the specific binding of [3H] PGE2 to the human EP4 receptor. Briefly, varying concentrations of NCEs were incubated with cell membrane fractions generated HEK293F cells transiently transfected with human EP4 receptor as described above. Each reaction consisted of 10 μg membrane protein and NCE in 50 mM Tris-HCl, pH-6.0 by NaOH, 10 mM $MgCl_2$ and 0.5 mM EDTA assay buffer. Radioligand, [3H] PGE2 (American Radiochemicals Inc. Specific Activity 180 Ci/mmol), at a final of 1 nM was added to each reaction where the final assay volume was 200 μL and concentration of DMSO was adjusted to 1%. Appropriate controls included total binding in the assay (vehicle control) and control for non-specific binding. Non-specific binding was evaluated by incubating the hEP4 protein with 10 μM unlabeled PGE2 under the same assay conditions as NCEs. The reaction was incubated at room temperature for 2 hours and terminated by harvesting the reaction contents to a PEI coated GF/C filter plate (PerkinElmer). The plate was washed four times with cold 50 mM Tris-HCl, pH-7.5 wash buffer and dried at 50° C. for 2 hours or at 37° C. overnight. [3H] PGE2 bound to the protein was quantified by the addition of 25 μL of Microscint PS (PerkinElmer) and plate was read on MicroBeta2 liquid Scintillation and luminescence counter (PerkinElmer). Data was analyzed using GraphPad Prism 5 (GraphPad Software Inc., San Diego, Calif.) where non-specific binding was normalized to 0% specific binding of [3]PGE2 and vehicle control (DMSO) was normalized to 100% specific binding of [3]PGE2. Binding affinity of NCEs, Ki, was generated using One site—Fit Ki equation in GraphPad Prism 5.

Functional Assay:

The functional assay for hEP4 activation and inhibition was carried out via the quantitative determination of agonist, PGE2, induced cAMP response using HTRF in a competitive immunoassay (Cisbio dynamic 2 kit). NCEs at varying concentrations were evaluated for inhibition of PGE2 induced increase in cAMP. Briefly, C6 glioma cells overexpressing hEP4 (Takeda) were cultured in DMEM (low glucose, pyruvate), 10% FBS (Gibco) and PenStep. The cells were harvested on the day of the assay, washed with HBSS+10 mM HEPES (pH 7.4)+0.1% BSA buffer and pre-incubated with varying concentrations of NCE. Each reaction contained 7000 cells and NCEs in HBSS+10 mM HEPES+0.1% BSA assay buffer along with PDE inhibitors IBMX and Ro 20-1724 (final concentration of each inhibitor 200 mM). Following 15 min pre-incubation, the cells were treated with EC80 concentration of agonist PGE2 for 30 min to induce cAMP. Final volume of the assay was 6 μL and DMSO concentration was maintained at 1%. The reaction was terminated with the addition of cAMP labeled with the dye d2 in lysis buffer according to manufacturers' protocol. This was followed by the addition of the anti-cAMP antibody labeled with Cryptate according to the manufacturers' protocol. The reaction was incubated at room temperature in dark for 45 min and the plate was evaluated for fluorescence at 665 nm (FRET) and 620 nm (cryptate emission) on a Flexstation III microplate reader (Molecular Devices, Sunnyvale, Calif.) Ex max: 313 nm; Em1: 620 nm; Em2: 665 nm. Data was analyzed using GraphPad Prism 5 (GraphPad Software Inc., San Diego, Calif.) where cells treated with agonist ($EC_{80}$) was normalized to 0% inhibition of hEP4 and cells treated with buffer (no agonist) was normalized to 100% inhibition of hEP4. $IC_{50}$ of NCEs was generated using non-linear regression—Log(inhibitor) vs. response equation in GraphPad Prism 5.

Table 9: Potency of compound in hEP4 radioligand binding assay at 300 nM and cell based assay (cAMP) at 1 μM

TABLE 9

| Example | hEP4 radioligand binding assay % Inhibition at 300 nM | hEP4 cell based assay (cAMP) % Inhibition at 1 μM |
|---|---|---|
| Example A46 | 12 | ND* |
| Example A47 | 12 | ND* |
| Example A48 | 28 | ND* |
| Example A49 | 17 | ND* |
| Example A50 | 26 | ND* |
| Example A51 | ND* (300 nM) 29 (1 μM) | ND* |
| Example B1 | 93 | 100 |
| Example B2 | 98 | 100 |
| Example B3 | 81 | 90 |
| Example B4 | 83 | 97 |
| Example B5 | 74 | 100 |
| Example B6 | 89 | 100 |
| Example B7 | 99 | 100 |
| Example B8 | 97 | 100 |
| Example B9 | 97 | 100 |
| Example B10 | 97 | 100 |
| Example B11 | 95 | 100 |
| Example B12 | 98 | 100 |
| Example B13 | 92 | 100 |
| Example B14 | 93 | 100 |
| Example B15 | 98 | 99 |
| Example B16 | 93 | 88 |
| Example B17 | 96 | 86 |
| Example B18 | 93 | 79 |
| Example B19 | 92 | 81 |
| Example B20 | 92 | 92 |
| Example B21 | 87 | 87 |
| Example B22 | 80 | 90 |
| Example B23 | 100 | 74 |
| Example B24 | 100 | 71 |
| Example B25 | 98 | 79 |
| Example B26 | 93 | 87 |
| Example B27 | 42 | ND* |
| Example B28 | 49 | ND* |
| Example B29 | 100 | 96 |
| Example B30 | 87 | 77 |
| Example B31 | 92 | 98 |
| Example B32 | 53 | 47 |
| Example B33 | 66 | 36 |
| Example B34 | 42.5 | ND* |
| Example B35 | 42.4 | ND* |
| Example B36 | 49 | ND* |
| Example B37 | 97 | 97 |
| Example B38 | 88 | ND* |
| Example B39 | 100 | 93 |
| Example B40 | 80 | 85 |
| Example B41 | 47 | ND* |
| Example B42 | 0.3 (300 nM) 26 (1 μM) | ND* |
| Example B43 | 10 | ND* |
| Example B44 | 93 | 92 |
| Example B45 | 100 | 98 |
| Example B46 | 87 | 95 |
| Example B47 | 60 | ND* |
| Example D1 | 85 | 98 |
| Example D2 | 87 | 92 |
| Example D3 | 73 | 84 |
| Example D4 | 92 | 93 |
| Example D5 | 88 | 90 |
| Example E1 | 92 | 91 |
| Example F1 | 100 | 90 |
| Example G1 | 100 | 92 |

*ND: Not determined

Experimental Example 2

Suppression of Arthritis Development in Adjuvant Induced Arthritis (AIA) Model in Female Lewis Rats Adjuvant arthritis was induced on day 1 in female Lewis rats (10-12 weeks) by intradermal injection of heat killed *Mycobacterium tuberculosis* in complete freund's adjuvant (CFA) intradermally (*Mycobacterium tuberculosis* 100 mg in 5 mL incomplete freunds adjuvant, 200 μL per rat). Animals were randomized into different treatment groups, each group consist of 8 animals based on clinical scores on day 14. The animals in control group were given CFA and in second control group were administered with CFA and vehicle (1% Tween-80+0.5% CMC, quantity sufficient, 3 ml/kg, PO), where as animals in experimental groups were treated with CFA and EP4 antagonist (Example B2 and Example B4) in therapeutic fashion orally twice a day (BID) from day 14 to day 23 at 0.1, 0.3, 1, 3, 10 and 30 mg/kg doses.

Evaluation of Disease Severity (Arthritis Score)

Figure 2:
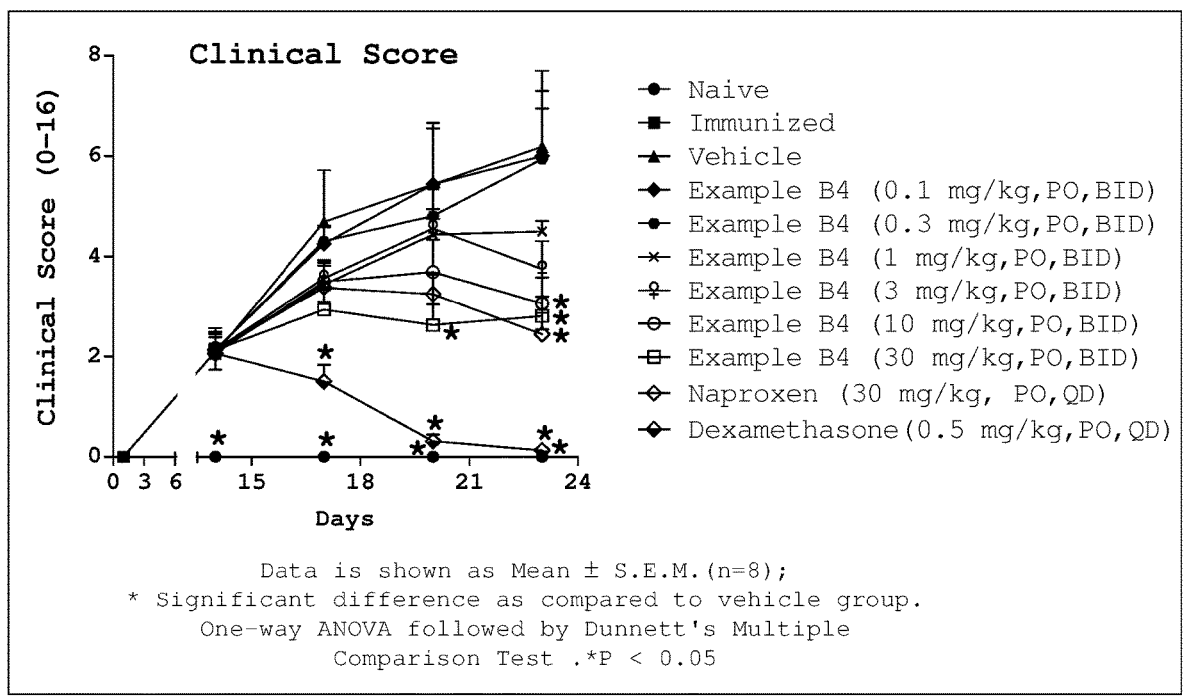
FIG. 2 shows suppression of arthritis development in adjuvant induced arthritis model when treated with the compound of Example B4.

Animals were evaluated for clinical symptoms and scored accordingly for inflamed paws and erythema. The scorer was blind to the treatment groups. Key findings for example B2 (Refer FIG. 1) and B4 (Refer FIG. 2) in rat arthritis model are as follows.

Rats treated with Example B2 showed 23, 45, 46, 67, 68 and 71% reduction in arthritis score at 0.1, 0.3, 1, 3, 10 and 30 mg/kg BID, doses respectively compared to vehicle treatment at the end of study period. $ED_{50}$ was 0.76 mg/kg, PO, BID.

Rats treated with Example B4 showed 3, 4, 27, 39, 51 and 55% reduction in arthritis score at 0.1, 0.3, 1, 3, 10 and 30 mg/kg BID, doses respectively compared to vehicle treatment at the end of study period. $ED_{50}$ was 8.8 mg/kg, PO, BID.

INDUSTRIAL APPLICABILITY

Compound (I) has a superior EP4 receptor antagonistic action, which may be useful as an agent for the prophylaxis or treatment of EP4 receptor associated diseases (e.g., rheumatoid arthritis, aortic aneurysm (e.g. abdominal aortic aneurysm, thoracic aortic aneurysm, thoracoabdominal aortic aneurysm etc.), endometriosis, ankylosing spondylitis, inflammatory breast cancer etc.) and the like.

This application is based on patent application No. 2244/DEL/2015 filed on Jul. 23, 2015 in India, the contents of which are encompassed in full herein.

The invention claimed is:

1. A compound represented by the formula (I)

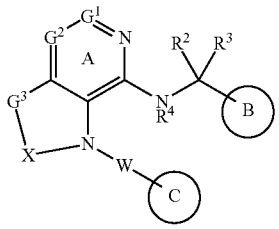

(I)

wherein
$G^1$ is a carbon atom,
$G^2$ is a carbon atom,
Ring A is pyridine,
$G^3$ is an oxygen atom,
X is ethylene,
$R^2$ and $R^3$ are each a hydrogen atom or a methyl group,
$R^4$ is a hydrogen atom,
Ring B is
  a $C_6$ aromatic hydrocarbon ring optionally further substituted by substituents selected from the group consisting of
    (a) a carboxy group,
    (b) 5-tetrazolyl,
    (c) a mono- or di-$C_1$-$C_6$ alkyl-carbamoyl group, and
    (d) a mono- or di-$C_1$-$C_6$ alkoxy-carbamoyl group, and
Ring C is a $C_6$ aromatic hydrocarbon ring, a $C_6$ cycloalkane, or a pyridine ring, each of which is optionally further substituted by 1 to 3 substituents selected from the group consisting of
    (a) a halogen atom,
    (b) an optionally halogenated $C_{1-6}$ alkyl group,
    (c) a $C_{1-6}$ alkoxy group, and
    (d) a $C_{6-14}$ aryl group, and
W is
  a $C_{1-4}$ alkyl group optionally substituted by an oxo group.

2. 4-[(1S)-1-[[4-[(3-Chlorophenyl)methyl]-2,3-dihydropyrido[4,3-b][1,4]oxazin-5-yl]amino]ethyl] benzoic acid or a salt thereof.

3. 4-[1-[[4-[(3,4-Difluorophenyl)methyl]-2,3-dihydropyrido[4,3-b][1,4]oxazin-5-yl]amino]cyclopropyl] benzoic acid or a salt thereof.

4. 4-[(1S)-1-[[4-[(4-Methoxyphenyl)methyl]-2,3-dihydropyrido[4,3-b][1,4]oxazin-5-yl]amino]ethyl] benzoic acid or a salt thereof.

5. A pharmaceutical composition comprising the compound or salt according to claim 1 and a pharmacologically acceptable carrier.

* * * * *

UNITED STATES PATENT AND TRADEMARK OFFICE
CERTIFICATE OF CORRECTION

PATENT NO. : 10,745,397 B2  
APPLICATION NO. : 15/746828  
DATED : August 18, 2020  
INVENTOR(S) : Dinesh Barawkar et al.

Page 1 of 1

It is certified that error appears in the above-identified patent and that said Letters Patent is hereby corrected as shown below:

On the Title Page

Item (22), please change the date of "PCT filed" from "July 26, 2016" to "July 22 2016"

Signed and Sealed this  
Twenty-ninth Day of December, 2020

Andrei Iancu  
*Director of the United States Patent and Trademark Office*